United States Patent
Bradley et al.

(10) Patent No.: US 11,707,056 B2
(45) Date of Patent: Jul. 25, 2023

(54) ANIMALS, REPERTOIRES AND METHODS

(71) Applicant: Kymab Limited, Cambridge (GB)

(72) Inventors: Allan Bradley, Cambridge (GB);
E-Chiang Lee, Cambridge (GB)

(73) Assignee: Kymab Limited, Cambridge (GB)

( * ) Notice: Subject to any disclaimer, the term of this patent is extended or adjusted under 35 U.S.C. 154(b) by 0 days.

(21) Appl. No.: 14/220,080

(22) Filed: Mar. 19, 2014

(65) Prior Publication Data

US 2015/0033369 A1    Jan. 29, 2015

Related U.S. Application Data

(60) Provisional application No. 61/818,836, filed on May 2, 2013.

(51) Int. Cl.
*A01K 67/027*    (2006.01)
*C07K 16/46*    (2006.01)

(52) U.S. Cl.
CPC ...... *A01K 67/0278* (2013.01); *A01K 67/0275* (2013.01); *A01K 67/0276* (2013.01); *C07K 16/462* (2013.01); *A01K 2207/15* (2013.01); *A01K 2217/072* (2013.01); *A01K 2217/15* (2013.01); *A01K 2227/105* (2013.01); *A01K 2267/01* (2013.01); *C07K 2317/21* (2013.01); *C07K 2317/24* (2013.01); *C07K 2317/56* (2013.01)

(58) Field of Classification Search
CPC .. C07K 16/00; C07K 16/462; C07K 16/1239; C07K 16/18; C07K 2317/14; C07K 2317/51; C07K 2317/92; C07K 16/1203; C07K 2317/21; C07K 2317/515; C07K 2317/52; C07K 2317/565; C07K 2317/567; C07K 16/1282; C07K 16/46; C07K 2317/007; C07K 16/007; C07K 2317/24; C07K 2317/56; A01K 67/0275; A01K 67/0278; A01K 67/0276; A01K 2207/15; A01K 2217/072; A01K 2217/15; A01K 2227/105; A01K 2267/01
USPC .............................. 800/18; 530/387.1, 387.3
See application file for complete search history.

(56) References Cited

U.S. PATENT DOCUMENTS

| | | | |
|---|---|---|---|
| 4,720,449 A | 1/1988 | Borror et al. | |
| 5,169,939 A | 12/1992 | Gefter et al. | 530/387.3 |
| 5,545,806 A | 8/1996 | Lonberg et al. | |
| 5,545,807 A | 8/1996 | Surani et al. | |
| 5,565,321 A | 10/1996 | Spriggs et al. | |
| 5,633,425 A | 5/1997 | Lonberg et al. | |
| 5,770,429 A | 6/1998 | Lonberg et al. | |
| 5,789,215 A | 8/1998 | Berns et al. | 435/172.3 |
| 5,807,715 A | 9/1998 | Morrison et al. | |
| 5,939,598 A | 8/1999 | Kucherlapati et al. | 800/25 |
| 5,948,600 A | 9/1999 | Roschger et al. | |
| 6,114,598 A | 9/2000 | Kucherlapati et al. | |
| 6,130,364 A | 10/2000 | Jakobovits et al. | |
| 6,162,963 A | 12/2000 | Kucherlapati et al. | |
| 6,319,906 B1 | 11/2001 | Bennett et al. | |
| 6,395,487 B1 | 5/2002 | Bradley et al. | |
| 6,461,818 B1 | 10/2002 | Bradley et al. | |
| 6,596,541 B2 * | 7/2003 | Murphy | A01K 67/0275 435/440 |
| 6,657,103 B1 | 12/2003 | Kucherlapati et al. | |
| 6,673,986 B1 | 1/2004 | Kucherlapati et al. | |
| 6,713,610 B1 | 3/2004 | Kucherlapati et al. | 530/388.23 |
| 6,833,268 B1 | 12/2004 | Green et al. | 435/320.1 |
| 6,992,235 B2 | 1/2006 | Bode et al. | |
| 6,998,514 B2 | 2/2006 | Brüggemann | 800/18 |
| 7,105,348 B2 | 9/2006 | Murphy et al. | |
| 7,119,248 B1 | 10/2006 | Rajewsky et al. | 800/6 |
| 7,205,140 B2 | 4/2007 | Gottschalk et al. | |
| 7,205,148 B2 | 4/2007 | Economides et al. | 435/462 |
| 7,262,028 B2 | 8/2007 | Van Berkel et al. | |
| 7,294,754 B2 | 11/2007 | Poueymirou et al. | |
| 7,435,871 B2 | 10/2008 | Green et al. | 800/18 |
| 7,501,552 B2 | 3/2009 | Lonberg et al. | 800/6 |
| 7,605,237 B2 | 10/2009 | Stevens et al. | |
| 7,605,238 B2 | 10/2009 | Korman et al. | |
| 7,910,798 B2 | 3/2011 | Tanamachi et al. | |
| 7,932,431 B2 | 4/2011 | Bruggemann | |
| 8,158,419 B2 | 4/2012 | Lonberg et al. | |
| 8,502,018 B2 | 8/2013 | Murphy et al. | 800/18 |
| 8,592,644 B2 | 11/2013 | Harriman et al. | |
| 8,642,835 B2 | 2/2014 | Macdonald et al. | |
| 8,697,940 B2 | 4/2014 | Macdonald et al. | |
| 8,754,287 B2 | 6/2014 | Macdonald et al. | |
| 8,771,988 B2 | 7/2014 | Goepfert et al. | |

(Continued)

FOREIGN PATENT DOCUMENTS

| | | | | |
|---|---|---|---|---|
| CA | 2 307 503 A1 | 11/2001 | | A61K 39/42 |
| CA | 2747534 A1 | 6/2010 | | |

(Continued)

OTHER PUBLICATIONS

Finn, C.A. Reproductive capacity and litter size in mice: Effect of age and environment. J. Reprod. Fertil. 6:205-214, (Year: 1963).*

(Continued)

*Primary Examiner* — Anne Marie S Wehbe
(74) *Attorney, Agent, or Firm* — Nutter McClennen & Fish LLP

(57) ABSTRACT

The present invention is directed to the concept of sectoring antibody gene segment repertoires in order to enable the development of novel, synthetic antibody chain repertoires not seen in nature. The present invention is also directed to the realisation of the inventors that sectoring can also alter gene segment expression by providing new arrangements of gene segment clusters relative to other gene segments and regulatory elements in transgenic immunoglobulin loci, thereby providing for new synthetic antibody chain sequence repertoires. The invention also relates to gene segment inversion.

34 Claims, 21 Drawing Sheets

Specification includes a Sequence Listing.

(56) References Cited

U.S. PATENT DOCUMENTS

| | | |
|---|---|---|
| 8,791,323 B2 | 7/2014 | Murphy et al. |
| 8,877,901 B2 | 11/2014 | Govindan |
| 8,962,913 B2 | 2/2015 | Murphy |
| 9,253,965 B2 | 2/2016 | Liang et al. |
| 9,434,782 B2 | 9/2016 | Bradley et al. |
| 9,445,581 B2 | 9/2016 | Bradley et al. |
| 9,447,177 B2 | 9/2016 | Bradley et al. |
| 9,504,236 B2 | 11/2016 | Bradley et al. |
| 9,505,827 B2 | 11/2016 | Bradley et al. |
| 9,783,593 B2 | 10/2017 | Bradley et al. |
| 9,783,618 B2 | 10/2017 | Friedrich et al. |
| 9,788,534 B2 | 10/2017 | Bradley et al. |
| 9,844,212 B2 | 12/2017 | Macdonald et al. |
| 9,896,516 B2 | 2/2018 | Bradley et al. |
| 9,924,705 B2 | 3/2018 | Liang et al. |
| 9,938,357 B2 | 4/2018 | Bradley et al. |
| 9,938,358 B2 | 4/2018 | Bradley et al. |
| 9,963,716 B2 | 5/2018 | Bradley et al. |
| 10,064,398 B2 | 9/2018 | Bradley et al. |
| 10,149,462 B2 | 12/2018 | Lee et al. |
| 10,165,763 B2 | 1/2019 | Bradley et al. |
| 10,226,033 B2 | 3/2019 | Bradley et al. |
| 10,251,377 B2 * | 4/2019 | Clube ................ C07K 16/00 |
| 10,605,808 B2 | 3/2020 | Logtenberg et al. |
| 10,667,501 B2 | 6/2020 | Germaschewski et al. |
| 10,730,930 B2 | 8/2020 | Bradley et al. |
| 10,774,155 B2 | 9/2020 | Bradley et al. |
| 10,966,412 B2 | 4/2021 | Lee et al. |
| 11,051,497 B2 | 7/2021 | Friedrich et al. |
| 11,128,131 B2 | 9/2021 | Yoshimura et al. ....... 530/387.3 |
| 11,297,810 B2 | 4/2022 | Bradley et al. |
| 11,297,811 B2 | 4/2022 | Clube |
| 11,399,522 B2 | 8/2022 | Lee et al. |
| 11,564,380 B2 | 1/2023 | Bradley et al. |
| 11,606,941 B2 | 3/2023 | Bradley et al. |
| 2002/0088016 A1 * | 7/2002 | Bruggemann ..... A01K 67/0278 800/18 |
| 2002/0183275 A1 | 12/2002 | Murphy et al. |
| 2003/0070185 A1 | 4/2003 | Jakobovits et al. |
| 2003/0108925 A1 | 6/2003 | Dix et al. |
| 2003/0167489 A1 | 9/2003 | Rajewsky et al. |
| 2003/0217373 A1 | 11/2003 | Green et al. ................ 800/6 |
| 2004/0128703 A1 | 7/2004 | Shizuya |
| 2004/0209268 A1 | 10/2004 | Azuma |
| 2004/0231012 A1 | 11/2004 | Bruggemann |
| 2005/0048621 A1 | 3/2005 | Grasso et al. |
| 2005/0260679 A1 | 11/2005 | Kellerman et al. |
| 2006/0008892 A1 * | 1/2006 | Yacoby-Zeevi .... A01K 67/0271 435/232 |
| 2006/0015949 A1 | 1/2006 | Lonberg et al. |
| 2006/0015957 A1 | 1/2006 | Lonberg et al. ............. 800/18 |
| 2006/0021074 A1 | 1/2006 | Kellermann et al. .......... 800/18 |
| 2006/0199204 A1 | 9/2006 | Dix et al. |
| 2007/0280945 A1 | 12/2007 | Stevens et al. ........... 424/145.1 |
| 2008/0098490 A1 | 4/2008 | Jakobovits et al. |
| 2009/0083870 A1 | 3/2009 | Horn et al. ................. 800/13 |
| 2009/0083879 A1 | 3/2009 | Dhugga |
| 2009/0093059 A1 | 4/2009 | Baszczynski et al. |
| 2009/0098134 A1 | 4/2009 | Buelow |
| 2009/0196112 A1 | 8/2009 | Cho ............................. 365/200 |
| 2009/0209036 A1 | 8/2009 | Reynaud et al. ............. 435/455 |
| 2009/0307787 A1 | 12/2009 | Grosveld et al. |
| 2010/0011450 A1 | 1/2010 | Garcia et al. |
| 2010/0069614 A1 | 3/2010 | Houtzager et al. ........ 530/387.1 |
| 2010/0146647 A1 | 6/2010 | Logtenberg et al. ............ 800/4 |
| 2010/0196367 A1 | 8/2010 | Day ........................... 424/130.1 |
| 2010/0330676 A1 | 12/2010 | Horowitz et al. |
| 2011/0119779 A1 | 5/2011 | Shizuya et al. |
| 2011/0138489 A1 | 6/2011 | Tanamachi et al. |
| 2011/0145937 A1 | 6/2011 | MacDonald et al. ............ 800/6 |
| 2011/0195454 A1† | 8/2011 | McWhirter |
| 2011/0236378 A1 | 9/2011 | Green et al. ............... 424/133.1 |
| 2011/0283376 A1 | 11/2011 | Murphy et al. |
| 2012/0021409 A1 | 1/2012 | McWhirter et al. |
| 2012/0070861 A1 | 3/2012 | Macdonald et al. ......... 435/91.1 |
| 2012/0073004 A1 | 3/2012 | Macdonald et al. |
| 2012/0096572 A1 | 4/2012 | Macdonald et al. |
| 2012/0167237 A1 | 6/2012 | Bradley et al. ................... 800/9 |
| 2012/0195910 A1 | 8/2012 | Wu et al. |
| 2012/0204278 A1 * | 8/2012 | Bradley ................. C07K 16/00 800/18 |
| 2012/0233715 A1 | 9/2012 | Kuroiwa et al. ................. 800/3 |
| 2012/0322108 A1 * | 12/2012 | Macdonald ........... C07K 16/22 435/69.6 |
| 2013/0039850 A1 | 2/2013 | Lonberg et al. ............. 424/1.49 |
| 2013/0096287 A1 | 4/2013 | Macdonald et al. |
| 2013/0102031 A1 | 4/2013 | King et al. ................... 435/69.6 |
| 2013/0160153 A1 | 6/2013 | Macdonald et al. |
| 2013/0198879 A1 | 8/2013 | Mcwhirter et al. |
| 2013/0212719 A1 | 8/2013 | Macdonald et al. |
| 2013/0243759 A1 | 9/2013 | Friedrich et al. |
| 2013/0247235 A1 | 9/2013 | Mcwhirter et al. |
| 2013/0254911 A1 | 9/2013 | Macdonald et al. |
| 2013/0263293 A1 | 10/2013 | Bradley et al. |
| 2013/0323790 A1 | 12/2013 | Macdonald et al. |
| 2013/0323791 A1 | 12/2013 | Macdonald et al. |
| 2013/0326647 A1 | 12/2013 | Macdonald et al. |
| 2013/0333057 A1 | 12/2013 | Macdonald et al. |
| 2014/0017228 A1 | 1/2014 | Macdonald et al. |
| 2014/0017782 A1 | 1/2014 | Murphy et al. |
| 2014/0041067 A1 | 2/2014 | Bradley et al. |
| 2014/0120582 A1 | 5/2014 | Bradley et al. |
| 2014/0130193 A1 | 5/2014 | Macdonald et al. |
| 2014/0130194 A1 | 5/2014 | Macdonald et al. |
| 2014/0137275 A1 | 5/2014 | Macdonald et al. |
| 2014/0150125 A1 | 5/2014 | Bradley et al. |
| 2014/0150126 A1 | 5/2014 | Bradley et al. |
| 2014/0182003 A1 | 6/2014 | Bradley et al. |
| 2014/0201854 A1 | 7/2014 | Bradley et al. |
| 2014/0201856 A1 | 7/2014 | Bradley et al. |
| 2014/0212416 A1 | 7/2014 | Friedrich et al. |
| 2014/0213773 A1 | 7/2014 | Macdonald et al. |
| 2014/0283150 A1 | 9/2014 | Bradley et al. |
| 2014/0323327 A1 | 10/2014 | Bradley et al. |
| 2014/0325690 A1 | 10/2014 | Bradley et al. |
| 2014/0331339 A1 | 11/2014 | Bradley et al. |
| 2014/0331343 A1 | 11/2014 | Bradley et al. |
| 2014/0331344 A1 | 11/2014 | Friedrich et al. |
| 2014/0356908 A1 | 12/2014 | Grosveld et al. |
| 2014/0359797 A1 | 12/2014 | Bradley et al. |
| 2015/0033369 A1 | 1/2015 | Bradley et al. |
| 2015/0033372 A1 | 1/2015 | Bradley et al. |
| 2015/0037337 A1 | 2/2015 | Friedrich et al. |
| 2015/0040250 A1 | 2/2015 | Bradley et al. |
| 2015/0082466 A1 | 3/2015 | Clube |
| 2015/0113669 A1 | 4/2015 | Bradley et al. |
| 2015/0133641 A1 | 5/2015 | Germaschewski et al. |
| 2015/0196015 A1 | 7/2015 | Macdonald et al. |
| 2015/0334998 A1 | 11/2015 | Bradley et al. |
| 2016/0044900 A1 | 2/2016 | Bradley et al. |
| 2016/0150768 A1 | 6/2016 | Bradley et al. |
| 2016/0219846 A1 | 8/2016 | Liang |
| 2016/0249592 A1 | 9/2016 | Bradley et al. |
| 2016/0345551 A1 | 12/2016 | Bradley et al. |
| 2016/0345552 A1 | 12/2016 | Bradley et al. |
| 2016/0353719 A1 | 12/2016 | Friedrich et al. |
| 2017/0051045 A1 | 2/2017 | Bradley et al. |
| 2017/0071174 A1 | 3/2017 | Bradley et al. |
| 2017/0081423 A1 | 3/2017 | Bradley et al. |
| 2017/0094956 A1 | 4/2017 | Bradley et al. |
| 2017/0096498 A1 | 4/2017 | Bradley et al. |
| 2017/0099815 A1 | 4/2017 | Bradley et al. |
| 2017/0099816 A1 | 4/2017 | Bradley et al. |
| 2017/0099817 A1 | 4/2017 | Bradley et al. |
| 2017/0101482 A1 | 4/2017 | Bradley et al. |
| 2017/0101483 A1 | 4/2017 | Bradley et al. |
| 2017/0105396 A1 | 4/2017 | Bradley et al. |
| 2017/0135327 A1 | 5/2017 | Lee |
| 2017/0320936 A1 | 11/2017 | Bradley et al. |
| 2017/0354131 A1 | 12/2017 | Bradley et al. |
| 2018/0030121 A1 | 2/2018 | Bradley et al. |
| 2018/0142006 A1 | 5/2018 | Logtenberg et al. |
| 2018/0282761 A1 | 10/2018 | Bradley et al. |
| 2018/0295821 A1 | 10/2018 | Friedrich et al. |

(56) References Cited

U.S. PATENT DOCUMENTS

| | | |
|---|---|---|
| 2018/0298112 A1 | 10/2018 | Bradley et al. |
| 2019/0174729 A1 | 6/2019 | Lee et al. |
| 2019/0208753 A1 | 7/2019 | Clube |
| 2019/0327946 A1 | 10/2019 | Bradley et al. |
| 2020/0205384 A1 | 7/2020 | Friedrich et al. |
| 2020/0214274 A1 | 7/2020 | Lee et al. |
| 2020/0267952 A1 | 8/2020 | Germaschewski et al. |
| 2020/0317751 A1 | 10/2020 | Bradley et al. |
| 2020/0317752 A1 | 10/2020 | Bradley et al. |
| 2020/0337280 A1 | 10/2020 | Bradley et al. |
| 2020/0352144 A1 | 11/2020 | Bradley et al. |
| 2020/0352145 A1 | 11/2020 | Bradley et al. |
| 2020/0375158 A1 | 12/2020 | Bradley et al. |
| 2021/0079118 A1 | 3/2021 | Bradley et al. |
| 2021/0204530 A1 | 7/2021 | Lee et al. |

FOREIGN PATENT DOCUMENTS

| | | | |
|---|---|---|---|
| CA | 2820824 A1 | 10/2012 | |
| CN | 102123582 A | 7/2011 | |
| CN | 104334732 A | 2/2015 | |
| DE | 10251918 A1 | 5/2004 | |
| EP | 1780272 A1 | 5/2007 | ............ C12N 15/00 |
| EP | 0937140 B1 | 9/2007 | |
| EP | 2517556 B1 | 10/2012 | |
| EP | 2517557 A2 | 10/2012 | |
| EP | 2550363 | 10/2012 | ............ C12N 15/85 |
| EP | 2147594 A1 | 11/2013 | |
| EP | 2480676 B1 | 4/2016 | |
| GB | 2398784 A | 9/2004 | .......... A01K 67/027 |
| GB | 2403475 A | 1/2005 | |
| JP | 2004524841 A | 8/2004 | |
| JP | 2005510253 A | 4/2005 | |
| JP | 2008507257 A | 3/2008 | |
| JP | 2010512749 A | 4/2010 | |
| JP | 2011525808 A | 9/2011 | |
| JP | 2012521211 A | 9/2012 | |
| JP | 2015-512634 A | 4/2015 | |
| KR | 20050042792 A | 5/2005 | |
| WO | WO-9004036 A1 | 4/1990 | |
| WO | WO-9100906 A1 | 1/1991 | |
| WO | WO 1991/10741 | 7/1991 | ............ C12P 21/06 |
| WO | 9203918 A1 | 3/1992 | |
| WO | 1993/12227 | 6/1993 | |
| WO | WO-9402602 A1 | 2/1994 | |
| WO | WO-9404667 A1 | 3/1994 | |
| WO | WO-9425585 A1 | 11/1994 | |
| WO | WO-9630498 A1 | 10/1996 | |
| WO | WO 1998/24884 | 6/1998 | ............ C12N 5/00 |
| WO | WO-9824893 A2 | 6/1998 | |
| WO | 9850431 A2 | 11/1998 | |
| WO | WO-9945962 A1 | 9/1999 | |
| WO | 0026373 A1 | 5/2000 | |
| WO | 0071585 A1 | 11/2000 | |
| WO | WO 2002/08409 A2 | 1/2002 | ............ C12N 15/00 |
| WO | WO-0236789 A2 | 5/2002 | |
| WO | WO 2002/043478 | 6/2002 | .......... A01K 67/027 |
| WO | WO 2002/053596 A2 | 7/2002 | ............ C07K 16/28 |
| WO | WO 2002/059263 A2 | 8/2002 | |
| WO | WO 2002/066630 A1 | 8/2002 | ............ C12N 15/00 |
| WO | WO 2002/070648 A2 | 9/2002 | |
| WO | WO-02070648 A2 | 9/2002 | |
| WO | WO 2003/006639 A1 | 1/2003 | ............ C12N 5/10 |
| WO | WO 2003/047336 A2 | 6/2003 | |
| WO | WO 2003/061363 A2 | 7/2003 | |
| WO | 2004009618 A2 | 1/2004 | |
| WO | 2004044150 A2 | 5/2004 | |
| WO | WO 2004/050838 A2 | 6/2004 | |
| WO | WO 2005/003364 A2 | 1/2005 | ............ C12N 15/90 |
| WO | WO-2005004592 A2 | 1/2005 | |
| WO | WO-2005058815 A2 | 6/2005 | |
| WO | WO-2005092926 A2 | 10/2005 | |
| WO | WO-2006008548 A2 | 1/2006 | |
| WO | 2006029459 A1 | 3/2006 | |
| WO | WO 2006/044492 | 4/2006 | ............ C12N 15/52 |
| WO | WO-2006055704 A2 | 5/2006 | |
| WO | WO-2006068953 A2 | 6/2006 | |
| WO | 2006117699 A2 | 11/2006 | |
| WO | WO 2006/122442 A1 | 11/2006 | ............ C12N 9/22 |
| WO | WO 2007/096779 A2 | 8/2007 | |
| WO | WO-2007085837 A1 | 8/2007 | |
| WO | WO 2007/117410 A2 | 10/2007 | .......... A01K 67/027 |
| WO | WO-2007143168 A2 | 12/2007 | |
| WO | WO-2008022391 A1 | 2/2008 | |
| WO | WO 2008/054606 A2 | 5/2008 | ............ C07K 16/00 |
| WO | WO 2008/070367 A2 | 6/2008 | ............ C12N 15/09 |
| WO | WO 2008/076379 A2 | 6/2008 | ............ C07K 16/18 |
| WO | WO-2008081197 A1 | 7/2008 | |
| WO | WO 2008/094178 A2 | 8/2008 | ............ C12Q 1/68 |
| WO | WO 2008/103474 A1 | 8/2008 | ............ C12N 15/13 |
| WO | 2008108918 A1 | 9/2008 | |
| WO | WO 2008/118970 A2 | 10/2008 | ............ A61K 48/00 |
| WO | WO 2008/122886 A2 | 10/2008 | ............ C12N 15/85 |
| WO | WO 2008/151081 A1 | 12/2008 | ............ C12N 15/13 |
| WO | WO 2009/013620 A2 | 1/2009 | |
| WO | WO 2009/018411 A1 | 2/2009 | ............ C07K 16/28 |
| WO | WO 2009/023540 A1 | 2/2009 | .......... A61K 39/395 |
| WO | WO 2009/076464 A2 | 6/2009 | ............ C12N 15/09 |
| WO | WO 2009/080254 A1 | 7/2009 | ............ C07K 16/46 |
| WO | WO 2009/094178 A2 | 7/2009 | ............ C09B 67/08 |
| WO | WO-2009097006 A2 | 8/2009 | |
| WO | WO-2009118524 A2 | 10/2009 | |
| WO | WO-2009129247 A2 | 10/2009 | |
| WO | WO 2009/143472 A2 | 11/2009 | ............ C07K 16/46 |
| WO | WO 2009/157771 A2 | 12/2009 | .......... A01K 67/027 |
| WO | WO 2010/039900 A2 | 4/2010 | ............ C12N 15/13 |
| WO | WO 2010/070263 A1 | 6/2010 | ............ C12N 15/85 |
| WO | WO 2011/163311 * | 6/2010 | |
| WO | WO-2010077854 A1 | 7/2010 | |
| WO | WO 2010/097385 A1 | 9/2010 | ............ C07K 16/24 |
| WO | WO-2010109165 A2 | 9/2010 | |
| WO | WO 2010/113039 A1 | 10/2010 | ............ C12N 5/00 |
| WO | WO 2011/004192 A1 | 1/2011 | ............ C07K 16/46 |
| WO | WO 2011/008093 A1 | 1/2011 | ............ C07K 16/00 |
| WO | 2011014469 A1 | 2/2011 | |
| WO | WO 2011/056864 A1 | 5/2011 | ............ C12P 21/06 |
| WO | WO-2011062206 A1 | 5/2011 | |
| WO | WO-2011062207 A1 | 5/2011 | |
| WO | WO-2011071957 A1 | 6/2011 | |
| WO | WO-2011072204 A1 | 6/2011 | |
| WO | WO 2011/097603 A1 | 8/2011 | ............ C12N 15/85 |
| WO | WO-2011146121 A1 | 11/2011 | |
| WO | 2011/163311 † | 12/2011 | |
| WO | 2011/163314 † | 12/2011 | |
| WO | WO 2011/158009 A1 | 12/2011 | .......... A01K 67/027 |
| WO | WO 2011/163311 A1 | 12/2011 | ............ C12N 15/85 |
| WO | WO 2011/163314 * | 12/2011 | |
| WO | WO 2011/163314 A1 | 12/2011 | ............ C12N 15/85 |
| WO | 2012/007167 A1 | 1/2012 | |
| WO | 2012023053 A2 | 2/2012 | |
| WO | WO 2012/018764 A1 | 2/2012 | ............ C12N 15/85 |
| WO | WO 2012/023053 A2 | 2/2012 | |
| WO | 2012064682 A1 | 5/2012 | |
| WO | 20121088313 A1 | 6/2012 | |
| WO | WO 2012/141798 A1 | 10/2012 | ............ C12N 15/85 |
| WO | WO 2012/148873 A2 | 11/2012 | .......... A01K 67/027 |
| WO | WO 2013/022782 A1 | 2/2013 | ............ C12N 15/85 |
| WO | 2013041846 A2 | 3/2013 | |
| WO | WO 2013/041844 A2 | 3/2013 | ............ C12N 15/85 |
| WO | WO 2013/041845 A2 | 3/2013 | ............ C12N 15/85 |
| WO | 2013045916 A1 | 4/2013 | |
| WO | WO 2013/059230 A1 | 4/2013 | ............ C12N 15/85 |
| WO | 2013061078 A1 | 5/2013 | |
| WO | WO 2013/061098 A2 | 5/2013 | ............ C12N 15/85 |
| WO | 2013079953 A1 | 6/2013 | |
| WO | WO 2013/096142 | 6/2013 | .......... A01K 67/027 |
| WO | WO 2013/116609 A1 | 8/2013 | .......... A01K 67/027 |
| WO | 2013130981 A1 | 9/2013 | |
| WO | WO-2013134263 A1 | 9/2013 | |
| WO | 2013/144566 A2 | 10/2013 | |
| WO | 2013144567 A1 | 10/2013 | |
| WO | 2013166236 A1 | 11/2013 | |
| WO | 2013171505 A1 | 11/2013 | |
| WO | WO-2013176772 A1 | 11/2013 | |

(56) References Cited

FOREIGN PATENT DOCUMENTS

| WO | WO-2014093622 A2 | 6/2014 |
|---|---|---|
| WO | 2014130690 A1 | 8/2014 |
| WO | 2015049517 A2 | 4/2015 |
| WO | 2019008123 A2 | 1/2019 |

OTHER PUBLICATIONS

Definition of "population" from Merriam Webster Dictionary https://www.merriam-webster.com/dictionary/population 2021.*

Definition of "population" from Dictionary.com https//www,dictionary.com/browse/population 2021.*

"DNA sequence of the human immunoglobulin D segment locus," GenBank, Nov. 14, 2005, URL:http://www.ncbi.nlm.nih.gov/nuccore/X97051.

Mattila, P.S., et al., "Extensive allelic sequence variation in the J region of the human immunoglobulin heavy chain gene locus,"European Journal of Immunology. vol. 25, Issue 9, pp. 2578-2582, Sep. 1995.

Macdonald, et al., "Precise and in situ genetic humanization of 6 Mb of mouse immunoglobulin genes," Proceedings of the National Academy of Sciences (USA), vol. 111, No. 14, 5147-5152, Apr. 8, 2014.

Adams. D., et al., "A Genome-Wide, End-Sequenced 129Sv BAC Library Resource for Targeting Vector Construction," Genomics, vol. 86, pp. 753-758, 2005.

Askew, R., et al., "Site-Directed Point Mutations in Embryonic Stem Cells: a Gene-Targeting Tag-and-Exchange Strategy," Molecular and Cellular Biology, pp. 4115-4124, Jul. 1993.

Auerbach, et al., "Establishment and chimera analysis of 129/SvEv- and C57BL/6-derived mouse embryonic stem cell lines," Biotechniques, vol. 29: pp. 1024-1032 (Nov. 2000).

Baker et al., "Homologous Recombination between Transferred and Chromosomal Immunoglobulin k Genes," Mol. Cell. Biology, pp. 4041-4047, Oct. 1988.

Barreto et al., "AID from bony fish catalyzes class switch recombination," Journal of Experimental Medicine, pp. 1-6, Sep. 12, 2005.

Bates et al., "Chromosomal position of a VH gene segment determines its activation and inactivation as a substrate for V(D)J recombination," The Journal of Experimental Medicine, vol. 204, No. 13, pp. 3247-3256, Dec. 24, 2007.

Beard, et al., "Efficient method to generate single-copy transgenic mice by site-specific integration in embryonic stem cells," Genesis (2006), vol. 44, pp. 23-28.

Beck et al., "Nucleotide sequence and exact localization of the neomycin phosphotransferase gene from transposon Tn5". Gene, vol. 19, pp. 327-336, Oct. 1982.

Berg et al., "Inverted repeats of Tn5 are transposable elements". PNAC USA, Genetics, vo. 79, pp. 2632-2635, Apr. 1982.

Bethke et al., "Segmental genomic replacement by Cre-mediated recombination: genotoxic stress activation of the p53 promoter in single-copy transformants," Nucleic Acids Research, vol. 25, No. 14, pp. 2828-2834, 1997.

Billiard, et al., "Ongoing D114-Notch signaling is required for T-cell homeostasis in the adult thymus," European Journal of Immunology, Aug. 4, 2011, vol. 41, pp. 2207-2216.

Bolland et al., "Antisense Intergenic Transcription Precedes IghD-to-J Recombination and is Controlled by the Intronic Enhancer Eμ," Mol. Cell. Biology, vol. 27, No. 15, pp. 5523-5533, Aug. 2007.

Bonin et al., "Isolation, Microinjection, and Transfer of Mouse Blastocysts" Methods in Molecular Biology, vol. 158, Gene Knockout Protocols, pp. 121-134.

Bonin et al., "Deletion of the IgH intronic enhancer and associated matrix attachment regions decreases, but does not abolish, class switching at the μ locus," Int. Immunol. vo. 10, No. 6, pp. 799-806, 1998.

Bradley et al., "Formation of germ-line chimaeras from embryo-derived teratocarcinoma cell lines," Nature Publishing Group, pp. 255-256, vol. 309, 1984.

Breden et al., "Comparison of Antibody Repertoires Produced by HIV-1 Infection, Other Chronic and Acute Infections, and Systemic Autoimmune Disease," PloS One. vol. 6, Issue 3, pp. 1-11, Mar. 2011.

Brocker et al., "Evolutionary divergence and functions of the ADAM and ADAMTS gene families" Human Genomics, vol. 4, No. 2, pp. 43-55, Oct. 2009.

Brüggemann, et al., "Human antibody production in transgenic mice: expression from 100 kb of the human IgH locus*," European Journal of Immunology, vol. 21, Issue 5, pp. 1323-1326, May 1991.

Brüggemann, "Human Antibody Expression in Transgenic Mice," Archivum Immunologiae et Therapiae Experimentalis, vol. 49, pp. 203-208, 2001.

Brüggemann et al., "Immunoglobulin heaw chain locus of the rat: Striking homology to mouse antibody genes," Proc. Natl. Acad. Sci. USA, Immunology, vol. 83, pp. 6075-6079, Aug. 1986.

Brüggemann et al., "A repertoire of monoclonal antibodies with human heavy chains from transgenic mice," Proc. Natl. Acad. Sci. USA, Immunology, vol. 86, pp. 6709-6713, Sep. 1989.

Buehr et al., "Capture of Authentic Embryonic Stem Cells from Rat Blastocysts," Cell, vol. 135, pp. 1287-1298, Dec. 26, 2008.

Cadinanos et al., "Generation of an inducible and optimized 12iggyback transposon system," Nucleic Acids Research, vol. 35, No. 12, Jun. 18, 2007.

Carstea, et al., "Germline competence of mouse ES and iPS cell lines: Chimera technologies and genetic background," World Journal of Stem Cells, Dec. 31, 2009; 1(1): pp. 22-29.

Chen et al., "B cell development in mice that lack one or both immunoglobulin χ light chain genes," The EMBO Journal, vo. 12, No. 3, pp. 821-830, 1993.

Chen et al., "Immunoglobulin Heavy Chain Gene Replacement: A Mechanism of Receptor Editing" Immunity, vol. 3, pp. 747-755, Dec. 1995.

Cho, "Testicular and epididymal ADAMs: expression and function during fertilization," Nature, vol. 9, pp. 550-560, Oct. 2012.

Choi et al., "Characterization and comparative genomic analysis of intronless Adams with testicular gene expression," Genomics 83, pp. 636-646, Aug. 2003.

Clark et al., "Trends in Antibody Sequence Changes During the Somatic Hypermutation Process," The Journal of Immunology, vol. 177, pp. 333-340, 2006.

Clark et al., "A Future for Transgenic Livestock," Nature Reviews, Genetics, vol. 4, pp. 825-833, Oct. 2003.

Colbere Garapin et al., "A New Dominant Hybrid Selective Marker for Higher Eukaryotic Cells". J Mol. Biol., vol. 150, No. 1, pp. 1-14, Jul. 25, 1981.

Collins, et al., "A mouse for all reasons," Cell, vol. 128, Issue 1, pp. 9-13 (Jan. 2007).

Combriato, et al., "Regulation of human Igλ light chain gene expression by NF-$_K$B1," Journal of Immunology, Issue 168, vol. 3, pp. 1259-1266, Feb. 1, 2002.

Conrath, et al., "Camel Single-domain Antibodies as Modular Building Units in Bispecific and Bivalent Antibody Constructs," The Journal of Biological Chemistry, vol. 276, No. 10, pp. 7346-7350, Mar. 9, 2001.

Copeland et al., "Recombineering: A Powerful New Tool for Mouse Functional Genomic," Nature Reviews, Genetics, vol. 2, pp. 769-869, Oct. 2001(10):769-79.

Corti et al., "A Neutralizing Antibody Selected from Plasma Cells That Binds to Group 1 and Group 2 Influenza A Hemagglutinins" Science, vol. 333, pp. 850-856, 2011.

Cuesta et al., "Multivalent antibodies: when design surpasses evolution," Trends Biotechnology, vol. 28, pp. 355-362, 2010.

De Saint Vincent et al., "Homologous recombination in mammalian cells mediates fonnation of a functional gene from two overlapping gene fragments," Proc. Natl. Acad. Sci., USA, Genetics, vol. 80, pp. 2002-2006, Apr. 1983.

DeChiara et al., "VelociMouse: Fully ES Cell-Derived FO-Generation Mice Obtained from the Injection of ES Cells into Eight-Cell-Stage Embryos," Gene Knockout Protocols: Second Edition, vol. 530, pp. 311-324, 2009.

(56) References Cited

OTHER PUBLICATIONS

DeChiara et al., "Producing Fully ES Cell-Derived Mice From Eight-Cell Stage Embryo Injections," Methods in Enzymology, vol. 476, Chapter 16, pp. 285-294, Jan. 2010.
Denome et al., "Patterns of polyadenylation site selection in gene constructs containing multiple polyadenylation signals," Mol. Cell Biol., vol. 8, No. 11, pp. 4829-4839, Nov. 1988.
Diez-Roux et al., "A High-Resolution Anatomical Atlas of the Transcriptome in the Mouse Embryo," PloS Biology, vol. 9, Issue 1, pp. 1-13, Jan. 2011.
Ding, et al., "Generation of high-affinity fully human anti-interleukin-8 antibodies from its cDNA by two-hybrid screening and affinity maturation in yeast," Protein Science, Oct. 2010; vol. 19, pp. 1957-1966.
DiNoia et al., "Molecular Mechanism of Antibody Somatic Hypermutation," Annu. Rev. Biochem, vol. 76, No. 1, pp. 1-22, 2007.
Doetschman et al., "Establishment of Hamster Blastocyst-Derived Embryonic Stem (ES) Cells," Developmental Biology, vol. 127, pp. 224-227, 1988.
Doetschman, et al., "Targeted mutation of the Hprt gene in mouse embryonic stem cells," Proceedings of the National Academy of Sciences of the United States of America, vol. 85, No. 22, pp. 8583-8587 Nov. 1988.
Doyle et al., "The construction of transgenic and gene knockout/knockin mouse models of human disease," Transgenic Research, Apr. 2012; 21(2): pp. 327-349.
Durbin et al., "A map of human genome variation from population-scale sequencing," Nature, vol. 467, pp. 1061-1074, Oct. 28, 2012.
Durdik et al., "Isotype switching by a microinjected µ immunoglobulin heavy chain gene in transgenic mice," PNAS USA Immunol, vol. 86, pp. 2346-2350, Apr. 1989.
Eisener-Dorman, et al., "Cautionary insights on knockout mouse studies: The gene or not the gene?," Brain, Behavior, and Immunity, vol. 23, No. 3, pp. 318-324, (Sep. 2009).
Ekiert et al., "A Highly Conserved Neutralizing Epitope on Group 2 Influenza A Viruses," Science, vol. 333, pp. 843-850, Aug. 12, 2011.
Evans, "Fertilin B and other ADAMs as integrin ligands: insights into cell adhesion and fertilization," BioEssays 23.7, pp. 628-639, 2001.
Featherstone et al., "The Mouse Immunoglobulin heavy Chain V-D Intergenic Sequence Contains Insulators That May Regulate Ordered V(D)J Recombination," The Journal of Biological Chemistry, vol. 285, No. 13, pp. 9327-9338, Mar. 26, 2010.
Feeney, "Genetic and Epigenetic Control of V Gene Rearrangement Frequency," V(D)J Recombination Advances in Experimental Medicine and Biology, 2009, vol. 650, pp. 73-81.
Fell et al., "Homologous recombination in hybridoma cells: heavy chain chimeric antibody produced by gene targeting." PNAS USA Immunology, vol. 86, pp. 8507-8511, Nov. 1989.
Feschotte et al., "DNA Transposons and the Evolution of Eukaryotic Genomes.," Annu Rev Genet., vol. 41, pp. 331-368, 2007.
Folger et al., "Patterns of Integration of DNA Microinjected into Cultured Mammalian Cells: Evidence for Homologous Recombination Between Injected Plasmid DNA Molecules," Mol. Cell Biol., vol. 2, No. 11, pp. 1372-1387, 1982.
Forconi et al., "The normal IGHV1-69-derived B-cell repertoire contains stereotypic patterns characteristic of unmutated CLL," vol. 115, pp. 71-77, 2010.
Fukita et al., "Somatic Hypermutation in the Heavy Chain Locus Correlates with Transcription," Immunity, vol. 9, pp. 106-114, Jul. 1998.
Gefter et al., "Expression of a VHC kappa chimaeric protein in mouse myeloma cells," Nature, pp. 364-367, May 24-30, 1984 (Abstract only).
Gerdes et al., "Physical Map of the mouse λ light chain and related loci," Immunogenetics, vol. 54, pp. 62-65, 2002.
Gerstein et al., "Isotype switching of an immunoglobulin heavy chain transgene occurs by DNA recombination between different chromosomes," Cell, vol. 63, No. 3, pp. 537-548, Nov. 1990.
Geurts et al., "Knockout Rats via Embryo Microinjection of Zinc-Finger Nucleases," Science, vol. 325, p. 433, Jul. 24, 2009.
Gluzman "SV40-Transformed Simian Cells Support the Replication of Early SV40 Mutants". Cell, vol. 23, pp. 175-182, Jan. 1981.
Goodhart, et al., "Rearrangement and expression of rabbit immunoglobulin kappa light chain gene in transgenic mice," Proceedings of the N ational Academy of Sciences (USA), vol. 84, No. 12, pp. 4229-4233, Jun. 1987.
Gorman et al., "The IgK 3' enhancer influences the ratio of Ig? Versus Ig? B lymphocytes" Immunity, vol. 5. pp. 241-252, Sep. 1996.
Gorny et al., "Human Anti-V3 HIV-1 Monoclonal Antibodies Encoded by the VHS-51/VL Lambda Genes Define a Conserved Antigenic Structure," PloSone, vol. 6, Issue 12, pp. 1-10, Dec. 2011.
Goyenechea et al., "Cells strongly expressing Ig(kappa) transgenes show clonal recruitment of hypermutation: a role for both MAR and the enhancers" The EMBO Journal, vol. 16, No. 13., pp. 3987-3994, 1997.
Gu et al., Independent Control of Immunoglobulin Switch Recombination at Individual Switch Regions Evidenced through Cre-loxP-Mediated Gene Targeting. Cell, vol. 73, pp. 1155-1164, Jun. 18, 1993.
Guerrero et al., "The bleomycin resistance gene of transposon Tn5 is an excellent marker for transformation of corynebacteria," Applied Microbiology Biotechnology, vol. 36, pp. 759-762, 1992.
Guntaka, "Transcription Termination and Polyadenylation in Retroviruses" Microbiological Review's, vol. 57, No. 3, pp. 511-521, Sep. 1993.
Green, "Antibody Engineering via Genetic Engineering of the Mouse: XenoMouse Strains are a. Vehicle for the Facile Generation of Therapeutic Human Monoclonal Antibodies," Journal of Immunological Methods, Dec. 10, 1999, vol. 231, Issues 1-2, pp. 11-23.
Han et al., "Comprehensive Analysis of Reproductive ADAMs: Relationship of ADAM4 and ADAM6 with an ADAM Complex Required for Fertilization in Mice," Biology of Reproduction 80, pp. 1001-1008, Jan. 7, 2009.
Hasty et al., "Target frequency and integration pattern for insertion and replacement vectors in embryonic stem cells," Molecular Cellular Biology, vol. 11, No. 9, pp. 4509-4517, Sep. 1991.
Hagiwara., Transgenic expression of VpreB-3 under the control of the immunoglobulin heavy chain enhancer and SV40 promoter, Kobe Journal of Medical Sciences, Feb. 1996, vol. 42, No. 1, pp. 43-59 (English Abstract).
Houvila et al., "Shedding light on ADAM metalloproteinases," Trends in Biochemical Sciences, vol. 30. No. 7, pages, Jul. 2005.
Hudziak et al., "Establishment of Mammalian Cell Lines Containing Multiple Nonsense Mutations and Functional Suppressor tRNA Genes," Cell, vol. 31, pp. 137-146, Nov. 1982.
Huang et al., "Structural Basis of Tyrosine Sulfation and VH-Gene Usage in Antibodies that Recognize the HIV Type 1 Coreceptor-Binding Site on gp120," PSNA, Mar. 2, 2004, vol. 101, No. 9, pp. 2706-2711.
Iglesias-Ussel, et al., "Forced expression of AID facilitates the isolation of class switch variants from hybridoma cells," Journal of Immunological Methods, Oct. 2006; 316(1-2), pp. 59-66.
Ivics et al., "The expanding universe of transposon technologies for gene and cell engineering," Mobile DNA, pp. 1-25, 2010.
Ivics et al., "The Sleeping Beauty Transposable Element: Evolution, Regulation and Genetic Applications," Curr. Issues Mol. Biol., vol. 6, pp. 43-56, 2004.
Izsvak et al., "Sleeping Beauty Transposition: Biology and Applications for Molecular Therapy," Molecular Therapy, vol. 9, No. 2, pp. 147-156, Feb. 2, 2004.
Jacob et al., "Gene targeting in the rat: advances and opportunities," Trends in Genetics, vol. 26, No. 12, pp. 510-518, Dec. 2010.
Jakobovits, et al., "From XenoMouse technology to panitumumab, the first fully human antibody product from transgenic mice," Nature Biotechnology, vol. 25, No. 10, pp. 1134-1143, Oct. 2007.
Janssens, et al., "Generation of heavy-chain-only antibodies in mice," Proceedings of the National Academy of Sciences (USA), Oct. 10, 2006, vol. 103, No. 41, pp. 15130-15135.

(56) References Cited

OTHER PUBLICATIONS

Jendreyko, et al., "Intradiabodies, Bispecific, Tetravalent Antibodies for the Simultaneous functional knockout of two cell surface receptors," The Journal of Biological Chemistry, vol. 278, pp. 47812-47819, Nov. 28, 2003.
Jung, et al., "Mechanism and Control of V(D)J Recombination at the Immunoglobulin Heavy Chain Locus," Annual Review of Immunology, Apr. 2006, vol. 24, pp. 541-570.
Kaminski, et al., "Antibody class switching differs among SJL, C57BL/6 and 129 mice," International Immunology, vol. 19, No. 4, pp. 545-556 (2007).
Kellerman, et al, "Developing the Xenomouse technology for evaluating immunogenicity , " AntibOZ 2 Conference. Australia, 2004.
Kim, et al., "CHO cells in biotechnology for production of recombinant proteins: current state and further potential" Appl. Microbiology Biotechnology, vol. 93, pp. 917-930, Dec. 9, 2011.
Kingzette et al., "Trans-chromosomal recombination within the Ig heavy chain switch region in B lymphocytes," Proc. Natl. Acad. Sci., vol. 95, pp. 11840-11845, Sep. 1998.
Kitamura et al., " A B cell-deficient mouse by targeted disruption of the membrane exon of the immunoglobulin chain gene," Nature, vol. 350, pp. 423-426, Apr. 1991.
Kohrer et al., "Import of amber and ochre suppressor tRNAs into mammalian cells: A general approach to site-specific insertion of amino acid analogues into proteins," PNAS USA, vol. 98, No. 25, pp. 214310-14315, Dec. 4, 2001.
Kostenuik, et al., Denosumab, a fully human monoclonal antibody to RANKL, inhibits bone resorption and increases BMD in knock-in mice that express chimeric (Murine/Human) RANKL, Journal of Bone and Mineral Research, vol. 24, No. 2, pp. 182-195, 2009.
Kotzamaris et al., Recombining overlapping BACs into a single larger BAC, BMC Biotechnology, pp. 1-10, 2004.
Krause, Epitope-Specific Human Influenza Antibody Repertoires Diversify by B Cell Intraclonal Sequence Divergence and Interclonal Convergence, The Journal of Immunology, pp. 3704-3711, Aug. 31, 2011.
Kruif et al., "Human Immunoglobulin Repertoires against Tetanus Toxoid Contain a Large and Diverse Fraction of High-Affinity Promiscuous Vh Genes," Journal of Molecular Biology, vol. 387, pp. 548-558, Feb. 11, 2009.
"Epididymal protein Rnase10 is required for post-testicular sperm maturation and male fertility," The FASEB Journal, pp. 4198-4209, 2012.
Kucherlapati et al., "Homologous recombination between plasmids in mammalian cells can be enhanced by treatment of input DNA," PNAS USA Genetics, vol. 81, pp. 3135-3157, May 1984.
Kuroiwa et al., "Sequential targeting of the genes encoding immunoglobulin and prion protein in cattle," Nature Genetics, vol. 36, No. 7, pp. 775-780, Jul. 2004.
Laventie, et al., "Heavy chain-only antibodies and tetravalent bispecific antibody neutralizing Staphylococcus aureus leukotoxins," Proceedings of the National Academy of Sciences (USA), Sep. 27, 2011; vol. 108, No. 39, pp. 16404-16409.
Lee et al., "Human C5aR knock-in mice facilitate the production and assessment of anti-inflammatory monoclonal antibodies," Nature Biotechnology, vol. 24, No. 10, pp. 1279-1284, Oct. 2006.
Li et al., "Transgenic mice with a diverse human T cell antigen receptor repertoire," Nature Medicine, vol. 16, No. 9, pp. 1029-1035, Sep. 2010.
Li et al., "The minimum Internal and external sequence requirements for transposition of the eukaryotic transformation vector 22iggyback," Mol. Genet. Genomics, vol. 266, pp. 190-198, 2001.
Li et al., "Crafting rat genomes with zinc fingers." Nature Biotechnology, vol. 29, No. 1, pp. 39-41, Jan. 2011.
Li et al., "Germline Competent Embrvonic Stem Cells Derived from Rat Blastocysts," Cell, vol. 135, pp. 1299-1310, Dec. 26, 2008.
Liao et al., "Generation of Induced Pluripotent Stem Cell Lines from Adult Rat Cells," Cell Stem Cell Brief Report, vol. 4, pp. 11-15, Jan. 9, 2009.
Luciw et al., "Location and Function of Retroviral and SV40 Sequences that Enhance Biochemical Transformation after Microinjection of DNA," Cell., vol. 33, pp. 705-176, Jul. 1983.
Luo et al., "Chromosomal transposition of a Tc1/mariner-like element in mouse embryonic stem cells," Proc. Natl. Acad. Sci. USA, Genetics, vol. 95, pp. 10769-10773, Sep. 1998.
Liu, et al., "Potent and Broad Anti-HIV-1 Activity Exhibited by a Glycosyl-Phosphatidylinositol-Anchored Peptide Derived from the CDR H3 of Broadly Neutralizing Antibody PG16," Journal of Virology, Sep. 2011, vol. 85, No. 17, pp. 8467-8476.
Lonberg, "Human antibodies from transgenic animals," Nature Biotechnology, vol. 23, No. 9, pp. 1117-1125. Sep. 2005.
Loveslati, et al., A study of Gm allotypes ad immunoglobulin heavy gamma IGHG genes in Berbers, Arabs and sub-Saharan Africans from Jerba Island, Tunisia Blackwell Science Ltd., Europran journal of Immunogenetics, vol. 28, pp. 531-538, 2001.
Luby, et al., "The μ switch region tandem repeats are important, but not required, for antibody class switch recombination," The Journal of Experimental Medicine, Jan. 15, 2001; 193(2): pp. 159-168.
Mack et al., "A small bispecific antibody construct expressed as a functional single-chain molecule with high tumor cell cytotoxicity," Proc. Natl. Acad. Sci. USA, Immunology, vol. 92, pp. 7021-7025, Jul. 1995.
Makris et al., "Mutational analysis of insertion sequence 50 (IS50) and transposon 5 (Tn5) ends," Proc. Natl. Acad. Sci. USA, Genetics, vol. 85, pp. 2224-2228, Apr. 1988.
Mallender et al., "Construction, Expression, and Activity of a Bivalent Bispecific Single-chain Antibody," The Journal of Biological Chemistry, vol. 269, No. 1, pp. 199-206, 1994.
Manis, et al., "Mechanism and control of class-switch recombination," Trends in Immunology, Jan. 2002, vol. 23, Issue 1, pp. 31-39.
Marcello et al., Lack of Tyrosylprotein Sulfotransferase-2 Activity Results in Altered Sperm-Egg Interactions and Loss of ADAM3 and ADAM6 in Epididymal Sperm, The Journal of Biological Chemistry, vol. 286, No. 15, pp. 13060-13070, Apr. 15, 2011.
Martensson et al., "Role of the surrogate light chain and the pre-B-cell receptor in mouse B-cell development," Immunology, vol. 101, pp. 435-441, 2000.
Maitta, et al., "Immunogenicity and Efficacy of *Cryptococcus neoformans* Capsular Polysaccharide Glucuronoxylomannan Peptide Mimotope-Protein Conjugates in Human Immunoglobulin Transgenic Mice," Infection and Immunity, vol. 72, No. 1, pp. 196-208, Jan. 2004.
Maul et al., "AID and Somatic Hypermutation," Advances in Immunology, vol. 105, pp. 159-191, 2010.
McCreath et al., "Production of gene-targeted sheep by nuclear transfer from cultured somatic cells," Nature, vol. 405, pp. 1066-1070, Jul. 29, 2000.
Mejia et al., "The Assembly of Large BACs by in Vivo Recombination," Genomics, vol. 70, pp. 165-170, 2000.
Mendez, et al., "Functional Transplant of Megabase Human Immunoglobulin Loci Recapitulates Human Antibody Response in Mice," Nature Genetics, Feb. 1997, vol. 15, pp. 146-156.
Milner, et al., "Polymorphism and utilization of Human $V_h$ Genes," Annals of the New York Academy of Sciences, vol. 764 pp. 50-61, Sep. 1995.
Mir, "Sequencing Genomes: From Individuals to Populations," Briefings in Functional Genomics Proteomics. vol. 8. No. 5, pp. 367-378, 2009.
Moreau et al., "The SV40 72 base repair repeat has a striking effect on gene expression both in SV40 and other chimeric recombinants," Nulcear Acids Research, vol. 9, No. 22, pp. 6047-6068, 1981.
Moreno et al., "The emerging role of matrix metalloproteases of the ADAM family in male germ cell apoptosis," Spermatogenesis, vol. 1, No. 3, pp. 195-208, Jul./Aug./Sep. 2011.
Mouellic et al., "Pattern of transcription of the homeo gene Hox-3.1 in the mouse embryo," Denes Dev., vol. 2, pp. 125-135, 1988.
Mortuza et al., "Immunoglobulin heavy-chain gene rearrangement in adult acute lymphoblastic leukemia reveals preferential usage of JH-proximal variable gene segments," Blood, vol. 97, No. 9, pp. 2716-2726, May 2001.

(56) References Cited

OTHER PUBLICATIONS

Murphy, "VelocImmune: immunoglobulin variable region humanized mice," Recombinant Antibodies for Immunotherapy. 1st ed. Cambridge: Cambridge University Press, pp. 100-108, 2009.

Murphy, et al., "Mice with megabase humanization of their immunoglobulin genes generate antibodies as efficiently as normal mice," PNAS, vol. 111, No. 14, pp. 5153-5158, Apr. 8, 2014.

Nadel, et al., "Sequence of the Spacer in the Recombination Signal Sequence Affects V(D)J Rearrangement Frequency and Correlates with Nonrandom Vk Usage In Vivo," J. Exp. Med., May 4, 1998, vol. 187, No. 9, pp. 1495-1503.

Nagle, "Regeneron helps make Sanofi VelocImmune to its 'weak' pipeline," Outsourcing-Pharmac.com, 2 pages, Dec. 3, 2007.

Nandi et al., "Regulated expression of genes inserted at the human chromosomal B-globin locus by homologous recombination," Proc. Natl. Sci. USA, Cell Biology, vol. 85, pp. 3845-3849, Jun. 1998.

Narayanan et al., "Bacterial Artificial Chromosome Mutagenesis Using Recombineering" Journal of Biomedicine and Biotechnology, vol. 2011, Article ID 971296, 10 pages, Dec. 9, 2010.

Nelson et al., "Development trends for human monoclonal antibody therapeutics," Nature Reviews, Drug Discovery, vol. 9, pp. 767-774, Oct. 2010.

Neuberger et al., "Somatic hypermutation," Current Opinion in Immunology, vol. 7, pp. 248-254, 1995.

Nicholson, et al., "Antibody Repertoires of Four- and Five-Feature Translocus Mice Carrying Human Immunoglobulin Heavy Chain and κ and λ Light Chain Yeast Artificial Chromosomes," The Journal of Immunology, Dec. 15, 1999, vol. 163, No. 12, pp. 6898-6906.

Niemann et al., "Transgenic farm animals: present and future," Rev. Sci Tech Off. Int Epiz., vol. 24, pp. 285-298, 2005.

Oancea et al., "Expression of the (Recombinant) Endogenous Immunoglobulin Heavy-Chain Locus requires the Intronic Matrix Attachment Regions," Molecular and Cellular Biology, vol. 17, No. 5, pp. 2658-2668, May 1997.

"Unidirectional Cre-mediated genetic inversion in mice using the mutant loxP pair lox66/lox71," Nucleic Acids Research, vol. 31, No. 22, pp. 1-7, 2003.

Ohlin, et al., "The human antibody repertoire to infectious agents: implications for disease pathogenesis," Molecular Immunology, vol. 40, Issue 1, pp. 1-11, Sep. 2003.

Osborn et al., "High-Affinity IgG Antibodies Develop Naturally in Ig-Knockout Rats Carrying Germline Human IgH/Ig k/Igλ Loci Bearing the Rat Ch Region," The Journal of Immunology, pp. 1481-1490, Feb. 15, 2013 (E Pub Jan. 9, 2013).

Osoegawa et al., "Bacterial Artificial Chromosome Libraries for Mouse Sequencing and Functional Analysis," Genome Research, pp. 16-28, 2000.

Pavlicek et al., "Ancient Transposable Elements, Processed Pseudogenes, and Endogenous Retroviruses," Genomic Disorders, pp. 57-72, 2006.

Pelham et al., "Expression of a Drosophila Heat Shock Protein in Mammalian Cells: Transient Association with Nucleoli after Heat Shock," Philosophical Transactions of the Royal Society, pp. 301-307, 1984.

Perlot et al., "Antisense transcripts from immunoglobulin heavy-chain locus V(D)J and switch regions," PNAS, vol. 105, No. 10, pp. 3843-3848, Mar. 11, 2008.

Perlot et al., "Cis-Regulatory Elements and Epigenetic Changes Control Genomic Rearrangements of the IgH Locus," Advances in Immunology, vol. 99, pp. 1-32, 2008.

Pettitt, et al., "Agouti C57BL/6N embryonic stem cells for mouse genetic resources," Nature Methods, vol. 6, No. 7, pp. 493-495 (Jul. 2009).

Plasterk et al., "Resident aliens: The Tc1/mariner superfamily of transposable elements," YIG, vol. 15, No. 8, pp. 326-333, Aug. 1999.

Ponsel, et al., "High Affinity, Developability and Functional Size: The Holy Grail of Combinatorial Antibody Library Generation," Molecules, vol. 16, No. 5, pp. 3675-3700, 2011.

Popov et al., "A Human Immunoglobulin λ Locus Is Similarly Well Expressed in Mice and Humans," Journal of Experimental Medicine, vol. 189, No. 10, pp. 1611-1619, May 17, 1999.

Pramanik, et al., Segmental duplication as one of the driving forces underlying the diversity of the human immunoglobulin heavy chain variable gene region, BMC Genomics, vol. 12, No. 78, 2011.

Primkoff et al., "Penetration, Adhesion, and Fusion in Mammalian Sperm-Egg Interaction," Science, vol. 296, pp. 2183-2185, Jun. 21, 2002.

Primakoff et al., "The ADAM Gene Family: surface proteins with adhesion and protease activity," Trends in Genetics, vol. 16, No. 2, pp. 83-87, Feb. 2000.

Puente et al., "Comparative genomic analysis of human and chimpanzee proteases," Genomics, vol. 86, pp. 638-647, 2005.

Prosser, et al., "Mosaic complementation demonstrates a regulatory role for myosin VIIa in actin dynamics of stereocilia," Molecular and Cellular Biology, Mar. 2008, vol. 28, No. 5, pp. 1702-1712.

Prosser, et al., "A resource of vectors and ES cells for targeted deletion of microRNAs in mice," Nature Biotechnology, vol. 29, No. 9, pp. 840-845, Sep. 2011.

Qu et al., "Gene Targeting of ErbB3 Using a Cre-Mediated Unidirectional DNA Inversion Strategy," Technology Report, Genesis, vol. 44, pp. 477-486, 2006.

Raynard et al., "Cis-acting regulatory sequences promote high-frequency gene conversion between repeated sequences in mammalian cells," Nucleic Acids Research, vol. 32, No. 19, pp. 5916-5927, Nov. 4, 2004.

Reddy et al., "Monoclonal antibodies isolated without screening by analyzing the variable-gene repertoire of plasma cells," Nature Biotechnology, vol. 28, No. 9, pp. 965-971, Sep. 2010.

Regeneron, "Big pharma vies for mice," Nature Biotechnology, Jun. 2007, vol. 25, No. 6, p. 613.

Retter, "Sequence and Characterization of the Ig Heavy Chain Constant and Partial Variable Region of the Mouse Strain 129S1," The Journal of Immunology, vol. 179, pp. 2419-2427, 2007.

Rivera, et al., "Genetic background and the dilemma of translating mouse studies to humans," Immunity, vol. 28, No. 1, pp. 1-4, Jan. 28, 2008.

Rodriguez, et al., "High-efficiency deleter mice show that FLPe is an alternative to Cre-loxP," Nature Genetics, vol. 25, pp. 139-140, Jun. 2000.

Rogozin et al., "Cutting Edge: DGYW/WRCH Is a Better Predictor of Mutability at G:c Bases in Ig Hypermutation Than the Widely Accepted RGYW/WRCY Motif and Probably Reflects a Two-Step Activation-Induced Cytidine Deaminase-Triggered Process," Journal of Immunology, vol. 172, pp. 3382-3384, 2004.

Sakai et al., "Recombination and transcription of the endogenous Ig heavy chain locus is effected by the Ig heavy chain intronic enhancer core region in the absence of the matrix attachment regions," Proc. Natl. Acad. Sci., vol. 96, pp. 1526-1531, Feb. 1999.

Sarkar et al., "Molecular evolutionary analysis of the widespread *piggyBac* transposon family and related "domesticated" sequences," Mol. Gen. Genomics, vol. 270, pp. 173-180, 2003.

Sasso et al., "Expression of the Immunoglobulin Vh Gene 51p1 Is Proportional to Its Germline Gene Copy Number." J. Clin. Invest., vol. 97, No. 9, pp. 2074-2080, May 1996.

Sasso, et al., "Ethnic differences in Polymorphism of an Immunoglobulin $V_h3$ gene," Journal of Clinical Investigation, vol. 96, No. 3, pp. 1591-1600, Sep. 1995

Sauer, "Functional Expression of the cre-lox Site-Specific Recombination System in the Yeast *Saccharomyces cerevisiae*," Molecular and Cellular Biology, vol. 7, No. 6, pp. 2087-2096, Jun. 1987.

Sauer et al., "Cre-stimulated recombination at loxP-containing DNA sequences placed into the mammalian genome," Nucleic Acids Research, vol. 17, No. 1, pp. 147-161, 1989.

Sauer et al., "Site-specific DNA recombination in mammalian cells by the Cre recombinase of bacteriophage P1," Proc. Natl. Acad. Sci. USA, Genetics, vol. 85, pp. 5166-5170, 1988.

Schnutgen et al., "A directional strategy for monitoring Cre-mediated recombination at the cellular level in the mouse", Nature Biotechnology, vol. 21, pp. 562-565, May 2003.

(56) References Cited

OTHER PUBLICATIONS

"Use of Mutated FLP Recognition Target (FRT) Sites for the Exchange of Expression Cassettes at Defined Chromosomal Loci," Biochemistry, vol. 33, pp. 12746-12751, 1994.
Schrock et al., "Comparative Genomic Hybridization (CGH)—Detection of Unbalanced Genetic Aberrations Using Conventional Micro-Array Techniques," Molecular Cytogenetics, Unit 8.12.1, Supplement 18, 30 pages, 2001.
Schroeder, et al., "Preferential utilization of conserved immunoglobulin heavy chain variable gene segments during human fetal life," Proc. Natl. Acad. Science USA, vol. 87, pp. 6146-6150, Aug. 1990.
Schweinfest et al., "A heat-shock-inducible eukaryotic expression vector," Gene. 71, pp. 207-210, 1988.
Scott, "Mice with a human touch," Nature Biotechnology, vol. 25, pp. 1075-1077, Dec. 2007.
Seed et al., "Purification of genomic sequences from bacteriophage libraries by recombination and selection in vivo," Nucleic Acids Research, vol. 11, No. 8, pp. 2427-2445, 1983.
Sen, et al., "Multiple nuclear factore interact with the immunoglobulin enhancer sequences, " Cell, vol. 46, pp. 705-716, Aug. 29, 1986.
Seong, et al., "To knockout in 129 or in C57BL/6: that is the question," Trends in Genetics, vol. 20, No. 2, pp. 59-62, Feb. 2004.
Serwe et al., "V(D)J recombination in B cells is impaired but not blocked by targeted deletion of the immunoglobulin heaw chain intron enhancer." The EMBO Journal, vol. 12, No. 6, pp. 2321-2327, 1993.
Shaul, et al., "Homologous recombination between a defective virus and a chromosomal sequence in mammalian cells," Proceedings of the National Academy of Sciences (USA), vol. 89, pp. 3781-3784, Jun. 1985.
Shimizu et al., "Immunoglobulin double-isotype expression by trans-mRNA in a human immunoglobulin transgenic mouse," Proc. Natl. Acad. Sci. USA, Immunology, vol. 86, pp. 8020-8023, Oct. 1989.
Shultz, et al., "Humanized mice in translational biomedical research," The Journal of Immunology, Feb. 2007, vol. 7, No. 2, pp. 118-130.
Sirac, et al., "Role of the monoclonal κ chain V domain and reversibility of renal damage in a transgenic model of acquired Fanconi syndrome," Blood, Jul. 15, 2006, vol. 108, No. 2, pp. 536-543.
Skarnes, et al., "A conditional knockout resource for the genome-wide study of mouse gene function," Nature, vol. 474, pp. 337-342, Jun. 16, 2011.
Simpson, et al., "Genetic variation among 129 substrains and its importance for targeted mutagenesis in mice," Nature Genetics, vol. 16, pp. 19-27.
"Expression of Genes Inserted at the Human B-Globin Locus By Homologous Recombination," Developmental Control of Globin Gene Expression, pp. 581-594, 1987.
Smithies, "Direct Alteration of a Gene in the Human Genome," J. Inher. Metab., Dis. 9, Suppl. 1, pp. 92-97, 1986.
Smithies et al., "Insertion of DNA sequences into the human chromosomal B-globin locus by homologous recombination," Nature, vol. 317, No. 19, pp. 230-234, Sep. 1985.
Sohn et al., "Somatic Hypermutation of an Immunoglobulin μ Heavy Chain Transgene," J. Exp. Med., vol. 177, pp. 493-504, Feb. 1993.
Song et al., "Accurate modification of a chromosomal plasmid by homologous recombination in human cells," Proc. Natl. Acad. Sci. USA, Genetics, vol. 84, pp. 6820-6824, Oct. 1987.
Sonoda et al., "B Cell Development under the Condition of Allelic Inclusion," Immunology, vol. 6, pp. 225-233, Mar. 1997.
Storb et al., "Physical Linkage of Mouse Genes by Pulsed-Field Gel Electrophoresis Suggests that the Rearrangement Process Favors Proximate Target Sequences," Molecular and Cellular Biology, vol. 9, No. 2, pp. 711-718, Feb. 1989.
Stevens et al., "Human Antibody Discovery, VelocImmune-A novel platform," Pharma Focus Asia, Clinical Trials Issue 8, pp. 1-5, 2008.
Taki et al., "Targeted Insertion of a Variable Region Gene into the Immunoglobulin Heavy Chain Locus," Science, vol. 262, pp. 1268-1271, Nov. 19, 1993.
Talbot et al., "Cell Adhesion and Fertilization: Steps in Oocyte transport, Sperm-Zona Pellucida Interactions, and Sperm-Egg Fusion," Biology of Reproduction 68, pp. 1-9, 2003.
Te Riele, et al., "Highly efficient gene targeting in embryonic stem cells through homologous recombination with isogenic DNA constructs," Proceedings of the National Academy of Sciences (USA), vol. 89, pp. 5128-5132, Jun. 1992.
Thomas et al., "High Frequency Targeting of Genes to Specific Sites in the Mammalian Genome," Cell, vol. 44, pp. 419-428, Feb. 14, 1986.
Thomas et al., "Introduction of homologous DNA sequences into mammalian cells induces mutations in the cognate gene" Nature, vol. 324, Nov. 1986.
Thomas et al., "Site-Directed Mutagenesis by Gene Targeting in Mouse Embryo-derived stem cells," Cell, vol. 51, pp. 503-512, Nov. 6, 1987.
Tomizuka, et al., "Double trans-chromosomic mice: Maintenance of two individual human chromosome fragments containing Ig heavy and k loci and expression of fully human antibodies," Proceedings of the National Academy of Sciences (USA), Jan. 18, 2000, vol. 97, No. 2, pp. 722-727.
Torres et al., "Laboratory protocols for conditional gene targeting", Institute for Genetics, University of Cologne, pp. 37-40, 1997.
Ungrin et al., "Strict control of telomerase activation using Cre-mediated inversion", BMC Biotechnology, vol. 6, pp. 1-9, 2006.
Valenzuela, et al., "High-throughput engineering of the mouse genome coupled with high-resolution expression analysis," Nature Biotechnology vol. 21, No. 6. p. 652-659 and vol. 21, No. 7, p. 822, (2003).
Van Spriel, et al., "Immunotherapeutic perspective for bispecific antibodies," Immunology Today, vol. 21. No. 8, pp. 391-397, Aug. 1, 2000.
Vassilieva et al., "Establishment of SSEA-1- and Oct-4 expressing rat embryonic stem-like cell lines and effects of cytokines of the IL-6 family on clonal growth," Experimental Cell Research, vol. 258, pp. 361-373, 2000.
Structure and expression of the human Immunoglobulin λ genes, J. Exp. Med., vol. 172, pp. 609-620, Aug. 1990.
Venken et al., "P[acman]: A BAC Transgenic Platform for Targeted Insertion of Large DNA Fragments in D. melanogaster," Science, vol. 314, pp. 1747-1751, Dec. 15, 2006.
Vora et al., "Altering the Antibody Repertoire via Transgene Homologous Recombination: Evidence for Global and Clone-autonomous Regulation of Antigen-driven B Cell Differentiation," J. Exp. Med., vol. 181, pp. 271-281, Jan. 1995.
Wallace et al., "Manipulating the Mouse Genome to Engineer Precise Functional Syntenic Replacements with Human Sequence," Cell, vol. 18, pp. 197-209, Jan. 12, 2007.
Wang et al., "AID upmutants isolated using a high-throughput screen highlight the immunity/cancer balance limiting DNA deaminase activity," Nature Structural & Molecular Biology, vol. 16, No. 7, Jul. 2009.
Wang et al., "Altering the spectrum of immunoglobulin V gene somatic hypeimutation by modifying the active site of AID," J. Exp. Med., vol. 207, No. 1, pp. 141-153, 2010.
Wang et al., "Catching a Moving Target," Science, Biochemistry, vol. 333, pp. 834-835, Aug. 21, 2011.
Wang, et al., "Chromosomal transposition of PiggyBac in mouse embryonic stem cells," Proceedings of the National Academy of Sciences (USA), (2008) vol. 105, No. 27, pp. 9290-9295.
Wang, et al., "Many human immunoglobulin heavy-chain IGHV gene polymorphisms have been reported in error," Immunology and Cell Biology, vol. 86, No. 2, pp. 111-115, Feb. 2008.
White, et al, "Genome-wide generation and systematic phenotyping of knockout mice revels new roles for many genes," Cell, vol. 154, Issue 2: pp. 452-464, Jul. 18, 2013.
Wilkie et al., "Analysis of the Integrant in MyK-103 Transgenic Mice in which Males Fail to Transmit the Integrant," Molecular and Cellular Biology, pp. 1646-1655, May 1987.

(56) References Cited

OTHER PUBLICATIONS

Williams et al., "Unequal VH Gene Rearrangement Frequency Within the Large Vh7183 Gene Family is not Due to Recombination Signal Sequence Variation, and Mapping of the Genes Shows a Bias of Rearrangement Base on Chromosomal Location," The Journal of Immunology, pp. 257-263, 2001.
Xu, et al., "Combinatorial surrobody libraries," Proceedings of the National Academy of Sciences (USA), (2008) vol. 105, No. 31, pp. 10756-10761.
Yancopoulous et al., "Preferential utilization of the most JH-proximal VH gene segments in pre-B-cell lines," Nature, vol. 311, pp. 727-733, 1984.
Yu, et al., Differential Usage of VH Gene Segments Is Mediated by cis Elements, The Journal of Immunology, Oct. 1, 1998, vol. 161, No. 7, pp. 3444-3454.
Zheng et al., Engineering Mouse Chromosomes with Cre-loxP: Range, Efficiency, and Somatic Applications, Molecular and Cellular Biology, vol. 20, No. 2, pp. 648-655, Jan. 2000.
Zou et al., "Cre-loxP-mediated gene replacement: a mouse strain producing humanized antibodies," Current Biology, vol. 4, No. 12, pp. 1099-1104, 1994.
"News in Brief," Nature Biotechnology, vol. 25, No. 6, p. 613, Jun. 2007.
GenBank Accession No. X97051 S64822, accessed Aug. 6, 2014, 29 pages.
Nucleotide Sequence RID Y55HBK1WH4, accessed Aug. 6, 2014, 2 pages.
U.S. Appl. No. 09/552,219, filed April 19, 2000, issued May 28, 2002 as U.S. Pat. No. 6,395,487.
U.S. Appl. No. 13/416,684; filed Mar. 9, 2012, issued Sep. 20, 2016 as U.S. No. 9,447,177.
U.S. Appl. No. 13/740,727, filed Jan. 14, 2013.
U.S. Appl. No. 13/846,672, filed Mar. 18, 2013.
U.S. Appl. No. 13/875,892, filed May 2, 2013.
U.S. Appl. No. 14/220,095, filed Mar. 19, 2014.
U.S. Appl. No. 14/226,698, filed Mar. 26, 2014.
U.S. Appl. No. 15/018,670, filed Feb. 8, 2016.
U.S. Appl. No. 15/095,315, filed Apr. 11, 2016.
U.S. Appl. No. 15/383,196, filed Dec. 19, 2016.
U.S. Appl. No. 15/383,202, filed Dec. 19, 2016.
Reference FOR_PAT002, as cited and submitted herewith, is believed to be the English language counterpart of Reference FOR_PAT001, as cited and submitted herewith.
Reference AC (US 6,595,541, as cited in the Initial Information Disclosure Statement filed Dec. 24, 2014) is believed to be the English language counterpart of Reference FOR_PAT004, as cited and submitted herewith.
Reference BV (WO 2003/047336, as cited and submitted in the Initial Information Disclosure Statement filed Dec. 24, 2014) is believed to be the English language counterpart of Reference FOR_PAT005, as cited and submitted herewith.
Reference FOR_PAT013, as cited and submitted herewith, is believed to be the English language counterpart of Reference FOR_PAT006, as cited and submitted herewith.
Reference FOR_PAT025, as cited and submitted herewith, is believed to be the English language counterpart of Reference FOR_PAT007, as cited and submitted herewith.
Reference NON_PAT037, as cited and submitted herewith, is believed to be the English translation of Reference NON_PAT038, as cited and submitted herewith.
Reference NON_PAT039, as cited and submitted herewith, is believed to be the English translation of Reference NON_PAT040, as cited and submitted herewith.
Reference NON_PAT042, as cited and submitted herewith, is believed to be the English translation of Reference NON_PAT041, as cited and submitted herewith.
1st International MUGEN Conference on Animal Models for Human Immunological Disease, Sep. 10-13, 2006—Athens Greece (Abstracts 1—52), 52 pages.
Adams D.J. et al., "Contemporary approaches for modifying the mouse genome," Physiological Genomics, vol. 34, 2008, pp. 225-238.
Adams D.J. et al., "Mutagenic Insertion and Chromosome Engineering Resource (MICER)," Nature Genetics, vol. 36 (8), Aug. 2004, pp. 867-871.
Affidavits Evidencing Murphy Slides as Printed Publication, 84 pages, dated Jun. 20, 2016.
Aguilera R.J. et al., "Characterization of immunoglobulin enhancer deletions in murine plasmacytomas," The EMBO Journal, 1985, vol. 4 (13B), pp. 3689-3693.
Ahmed T., "Sanofi-aventis and Regeneron Extend Therapeutic Antibody Agreement," PharmaDeals Review, Nov. 2009, vol. 11, p. 115.
Arnaout R., et al., "High-Resolution Description of Antibody Heavy-Chain Repertoires in Humans," PLoS One, Aug. 2011, vol. 6 (8), pp. e22365-1-e22365-8.
Arthur J.S. et al., "Gene-Targeting Vectors," Chapter 9, Transgenesis Techniques, Principles and Protocols, Third edition, 2009 (24 pages, including cover sheet, copyright and preface pages and table of contents), pp. 127-144.
Asenbauer H. et al., "The immunoglobulin lambda light chain enhancer consists of three modules which synergize in activation of transcription," European Journal of Immunology, 1999, vol. 29, pp. 713-724.
Atlas of Genetics and Cytogenetics in Oncology and Haematology, VPREB1 (pre-B lymphocyte 1), 5 pages. [Retrieved online at http://atlasgeneticsoncolgy.org/Genes/GC_VPREB1.html on May 25, 2015].
Avery S., Attorney for Applicant, Third-Party Pre-Issuance Submission Under 37 CFR Section 1.290 in U.S. Appl. No. 14/517,755, dated Jun. 26, 2015, 16 pages.
Baer A. et al., "Coping with kinetic and thermodynamic barriers: RMCE, an efficient strategy for the targeted integration of transgenes," Current Opinions in Biotechnology, Oct. 2001, vol. 12(5), pp. 473-480.
Baker A.M., et al., "Adaptation of TCR Expression Vectors for the Construction of Mouse-Human Chimeric MBP-Specific TCR Transgenes," Journal of Neuroscience Research, 1996, vol. 45 (4), pp. 487-491.
Beck J.A., et al., "Genealogies of mouse inbred strains," Nature Genetics, 2000, vol. 24, pp. 23-25 (with supporting table and chart).
Beerli R.R., et al., "Mining Human Antibody Repertoires," mAbs, Jul./Aug. 2010, vol. 2 (4), pp. 365-378.
Bentham, A., Attorneys for Regeneron Pharmaceuticals, Inc., Opposition against EP2421357B1 in the name of Kymab Ltd. pertaining to Application No. 10734546.4, dated Jan. 9, 2017, 13 pages.
Bhattacharya P., et al., "Switch Region Identity Plays an Important Role in Ig Class Switch Recombination," Journal of Immunology, 2010, vol. 184 (11), pp. 6242-6248.
Birling M.C. et al., "Site-Specific Recombinases for Manipulation of the Mouse Genome," Chapter 16, Transgenesis Techniques, Principles and Protocols, Third edition, 2009 (25 pages, including cover sheet, copyright and preface pages and table of contents), pp. 245-263.
Blankenstein T. et al., "Immunoglobulin $V_H$ Region Genes of the Mouse are Organized in Overlapping Clusters," European Journal of Immunology, 1987, vol. 17 (9), pp. 1351-1357.
Board of Appeal of the European Patent Office, Datasheet for the Decision of Nov. 9, 2015 for Application No. 02709544.7, Case T 2220/14—3.3.08, 83 pages.
Bode J., et al., "The Transgeneticist's Toolbox: Novel Methods for the Targeted Modification of Eukaryotic Genomes," Biological Chemistry, Sep./Oct. 2000, vol. 381 (9-10), pp. 801-813.
Bogen B., et al., "A Rearranged $\lambda_2$ Light Gene Chain Retards but does not Exclude x and $\lambda_1$ Expression," European Journal of Immunology, 1991, vol. 21 (10), pp. 2391-2395.
Bransteitter R., et al., "Activation-Induced Cytidine Deaminase Deaminates Deoxycytidine on Single-Stranded DNA but Requires the Action of RNase," Proceedings of the National Academy of Sciences of the U.S.A., Apr. 2003, vol. 100 (7), pp. 4102-4107.

(56) References Cited

OTHER PUBLICATIONS

Brault V., et al., "Modeling Chromosomes in Mouse to Explore the Function of Genes, Genomic Disorders, and Chromosonal Organization," *PLoS Genetics*, Jul. 2006, vol. 2 (7), pp. e86-1-e86-9.

Brezinschek H.P., et al., "Analysis of the Human V, Gene Repertoire," *Journal of Clinical Investigation*, 1997, vol. 99 (10), pp. 2488-2501.

Brüggemann M., et al., "The Immunogenicity of Chimeric Antibodies," *The Journal of Experimental Medicine*, Dec. 1989, vol. 170 (6), pp. 2153-2157.

Brüggemann M., et al., "Strategies for Expressing Human Antibody Repertoires in Transgenic Mice," *Immunology Today*, Aug. 1996, vol. 17 (8), pp. 391-397.

Briney B.S., et al., "Human Peripheral Blood Antibodies with Long HCDR3s are Established Primarily at Original Recombination using a Limited Subset of Germline Genes," *PLoS One*, 2012, vol. 7 (5), pp. e36750-1-e36750-13.

Brüggemann M., et al., "Human Monoclonal Antibodies from Translocus Mice," *Molecular Biology of B Cells*, Chapter 34, 2003, pp. 547-561.

Butler J.E., et al., "Immunoglobulin Diversity, B-Cell and Antibody Repertoire Development in Large Farm Animals," *Revue scientifique et technique* (International Office of Epizootics), 1998, vol. 17(7), pp. 43-70.

Call L.M., et al., "A Cre-*lox* recombination system for the targeted integration of circular yeast artificial chromosomes into embryonic stem cells," *Human Molecular Genetics*, 2000, vol. 9 (12), pp. 1745-1751.

Carter T.C., et al., "Standardized Nomenclature for Inbred Strains of Mice," *Cancer Research*, 1952, vol. 12 (8), pp. 602-613.

Casrouge A., et al., "Size Estimate of the αβ TCR Repertoire, of Naive Mouse Splenocytes," *The Journal of Immunology*, 2000, vol. 164 (11), pp. 5782-5787.

Chan A.C., et al., "Therapeutic Antibodies for Autoimmunity and Inflammation," *Nature Reviews Immunology*, 2010, vol. 10 (5), pp. 301-316.

Chen Y., "*PiggyBac* Transposon-Mediated, Reversible Gene Transfer in Human Embryonic Stem Cells," *Stem Cells and Development*, Nov. 2010, vol. 19 (6), 9 pages.

Chia R., et al., "The origins and uses of mouse outbred stocks," *Nature Genetics*, 2005, vol. 37 (11), pp. 1181-1186.

Chinese Patent Office, First Office Action (English Translation) for Chinese Application No. 201180039668.1, dated Jan. 3, 2014, 6 pages.

Chinese Patent Office, First Office Action for Chinese Patent Application No. 201180039668.1, dated Jan. 3, 2014, 6 pages.

Chinese Patent Office, Office Action (English Translation) for Chinese Patent Application No. 201380029744.1, dated Nov. 10, 2016, 2 pages.

Chinese Patent Office, Office Action for Chinese Patent Application No. 201380027944.1, dated Nov. 10, 2016, 5 pages.

Chinese Patent Office, Search Report, Chinese Patent Application No. 201180039668.1, dated Jan. 3, 2014, 2 pages.

Chinese Patent Office, Search Report (English Translation), Chinese Patent Application No. 201180039668.1, dated Jan. 3, 2014, 1 page.

Clark M.R., "IgG Effector Mechanisms," *Chemical Immunology*, 1997, vol. 65, pp. 88-110.

Corbett S.J., et al., "Sequence of the Human Immunoglobulin Diversity (D) Segment Locus: A Systematic Analysis Provides No Evidence for the Use of DIR Segments, Inverted D Segments, "Minor" D Segments or D-D Recombination," *Journal of Molecular Biology*, 1997, vol. 270 (4), pp. 587-597.

Crouch E.E., et al., "Regulation of AID expression in the Immune Response," *Journal of Experimental Medicine*, May 2007, vol. 204 (5), pp. 1145-1156.

Davies N.P., et al., "Creation of Mice Expressing Human Antibody Light Chains by Introduction of a Yeast Artificial Chromosome Containing the Core Region of the Human Immunoglobulin κ Locus," *Nature Biotechnology*, Aug. 1993, vol. 11 (8), pp. 911-914.

De Bono B., et al., "$V_H$ Gene Segments in the Mouse and Human Genomes," *Journal of Molecular Biology*, 2004, vol. 342 (1), pp. 131-143.

De Wildt R.M. et al., "Analysis of Heavy and Light Chain Pairings Indicates that Receptor Editing Shapes the Human Antibody Repertoire," *Journal of Molecular Biology*, 1999, vol. 285, pp. 895-901.

Declerck P. et al., "Generation of Monoclonal Antibodies against autologous Proteins in Gene-inactivated Mice," *The Journal of Biological Chemistry*, Apr. 1995, vol. 270 (15), pp. 8397-8400.

Deftos, M., et al., "Defining the Genetic Origins of Three Rheumatoid Synovium-derived IgG Rheumatoid Factors," *Journal of Clinical Investigations*, Jun. 1994, vol. 93, pp. 2545-2553.

Deng C., et al., "Reexamination of Gene Targeting Frequency as a Function of the Extent of Homology Between the Targeting Vector and the Target Locus," *Molecular and Cellular Biology*, Aug. 1992, vol. 12 (8), pp. 3365-3371.

Donohoe M.E., et al., "Transgenic Human λ5 Rescues the Murine λ5 Nullizygous Phenotype," *Journal of Immunology*, 2000, vol. 164, pp. 5269-5276.

Ebert A., et al., "The Distal $V_H$ Gene Cluster of the Igh Locus Contains Distinct Regulatory Elements with Pax5 Transcription Factor-Dependent Activity In Pro-B Cells," *Immunity*, Feb. 2011, vol. 34 (2), pp. 175-187.

Edwards D.R., et al., "The ADAM Metalloproteinases," *Molecular Aspects of Medicine*, 2008, vol. 29 (5), pp. 258-289.

Engel H., et al., "Expression level of a transgenic 2 chain results in isotype exclusion and commitment to B1 cells," *European Journal of Immunology*, 1998, vol. 28, pp. 2289-2299.

European Patent Office, Alessandro Brero, Authorized officer, International Search Report for Application No. PCT/GB2012/052296, dated May 17, 2013, 30 pages, *together with the Written Opinion of the International Searching Authority*.

European Patent Office, Alessandro Brero, Authorized officer, International Search Report for Application No. PCT/GB2012/052297, dated Jun. 19, 2013, 24 pages, *together with the Written Opinion of the International Searching Authority*.

European Patent Office, Alessandro Brero, Authorized Officer, International Search Report for Application No. PCT/GB2012/052298, dated Jun. 13, 2013, 21 pages, *together with the Written Opinion of the International Searching Authority*.

European Patent Office, Examination Report for Application No. 12762378.3, dated Jun. 8, 2016, 5 pages.

European Patent Office, Extended European Search Report for Application No. 16189625.3, dated Nov. 23, 2016, 8 pages.

European Patent Office, Communication pursuant to Rule 114(2) EPC regarding 14772198.9, dated Mar. 30, 2016, 16 pages.

European Patent Office, European Search Report for Application No. 12194977.0, dated Jul. 5, 2013, 4 pages.

European Patent Office, Extended European Search Report for Application No. 12171791.2, dated Jun. 18, 2013, 5 pages.

European Patent Office, Extended European Search Report for Application No. 12171793.8 dated Jun. 21, 2013, 8 pages.

European Patent Office, Extended European Search Report for Application No. 12194970.5, dated Jan. 23, 2013, 9 pages.

European Patent Office, Extended European Search Report for Application No. 12194977.0, dated Jul. 17, 2013, 8 pages.

European Patent Office, Extended European Search Report for Application No. 12195041.4, dated Nov. 18, 2013, 8 pages.

European Patent Office, Extended European Search Report for Application No. 14170196.1, dated Oct. 8, 2014, 8 pages.

European Patent Office, Extended European Search Report for Application No. 14176740.0, dated Oct. 15, 2014, 7 pages.

European Patent Office, Extended European Search Report for Application No. 15188522.5 dated Feb. 2, 2016, 15 pages.

European Patent Office, Extended European Search Report for Application No. 16151215.7, dated Mar. 16, 2016, 11 pages.

European Patent Office, F. Chambonnet, Authorized officer, International Search Report for Application No. PCT/GB2012/052380, dated Jan. 3, 2013, 17 pages, *together with the Written Opinion of the International Searching Authority*.

European Patent Office, Gaby Brouns, Authorized officer, International Search Report for Application No. PCT/GB2012/052956,

(56) References Cited

OTHER PUBLICATIONS dated Mar. 1, 2013, 14 pages, *together with the Written Opinion of the International Searching Authority.*
European Patent Office, Gaby Brouns, Authorized officer, International Search Report for Application No. PCT/GB2012/052960, dated Apr. 29, 2013, 19 pages, *together with the Written Opinion of the International Searching Authority.*
European Patent Office, Gaby Brouns, Authorized officer, International Search Report for Application No. PCT/GB2013/050682, dated Sep. 25, 2013, 16 pages, *together with the Written Opinion of the International Searching Authority.*
European Patent Office, Gaby Brouns, Authorized officer, International Search Report for Application No. PCT/GB2013/050683, dated Jul. 9, 2013, 11 pages, *together with the Written Opinion of the International Searching Authority.*
European Patent Office, Gaby Brouns, Authorized officer, International Search Report for Application No. PCT/GB2013/051280, dated Nov. 15, 2013, 19 pages, *together with the Written Opinion of the International Searching Authority.*
European Patent Office, Examination Report for Application No. 12795841.1, dated Feb. 12, 2016, 5 pages.
European Patent Office, Examination Report for Application No. 13711119.1, dated Dec. 17, 2015, 6 pages.
European Patent Office, Examination Report for Application No. 13711119.1, dated Jul. 13, 2016, 6 pages.
European Patent Office, International Searching Authority, Examiners Report on Allowable Claims for Application No. PCT/GB2010/051122, datedJan. 2004, 1 page.
European Patent Office, James Bretherick, Primary Examiner, Examination Report for Application No. 12778780.2, dated Oct. 14, 2016, 3 pages.
European Patent Office, Extended European Search Report for Application No. 14196645.7, dated Jun. 26, 2015, 12 pages.
European Patent Office, Julien Landre, Authorized officer, International Search Report for Application No. PCT/GB2012/052670, dated Feb. 14, 2013, 12 pages, *together with the Written Opinion of the International Searching Authority.*
European Patent Office, Laurent Deleu, Authorized Officer, International Preliminary Report on Patentability Chapter II for Application No. PCT/GB2010/051122, date of completion Nov. 2, 2011, 33 pages.
European Patent Office, Laurent Deleu, Authorized officer, International Search Report for Application No. PCT/GB2010/051122, dated Sep. 29, 2010, 9 pages, *together with the Written Opinion of the International Searching Authority.*
European Patent Office, Laurent Deleu, Authorized officer, International Search Report for Application No. PCT/GB2011/050019, dated May 16, 2011, 12 pages, *together with the Written Opinion of the International Searching Authority.*
European Patent Office, Examination Report for Application No. 12194970.5, dated Sep. 23, 2013, 6 pages.
European Patent Office, Examination Report for Application No. 14176740.0, dated Jun. 6, 2016, 5 pages.
European Patent Office, Examination Report for Application No. 14176740.0, dated Oct. 23, 2015, 5 pages.
European Patent Office, Notice of opposition to a European patent, pertaining to Application No. 10734546.4, dated Jan. 23, 2013, 41 pages.
European Patent Office, Opposition against EP2421357 Animal Models and Therapeutic Molecules in the name of Kymab Limited pertaining to Application No. 10734546.4, dated Oct. 23, 2013, 44 pages.
European Patent Office, Opposition against EP2517557 Animal Models and Therapeutic Molecules in the name of Kymab Limited pertaining to Application No. 12171793.8, dated Jan. 17, 2017, 39 pages.
European Patent Office, Statement of Fact and Arguments in Support of Opposition pertaining to Application No. 10734546.4, dated Oct. 22, 2013, 41 pages.
European Patent Office, Invitation to Pay Additional Fees and, Where Applicable, Protest Fee, Application No. PCT/GB2012/052296, mailed on Jan. 24, 2013, 9 pages.
Feng Y.Q., et al., "Site-Specific Chromosomal Integration in Mammalian Cells: Highly Efficient CRE Recombinase-Mediated Cassette Exchange," *Journal of Molecular Biology*, 1999, vol. 292 (4), pp. 779-785.
Festing, M.F.W., et al., "Revised nomenclature for strain 129 mice," *Mammalian Genome*, 1999, vol. 10, p. 836.
Fleischer B., et al., "Reactivity of Mouse T-Cell Hybridomas Expressing Human Vp Gene Segments With *Staphylococcal* and *Streptococcal* Superantigens," *Infection and Immunity*, Mar. 1996, vol. 64 (3), pp. 987-994.
French Patent Office, INPI, Laurent Deleu, Authorized officer, International Search Report for Patent Application No. 1359518, dated Aug. 20, 2014, 3 pages.
Friedrich G., Statement of Dr. Glenn Friedrich, dated Mar. 3, 2016, 4 pages.
Fujieda S., et al., "Multiple Types of Chimeric Germ-Line Ig Heavy Chain Transcripts in Human B Cells: Evidence for Trans-Splicing of Human Ig RNA," *Journal of Immunology*, 1996, vol. 157 (8), pp. 3450-3459.
Gallo M.L., et al., "The Human Immunoglobulin Loci Introduced into Mice: V (D) and J Gene Segment Usage Similar to that of Adult Humans," *European Journal of Immunology*, 2000, vol. 30 (2), pp. 534-540.
Gama Sosa M.A., et al., "Animal Transgenesis: An Overview," *Brain Structure and Function*, 2010, vol. 214 (2-3), pp. 91-109.
Gavilondo J.V., et al., "Antibody Engineering at the Millennium," *BioTechniques*, Jul. 2000, vol. 29 (1), pp. 128-145.
Genbank (D. Muzny et al.), "Rattus norvegicus clone CH230-30N12, * Sequencing in Progress *, 6 unordered pieces," Accession No. AC111740, Nov. 9, 2002, 42 pages. [Retrieved from the Internet: http://www.ncbi.nlm.nih.gov/nuccore/AC111740 on Feb. 28, 2013].
Genbank, "DNA Sequence of the Human Immunoglobulin D Segment Locus," Accession No. x97051.1 S64822, updated Mar. 3, 2015, 26 pages.
Genbank, "*Homo sapiens* immunoglobulin heavy-chain (IGHV2-5) gene, IGHV2-5*10 allele, partial sequence," Accession No. KF698731.1, dated Nov. 18, 2013, 1 page.
Genbank, "Mus musculus strain 129S1/SvlmJ chromosome 12 genomic sea locus group 129S1/SvlmJ 129S1/SVIMJ_MMCHR12_CTG1," NCBI Reference Sequence No. NT_114985.3, dated May 5, 2014, 1 page.
Giallourakis C.C., et al., "Elements Between the IgH Variable (V) and Diversity (D) Clusters Influence Antisense Transcription and Lineage-Specific V(D)J Recombination," *Proceedings of the National Academy of Sciences of the U.S.A.*, 2010, vol. 107 (51), pp. 22207-22212.
Giraldo P., et al., "Size Matters: Use of YACs, BACs and PACs in Transgenic Animals," *Transgenic Research*, 2001, vol. 10 (2), pp. 83-103.
Giusti A.M., et al., "Hypermutation is Observed only in Antibody H Chain V Region Transgenes that have Recombined with Endogenous Immunoglobulin H DNA: Implications for the Location of *cis*-acting Elements Required for Somatic Mutation," *The Journal of Experimental Medicine*, Mar. 1993, vol. 177 (3), pp. 797-809.
Glanville J., et al., "Naive Antibody Gene-Segment Frequencies are Heritable and Unaltered by Chronic Lymphocyte Ablation," *Proceedings of the National Academy of Sciences of the U.S.A*, Dec. 2011, vol. 108 (50), p. 20066-20071.
Glaser S. et al., "Current issues in mouse genome engineering," *Nature Genetics*, Nov. 2005, vo. 37 (11), pp. 1187-1193.
Goldman I.L., et al., "Transgenic Animals in Medicine: Integration and Expression of Foreign Genes, Theoretical and Applied Aspects," *Medical Science Monitor*, 2004, vol. 10 (11), pp. RA274-RA285.
Gratz S. et al., "Genome Engineering of *Drosophila* with the CRISPR RNA-Guided Cas9 Nuclease," *Genetics*, Aug. 2013, vol. 194, pp. 1029-1035.
Green L.L., et al., "Antigen-Specific Human Monoclonal Antibodies from Mice Engineered with Human Ig Heavy and Light Chain YACs," *Nature Genetics*, May 1994, vol. 7 (1), pp. 13-21.

(56) References Cited

OTHER PUBLICATIONS

Green L.L., et al., "Regulation of B Cell Development by Variable Gene Complexity in Mice Reconstituted with Human Immunoglobulin Yeast Artificial Chromosomes," *The Journal of Experimental Medicine*, Aug. 1998, vol. 188 (3), pp. 483-495.
Grippo V., et al., "The Heavy Chain Variable Segment Gene Repertoire in Chronic Chagas' Heart Disease," *The Journal of Immunology*, Dec. 2009, vol. 182 (12), pp. 8015-8025.
Grund M., European Patent Attorney, Grund Intellectual Property Group, Third-Party Observations according to Article 115 EPC regarding 11705964.2, dated Apr. 30, 2014, 4 pages.
Grund M., European Patent Attorney, Grund Intellectual Property Group, Third-Party Observations according to Article 115 EPC regarding 11705964.2, dated Aug. 5, 2016, 11 pages.
Grund M., European Patent Attorney, Grund Intellectual Property Group, Third-Party Observations according to Article 115 EPC regarding 11705964.2, dated Oct. 9, 2013, 8 pages.
Grund M., European Patent Attorney, Grund Intellectual Property Group, Third-Party Observations according to Article 115 EPC regarding 12171791.2, dated Aug. 4, 2014, 6 pages.
Grund M., European Patent Attorney, Grund Intellectual Property Group, Third-Party Observations according to Article 115 EPC regarding 12171791.2, dated Dec. 19, 2014, 7 pages.
Grund M., European Patent Attorney, Grund Intellectual Property Group, Third-Party Observations according to Article 115 EPC regarding 12171791.2, dated Feb. 26, 2014, 9 pages.
Grund M., European Patent Attorney, Grund Intellectual Property Group, Third-Party Observations according to Article 115 EPC regarding 12171793.8, dated Jun. 25, 2014, 7 pages.
Grund M., European Patent Attorney, Grund Intellectual Property Group, Third-Party Observations according to Article 115 EPC regarding 12194970.5, dated Apr. 25, 2014, 6 pages.
Grund M., European Patent Attorney, Grund Intellectual Property Group, Third-Party Observations according to Article 115 EPC regarding 12194970.5, dated Aug. 12, 2014, 5 pages.
Grund M., European Patent Attorney, Grund Intellectual Property Group, Third-Party Observations according to Article 115 EPC regarding 12194970.5, dated Mar. 5, 2014, 9 pages.
Grund M., European Patent Attorney, Grund Intellectual Property Group, Third-Party Observations according to Article 115 EPC regarding 12194970.5, dated Nov. 15, 2013, 6 pages.
Grund M., European Patent Attorney, Grund Intellectual Property Group, Third-Party Observations according to Article 115 EPC regarding 12194970.5, dated Sep. 9, 2013, 11 pages.
Grund M., European Patent Attorney, Grund Intellectual Property Group, Third-Party Observations according to Article 115 EPC regarding 12194977.0, dated Mar. 26, 2014, 4 pages.
Grund M., European Patent Attorney, Grund Intellectual Property Group, Third-Party Observations according to Article 115 EPC regarding 12194977.0, dated May 12, 2015, 5 pages.
Grund M., European Patent Attorney, Grund Intellectual Property Group, Third-Party Observations according to Article 115 EPC regarding 12195041.4, dated Jul. 30, 2014, 5 pages.
Grund M., European Patent Attorney, Grund Intellectual Property Group, Third-Party Observations according to Article 115 EPC regarding 12762377.5, dated Feb. 12, 2016, 8 pages.
Grund M., European Patent Attorney, Grund Intellectual Property Group, Third-Party Observations according to Article 115 EPC regarding 12762377.5, dated May 22, 2015, 7 pages.
Grund M., European Patent Attorney, Grund Intellectual Property Group, Third-Party Observations according to Article 115 EPC regarding 12762378.3, dated Feb. 15, 2017, 6 pages.
Grund M., European Patent Attorney, Grund Intellectual Property Group, Third-Party Observations according to Article 115 EPC regarding 12772122.3, dated Mar. 12, 2015, 5 pages.
Grund M., European Patent Attorney, Grund Intellectual Property Group, Third-Party Observations according to Article 115 EPC regarding 12772122.3, dated May 17, 2016, 7 pages.
Grund M., European Patent Attorney, Grund Intellectual Property Group, Third-Party Observations according to Article 115 EPC regarding 12795606.8, dated Aug. 22, 2014, 8 pages.
Grund M., European Patent Attorney, Grund Intellectual Property Group, Third-Party Observations according to Article 115 EPC regarding 12795606.8, dated Feb. 26, 2014, 6 pages.
Grund M., European Patent Attorney, Grund Intellectual Property Group, Third-Party Observations according to Article 115 EPC regarding 12795606.8, dated Mar. 26, 2015, 4 pages.
Grund M., European Patent Attorney, Grund Intellectual Property Group, Third-Party Observations according to Article 115 EPC regarding 13711119.1, dated Dec. 9, 2015, 7 pages.
Grund M., European Patent Attorney, Grund Intellectual Property Group, Third-Party Observations according to Article 115 EPC regarding 13711119.1, dated Jul. 5, 2016, 7 pages.
Grund M., European Patent Attorney, Grund Intellectual Property Group, Third-Party Observations according to Article 115 EPC regarding 13711120.9, dated May 17, 2016, 11 pages.
Grund M., European Patent Attorney, Grund Intellectual Property Group, Third-Party Observations according to Article 115 EPC regarding 14176740.0, dated Aug. 10, 2015, 13 pages.
Grund M., European Patent Attorney, Grund Intellectual Property Group, Third-Party Observations according to Article 115 EPC regarding 14176740.0, dated Nov. 2, 2016, 4 pages.
Grund M., European Patent Attorney, Grund Intellectual Property Group, Third-Party Observations according to Article 115 EPC regarding 16189625.3, dated Mar. 23, 2017, 5 pages.
Grund M., European Patent Attorney, Grund Intellectual Property Group, Third-Party Observations regarding Application No. PCT/GB2012/052297, dated Jan. 17, 2014, 3 pages.
Grund M., European Patent Attorney, Grund Intellectual Property Group, Third-Party Observations regarding Application No. PCT/GB2012/052298, dated Jan. 17, 2014, 4 pages.
Grund M., European Patent Attorney, Grund Intellectual Property Group, Third-Party Observations regarding Application No. PCT/GB2012/052380, dated Jan. 24, 2014, 4 pages.
Grund M., European Patent Attorney, Grund Intellectual Property Group, Third-Party Observations regarding Application No. PCT/GB2012/052956, dated Mar. 26, 2014, 2 pages.
Grund M., European Patent Attorney, Grund Intellectual Property Group, Third-Party Observations regarding Application No. PCT/GB2012/052960, dated Apr. 2, 2014, 3 pages.
Grund M., European Patent Attorney, Grund Intellectual Property Group, Third-Party Observations regarding Application No. PCT/GB2013/050682, dated Jul. 28, 2014, 3 pages.
Grund M., European Patent Attorney, Grund Intellectual Property Group, Third-Party Observations regarding Application No. PCT/GB2013/050683, dated Jul. 28, 2014, 2 pages.
Grund M., European Patent Attorney, Grund Intellectual Property Group, Third-Party Observations regarding Application No. PCT/US2012/026416, dated Jun. 6, 2013, 2 pages.
Grund M., European Patent Attorney, Grund Intellectual Property Group, Third-Party Observations according to Article 115 EPC regarding 11705964.2, dated Feb. 26, 2015, 5 pages.
Grund M., European Patent Attorney, Grund Intellectual Property Group, Third-Party Observations according to Article 115 EPC regarding 16151215.7, dated Mar. 1, 2017, 4 pages.
Guan C. et al., "A Review of Current Large-Scale Mouse Knockout Efforts," *Genesis*, vol. 48, 2010, pp. 73-85.
Guirouilh-Barbat J. et al., "Is homologous recombination really an error-free process?", *Frontiers in Genetics*, Jun. 2014, vol. 5 (175), 15 pages.
Guo, Y., et al., "A Preliminary Analysis of the Immunoglobulin Genes in the African Elephant (*Loxodonta africana*);" *PLoS ONE*, Feb. 2011, vol. 6 (2), pp. e16889-1-e16889-14.
Hamers-Caterman C. et al., "Naturally occurring antibodies devoid of light chains," *Nature*, Jun. 1993, vol. 363, pp. 446-448.
Harding F.A., et al., "Class Switching in Human Immunoglobulin Transgenic Mice," *Annals of the New York Academy of Sciences*, 1995, vol. 764, pp. 536-546.
Hendricks J., et al., "Organization of the Variable Region of the Immunoglobulin Heavy-Chain Gene Locus of the Rat," *Immunogenetics*, 2010, vol. 62 (7), pp. 479-486.

(56) References Cited

OTHER PUBLICATIONS

Herschbach, Jarrell B., Third-Party Pre-Issuance Submission Under 37 CFR Section 1.290 in U.S. Appl. No. 14/052,259, dated Aug. 6, 2014, 7 pages.
Hewitt S.L., et al., "Association between the *Igk* and *Igh* immunoglobulin loci mediated by the 3' *Igk* Enhancer Induces 'decontraction' of the *Igh* locus in pre-B cells," *Nature Immunology*, Apr. 2008, vol. 9 (4), pp. 396-404.
Hong J. et al., "Derivation and Characterization of Embryonic Stem Cells Lines Derived from Transgenic Fischer 344 and Dark Agouti Rats," *Stem Cells and Development*, 2012, vol. 21 (6), pp. 1571-1586.
Houdebine L.M., "The Methods to Generate Transgenic Animals and to Control Transgene Expression," *Journal of Biotechnology*, 2002, vol. 98 (2-3), pp. 145-160.
Houdebine L.M., "Transgenic Animal Models in Biomedical Research," *Methods in Molecular Biology*, Chapter 10, 2007, vol. 360, pp. 163-202.
Houldsworth J., et al., "Comparative Genomic Hybridization: An Overview," *The American Journal of Pathology*, Dec. 1994, vol. 145 (6), pp. 1253-1260.
Hsu E., et al., "The plasticity of immunoglobulin gene systems in evolution," *Immunology Reviews*, vol. 210, Apr. 2006, pp. 8-26.
Huang, D., et al., "Sequence Analyses of Three Immunoglobulin G Anti-virus Antibodies Reveal Their Utilization of Autoantibody-related Immunoglobulin Vh Genes, but Not Vλ Genes," *Journal of Clinical Investigations*, Dec. 1992, vol. 90, pp. 2197-2208.
Huber V.C. et al., "Distinct Contributions of Vaccine-Induced Immunoglobulin G1 (IgG1) and IgG2a Antibodies to Protective Immunity Against Influenza," *Clinical and Vaccine Immunology*, 2006, vol. 13(9), pp. 981-990.
Jakobovits A., "Production of Fully Human Antibodies by Transgenic Mice," *Current Opinion in Biotechnology*, 1995, vol. 6 (5), pp. 561-566.
Jakobovits A., "The Long-Awaited Magic Bullets: Therapeutic Human Monoclonal Antibodies from Transgenic Mice," *Expert Opinion Investigational Drugs*, 1998, vol. 7 (4), pp. 607-614.
Janeway C.A. et al., "The rearrangement of antigen-receptor gene segments controls lymphocyte development," Immunobiology: The Immune System in Health and Disease, 5th Edition, Aug. 2015, 13 pages. [Retrieved from the Internet: http://www.ncbi.nlm.nih.gov/books/NBK27113/].
Janeway et al., "Structural Variation in Immunoglobulin Constant Regions," Immunobiology: *The Immune System in Health and Disease*, 5th Edition, 2001, 5 pages.
Jasper, P.J., et al., "B lymphocyte deficiency in IgH-transgenic rabbits," European Journal of *Immunology*, 2007, vol. 37, pp. 2290-2299.
Jessen K.A., et al., "Molecular Analysis of Metastasis in a Polyomavirus Middle T Mouse Model: the Role of Osteopontin," *Breast Cancer Research*, 2004, vol. 6 (3), pp. R157-R169.
Johnston C.M., et al., "Complete Sequence Assembly and Characterization of the C57BL/6 Mouse Ig Heavy Chain V Region," *The Journal of Immunology*, 2006, vol. 176 (7), pp. 4221-4234.
Jones, B.T., Attorney for Applicant, Third-Party Pre-Issuance Submission Under 37 CFR Sec. 1.290 in U.S. Appl. No. 15/016,211, dated Oct. 4, 2016, 59 pages.
Jones, B.T., Attorney for Applicant, Third-Party Pre-Issuance Submission Under 37 CFR Sec. 1.290 in U.S. Appl. No. 15/018,670, dated Aug. 12, 2016, 26 pages.
Jones, B.T., Attorney for Applicant, Third-Party Pre-Issuance Submission Under 37 CFR Sec. 1.290 in U.S. Appl. No. 15/095,315, dated Sep. 16, 2016, 26 pages.
Jones, B.T., Attorney for Applicant, Third-Party Pre-Issuance Submission Under 37 CFR Sec. 1.290 in U.S. Appl. No. 15/232,122, dated Mar. 13, 2017, 32 pages.
Jones, B.T., Attorney for Applicant, Third-Party Pre-Issuance Submission Under 37 CFR Sec. 1.290 in U.S. Appl. No. 15/214,963, dated Mar. 2, 2017, 42 pages.
Karu A.E., et al., "Recombinant Antibody Technology," ILAR Journal / National Research Council, *Institute of Laboratory Animal Resources*, 1995, vol. 37 (3), pp. 132-141.
Kaushik A., et al., "Novel Insight into Antibody Diversification from Cattle," Veterinary *Immunology and Immunopathology*, 2002, vol. 87 (3-4), pp. 347-350.
Kawasaki, K., et al., "One-Megabase Sequence Analysis of the Human Immunoglobulin λ Gene Locus," *Genome Research*, 1997, vol. 7, pp. 250-261.
Kenter A.L., et al., "Three-Dimensional Architecture of the IgH Locus Facilitates Class Switch Recombination," *Annals of the New York Academy of Sciences*, 2012, vol. 1267, pp. 86-94.
Kim T., et al., "Expression and Relationship of Male Reproductive ADAMs in Mouse," *Biology of Reproduction*, 2006, vol. 74 (4), pp. 744-750.
Kindt T.J. et al., "Organization and Expression of Immunoglobulin Genes," Chapter 5, *Immunology*, Sixth edition, 2007 (36 pages, including cover sheet and copyright page), pp. 111-144.
Kondo S., "Highly improved Gene Targeting by Germline-Specific Cas9 Expression in *Drosophila*," *Genetics*, vol. 195, Nov. 2013, 1 page (Abstract).
Kondo S., "Highly improved Gene Targeting by Germline-Specific Cas9 Expression in *Drosophila*," *Genetics*, vol. 195, Nov. 2013, pp. 715-721.
Kouskoff V., et al., "Cassette Vectors Directing Expression of T Cell Receptor Genes in Transgenic Mice," *Journal of Immunological Methods*, 1995, vol. 180 (2), pp. 273-280.
Kuraoka M., et al., "AID Expression During B-Cell Development: Searching for Answers," *Immunologic Research*, 2011, vol. 49 (1-3), pp. 3-13.
Kuzin I.I. et al., "Requirement for enhancer specificity in immunoglobulin heavy chain locus regulation," *Journal of Immunology*, Jun. 2008, vol. 180 (11), pp. 7443-7450.
Laffleur B., et al., "Production of Human or Humanized Antibodies in Mice," Chapter 9, *Methods in Molecular Biology*, 2012, vol. 901, pp. 149-159.
Largaespada D.A., "Transposon Mutagenesis in Mice," *Methods in Molecular Biology*, vol. 530, 2009, pp. 379-390.
Lee E.C., et al., "Complete Humanization of the Mouse Immunoglobulin Loci Enables Efficient Therapeutic Antibody Discovery," *Nature Biotechnology*, 2014, vol. 32 (4), pp. 356-363.
Lee E.C., et al., "The Application of Transgenic Mice for Therapeutic Antibody Discovery," *Methods in Molecular Biology*, Chapter 8, 2012, vol. 901, pp. 137-148.
Lefranc M., Appendix 1P, Abbreviations and Useful Data, "Nomenclature of the Human Immunoglobulin Genes," *Current Protocols in Immunology*, 2000, Supp. 40, pp. A.1P.1-A.1P.37.
Lefranc M.P., et al.," IGHJ group," The Immunoglobulin FactsBook, IMGT, the international ImMunoGeneTics database, May 2001, 4 pages (including cover sheet and copyright pages).
Lefranc M.P. et al., "Immunoglobulin Lambda (IGL) Genes of Human and Mouse," *Molecular Biology of B Cells*, Chapter 4, p. 47, 2004 (Edtrs. Honjo et al.).
Lefranc M.P., "Nomenclature of the Human Immunoglobulin Heavy (IGH) Genes," *Experimental and Clinical Immunogenetics*, 2001, vol. 18 (2), pp. 100-116.
Lefranc M.P., "Nomenclature of the Human Immunoglobulin Kappa (IGK) Genes," *Experimental and Clinical Immunogenetics*, 2001, vol. 18 (3), pp. 161-174.
Lefranc M.P., "Nomenclature of the Human Immunoglobulin Lambda (IGL) Genes," *Experimental and Clinical Immunogenetics*, 2001, vol. 18 (4), pp. 242-254.
Levin A.M. et al., "Optimizing the affinity and specificity of proteins with molecular display," *Molecular Biosystems*, 2006, vol. 2, pp. 49-57.
Li H., et al., "Genetic Diversity of the Human Immunoglobulin Heavy Chain $V_H$ Region," *Immunological Reviews*, Dec. 2002, vol. 190, pp. 53-68.
Li M., Second Declaration of Dr. Meng (Amy) Li, dated Sep. 5, 2016, 2 pages.
Liang Q. et al., "Extensive genomic copy number variation in embryonic stem cells," *Proceedings of the National Academy of Sciences of the U.S.A.*, Nov. 2008, vol. 105 (45), pp. 17453-17456.

(56) References Cited

OTHER PUBLICATIONS

Little M., et al., "Generation of a Large Complex Antibody Library from Multiple Donors," *Journal of Immunological Methods*, 1999, vol. 231 (1-2), pp. 3-9.

Lonberg N., "Fully Human Antibodies from Transgenic Mouse and Phage Display Platforms," *Current Opinion in Immunology*, 2008, vol. 20 (4), pp. 450-459.

Lyon C., Attorney for Applicant, Third-Party Pre-Issuance Submission Under 37 CRF Sec. 1.290 in U.S. Appl. No. 14/056,700, dated Nov. 28, 2014, 6 pages.

Lyon C., Attorney for Applicant, Third-Party Pre-Issuance Submission Under 37 CFR Sec. 1.290 in U.S. Appl. No. 14/056,707, dated Nov. 28, 2014, 10 pages.

Lyon C., Attorney for Applicant, Third-Party Pre-Issuance Submission Under 37 CFR Sec. 1.290 in U.S. Appl. No. 13/846,672, dated Mar. 17, 2015, 32 pages.

Lyon C., Attorney for Applicant, Third-Party Pre-Issuance Submission Under 37 CFR Sec. 1.290 in U.S. Appl. No. 13/875,892, dated May 5, 2015, 49 pages.

Lyon C., Attorney for Applicant, Third-Party Pre-Issuance Submission Under 37 CFR Sec. 1.290 in U.S. Appl. No. 13/886,511, dated May 5, 2015, 18 pages.

Lyon C., Attorney for Applicant, Third-Party Pre-Issuance Submission Under 37 CFR Sec. 1.290 in U.S. Appl. No. 14/040,405, dated Jan. 16, 2015, 18 pages.

Lyon C., Attorney for Applicant, Third-Party Pre-Issuance Submission Under 37 CFR Sec. 1.290 in U.S. Appl. No. 14/040,427, dated Jan. 16, 2015, 20 pages.

Lyon C., Attorney for Applicant, Third-Party Pre-Issuance Submission Under 37 CFR Sec. 1.290 in U.S. Appl. No. 14/056,434, dated Dec. 15, 2014, 6 pages.

Lyon C., Attorney for Applicant, Third-Party Pre-Issuance Submission Under 37 CFR Sec. 1.290 in U.S. Appl. No. 14/080,630, dated Oct. 31, 2014, 8 pages.

Lyon C., Attorney for Applicant, Third-Party Pre-Issuance Submission Under 37 CFR Sec. 1.290 in U.S. Appl. No. 14/137,902, dated Nov. 13, 2014, 9 pages.

Lyon C., Attorney for Applicant, Third-Party Pre-Issuance Submission Under 37 CFR Sec. 1.290 in U.S. Appl. No. 14/220,095, dated Aug. 4, 2015, 19 pages.

Lyon C., Attorney for Applicant, Third-Party Pre-Issuance Submission Under 37 CFR Sec. 1.290 in U.S. Appl. No. 14/220,099, dated Apr. 29, 2015, 43 pages.

Lyon C., Attorney for Applicant, Third-Party Pre-Issuance Submission Under 37 CFR Sec. 1.290 in U.S. Appl. No. 14/226,706, dated Jul. 28, 2015, 53 pages.

Lyon C., Attorney for Applicant, Third-Party Pre-Issuance Submission Under 37 CFR Sec. 1.290 in U.S. Appl. No. 14/263,158, dated Apr. 29, 2015, 16 pages.

Lyon C., Attorney for Applicant, Third-Party Pre-Issuance Submission Under 37 CFR Sec. 1.290 in U.S. Appl. No. 14/263,176, dated Apr. 29, 2015, 16 pages.

Lyon C., Attorney for Applicant, Third-Party Pre-Issuance Submission Under 37 CFR Sec. 1.290 in U.S. Appl. No. 14/497,054, dated Oct. 21, 2015, 81 pages.

Lyon C., Attorney for Applicant, Third-Party Pre-Issuance Submission Under 37 CFR Sec. 1.290 in U.S. Appl. No. 14/498,685, dated Sep. 18, 2015, 37 pages.

Lyon C., Attorney for Applicant, Third-Party Pre-Issuance Submission Under 37 CFR Sec. 1.290 in U.S. Appl. No. 14/516,461, dated Aug. 4, 2015, 27 pages.

Lyon C., Attorney for Applicant, Third-Party Pre-Issuance Submission Under 37 CFR Sec. 1.290 in U.S. Appl. No. 14/543,359, dated Nov. 13, 2015, 36 pages.

Lyon C., Attorney for Applicant, Third-Party Pre-Issuance Submission Under 37 CFR Sec. 1.290 in U.S. Appl. No. 14/226,698, dated Jun. 3, 2015, 53 pages.

Ma B., et al., "Human Antibody Expression in Transgenic Rats: Comparison of Chimeric IgH Loci with Human $V_H$, D and $J_H$ but Bearing Different Rat C-Gene Regions," *Journal of Immunological Methods*, 2013, vols. 400-401, pp. 78-86.

MacDonald L., Curriculum Vitae of Lynn E. MacDonald, Ph.D., 3 pages.

MacDonald L., Declaration of Lynn E. MacDonald with Exhibits, dated Feb. 3, 2015, relating to International Application No. PCT/US02/04500 (Published as WO02/066630 A1), 13 pages.

Macdonald L., Declaration of Lynne E. Macdonald, dated Jun. 29, 2016, 4 pages.

MacDonald L., et al., Expanded Poster: Velocigene Technology Extended to Humanization of Several Megabases of Complex, Sep. 2006, 6 pages.

MacDonald L., et al., Poster: Velocigene Technology Extended to Humanization of Several Megabases of Complex and evidence of unavailability, Sep. 2006, 42 pages.

MacDonald L., et al., "Velocigene Technology Extended to Humanization of Several Megabases of Complex Gene Loci," (Abstract-21) 1st International MUGEN Conference on Animal Models for Human Immunological Disease, Athens Greece, Sep. 10-13, 2006, 1 page.

Magadan S., et al., "Production of Antigen-Specific Human Monoclonal Antibodies: Comparison of Mice Carrying IgH/K or IgH/$_K$/λ transloci," *Biotechniques*, 2002, vol. 33 (3), pp. 680, 682, 684 passim.

Marchalonis J.J. et al., "Emergence of the immunoglobulin family: conservation in protein sequence and plasticity in gene organization," *Glycobiology*, vol. 6, 1996, pp. 657-663.

Martinez C., et al., "The Mouse (*Mus musculus*) Immunoglobulin Kappa Variable (IGKV) Genes and Joining (IGKJ) Segments," *Experimental and Clinical Immunogenetics*, Jul. 1998, vol. 15, pp. 184-193.

Martinez P., et al., "Antibody Synthesis *in Vitro*," *Encyclopedia of Life Sciences*, 2005, pp. 1-8.

Martinez-Jean C., et al., "Nomenclature and Overview of the Mouse (*Mus musculus* and *Mus* sp.) Immunoglobulin Kappa (IGK) Genes," *Experimental and Clinical Immunogenetics*, 2001, vol. 18(4), pp. 255-279.

Matthews V.B., et al., "A Locus Affecting Immunoglobulin Isotype Selection (*Igis*1) Maps to the MHC Region in C57BL, BALB/c and NOD Mice," *Immunology and Cell Biology*, 2001, vol. 79 (6), pp. 576-582.

McMurry M.T., et al., "Enhancer Control of Local Accessibility to V(D)J Recombinase," *Molecular and Cellular Biology*, Aug. 1997, vol. 17 (8), pp. 4553-4561.

Mester G., European Patent Attorney, Grund Intellectual Property Group, Third-Party Observations according to Article 115 EPC regarding EP 12778780.2, dated Sep. 30, 2016, 5 pages.

Mgi, "Guidelines for Nomenclature of Mouse and Rat Strains," International Committee on Standardized Genetic Nomenclature for Mice / Rat Genome and Nomenclature Committee; Chairpersons: J.T. Eppig and G. Levan, Oct. 2011, 11 pages. [printed: Mar. 6, 2012—http://www.informatics.jax.org/mgihome/nomen/strains.shtml)].

Mills F., et al., "Enhancer Complexes Located Downstream of Both Human Immunoglobulin Cα Genes," *The Journal of Experimental Medicine*, Sep. 1997, vol. 186 (6), pp. 845-858.

Minaee S., et al., "Mapping and Functional Analysis of Regulatory Sequences in the Mouse λ5-VpreB1 Domain," *Molecular Immunology*, 2005, vol. 42 (11), pp. 1283-1292.

Müller U., "Ten Years of Gene Targeting: Targeted Mouse Mutants, from Vector Design to Phenotype Analysis," *Mechanisms of Development*, 1999, vol. 82 (1-2), pp. 3-21.

Moffatt S. et al., "PEGylated J591 mAb loaded in PLGA-PEG-PLGA tri-block copolymer for targeted delivery: In vitro evaluation in human prostate cancer cells," *International Journal of Pharmaceutics*, 2006, vol. 317, pp. 10-13.

Monaco A.P., et al., "YACs, BACs, PACs and MACs: Artificial Chromosomes as Research Tools," *Trends in Biotechnology*, Jul. 1994, vol. 12 (7), pp. 280-286.

Moran N., et al., "Mouse Platforms Jostle for Slice of Humanized Antibody Market," *Nature Biotechnology*, Apr. 2013, vol. 31 (4), pp. 267-268.

(56) References Cited

OTHER PUBLICATIONS

Mullins, L.J., et al., "Transgenesis in the Rat and Larger Mammals," Perspective Series: Molecular Medicine in Genetically Engineered Animals, *Journal of Clinical Investigation*, Apr. 1996, vol. 97 (7), pp. 1557-1560.

Munoz M. et al., "Constraints to Progress in Embryonic Stem Cells from Domestic Species," *Stem Cell Review and Reports*, 2009, vol. 5, pp. 6-9.

Murphy A., "Declaration of Andrew J. Murphy," including Slide Presentation dated Nov. 3, 2009, at Wellcome Trust Advanced Course: Genetic Manipulation of ES Cells, in Hirixton, UK, entitled "BAC-based Modifications of the Mouse Genome: The Big and the Backward," cited in an IDS in U.S. Appl. No. 14/192,051 of MacDonald et al., dated Oct. 6, 2014, 62 pages.

Murphy D., "BAC-based Modifications of the Mouse Genome: The Big and the Backward," The Advanced Course: Genetic Manipulation of ES Cells, dated Nov. 3, 2009, VP Target Discovery, Regeneron Pharmaceuticals, 58 pages.

Murphy et al., The Generation of Lymphocyte Antigen Receptors, Chapter 4, excerpt from *Janeway's Immunobiolog*, Seventh edition, 2008, p. 158.

Muyrers J.P., et al., "Rapid Modification of Bacterial Artificial Chromosomes by ET-Recombination," *Nucleic Acids Research*, 1999, vol. 27 (6), pp. 1555-1557.

Narayanan K., et al., "Efficient and Precise Engineering of a 200 kb β-Globin Human/Bacterial Artificial Chromosome in *E. coli* DH10B using an Inducible Homologous Recombination System," *Gene Therapy*, 1999, vol. 6 (3), pp. 442-447.

Neuberger M.S., et al., "Isotype Exclusion and Transgene Down-Regulation in Immunoglobulin-λ Transgenic Mice," *Nature*, Mar. 1989, vol. 338 (6213), pp. 350-352.

Neuberger M.S., "Expression and regulation of immunoglobulin heavy chain gene transfected into lymphoid cells," *The EMBO Journal*, 1983, vol. 2 (8), pp. 1373-1378.

New Zealand Patent Office, Simon Maguire, Authorized Officer, Further Examination Report for Patent No. 623756, dated Sep. 9, 2015, 3 pages.

Ohm-Laursen L., et al., "Identification of Two New Alleles, *IGHV3-23*04* and *IGHJ6*04*, and the Complete Sequence of the *IGHV3-h* Pseudogene in the Human Immunoglobulin Locus and their Prevalences in Danish Caucasians," *Immunogenetics*, 2005, vol. 57 (9), pp. 621-627.

Oumard A. et al., "Recommended method for chomosome exploitation: RMCE-based cassette-exchange systems in animal cell biotechnology," *Cytotechnology*, 2006, vol. 50, pp. 93-108.

Parng C.L., et al., "Gene Conversion Contributes to Ig Light Chain Diversity in Cattle," *Journal of Immunology*, 1996, vol. 157 (12), pp. 5478-5486.

Pear W.S., et al., "Localization of the Rat Immunoglobulin Heavy Chain Locus to Chromosome 6," *Immunogenetics*, 1986, vol. 23 (6), pp. 393-395.

Pera, M.F., et al., "Human embryonic stem cells," *Journal of Cell Science*, 2000, vol. 113, pp. 5-10.

Perez-Luz S. et al., "Factor VIII mRNA expression from a BAC carrying the intact locus made by homologous recombination," *Genomics*, 2007, vol. 90, pp. 610-619.

Pettersson S., et al., "A second B cell-specific enhancer 3' of the immunoglobulin heavy-chain locus," *Nature*, Mar. 1990, vol. 344, pp. 165-168.

Pobursky K., Third-Party Pre-Issuance Submission Under 37 CFR 1.290 in U.S. Appl. No. 13/843,528, dated Mar. 18, 2014, 14 pages.

Pobursky K., Third-Party Pre-Issuance Submission Under 37 CFR 1.290 in U.S. Appl. No. 13/433,084, dated Apr. 1, 2014, 15 pages.

Pobursky K., Third-Party Pre-Issuance Submission Under 37 CFR 1.290 in U.S. Appl. No. 13/434,361, dated Apr. 1, 2014, 15 pages.

Pobursky K., Third-Party Pre-Issuance Submission Under 37 CFR 1.290 in U.S. Appl. No. 13/740,727, dated May 27, 2014, 25 pages.

Presta L., "Molecular engineering and design of therapeutic antibodies," *Current Opinion in Immunology*, 2008, vol. 20, pp. 460-470.

Printout of PDF file available from the University of California website presented in support of European opposition in the name of Kymab Ltd. pertaining to Application No. EP12171793.8 as filed on Jan. 19, 2017, 4 pages. [http://www.research.uci.edu/facilities-services/tmf/presentations/Mouse_ES_CellLine].

Pruzina S., et al., "Human Monoclonal Antibodies to HIV-1 gp140 from Mice Bearing YAC-Based Human Immunoglobulin Transloci," *Protein Engineering, Design & Selection*, 2011, vol. 24 (10), pp. 791-799.

Qi N.R., et al., "A New Transgenic Rat Model of Hepatic Steatosis and the Metabolic Syndrome," *Hypertension*, 2005, vol. 45 (5), pp. 1004-1011.

Ramírez-Solis R., et al., "Chromosome Engineering in Mice," *Nature*, Dec. 1995, vol. 378 (6558), pp. 720-724.

Ramsden D.A., et al., "Conservation of Sequence in Recombination Signal Sequence Spacers," *Nucleic Acids Research*, 1994, vol. 22 (10), pp. 1785-1796.

Ray P., et al., "Ectopic Expression of a c-$kit^{VV42}$ Minigene in Transgenic Mice: Recapitulation of W Phenotypes and Evidence for c-*kit* Function in Melanoblast Progenitors," *Genes & Development*, 1991, vol. 5 (12A), pp. 2265-2273.

Regeneron Pharmaceuticals, Inc., Press Release—"Astellas Licenses Regeneron's Velocimmune Technology for Discovering Human Monoclonal Antibodies," dated Mar. 30, 2007, 2 pages.

Regeneron Pharmaceuticals, Inc., Press Release—"AstraZeneca Licenses Regeneron's VelocImmune Technology for Discovering Human Monoclonal Antibodies—AstraZeneca Is First Licensee of Novel Velocimmune Technology License Fees Total up to $120 Million Over Six Years," Feb. 5, 2007, 2 pages.

Regeneron Pharmaceuticals, Inc., Press Release—"Regeneron Initiates Major Global Collaboration with Sanofi-aventis of Develop and Commercialize Fully-Human Therapeutic Antibodies," Nov. 29, 2007, 2 pages.

Ren S.Y., et al., "Targeted Insertion Results in a Rhombomere 2-Specific *Hoxa*2 Knockdown and Ectopic Activation of *Hoxa*1 Expression," *Developmental Dynamics*, 2002, vol. 225 (3), pp. 305-315.

Renaut L. et al., "Affinity Maturation of Antibodies: Optimized Methods to Generate High-Quality ScFv Libraries and Isolate IgG Candidates by High-Throughput Screening," *Antibody Engineering: Methods and Protocols*, Chapter 26, Second Edition, 2012, vol. 907, pp. 451-461.

Ricker M., European Patent Attorney, Opposition against EP2421357B1 in the name of Kymab Limited Statement of Facts and Arguments pertaining to Application No. 10734546.4, dated Oct. 23, 2013, 29 pages.

Ristevski S., "Making Better Transgenic Models: Conditional, Temporal, and Spatial Approaches," *Molecular Biotechnology*, 2005, vol. 29 (2), pp. 153-163.

Rosner K., et al., "Third Complementarity-Determining Region of Mutated $V_H$ Immunoglobulin Genes Contains Shorter V, D, J, P, and N Components than Non-Mutated Genes," *Immunology*, 2001, vol. 103 (2), pp. 179-187.

Rourke J., Declaration of Jeffrey Rourke, Registered Patent Attorney for Regeneron Pharmaceuticals, Inc.—In the matter of Patent Acceptance 2011266843 in the Name of Kymab Limited and in the Matter of Opposition thereto by Regeneron Pharmaceuticals, Inc., dated Jan. 29, 2016, 5 pages.

Rusk N., "Making Mice at High Speed," *Nature Methods*, Mar. 2007, vol. 4 (3), pp. 196-197.

Sabbattini P., et al., "Analysis of Mice with Single and Multiple Copies of Transgenes Reveals a Novel Arrangement for the λ5-$V_{preB1}$ Locus Control Region," *Molecular and Cellular Biology*, Jan. 1999, vol. 19 (1), pp. 671-679.

Scapini P., et al., "Myeloid Cells, BAFF, and IFN-γ Establish an Inflammatory Loop that Exacerbates Autoimmunity in Lyn-Deficient Mice," *The Journal of Experimental Medicine*, Jul. 2010, vol. 207 (8), pp. 1757-1773.

Schonewald, S.L., Attorney for Applicant, Third-Party Pre-Issuance Submission Under 37 CFR Sec. 1.290 in U.S. Appl. No. 14/220,074, dated Jul. 12, 2016, 46 pages.

(56) References Cited

OTHER PUBLICATIONS

Schonewald, S.L., Attorney for Applicant, Third-Party Pre-Issuance Submission Under 37 CFR Sec. 1.290 in U.S. Appl. No. 14/750,870, dated Aug. 10, 2016, 34 pages.
Schonewald, S.L., Attorney for Applicant, Third-Party Pre-Issuance Submission Under 37 CFR Sec. 1.290 in U.S. Appl. No. 14/818,162, dated May 24, 2016, 47 pages.
Schroeder, Jr. H.W., "Similarity and divergence in the development and expression of the mouse and human antibody repertoires," *Developmental and Comparative Immunology*, vol. 30, 2006, pp. 119-135.
Seals D.F., et al., "The ADAMs Family of Metalloproteases: Multidomain Proteins with Multiple Functions," *Genes & Development*, 2003, vol. 17 (1), pp. 7-30.
Seidl K.J., et al., "An Expressed $Neo^r$ Cassette Provides Required Functions of the 1γ2b Exon for Class Switching," *International Immunology*, 1998, vol. 10 (11), pp. 1683-1692.
Seidl K.J., et al., "Position-Dependent Inhibition of Class-Switch Recombination by $PGK-neo^r$ Cassettes Inserted into the Immunoglobulin Heavy Chain Constant Region Locus," *Proceedings of the National Academy of Sciences of the U.S.A.*, Mar. 1999, vol. 96 (6), pp. 3000-3005.
Sekiguchi J., et al., "The Mechanism of V(D)J Recombination," *Molecular Biology of B Cells*, Chapter 5, 2004, pp. 61-82.
Sequence Listing to WO2008054606A2, 163 pages.
Shi B., et al., "Comparative Analysis of Human and Mouse Immunoglobulin Variable Heavy Regions from IMGT/LIGM-DB with IMGT/HighV-QUEST," *Theoretical Biology and Medical Modelling*, 2014, vol. 11, pp. 1-11.
Shi Y.P., et al., "The Mapping of Transgenes by Fluorescence in Situ Hybridization on G-Banded Mouse Chromosomes," *Mammalian Genome*, 1994, vol. 5 (6), pp. 337-341.
Shih H.H., "Discovery Process for Antibody-Based Therapeutics," *Development of Antibody-Based Therapeutics*, Chapter 2, 2012, pp. 9-32.
Shore, D.E., Attorney for Applicant, Third-Party Pre-Issuance Submission Under 37 CFR Sec. 1.290 in U.S. Appl. No. 14/543,359, filed Mar. 3, 2017, 16 pages.
Sigmund C.D., "Viewpoint: Are Studies in Genetically Altered Mice Out of Control?," *Arteriosclerosis, Thrombosis, and Vascular Biology*, Jun. 2000, vol. 20 (6), pp. 1425-1429.
Smith K.R., "Gene Transfer in Higher Animals: Theoretical Considerations and Key Concepts," *Journal of Biotechnology*, 2002, vol. 99 (1), pp. 1-22.
Sopher B. et al., "Efficient recombination-based methods for bacterial artificial chromosome fusion and mutagenesis," *Gene*, 2006, vol. 371, pp. 136-143.
Sorrell D.A. et al., "Targeted modification of mammalian genomes," *Biotechnology Advances*, vol. 23, 2005, pp. 431-469.
Soukharev S., et al., "Segmental Genomic Replacement in Embryonic Stem Cells by Double *Lox* Targeting," *Nucleic Acids Research*, 1999, vol. 27 (18), pp. e21.
Spanopoulou E., et al., "Functional Immunoglobulin Transgenes Guide Ordered B-Cell Differentiation in Rag-1-Deficient Mice," *Genes & Development*, 1994, vol. 8 (9), pp. 1030-1042.
Stavnezer J., et al., "Mechanism and Regulation of Class Switch Recombination," *Annual Review of Immunology*, 2008, vol. 26, pp. 261-292.
Stephen R., Kymab Limited Statement of Facts and Evidence in opposition to EP2550363, Olswang LLP, dated Sep. 10, 2015, 22 pages.
Stephen R., Olswang, Response to Examination Report dated Jun. 6, 2016 for Application No. 14176740.0, as filed with the European Patent Office on Oct. 10, 2016, 4 pages.
Stephen R., Olswang, Response to Search Report dated Oct. 15, 2014 for Application No. 14176740.0, as filed with the European Patent Office on May 12, 2015, 4 pages.
Stephen R., Olswang, Response to Third-Party Observations dated Aug. 10, 2015 and Examination Report dated Oct. 23, 2015 for Application No. 14176740.0, as filed with the European Patent Office on Apr. 23, 2016, 6 pages.
Stevens S., et al., Expanded Poster—VelocImmune[TM]: Humanization of immunoglobulin loci using VelociGene technology, Sep. 2006, 6 pages.
Stevens S., et al., Poster: "VelocImmune[TM]: Humanization of immunoglobulin loci using VolociGene technology" and evidence of unavailability, Sep. 2006, 42 pages.
Stevens S. et al., "Velocimmune: Humanization of Immunoglobulin Loci Using Velocigene Technology," (Abstract—4) Presented at 1st International MUGEN Conference on Animal Models for Human Immunological Disease, Athens, Greece, Sep. 10-13, 2006, 1 page.
Sun Y. et al., "Repertoire of Human Antibodies against the Polysaccharide Capsule of *Streptococcus pneumoniae* Serotype 6B," *Infection and Immunity*, Mar. 1999, vol. 67 (3), pp. 1172-1179.
Suárez E., et al., "Rearrangement of Only One Human IGHV Gene is Sufficient to Generate a Wide Repertoire of Antigen Specific Antibody Responses in Transgenic Mice," *Molecular Immunology*, 2006, vol. 43 (11), pp. 1827-1835.
Takeda S., et al., "Construction of Chimaeric Processed Immunoglobulin Genes Containing Mouse Variable and Human Constant Region Sequences," *Nature*, Apr. 1985, vol. 314 (6010), pp. 452-454.
Tan L.K., et al., "A Human-Mouse Chimeric Immunoglobulin Gene with a Human Variable Region is Expressed in Mouse Myeloma Cells," *Journal of Immunology*, Nov. 1985, vol. 135 (5), pp. 3564-3567.
Tanimoto Y., et al., "Embryonic Stem Cells Derived from C57BL/6J and C57BL/6N Mice," *Comparative Medicine*, Aug. 2008, vol. 58 (4), pp. 347-352.
Taylor L.D., et al., "Human Immunoglobulin Transgenes Undergo Rearrangement, Somatic Mutation and Class Switching in Mice that Lack Endogenous IgM," *International Immunology*, 1994, vol. 6 (4), pp. 579-591.
The Jackson Laboratory, "Breeding Strategies for Maintaining Colonies of Laboratory Mice," *A Jackson Laboratory Resource Manual*, 2007, pp. 1-29.
Thykjaer T., et al., "Gene Targeting Approaches Using Positive-Negative Selection and Large Flanking Regions," *Plant Molecular Biology*, 1997, vol. 35 (4), pp. 523-530.
Tonegawa S., "Somatic Generation of Antibody Diversity," Nature, Apr. 1983, vol. 302 (5909), pp. 575-581.
Tong C., et al., "Production of p53 gene knockout rats by homologous recombination in embryonic stem cells," *Nature*, Sep. 2010, vol. 467 (7312), pp. 211-213.
Tuaillon N., et al., "Human immunoglobulin heavy-chain minilocus recombination in transgenic mice: Gene-segment use in μ and γ transcripts," *Proceedings of the National Academy of Sciences of the U.S.A.*, Apr. 1993, vol. 90, pp. 3720-3724.
Tucker P.W., et al., "Mouse IgA Heavy Chain Gene Sequence: Implications for Evolution of Immunoglobulin Hinge Axons," *Proceedings of the National Academy of Sciences of the U.S.A.*, Dec. 1981, vol. 78 (12), pp. 7684-7688.
United Kingdom Intellectual Property Office, Combined Search and Examination Report under Sections 17 and 18(3) for Application No. GB1317410.7, dated Nov. 21, 2013, 8 pages.
United Kingdom Intellectual Property Office, Combined Search and Examination Report under Sections 17 and 18(3) for Application No. GB1317447.9, dated Jan. 14, 2014, 7 pages.
United Kingdom Intellectual Property Office, Corrected Search Report Under Section 17 for Application No. GB1122047.2, dated Apr. 20, 2012, 5 pages.
United Kingdom Intellectual Property Office, Search Report under Secdtion 17 for Application No. GB1116122.1, dated Feb. 2, 2012, 1 page.
Urquhart-Dykes & Lord LLP, Third-Party Observation for Application No. EP20140772198, dated Dec. 14, 2015, 8 pages.
USPTO, Excerpts from U.S. Appl. No. 14/682,859, filed Apr. 9, 2015, including Applicant-initiated Interview Summary; Amendments to the Claims and Information Disclosure Statement, 14 pages.

(56) References Cited

OTHER PUBLICATIONS

Van Der Weyden L. et al., "Mouse Chromosome Engineering for Modeling Human Disease," *Europe PMC Funders Group*, Author Manuscript, Dec. 2008, 32 pages.
Van Dijk M., Declaration of Marcus Van Dijk with exhibits, Apr. 30, 2016, 139 pages.
Van Loo, P.F., et al., "Surrogate-Light-Chain Silencing Is Not Critical for the Limitation of Pre-B Cell Expansion but Is for the Termination of Constitutive Signaling," *Immunity*, Sep. 2007, vol. 27, pp. 468-480.
Van Snick J.L., et al., "Genetic Control of Rheumatoid Factor Production in the Mouse. Role of Genes Linked to the Immunoglobulin Heavy Chain Locus and to the Major Histocompatibility Complex," *Arthritis and Rheumatism*, Sep. 1983, vol. 26 (9), pp. 1085-1090.
Vieira P. et al., "The half-lives of serum immunoglobulins in adult mice," *European Journal of Immunology*, 1988, vol. 18, pp. 313-316.
Vollmer J., et al., "Antigen Contacts by Ni-Reactive TCR: Typical a Chain Cooperation Versus Alpha Chain-Dominated Specificity," *International Immunology*, 2000, vol. 12 (12), pp. 1723-1731.
Wagner S.D., et al., "Antibodies Generated from Human Immunoglobulin Miniloci in Transgenic Mice," *Nucleic Acids Research*, 1994, vol. 22 (8), pp. 1389-1393.
Wang X., et al., "Recombination, transcription, and diversity of a partially germline-joined VH in a mammal," *Immunogenetics*, 2012, vol. 64, pp. 713-717.
Wasserman R., et al., "The Pattern of Joining ($J_H$) Gene Usage in the Human IgH Chain Is Established Predominantly at the B PreCursor Cell Stage," *The Journal of Immunology*, Jul. 1992, vol. 149(2), pp. 511-516.
Waterhouse P., et al., "Combinatorial Infection and *in Vivo* Recombination: a Strategy for Making Large Phage Antibody Repertoires," *Nucleic Acids Research*, 1993, vol. 21 (9), pp. 2265-2266.
Waterston R.H., et al., "Initial Sequencing and Comparative Analysis of the Mouse Genome," *Nature*, Dec. 2002, vol. 420 (6915), pp. 520-562.
Webpage corroborating non-confidential nature of 2006 MUGEN Conference, Athens (www.mugen.noe.org), accessed Aug. 9, 2016, 4 pages.
Weichhold G.M., et al., "Megabase Inversions in the Human Genome as Physiological Events," *Nature*, Sep. 1990, vol. 347 (6288), pp. 90-92.
Weichhold G.M., et al., "The Human Immunoglobulin κ Locus Consists of Two Copies that are Organized in Opposite Polarity," *Genomics*, 1993, vol. 16 (2), pp. 503-511.
Weiner L.M., "Fully Human Therapeutic Monoclonal Antibodies," *Journal of Immunology*, Jan./Feb. 2006, vol. 29 (1), pp. 1-9.
Wikipedia, "Monoclonal antibody," 2008, 8 pages.
Wikipedia, "Polyclonal antibodies," 2008, 5 pages.
Wilke K., et al., "Diagnosis of Haploidy and Triploidy Based on Measurement of Gene Copy No. by Real-Time PCR," *Human Mutation*, 2000, vol. 16 (5), pp. 431-436.
Williams K., Attorney for Applicant, Third-Party Pre-Issuance Submission Under 37 CFR 1.290 in U.S. Appl. No. 14/600,829, dated Apr. 1, 2016, 18 pages.
Williams K., Attorney for Applicant, Third-Party Pre-Issuance Submission Under 37 CFR 1.290 in U.S. Appl. No. 14/679,949, dated Apr. 1, 2016, 18 pages.
Wuerffel R., et al., "S-S Synapsis During Class Switch Recombination is Promoted by Distantly Located Transcriptional Elements and Activation-Induced Deaminase," *Immunity*, Nov. 2007, vol. 27 (5), pp. 711-722.
Xu Y., et al., "Deletion of the Igκ Light Chain Intronic Enhancer/Matrix Attachment Region Impairs but does not Abolish VκJκ Rearrangement," *Immunity*, Apr. 1996, vol. 4 (4), pp. 377-385.
Yamada M., et al., "Preferential Utilization of Specific Immunoglobulin Heavy Chain Diversity and Joining Segments in Adult Human Peripheral Blood B Lymphocytes," *Journal of Experimental Medicine*, Feb. 1991, vol. 173, pp. 395-407.

Yang X.W., et al., "Homologous Recombination Based Modification in *Escherichia coli* and Germline Transmission in Transgenic Mice of a Bacterial Artificial Chromosome," *Nature Biotechnology*, Sep. 1997, vol. 15 (9), pp. 859-865.
Yu Y., et al., "Engineering Chromosomal Rearrangements in Mice," *Nature Reviews Genetics*, 2001, vol. 2(10), pp. 780-790.
Zemlin M., et al., "Expressed Murine and Human CDR-H3 Intervals of Equal Length Exhibit Distinct Repertoires that Differ in their Amino Acid Composition and Predicted Range of Structures," *Journal of Molecular Biology*, 2003, vol. 334 (4), pp. 733-749.
Zhang X. et al., "Combination of overlapping bacterial artificial chromosones by a two-step recombinogenic engineering method," *Nucleic Acids Research*, 2003, vol. 31 (15), pp. e81-1-e81-6.
Zhang Y., et al., "A New Logic for DNA Engineering Using Recombination in *Escherichia coli*," *Nature Genetics*, 1998, vol. 20 (2), pp. 123-128.
Zhao S., "A Comprehensive BAC Resource," *Nucleic Acids Research*, 2001, vol. 29 (1), pp. 141-143.
Zhao Y. et al., "Physical Mapping of the Bovine Immunoglobulin Heavy Chain Constant Region Gene Locus," *Journal of Biological Chemistry*, Sep. 2003, vol. 278 (37), pp. 35024-35032.
Zheng J., et al., "Immunoglobulin Gene Transcripts Have distinctive VκDJκ Recombination Characteristics in Human Epithelial Cancer Cells", *The Journal of Biological Chemistry*, Mar. 2009, vol. 284 (20), pp. 13610-13619.
Zou X., et al., "Removal of the BiP-Retention Domain in Cµ Permits Surface Deposition and Developmental Progression Without L-Chain," *Molecular Immunology*, 2008, vol. 45 (13), pp. 3573-3579.
Zou X., et al., "Subtle differences in antibody responses and hypermutation of λ light chains in mice with a disrupted x contant region," *European Journal of Immunology*, 1995, vol. 25, pp. 2154-2162.
U.S. Appl. No. 14/080,630, filed Nov. 14, 2013.
U.S. Appl. No. 14/226,706, filed Mar. 26, 2014.
U.S. Appl. No. 14/263,158, filed Apr. 28, 2014.
U.S. Appl. No. 14/263,176, filed Apr. 28, 2014.
U.S. Appl. No. 14/498,685, filed Sep. 26, 2014.
U.S. Appl. No. 14/516,461, filed Oct. 16, 2014.
U.S. Appl. No. 14/543,359, filed Nov. 17, 2014.
U.S. Appl. No. 15/088,805, filed Apr. 1, 2016.
U.S. Appl. No. 15/656,897, filed Jul. 21, 2017.
U.S. Appl. No. 15/690,183, filed Aug. 29, 2017.
U.S. Appl. No. 15/948,709, filed Apr. 9, 2018.
1st International MUGEN Conference on Animal Models for Human Immunological Disease, Sep. 10-13, 2006—Athens Greece (Scientific Programme & Presentations), 4 pages.
Adekar S.P., et al., "A Natural Human IgM Antibody that Neutralizes Botulinum Neurotoxin *in vivo*," *Hybridoma*, 2008, vol. 27 (2), pp. 65-69.
Aizenshtein E., et al., "Immunological complex for enhancement of innate immune response in passive vaccination," *Vaccine*, Jan. 2013, vol. 31 (4), pp. 626-631 [abstract only—1 page].
Australian IP Office, Examination Report No. 1 for Standard Patent Application for Application No. 2016244295, dated Aug. 18, 2017, 4 pages.
Australian IP Office, Notification of material filed by a third-party for Application No. 2012311288 in the name of Kymab Ltd., Applicant, dated Nov. 20, 2017, 14 pages.
Baxendale H.E., et al., "Natural human antibodies to pneumococcus have distinctive molecular characteristics and protect against pneumococcal disease," *Clinical and Experimental Immunology*, 2007, vol. 151, pp. 51-60.
Bornstein G.G. et al., "Development of a new fully human anti-CD20 monoclonal antibody for the treatment of B-cell malignancies", *Investigational New Drugs*, 2010, vol. 28, pp. 561-574.
Boyd S.D., et al., "Individual Variation in the Germline Ig Gene Repertoire Inferred from Variable Region Gene Rearrangements," *The Journal of Immunology*, Jun. 2010, vol. 184 (12), pp. 6986-6992.
Bradley A., Declarations of Allan Bradley (Tanamachi/Grosveld), as submitted in U.S. Appl. No. 13/416,684, 5 pages.

(56) References Cited

OTHER PUBLICATIONS

Bradley A., Declaration of Allan Bradley (commercial success), with exhibits, as submitted in U.S. Appl. No. 13/416,684, dated Feb. 12, 2015, 15 pages.

Bradley A., Declaration of Allan Bradley (mouse strain), with exhibits, as submitted in U.S. Appl. No. 13/416,684, dated Feb. 12, 2015, 68 pages.

Bradshaw, et al., "Handbook of Cell Signalling," 2010, Chapter 5, p. 33 (excerpt).

Brüggemann M., et al., "Selection Strategies III: Transgenic Mice," in *Handbook of Therapeutic Antibodies—Technologies, Emerging Developments and Approved Therapeutics*, 2010, Chapter 4, pp. 69-91.

Brüggemann M., "The Preparation of Human Antibodies from Mice Harbouring Human Immunoglobulin Loci," *Transgenic Animals. Generation and Use*, 1997, Chapter 58, Part IV, Section A, pp. 397-402 (including cover and copyright pages).

Burton D.R., et al., "Antibody vs. HIV in a clash of evolutionary titans," *Proceedings of the National Academy of Sciences of the U.S.A*, Oct. 2005, vol. 102 (42), pp. 14943-14948.

Calame K., et al., "Regulation of immunoglobulin gene transcription," *Immunoglobulin Genes*, $2^{nd}$ edition, Chapter 18, 1995, pp. 397-422.

Camboni M., et al., "Active and passive immunization strategies based on the SDPM1 peptide demonstrate pre-clinical efficacy in the APPswePSEN1dE9 mouse model for Alzheimer's disease," *Neurobiology of Disease*, Feb. 2014, vol. 52, pp. 31-43 [abstract only—2 pages].

Collins A.M., et al., "The reported germline repertoire of human immunoglobulin kappa chain genes is relatively complete and accurate," *Immunogenetics*, 2008, vol. 60, pp. 669-676.

Collis A.V.J., et al., "Analysis of the Antigen Combining Site: Correlations Between Length and Sequence Composition of the Hypervariable Loops and the Nature of the Antigen," *Journal of Molecular Biology*, 2003, vol. 325, pp. 337-354.

Davis C.G., et al., "Production of Human Antibodies from Transgenic Mice," *Antibody Engineering, Methods and Protocols, Methods in Mol. Biol.*, Chapter 10, 2004, pp. 191-200.

Delves P.J., et al., "Antibodies," Chapter 3, *Roitt's Essential Immunology*, Eleventh edition, 2006, pp. 37-60.

D'eustachio P., et al., "Mouse Chromosome 12," *Mammalian Genome*, 1998, vol. 8, pp. S241-257.

Dörner T., et al., "Delineation of Selective Influences Shaping the Mutated Expressed Human Ig Heavy Chain Repertoire," *The Journal of Immunology*, Mar. 1998, vol. 160 (6), pp. 2831-2841.

Dörner T., et al., "Analysis of the targeting of the hypermutational machinery and the impact of subsequent selection on the distribution of nucleotide changes in human $V_H DJ_H$ rearrangements," *Immunologic Reviews*, Apr. 1998, vol. 162 (1), pp. 161-171.

Dörner T., et al., "Somatic hypermutation of human immunoglobulin heavy chain genes: targeting of RGYW motifs on both DNA strands," *European Journal of Immunology*, 1998, vol. 28, pp. 3384-3396.

Dubel S., "Therapeutic Antibodies—From Past to Future," in *Handbook of Therapeutic Antibodies—Technologies, Emerging Developments and Approved Therapeutics*, 2010, Chapter 1 (excerpt: pp. 3-5).

European Patent Office, Examination Report for Application No. 13723933.1, dated Jan. 17, 2018, 6 pages.

European Patent Office, Examination Report for Application No. 15188522.5, dated Aug. 11, 2017, 6 pages. Considered.

European Patent Office, Extended European Search Report for Application No. 17174426.1, dated Sep. 14, 2017, 10 pages, considered.

European Patent Office, Extended European Search Report for Application No. 17196214.5, dated Jan. 2, 2018, 13 pages. Considered.

European Patent Office, Examination Report for Application No. 16151215.7, dated Jan. 23, 2017, 5 pages. Considered.

European Patent Office, Opposition against EP2604110 Animal Models and Therapeutic Molecules in the name of Kymab Limited pertaining to Application No. 12194777.0, dated Aug. 28, 2017, 73 pages. Considered.

European Patent Office, Opposition against EP2758535 Antibodies, Variable Domains and Chains Tailored for Human Use in the name of Kymab Limited pertaining to Application No. 12772122.3, dated Aug. 9, 2017, 75 pages. Considered.

European Patent Office, Opposition against EP2798950 Animal Models and Therapeutic Molecules in the name of Kymab Limited pertaining to Application No. 14170196.1, dated Jan. 18, 2018, 33 pages. Considered.

Evans M.J., Declaration of Martin J. Evans, with Appendices, dated Dec. 23, 2016, 99 pages.

Forsman A., et al., "Llama Antibody Fragments with Cross-Subtype Human Immunodeficiency Virus Type I (HIV-1)-Neutralizing Properties and High Affinity for HIV-1 gp120," *Journal of Virology*, Dec. 2008, vol. 82 (24), pp. 12069-12081.

Frigerio B., et al., "Antibody Engineering as Opportunity for Selection and Organization of Anti- HIV Therapeutic Agents," *The Open Autoimmunity Journal*, 2010, vol. 2, pp. 127-138.

Genbank, "Homo sapiens partial IGHJ6 gene for immunoglobulin heavy joining 6, exon 1, allele 4," AJ879487.1, dated Jul. 26, 2016, 1 page.

Giudicelli V., et al., "IMGT/GENE-DB: a comprehensive database for human and mouse immunoglobulin and T cell receptor genes," *Nucleic Acids Research*, 2005, vol. 33, pp. D256-D261.

Grandea A.G., III., et al., "Human antibodies reveal a protective epitope that is highly conserved among human and nonhuman influenza A viruses," *Proceedings of the National Academy of Sciences of the U.S.A.*, Jul. 2010, vol. 107 (28), pp. 12658-12663.

Grund M., European Patent Attorney, Grund Intellectual Property Group, Third-Party Observations according to Article 115 EPC regarding 12762377.5, dated Jun. 20, 2017, 4 pages.

He Y., et al., "Efficient Isolation of Novel Human Monoclonal Antibodies with Neutralizing Activity Against HIV-1 from Transgenic Mice Expressing Human Ig Loci," *The Journal of Immunology*, 2002, vol. 169, pp. 595-605.

HGNC (HUGO Gene Nomenclature Committee), "Gene Family: Immunoglobulin Heavy Locus at 14q32.33 (IGH)," 4 pages. [retrieved on Jul. 31, 2017 at http://www.genenames.org/cgi-bin/genefamilies/set/349].

Hülseweh B., et al., "Human-like antibodies neutralizing Western equine encephalitis virus," *mAbs*, May/Jun. 2014, vol. 6 (3), pp. 718-727.

Imbimbo B.P., et al., "Solanezumab for the treatment of mild-to-moderate Alzheimer's disease," *Expert Review of Clinical Immunology*, Feb. 2012, vol. 8 (2), pp. 135-149 [abstract only—1 page].

IMGT, *the International ImMunoGeneTics Information system database*, IMGT/GENE-DB entry for Homo sapiens IGHD3-9, 2007, 2 pages.

IMGT, *the International ImMunoGeneTics Information system database*, "Alignment of alleles: Human IGHJ6," dated Jun. 29, 2011, 1 page.

IMGT, *the International ImMunoGeneTics Information system database*, IMGT/GENE-DB entry for Homo sapiens IGHJ6, dated Jul. 26, 2017, version 3.1.17, 4 pages.

IMGT, *the International ImMunoGeneTics Information system database*, "IMGT/GENE-DB reference sequences," Nucleotide sequences of the four human IGHJ6 alleles, dated Jul. 26, 2017, version 3.1.17, 1 page.

IMGT, *the International ImMunoGeneTics Information system database*, "IMGT/GENE-DB reference sequences," Amino acid sequences of the four human IGHJ6 alleles, dated Jul. 26, 2017, version 3.1.17, 7 pages.

Jackson S.M., et al., "Human B Cell Subsets," *Advances in Immunology*, Chapter 5, 2008, vol. 98, pp. 151-224.

Jones B.T., Attorney for Applicant, Third-Party Pre-Issuance Submission Under 37 CFR Sec. 1.290 in U.S. Appl. No. 15/251,969, filed May 4, 2017, 22 pages.

Jones B.T., Attorney for Applicant, Third-Party Pre-Issuance Submission Under 37 CFR Sec. 1.290 in U.S. Appl. No. 15/360,502, filed May 8, 2017, 40 pages.

(56) References Cited

OTHER PUBLICATIONS

Jones B.T., Attorney for Applicant, Third-Party Pre-Issuance Submission Under 37 CFR Sec. 1.290 in U.S. Appl. No. 15/383,101, filed May 30, 2017, 32 pages.
Jones B.T., Attorney for Applicant, Third-Party Pre-Issuance Submission Under 37 CFR Sec. 1.290 in U.S. Appl. No. 15/383,188, filed May 30, 2017, 33 pages.
Jones B.T., Attorney for Applicant, Third-Party Pre-Issuance Submission Under 37 CFR Sec. 1.290 in U.S. Appl. No. 15/383,196, filed May 8, 2017, 25 pages.
Jones B.T., Attorney for Applicant, Third-Party Pre-Issuance Submission Under 37 CFR Sec. 1.290 in U.S. Appl. No. 15/383,202, filed May 3, 2017, 23 pages.
Kim S.J., et al., "Antibody Engineering for the Development of Therapeutic Antibodies," *Mol. Cells*, 2005, vol. 20 (1), pp. 17-29.
Kriangkum J., et al., "Molecular Characterization of Waldenstrom's Macroglobulinemia Reveals Frequent Occurrence of Two B-Cell Clones Having Distinct IgH VDJ Sequences," *Clinical Cancer Research*, Apr. 2007, vol. 13 (7), pp. 2005-2013.
Lee E., et al., "Use of IGHJ and IGHD gene mutations in analysis of immunoglobulin sequences for the prognosis of chronic lymphocytic leukemia," *Leukemia Research*, 2007, vol. 31, pp. 1247-1252.
Lonberg N., et al., "Antigen-specific human antibodies from mice comprising four distinct genetic modifications," *Nature*, Apr. 1994, vol. 368, pp. 856-859.
Lonberg N., et al., "Human Antibodies from Transgenic Mice," *Intern. Rev. Immunol.*, 1995, vol. 13, pp. 65-93.
Lonberg N., "Human Monoclonal Antibodies from Transgenic Mice," *Therapeutic Antibodies. Handbook of Experimental Pharmacology*, 2008, pp. 69-97.
Magdelaine-Beuzelin C., et al., "Structure-function relationships of the variable domains of monoclonal antibodies approved for cancer treatment," *Critical Reviews in Oncology/Hematology*, 2007, vol. 64, pp. 210-225.
Mårtensson I.L., et al., "The pre-B-cell receptor," *Current Opinion in Immunology*, 2007, vol. 19, pp. 137-142.
Meier I.D., et al., "Short DNA sequences inserted for gene targeting can accidentally interfere with off-target gene expression," *The FASEB Journal*, Research Communication, Jun. 2010, vol. 24, pp. 1714-1724.
Missirlis P.I., et al., "A high-throughout screen identifying sequence and promiscuity characteristics of the *loxP* spacer region in Cre-mediated recombination," *BMC Genomics*, Apr. 2006, vol. 7(73), 13 pages.
O'Dea, T.P., Attorney for Applicant, Third-Party Pre-Issuance Submission Under 37 CFR Sec. 1.290 in U.S. Appl. No. 15/383,342, filed Aug. 7, 2017, 32 pages.
O'Dea, T.P., Attorney for Applicant, Third-Party Pre-Issuance Submission Under 37 CFR Sec. 1.290 in U.S. Appl. No. 15/385,348, filed Jul. 28, 2017, 48 pages.
O'Dea, T.P., Attorney for Applicant, Third-Party Pre-Issuance Submission Under 37 CFR Sec. 1.290 in U.S. Appl. No. 15/385,372, filed Jul. 28, 2017, 48 pages.
Okada A., et al., "The variable region gene assembly mechanism," *Immunoglobulin Genes*, 2$^{nd}$ edition, Chapter 10, 1995, pp. 205-234.
Pinaud E., et al., "The IgH Locus 3' Regulatory Region: Pulling the Strings from Behind," *Advances in Immunology*, Chapter 2, 2011, vol. 11, pp. 27-70.
Potter K.N., et al., "Features of the overexpressed V1-69 genes in the unmutated subset of chronic lymphocytic leukemia are distinct from those in the healthy elderly repertoire," *Blood*, Apr. 2003, vol. 101 (8), pp. 3082-3084.
Prak E.T.L, et al., "B cell receptor editing in tolerance and autoimmunity," *Annals of the New York Academy of Sciences*, Jan. 2011, vol. 1217, pp. 96-121.
Raaphorst F.M., et al., "Human Ig heavy chain CDR3 regions in adult bone marrow pre-B cells display an adult phenotype of diversity: evidence for structural selection of $D_H$ amino acid sequences," *International Immunology*, Oct. 1997, vol. 9 (10), pp. 1503-1515.
Ren L., et al., "Silencing of the immunoglobulin heavy chain locus by removal of all eight constant-region genes in a 200-kb region," *Genomics*, Aug. 2004, vol. 84, pp. 686-695.
Ricker M., European Patent Attorney, Opposition against EP2758535 in the name of Kymab Limited Statement of Facts and Arguments pertaining to Application No. 12772122.3, dated Aug. 9, 2017, 42 pages.
Rock E.P., et al., "CDR3 Length in Antigen-specific Immune Receptors", *Journal of Experimental Medicine*, Jan. 1994, vol. 179, pp. 323-328.
Rudolf M.P., et al., "Molecular basis for nonanaphylactogenicity of a monoclonal anti-IgE antibody," *Journal of Immunology*, Jul. 2010, vol. 165 (2), pp. 813-819.
Ruiz M., et al., "The Human Immunoglobulin Heavy Diversity (IGHD) and Joining (IGHJ) Segments," *Experimental and Clinical Immunogenetics*, 1999, vol. 16, pp. 173-184.
Russell N.D., et al., "Production of Protective Human Antipneumococcal Antibodies by Transgenic Mice with Human Immunoglobulin Loci," *Infection and Immunity*, Apr. 2000, vol. 68 (4), pp. 1820-1826.
Schonewald S.L., Attorney for Applicant, Third-Party Pre-Issuance Submission Under 37 CFR Sec. 1.290 in U.S. Appl. No. 14/935,010, dated Aug. 19, 2016, 27 pages.
Shore D.E., Attorney for Applicant, Third-Party Pre-Issuance Submission Under 37 CFR Sec. 1.290 in U.S. Appl. No. 15/088,805, filed Nov. 17, 2017, 44 pages.
Shore D.E., Attorney for Applicant, Third-Party Pre-Issuance Submission Under 37 CFR Sec. 1.290 in U.S. Appl. No. 15/199,575, filed May 31, 2017, 37 pages.
Shore D.E., Attorney for Applicant, Third-Party Pre-Issuance Submission Under 37 CFR Sec. 1.290 in U.S. Appl. No. 15/690,183, filed Feb. 28, 2018, 60 pages.
Siman-Tov D.D., et al., "Differentiation of a passive vaccine and the humoral immune response toward infection: Analysis of phage displayed peptides," *Vaccine*, Jan. 2006, vol. 24, pp. 607-612.
Stein R., et al., "Characterization of a humanized IgG4 anti-HLA-DR monoclonal antibody that lacks effector cell functions but retains direct antilymphoma activity and increases the potency of rituximab," *Blood*, Oct. 2006, vol. 108 (8), pp. 2736-2744.
Suárez E., et al., "Human monoclonal antibodies produced in transgenic BABκ,λ mice recognising idiotypic immunoglobulins of human lymphoma cells," *Molecular Immunology*, 2004, vol. 41, pp. 519-526.
Taylor L.D., et al., "A transgenic mouse that expresses a diversity of human sequence heavy and light chain immunoglobulins," *Nucleic Acids Research*, 1992, vol. 20 (23), pp. 6287-6295.
Table S1 (from Breden F., et al., "Comparison of Antibody Repertoires Produced By HIV-1 Infection, Other Chronic and Acute Infections, and Systemic Autoimmune Disease," *PLoS One*, 2011, vol. 6 (3), pp. e16857-1-e16857—11.), 60 pages.
Table S2 (from Breden F., et al., "Comparison of Antibody Repertoires Produced By HIV-1 Infection, Other Chronic and Acute Infections, and Systemic Autoimmune Disease," *PLoS One*, 2011, vol. 6 (3), pp. e16857-1-e16857—11.), 14 pages.
Xiao X., et al., "Germline-like predecessors of broadly neutralizing antibodies lack measurable binding to HIV-1 envelope glycoproteins: Implications for evasion of immune responses and design of vaccine immunogens," *Biochemical and Biophysical Communications*, 2009, vol. 390, pp. 404-409.
Zhu Z., et al., "Cross-Reactive HIV-1-Neutralizing Human Monoclonal Antibodies Identified from a Patient with 2F5-Like Antibodies," *Journal of Virology*, Nov. 2011, vol. 85 (21), pp. 11401-11408.
Zwick M.B., et al., "The Long Third Complementarity-Determining Region of the Heavy Chain Is Important in the Activity of the Broadly Neutralizing Anti-Human Immunodeficiency Virus Type 1 Antibody 2F5," *Journal of Virology*, Mar. 2004, vol. 78 (6), pp. 3155-3161.
Wozniak-Knopp G., et al., "Introducing antigen-binding sites in structural loops of immunoglobulin constant domains: Fc fragments with engineered HER2/neu-binding sites and antibody properties," *Protein Engineering Design & Selection*, 2010, vol. 23(4), pp. 289-297.

(56) References Cited

OTHER PUBLICATIONS

Grund M., European Patent Attorney, Grund Intellectual Property Group, Third-Party Observations According to Article 115 EPC regarding 17196235.0, dated Nov. 27, 2018, 22 pages.

Grund M., European Patent Attorney, Grund Intellectual Property Group, Third-Party Observations according to Article 115 EPC regarding 19207052.2, dated Aug. 19, 2020, 4 pages.

Gutterson N.I., et al., "Replacement and Amplification of Bacterial Genes With Sequences Altered in Vitro," Proc. Natl. Acad. Sci. USA, Aug. 1983, vol. 80(16), pp. 4894-4898.

Hasty P., et al., "Introduction of a Subtle Mutation Into the Hox-2.6 Locus in Embryonic Stem Cells," Nature, Mar. 1991, vol. 350(6315), pp. 243-246.

Ichihara Y., et al., "Organization of Human Immunoglobulin Heavy Chain Diversity Gene Loci," The EMBO Journal, 1988, vol. 7, No. 13, pp. 4141-4150.

Ignatovich O. et al., "The creation of diversity in the human immunoglobulin V(lambda) repertoire," Journal of Molecular Biology, Apr. 1997, vol. 268, pp. 69-77.

Ignatovich O., et al., "Dominance of intrinsic genetic factors in shaping the human immunoglobulin V? repertoire", Journal of Molecular Biology, Nov. 1999, vol. 294, pp. 457-465.

International Bureau of WIPO, Examiner Isabella Machill, Third-Party Observations regarding Application No. PCT/EP2018/068309, dated Aug. 14, 2019, 6 pages.

Tzhaki J.E., et al., "Construction by Gene Targeting in Human Cells of a Conditional CDC2 Mutant That Rereplicates Its DNA,", Nature Genetics, Mar. 1997, vol. 15(3), pp. 258-265.

Tzhaki J.E., et al., "Targeted Breakage of a Human Chromosome Mediated by Cloned Human Telomeric DNA," Nature Genetics, Dec. 1992, vol. 2(4), pp. 283-287.

Ivanov I.I., et al., "Development of the Expressed Ig CDR-H3 Repertoire Is Marked by Focusing of Constraints in Length, Amino Acid Use, and Charge That Are First Established in Early B Cell Progenitors," The Journal of Immunology, Jun. 2005, vol. 174, pp. 7773-7780.

Janeway C.A. et al., "Chapter 3: Structure of the Antibody Molecule and the Immunoglobulin Genes," excerpts from Immunobiology: The Immune System in Health and Disease, 4th Edition, 1999, 4 pages.

Japanese Patent Office, Decision of Rejection—Application No. 2017-021028, dated Sep. 9, 2019, together with English translation, 9 pages.

Japanese Patent Office, Pre-Appeal Report—Application No. 2017-021028—Appeal No. 2020-000300, mailed Mar. 17, 2020, together with English translation, 13 pages.

Japanese Patent Office, Notice of Reasons for Rejection—Application No. 2016-548441, dated Aug. 5, 2019, together with English translation, 12 pages.

Japanese Patent Office, Notice of Reasons for Rejection—Application No. 2018-088749, dated May 27, 2019, together with English translation, 11 pages.

Japanese Patent Office, Notice of Reasons for Rejection—Application No. 2017-021028, dated Dec. 21, 2018, together with English translation, 11 pages.

Japanese Patent Office, Notice of Reasons for Rejection—Application No. 2017-017360, dated Mar. 19, 2018, together with English translation, 7 pages.

Kelley S.K., et al., "Preclinical Pharmacokinetics, Pharmacodynamics, and Activity of a Humanized Anti-CD40 Antibody (SGN-40) in Rodents and Non-Human Primates," British Journal of Pharmacology, 2006, vol. 148, pp. 1116-1123.

Koller B.H., et al. "Altering Genes in Animals by Gene Targeting," Annu. Rev. Immunol., 1992, vol. 10, pp. 705-730.

Kotzamanis G., et al., "Construction of human artificial chromosome vectors by recombineering," Gene, 2005, vol. 351, pp. 29-38.

Kumar R., et al., "A novel strategy for efficient production of anti-V3 human scFvs against HIV-1 clade C," BMC Biotechnology, Nov. 2012, vol. 12 (87), 15 pages.

Kuzminov A., "DNA Replication Meets Genetic Exchange: Chromosomal Damage and Its Repair by Homologous Recombination," Proc. Natl. Acad. Sci. U.S.A., Jul. 2001, vol. 98(15), pp. 8461-8468.

Law M., et al., "Antibodies Against Viruses: Passive and Active Immunization," Current Opinion in Immunology, Aug. 2008, vol. 20(4), pp. 486-492.

Lee, E-Chiang, "Declaration of E-Chiang Lee," Jun. 13, 2016, 8 pages.

Lerner, R.A., "Rare antibodies from combinatorial libraries suggests an S.O.S. component of the human mmunological repertoire," Mol. BioSyst, Apr. 2011, vol. 7(4), pp. 1004-1012.

Li Z., et al., "The generation of antibody diversity through somatic hypermutation and class switch recombination," Genes & Development, 2004, vol. 18, pp. 1-11.

Logtenberg T., "Antibody Cocktails: Next-Generation Biopharmaceuticals With Improved Potency," Trends in Biotechnology, Sep. 2007, vol. 25(9), pp. 390-394.

Macdonald L., Declaration of Lynne E. Macdonald, dated May 16, 2018, including Annex 1, 10 pages.

Mårtensson I.L., et al., "Role of the Surrogate Light Chain and the Pre-B-Cell Receptor in Mouse B-Cell Development," Immunology, 2000, vol. 101 (4), pp. 435-441.

Mitra R., et al., "PiggyBac can bypass DNA synthesis during cut and paste transposition," The EMBO Journal, 2008, vol. 27, pp. 1097-1109.

Morrison S.L., et al. "Vectors and Approaches for the Eukaryotic Expression of Antibodies and Antibody Fusion Proteins" Antibody Engineering, 2nd Edition, Chapter 9, 1995, 31 pages.

Muramatsu M., et al., "Specific Expression of Activation-induced Cytidine Deaminase (AID), a Novel Member of the RNA-editing Deaminase Family in Germinal Center B Cells," 1999, The Journal of Biological Chemistry, vol. 274 (26), pp. 18470-18476.

Muyrers J.P.P., et al., "Techniques: Recombinogenic engineering—new options for cloning and manipulating DNA," Trends in Biochemical Sciences, May 2001, vol. 26(5), pp. 325-331.

Newcombe C., et al., "Antibody production: Polyclonal-derived biotherapeutics," Journal of Chromatography B, 2007 vol. 848, pp. 2-7.

Ogle, Ph.D., J.M., European Patent Attorney of Hoffman Eitle, Opposition to EP 2 792 236 (Application No. 14176740.0) dated Feb. 28, 2020, 56 pages.

Ogle, Ph.D., J.M., European Patent Attorney of Hoffman Eitle, Reply to Statement of Grounds of Appeal In re Opposition against EP2758535 dated Feb. 26, 2020, 80 pages.

Ogle, Ph.D., J.M., European Patent Attorney of Hoffman Eitle, Reply to Statement of Grounds of Appeal (Corrected Version) In re Opposition against EP2758535 dated Feb. 26, 2020, 83 pages.

Ogle, Ph.D., J.M., European Patent Attorney of Hoffman Eitle, Written Submission in preparation to/during oral proceedings In re Opposition against EP2792236 dated Apr. 17, 2020, 14 pages.

Perera, W.S., et al., "Comparison between hybridoma and Fab/phage anti-RhD: Their V gene usage and pairings," Disease Markers, 2000, vol. 16, pp. 15-19.

Porter A., Resume Imperial College London, retrieved from the Internet under https://www.imperial.ac.uk/people/andy.porter on May 21, 2020, 2 pages.

Porter A.C., et al., "Role of the B Subunit of the *Escherichia coli* Proton-Translocating ATPase. A Mutagenic Analysis," Journal of Biological Chemistry, Jul. 1985, vol. 260(13), pp. 8182-8187.

Porter, Andrew, First Declaration (Evidence in Support of Opposition thereto by Regeneron Pharmaceuticals, Inc.) for Application No. 14176740.0, dated Oct. 11, 2018, 31 pages.

Porter, Andrew, Second Decarlaration (Evidence in Support of Opposition thereto by Regeneron Pharmaceuticals, Inc.) for Application No. 14176740.0, dated Apr. 14, 2020, 8 pages.

Porteus M., "Using Homologous Recombination to Manipulate the Genome of Human Somatic Cells," Biotechnology and Genetic Engineering Reviews, 2007, vol. 24, pp. 195-212.

Richardson, C. et al., "Molecular Basis of 9G4 B cell Autoreactivity in Human Systemic Lupus Erythematosus," The Journal of Immunology, vol. 191(10), pp. 4926-4939 (Nov. 2013).

(56) References Cited

OTHER PUBLICATIONS

Rojas G., et al., "Efficient Construction of a Highly Useful Phage-Displayed Human Antibody Repertoire", Biochemical and Biophysical Research Communications, Nov. 2005, vol. 336(4), pp. 1207-1213.
Rothstein R., "Targeting, Disruption, Replacement, and Allele Rescue: Integrative DNA Transformation in Yeast," Methods in Enzymology, 1991, vol. 194, pp. 281-301.
Rubinstein M., et al., "Introduction of a Point Mutation Into the Mouse Genome by Homologous Recombination in Embryonic Stem Cells Using a Replacement Type Vector With a Selectable Marker," Nucleic Acids Research, Jun. 1993, vol. 21(11), pp. 2613-2617.
[No Author Listed] IMGT Repertoire (IG and TR), Gene table: human (*Homo sapiens*) IGHD, created Apr. 18, 1997, last updated Jan. 17, 2020, 3 pages. [retrieved from the internet under: http://www.imgt.org/IMGTrepertoire/].
An Z., "Therapeutic Monoclonal Antibodies from Bench to Clinic", 2009, 4 pages.
Anderson P.S. et al., "Extensive restrictions in the VH sequence usage of the human antibody response against the Rhesus D Antigen," Molecular Immunology, Jan. 2007, vol. 44, pp. 412-422.
Balbás P., et al., "Chromosomal Editing in *Escherichia coli*. Vectors for DNA Integration and Excision," Molecular Biotechnology, Sep. 2001, vol. 19(1), pp. 1-12.
Bentham A., J.A. Kemp, European Patent Attorney, Final Written Submissions for Application No. 12171793.8, dated May 17, 2018, 20 pages.
Bentham A., J.A. Kemp, European Patent Attorney, Statement of Fact and Arguments in Support of Opposition against EP2517557 in the name of Kymab Limited pertaining to Application No. 12171793.8, dated Jan. 11, 2017, 32 pages.
Bostrom J., et al., "Variants of the Antibody Herceptin That Interact with HER2 and VEGF at the Antigen Binding Site," Science, Mar. 2009, vol. 323, pp. 1610-1614.
Bradley A., et al., "Modifying the Mouse: Design and Desire," Biotechnology, May 1992, vol. 10(5), pp. 534-539.
Brazilian Patent Office, Lúcia Aparecida Mendonca, Preliminary Office Action for Application No. BR112012000536-7, dated Jul. 7, 2010, 12 pages.
Brazilian Patent Office, Lucia Aparecida Mendonca, Preliminary Office Action (English translation) for Application No. BR112012000536-7, dated Jul. 7, 2010, 1 page.
Canadian IP Office, Office Action for Application No. 2,857,569, dated Jan. 14, 2019, 6 pages.
Canadian IP Office, Protest and Submission of Prior Art, Application No. 2,802,591, dated Nov. 13, 2019, 18 pages.
Carpenter A.J., et al., "Construction, Characterization, and Complementation of a Conditional-Lethal DNA Topoisomerase llalpha Mutant Human Cell Line," Molecular Biology of the Cell, Dec. 2004, vol. 15(12), pp. 5700-5711.
Chapal, N. et al., "Thyroid Peroxidase Autoantibodies Obtained from Random Single Chain Fv Libraries Contain the Same Heavy/Light Chain Combinations as Occur in Vivo," Endocrinology, 2001, vol. 142(11), pp. 4710-4750.
Chinese Patent Office, First Office Action for Application No. 201610821299.6, dated Jun. 23, 2020, 15 pages.
Chinese Patent Office, First Office Action (English translation) for Application No. 201610821299.6, dated Jun. 23, 2020, 19 pages.
Dafhnis-Calas F., et al., "Iterative in vivo assembly of large and complex transgenes by combining the activities of φC31 integrase and Cre recombinase," Nucleic Acids Research, Dec. 2005, vol. 33(22), pp. e189-1-e189-14.
De Kruif J., et al., "Human Immunoglobulin Repertoires Against Tetanus Toxoid Contain a Large and Diverse Fraction of High-Affinity Promiscuous VH Genes," Journal of Molecular Biology, 2009, vol. 387 (3), pp. 548-558.
Decloux A.M., Attorney for Applicant, Amendment and Response After Final Rejection—U.S. Appl. No. 13/846,672, filed May 10, 2016, 20 pages.

Defranco, Anthony L., Ph.D., Declaration, dated Sep. 9, 2019, 113 pages.
Deonarain R., et al., "Impaired Antiviral Response and Alpha/Beta Interferon Induction in Mice Lacking Beta Interferon," Journal of Virology, Apr. 2000, vol. 74(4), pp. 3404-3409.
Dewitt W.S., et al., "A Public Database of Memory and Naive B-Cell Receptor Sequences," PLOS ONE, Aug. 2016, 18 pages.
Ejima D., "Effective elution of antibodies by arginine and arginine derivatives in affinity col. chromatography," Analytical Biochemistry, 2005, vol. 345, pp. 250-257.
England, Nicholas Dr., 37 C.F.R. Rule 1.132 Declaration, dated Dec. 21, 2016, 6 pages.
European Patent Office, Decision rejecting the opposition (Art. 101(2) EPC) for Application No. 10 010 741.6, dated Apr. 25, 2018, 44 pages.
European Patent Office, Examination Report for Application No. 13723933.1, dated Mar. 18, 2020, 7 pages.
European Patent Office, Extended European Search Report for Application No. 18153171.6, dated Jun. 28, 2018, 15 pages.
European Patent Office, Irmgard Scheffzyk, Authorized officer, International Search Report for Application No. PCT/EP2018/068309, dated Jan. 15, 2019, 14 pages, together with the Written Opinion of the International Searching Authority.
European Patent Office, Examination Report for Application No. 17174426.1, dated Feb. 5, 2020 (with Annex), 11 pages.
European Patent Office, Notice of Opposition to a European Patent EP2517557 in the name of Kymab Limited pertaining to Application No. 12171793.8, dated Jan. 11, 2017, 7 pages.
European Patent Office, Notice of Opposition to a European Patent EP2758534 in the name of Kymab Limited pertaining to Application No. 12762377.5, dated May 4, 2020, 6 pages.
Ewert H.T., et al., "Biophysical Properties of human antibody variable domains," J. Mol. Biol., Jan. 2003, vol. 325 (3), pp. 531-553.
Finn C.A., "Reproductive Capacity and Litter Size in Mice: Effect of Age and Environment," J. Reprod. Fertil., 1963, vol. 6, pp. 205-214.
Genbank "Immunoglobulin Heavy Chain Variable Region (*Homo sapiens*)," Accession No. BAA75060, dated Jul. 2, 2008, 1 page.
Genbank, "*H.sapiens* immunoglobulin heavy chain J region, B1C haplotype," Accession No. X86356, 2 pages.
Genbank, "*Homo sapiens* DNA, immunoglobulin heavy-chain variable region, complete sequence, 5 of 5," AB019441.1, dated Jun. 18, 2018, 36 pages.
Genbank, "Human Ig germline J6-region, partial cds," Accession No. M63030, 1 page.
Gibson D.G., et al., "Complete Chemical Synthesis, Assembly, and Cloning of a Mycoplasma genitalium Genome," Science, Feb. 2008, vol. 319, pp. 1215-1220.
Goding J.W., "Differences Between Conventional and Monoclonal Serology," Monoclonal Antibodies: Principles and Practice, Production and Application of Monoclonal Antibodies in Cell Biology, Biochemistry and Immunology, 1996, Third Edition, Section 7.3, pp. 129-130.
Goodnow, Christopher Carl, Declaration (Evidence in Support of Opposition thereto by Regeneron Pharmaceuticals Inc. for Application No. 2011266843), dated Jan. 29, 2016, 21 pages.
Goodnow, Christopher Carl, Second Declaration (Evidence in Support of Opposition thereto by Regeneron Pharmaceuticals, Inc. for Application No. 2011266843), dated Jul. 4, 2016, 9 pages.
Goodnow, Christopher Carl, Third Declaration (Evidence in Support of Opposition thereto by Regeneron Pharmaceuticals, Inc. for Application No. 2011266843), dated Aug. 29, 2017, 7 pages.
Gondo Y., et al., Next-generation gene targeting in the mouse for functional genomics, BMB reports, Jul. 2009, vol. 42(6), pp. 315-323.
Grund M., European Patent Attorney, Grund Intellectual Property Group, Third-Party Observations according to Article 115 EPC regarding 12171793.8, dated Mar. 17, 2015, 4 pages.
Grund M., European Patent Attorney, Grund Intellectual Property Group, Third-Party Observations according to Article 115 EPC regarding 12171793.8, dated May 22, 2015, 5 pages.

(56) References Cited

OTHER PUBLICATIONS

Grund M., European Patent Attorney, Grund Intellectual Property Group, Third-Party Observations according to Article 115 EPC regarding 12171793.8, dated Oct. 10, 2013, 10 pages.
Grund M., European Patent Attorney, Grund Intellectual Property Group, Third-Party Observations according to Article 115 EPC regarding 14781635.9, dated May 18, 2018, 4 pages.
Grund M., European Patent Attorney, Grund Intellectual Property Group, Third-Party Observations according to Article 115 EPC regarding 15188522.5, dated Mar. 13, 2019, 3 pages.
Grund M., European Patent Attorney, Grund Intellectual Property Group, Third-Party Observations according to article 115 EPC regarding 17174426.1, dated Feb. 11, 2019, 5 pages.
Grund M., European Patent Attorney, Grund Intellectual Property Group, Third-Party Observations according to Article 115 EPC regarding 17174426.1, dated Jun. 27, 2018, 7 pages.
Sabouri, Z., et al., "Redemption of autoantibodies on anergic B cells by variable-region glycosylation and mutation away from self-reactivity," Proceedings of the National Academy of Sciences of the United States of America, Early Edition, May 2014, pp. E2567-E2575.
Schaller, M. et al., "The splenic autoimmune response to ADAMTS13 in thrombotic thrombocytopenic purpura contains recurrent antigen-binding CDR3 motifs," Blood, Nov. 2014, vol. 124(23), pp. 3469-3479.
Scherer S., et al., "Replacement of Chromosome Segments With Altered DNA Sequences Constructed in Vitro," Proc. Natl. Acad. Sci. USA, Oct. 1979, vol. 7 6(10), pp. 4951-4955.
Schonewald, Stephanie L., Choate Hall & Stewart LLP, Petition for Inter Partes Review—AIA Review No. IPR2019-01577, filed Sep. 20, 2019, 86 pages.
Schonewald, Stephanie L., Choate Hall & Stewart LLP, Petition for Inter Partes Review—AIA Review No. IPR2019-01578, filed Sep. 20, 2019, 83 pages.
Schonewald, Stephanie L., Choate Hall & Stewart LLP, Petition for Inter Partes Review—AIA Review No. IPR2019-01579, filed Sep. 20, 2019, 84 pages.
Schonewald, Stephanie L., Choate Hall & Stewart LLP, Petition for Inter Partes Review—AIA Review No. IPR2019-01580, filed Sep. 20, 2019, 87 pages.
Schonewald, Stephanie L., Choate Hall & Stewart LLP, Petition for Inter Partes Review—AIA Review No. IPR2020-00389, filed Jan. 3, 2020, 89 pages.
Sharan S.K., et al., "Recombineering: a homologous recombination-based method of genetic engineering," Nature Protocols, 2009, vol. 4(2), pp. 206-223.
Shaw, D.J., J.A. Kemp, European Patent Attorney, Response to Summons to attend Oral Proceedings In re Opposition against EP2757875 in the name of Kymab Limited pertaining to Application No. 12762378.8, dated Apr. 16, 2020, 21 pages.
Shore D.E., Attorney for Applicant, Third-Party Pre-Issuance Submission Under 37 CFR Sec. 1.290 in U.S. Appl. No. 15/656,897, filed May 4, 2018, 55 pages.
Shore D.E., Attorney for Applicant, Third-Party Pre-Issuance Submission Under 37 CFR Sec. 1.290 in U.S. Appl. No. 15/786,281, filed Jun. 27, 2018, 63 pages.
Shore D.E., Attorney for Applicant, Third-Party Pre-Issuance Submission Under 37 CFR Sec. 1.290 in U.S. Appl. No. 15/786,281, filed Jun. 27, 2018 (Second Submission), 62 pages.
Shore D.E., Attorney for Applicant, Third-Party Pre-Issuance Submission Under 37 CFR Sec. 1.290 in U.S. Appl. No. 15/786,281, filed Jun. 27, 2018 (Third Submission), 53 pages.
Shore D.E., Attorney for Applicant, Third-Party Pre-Issuance Submission Under 37 CFR Sec. 1.290 in U.S. Appl. No. 15/948,709, filed Jan. 10, 2019, 43 pages.
Shore D.E., Attorney for Applicant, Third-Party Pre-Issuance Submission Under 37 CFR Sec. 1.290 in U.S. Appl. No. 15/955,216, dated Feb. 5, 2019, 52 pages.
Shore D.E., Attorney for Applicant, Third-Party Pre-Issuance Submission Under 37 CFR Sec. 1.290 in U.S. Appl. No. 16/216,666, filed Dec. 11, 2019, 42 pages.
Shore D.E., Attorney for Applicant, Third-Party Pre-Issuance Submission Under 37 CFR Sec. 1.290 in U.S. Appl. No. 16/353,870, filed Dec. 20, 2019, 104 pages.
Shore, D.E., Attorney for Applicant, Third-Party Pre-Issuance Submission Under 37 CFR Sec. 1.290 in U.S. Appl. No. 16/296,033, filed Jul. 14, 2020, 75 pages.
Shore, D.E., Attorney for Applicant, Third-Party Pre-Issuance Submission Under 37 CFR Sec. 1.290 in U.S. Appl. No. 16/296,033, filed Jul. 14, 2020, 78 pages (2nd Submission).
Siegel, D.L. et al., "Section 5: Structural/genetic analysis of mAbs to blood group antigens. Coordinator's Report," Transfus. Clin. Biol., 2002, vol. 9, pp. 83-97.
Sleeman, Mark W., First Declaration (Evidence in Support of Opposition thereto by Regeneron Pharmaceuticals, Inc. for Application No. 2011266843), dated Jan. 29, 2016, 24 pages.
Sleeman, Mark W., Second Declaration (Evidence in Support of Opposition thereto by Regeneron Pharmaceuticals, Inc. for Application No. 2011266843), dated Jul. 4, 2016, 7 pages.
Sleeman, Mark W., Third Declaration (Evidence in Support of Opposition thereto by Regeneron Pharmaceuticals, Inc. for Application No. 2011266843), dated Jan. 25, 2018, 9 pages.
Sosio M., et al., "Assembly of large genomic segments in artificial chromosomes by homologous recombination in *Escherichia coli*," Nucleic Acids Research, 2001, vol. 29(7), pp e37-1-e37-8.
Stacey A., et al., "Use of Double-Replacement Gene Targeting to Replace the Murine α-Lactalbumin Gene with Its Human Counterpart in Embryonic Stem Cells and Mice," Molecular and Cellular Biology, Feb. 1994, vol. 14(2), pp. 1009-1016.
Stephen R., Olswang LLP, Response to Examination Report dated Jun. 6, 2016 to the European Patent Office with corresponding claims for Application No. 14176740.0, dated Oct. 10, 2016, 11 pages.
Stephen R., Olswang LLP, Response to Search Report dated Oct. 15, 2014 to the European Patent Office with corresponding claims for Application No. 14176740.0, dated May 12, 2015, 10 pages.
Stephen R., Olswang LLP, Response to Third-Party Observations dated Aug. 10, 2015 and Examination Report dated Oct. 23, 2015 to the European Patent Office with corresponding claims for Application No. 14176740.0, dated Apr. 23, 2016, 13 pages.
Stephen R., Olswang LLP, Response to Appeal filed by Regeneron Pharmaceuticals, Inc. for Application No. 14170196.1, as filed with the European Patent Office dated Mar. 12, 2020, 23 pages.
Stephen R., Olswang LLP, Response to Examination Report dated Nov. 10, 2016 to the European Patent Office with corresponding claims for Application No. 14176740.0 on Mar. 17, 2017, 13 pages.
Stephen R., Olswang LLP, Response to Grounds of Appeal dated Dec. 14, 2018 for Application No. 12171793.8 (Patent No. EP2517557), as filed with the European Patent Office on Apr. 29, 2019, 17 pages.
Stephen R., Olswang LLP, Response to Opposition (as filed by Regeneron Pharmaceuticals, Inc. on Jan. 11, 2017) for Application No. 12171793.8, as filed with the European Patent Office on Jun. 23, 2017, 8 pages.
Stephen R., Olswang LLP, Response to Opposition in the name of Kymab Limited filed against EP2758535B1, dated Mar. 22, 2018, 26 pages.
Stephen R., Olswang LLP, Response to Summons and Preliminary Opinion pertaining to Patent No. EP 2517557 for Application No. 12171793.8, as filed with the European Patent Office on May 17, 2018, 4 pages.
Stephen R., Olswang LLP, Response to Third-Party Observations for Application No. 12171793.8, as filed with the European Patent Office on Apr. 17, 2015, 3 pages.
Sullivan P.M., et al., "Targeted Replacement of the Mouse Apolipoprotein E Gene with the Common Human APOE3 Allele Enhances Diet-induced Hypercholesterolemia and Atherosclerosis," The Journal of Biological Chemistry, 1997, vol. 272, No. 2, pp. 17972-17980.
Traggiai, E. et al., "An efficient method to make human monoclonal antibodies from memory B cells: potent neutralization of SARS coronavirus", Nature Medicine, Aug. 2004, vol. 10(8), pp. 871-875.

(56) References Cited

OTHER PUBLICATIONS

U.S. Patent and Trademark Office, Before the Patent and Appeal Board, AIA Review No. IPR2019-01577, Decision (Denying Institution of Inter Parties Review 35 U.S.C. Sec. 314), dated Apr. 1, 2020, 20 pages.

U.S. Patent and Trademark Office, Before the Patent and Appeal Board, AIA Review No. PR2019-01578, Decision (Denying Institution of Inter Parties Review 35 U.S.C. Sec. 314), dated Apr. 1, 2020, 17 pages.

U.S. Patent and Trademark Office, Before the Patent and Appeal Board, AIA Review No. IPR2019-01579, Decision (Denying Institution of Inter Parties Review 35 U.S.C. Sec. 314), dated Mar. 20, 2020,20 pages.

U.S. Patent and Trademark Office, Before the Patent and Appeal Board, AIA Review No. IPR2019-01580, Decision (Denying Institution of Inter Parties Review 35 U.S.C. Sec. 314), dated Mar. 18, 2020, 26 pages.

U.S. Patent and Trademark Office, Before the Patent and Appeal Board, AIA Review No. IPR2020-00389, Decision (Denying Institution of Inter Parties Review 35 U.S.C. Sec. 314), dated May 26, 2020, 21 pages.

Valancius V., et al., "Testing an "In-Out" Targeting Procedure for Making Subtle Genomic Modifications in Mouse Embryonic Stem Cells," Molecular and Cellular Biology, Mar. 1991, vol. 11(3), pp. 1402-1408.

Van Dijk, Marcus, Third Declaration (Evidence in Support of Opposition thereto by Regeneron Pharmaceuticals, Inc. for Application No. 2011266843), dated Mar. 28, 2018, 6 pages.

Wu H., et al., "Double replacement: Strategy for efficient introduction of subtle mutations into the murine Colla-1 gene by homologous recombination in embryonic stem cells," Proc. National Academy of Sciences of the U.S.A., Mar. 1994, vol. 91, pp. 2819-2823.

Ku Z., et al., "Site-specific recombination in *Schizosaccharomyces pombe* and systematic assembly of a 400kb transgene array iin mammalian cells using the integrase of Steptomyces phage φBt1," Nucleic Acids Research, Dec. 2007, vol. 36(1), pp. e9-1-e9-9.

Yusa K., et al., "Generation of transgene-free induced pluripotent mouse stem cells by the piggyBac transposon," Nature Methods, May 2009, vol. 6, Issue No. 5, pp. 363-371.

Yusa K., et al., "Targeted gene correction of α1-antitrypsin deficiency in induced pluripotent stem cells," Nature, Oct. 2011, vol. 478, Issue No. 7369, pp. 391-394.

U.S. Appl. No. 13/886,511, filed May 3, 2013.

[No Author Listed] Exemplary allele distribution for IgHV3-72 (3 pages) [retrieved from the internet Apr. 29, 2021: http://www.imgt.org/IMGTrepertoire/Proteins/taballeles/human/IGH/IGHV/Hu_IGHVall.html].

[No Author Listed] Exemplary allele distribution for IgHV3-73 (3 pages) [retrieved from the internet Apr. 29, 2021: http://www.imgt.org/IMGTrepertoire/Proteins/taballeles/human/IGH/IGHV/Hu_IGHVall.html].

[No Author Listed] IMGT Repertoire (IG and TR), Gene table: human (*Homo sapiens*) IGHJ4, created Oct. 17, 1997, last updated Mar. 30, 2021, 606 pages. [retrieved from the internet under: http://www.imgt.org/IMGTrepertoire/Proteins/alleles/index.php?species=Homo%20sapiens&group=IGHJ&gene=IGHJ4].

Betz A.G., et al., "Elements Regulating Somatic Hypermutation of an Immunoglobulin ? Gene: Critical Role for the Intron Enhancer/Matrix Attachment Region," Cell, Apr. 1994, vol. 77, pp. 239-248.

Brevini T.A.L., "Embryonic Stem Cells in Domestic Animals, No shortcuts to pig embryonic stem cells," ScienceDirect/Theriogenology, vol. 74, 2010, pp. 544-550.

Chen J., et al., "RAG-2-deficient blastocyst complementation: An assay of gene function in lymphocyte development," Proceedings of the National Academy of Sciences of the U.S.A., Immunology, May 1993, vol. 90, pp. 4528-4532.

Daukss, Dana M., Third-Party Pre-Issuance Submission Under 37 CFR 1.290 in U.S. Appl. No. 16/721,326, dated Mar. 25, 2021, 36 pages.

Daukss, Dana M., Third-Party Pre-Issuance Submission Under 37 CFR 1.290 in U.S. Appl. No. 16/721,326, dated Mar. 25, 2021, 30 pages (Second Submission).

Daukss, Dana M., Third-Party Pre-Issuance Submission Under 37 CFR 1.290 in U.S. Appl. No. 16/725,707, dated Dec. 28, 2020, 46 pages.

Daukss, Dana M., Third-Party Pre-Issuance Submission Under 37 CFR 1.290 in U.S. Appl. No. 16/869,416, dated Apr. 6, 2021, 28 pages.

Daukss, Dana M., Third-Party Pre-Issuance Submission Under 37 CFR 1.290 in U.S. Appl. No. 16/870,365, dated Mar. 15, 2021, 36 pages.

Daukss, Dana M., Third-Party Pre-Issuance Submission Under 37 CFR 1.290 in U.S. Appl. No. 16/870,365, dated Mar. 15, 2021, 45 pages (Second Submission).

Daukss, Dana M., Third-Party Pre-Issuance Submission Under 37 CFR 1.290 in U.S. Appl. No. 16/886,057, dated Apr. 1, 2021, 31 pages.

Daukss, Dana M., Third-Party Pre-Issuance Submission Under 37 CFR 1.290 in U.S. Appl. No. 16/886,394, dated Apr. 1, 2021, 33 pages.

Daukss, Dana M., Third-Party Pre-Issuance Submission Under 37 CFR 1.290 in U.S. Appl. No. 16/905,537, dated Apr. 23, 2021, 47 pages.

Daukss, Dana M., Third-Party Pre-Issuance Submission Under 37 CFR 1.290 in U.S. Appl. No. 16/905,557, dated Mar. 9, 2021, 67 pages.

Daukss, Dana M., Third-Party Pre-Issuance Submission Under 37 CFR 1.290 in U.S. Appl. No. 16/905,557, dated Mar. 9, 2021, 63 pages (Second Submission).

Defranco, Anthony L., Ph.D., Declaration, Interparties Review AIA No. IPR2019-01578 (U.S. Pat. No. 9,434,782), dated Sep. 9, 2019, 121 pages.

Defranco, Anthony L., Ph.D., Declaration, Interparties Review AIA No. IPR2019-01579 (U.S. Pat. No. 9,447,177), dated Sep. 20, 2019, 103 pages.

Ebersbach H., et al., "Antigen Presentation for the Generation of Binding Molecules," Methods of Molecular Biology, 2012, Chaper 1: Antigen Presentation for the Generation of Binding Molecules, pp. 1-10 (including cover and copyright pages).

European Patent Office, Examination Report for Application No. 13723933.1, dated Feb. 21, 2019, 7 pages.

European Patent Office, Examination Report for Application No. 18743421.2, dated Feb. 26, 2021, 3 pages.

European Patent Office, Extended European Search Report for Application No. 20188009.3, dated May 3, 2021, 17 pages.

European Patent Office, Notice of Opposition, together with Statement of Fact and Arguments in Support of Opposition related to European Patent EP2989894 in the name of Kymab Limited pertaining to Application No. 15188522.5, dated May 17, 2021, 34 pages.

European Patent Office, Notice of Opposition,.together with Ground of Opposition and accompanying cited documents, related to European Patent EP3128009 in the name of Kymab Limited pertaining to Application No. 16189625.3, dated May 6, 2021, 55 pages.

European Patent Office, Minutes of the oral proceedings before the Opposition Division, relating to Application No. EP12716101.6 (Patent No. EP2550363), with supporting documents, dated May 26, 2017, 62 pages.

Friedrich G., Statement of Dr. Glenn Friedrich, dated Mar. 31, 2014, 9 pages.

Friedrich G., Statement of Dr. Glenn Friedrich, dated Oct. 16, 2014, 9 pages.

Genbank, *Homo sapiens* immunoglobulin heavy chain (IGH.1@) on chromosome 14, NCBI Ref. Sequence No. NG_001019.1, dated Jun. 26, 2002, 261 pages.

Genbank, "Mus musculus Ig kappa germline J-C region: J1-5 and C genes, and flanks," GenBank No. L80040.1, dated Sep. 2, 2003, 5 pages.

Genbank, Mus musculus immunoglobulin heavy chain locus constant region and partial variable region, strain 129S1, NCBI Reference Sequence No. AJ851868.3, dated Jul. 26, 2007, 23 pages.

(56) References Cited

OTHER PUBLICATIONS

Hasty P., et al., "Gene targeting, principles, and practice in mammalian cells," Gene Targeting, A Practical Approach, 2nd Edition, Oxford, 2000, pp. 1-175, including cover pages (XP055500641).
Jefferis R., et al., "Human immunoglobulin allotypes," mAbs,vol. 1, Issue No. 4, pp. 1-7 (Jul./Aug. 2009).
Kilpatrick K.E., et al., "Rapid Development of Affinity Matured Monoclonal Antibodies Using RIMMS," Hybridoma, 1997, vol. 16, Issue No. 4, pp. 381-389.
Little M., et al., "Of mice and men: hybridoma and recombinant antibodies," Review Immunology Today, Aug. 2000, vol. 21, Issue No. 8, pp. 364-370.
Liu X., et al., "Trisomy Eight in ES Cells Is a Common Potential Problem in Gene Targeting and Interferes With Germ Line Transmission," Developmental Dynamics, vol. 209, 1997, pp. 85-91.
Murphy A., "Declaration of Andrew J. Murphy," including Slide Presentation dated Nov. 3, 2009, at Wellcome Trust Advanced Course: Genetic Manipulation of ES Cells, in Hirixton, UK, entitled "BAC-based Modifications of the Mouse Genome: The Big and the Backward," including course timetables, 72 pages.
Odegard V.H., et al., "Targeting of somatic hypermutation," Nature Reviews—Immunology, Aug. 2006, vol. 6, pp. 573-583.
Ozawa T., et al., "Amplification and analysis of cDNA generated from a single cell by 5'-RACE: application to isolation of antibody heavy and light chain variable gene sequences from single B cells," BioTechniques—Short Technical Reports, 2006, vol. 40, Issue No. 4, pp. 469-478.
Ploegh, Hidde Dr., Declaration, submittted in U.S. Appl. No. 14/046,291 (now U.S. Pat. No. 10,526,630) dated Jul. 12, 2018, 123 pages.
Ronal D., et al., "Variegated Expression of the Endogenous Immunoglobulin Heavy-Chain Gene in the Absence of the Intronic Locus Control Region," Molecular and Cellular Biology, Oct. 1999, vol. 19, Issue No. 10, pp. 7031-7040.
Roskos L.K., et al.,"Human Antiglobulin Responses," Measuring Immunity, Dec. 2005, Chapter 13, pp. 172-186.
Sheng Y., et al., "Transformation of *Escherichia coli* with large DNA molecules by electroporation," Nucleic Acids Research, 1995, vol. 23, Issue No. 11, pp. 1990-1996.
Shiokawa S., et al., "IgM Heavy Chain Complementarity-Determining Region 3 Diversity Is Constrained by Genetic and Somatic Mechanisms Until Two Months After Birth," Journal of Immunology, May 1999, vol. 162, Issue No. 10, pp. 6060-6070.
Tung J.W., "Phenotypically distinct B cell development pathways map to the three B cell lineages in the mouse," Proceedings of the National Academy of Sciences of the U.S.A., Apr. 2006, vol. 103(16), pp. 6293-6298.
Winter D.B., et al., "Insertion of 2 KB of Bacteriophage DNA Between an Immunoglobulin Promoter and Leader Exon Stops Somatic Hypermutation in a κ Transgene," Molecular Immunology, 1997, vol. 34, Issue No. 5, pp. 359-366.
Woloschak G.E., et al., "Regulation of κ / λ Immunoglobulin Light Chain Expression in Normal Murine Lymphocytes," Moleular Immunology, 1987, vol. 24, Issue No. 7, pp. 751-757.
Brezinschek H.P., et al., "Analysis of the Heavy Chain Repertoire of Human Peripheral B Cells Using Single-Cell Polymerase Chain Reaction," The Journal of Immunology, vol. 155, 1995, pp. 190-202.
Daukss, Dana M., Third-Party Pre-Issuance Submission Under 37 CFR 1.290 in U.S. Appl. No. 16/870,413, dated Jun. 1, 2021, 34 pages.
Daukss, Dana M., Third-Party Pre-Issuance Submission Under 37 CFR 1.290 in U.S. Appl. No. 16/870,413, dated Jun. 1, 2021, 40 pages (Second Submission).
Elsen H.N., et al., "Variations in Affinities of Antibodies during the Immune Response," Biochemistry, Feb. 1964, vol. 3, Issue No. 7, pp. 996-1008.
Khodarovich Y.M., et al., "Expression of Eukaryotic Recombinant Proteins and Deriving Them from the Milk of Transgenic Animals," Applied Biochemistry and Microbiology, Problems and Aspects, 2013, vol. 49, Issue No. 9, pp. 711-722.
Hjelm B., et al., "Generation of monospecific antibodies based on affinity capture of polyclonal antibodies," Protein Science, 2011, vol. 20, pp. 1824-1835.
Maksimenko O.G., et al., "Use of Transgenic Animals in Biotechnology: Prospect and Problems," ACTA Naturae, Reviews, 2013, vol. 5, Issue No. 1, pp. 33-46.
Patil V.M., et al., "Transgenic animals and drug development: A review," Indian Journal of Public Health Research & Development, Jun. 2011, vol. 2, Issue No. 1, pp. 106-109.
Ravetch, J.V., et al., "Structure of the human immunoglobulin μ locus: Characterization of embryonic and rearranged J and D genes," Cell, Dec. 1981, vol. 27, Issue No. 3, Part 2, pp. 583-591.
Stephen, R., Cameron McKenna Nabarro Olswang LLP, Response to Opposition to EP 3028564 (Application No. 16151214.0) with supporting documents, dated Nov. 16, 2018, 164 pages.
Throsby M., et al., "Heterosubtypic Neutralizing Monoclonal Antibodies Cross-Protective against H5N1 and H1N1 Recovered from Human IgM+ Memory B Cells," PLoS One, Dec. 2008, vol. 3, Issue No. 12, pp. e3942-1-e3942-15.
Volpe J.M., et al., "Large-scale analysis of human heavy chain V(D)J recombination patterns," Immunome Research, 2008, vol. 4, Issue No. 3, 10 pages.
Voronina V.A., et al., "Deletion of Adam6 in Mus musulus leads to male subfertility an deficits in sperm ascent into the oviduct," Biology of Reproduction, 2019, vol. 100, Issue No. 3, pp. 686-696.
Xu J.L., et al., "Diversity in the CDR3 Region of VH Is Sufficient for Most Antibody Specificities," Immunity, vol. 13, Jul. 2000, pp. 37-45.
Yang C., et al., "Mutant PFN1 causes ALS phenotypes and progressive motor neuron degeneration in mice by a gain of toxicity," Proceedings of the National Academy of Sciences of the U.S.A., Sep. 2016, vol. 113, Issue No. 41, pp. E6209-E6218.
U.S. Appl. No. 14/220,074, filed Mar. 19, 2014.
U.S. Appl. No. 14/226,698, filed Mar. 26, 2014, issued May 8, 2018 as U.S. Pat. No. 9,963,716.
U.S. Appl. No. 14/818,162, filed Aug. 4, 2015.
U.S. Appl. No. 15/232,122, filed Aug. 9, 2016.
U.S. Appl. No. 15/383,188, filed Dec. 19, 2016.
U.S. Appl. No. 16/216,666, filed Dec. 11, 2018.
U.S. Appl. No. 16/296,033, filed Mar. 7, 2019.
U.S. Appl. No. 16/353,870, filed Mar. 14, 2019.
U.S. Appl. No. 17/180,258, filed Feb. 18, 2021.
[No Author Listed] IMGT Repertoire, Gene table: Protein display: Human IGH C-Regions, last updated Jun. 9, 2021, 1 page [retrieved from the internet under: http://www.imgt.org/IMGTrepertoire/Proteins/protein/human/IGH/IGHC/Hu_IGHCallgenes.html].
Almagro J.C., et al., "Therapeutic Monoclonal Antibodies from Bench to Clinic," Part IV—Antibody Engineering, Chapter 13: Antibody Engineering: Humanization, Affinity Maturation, and Selection Techniques, 2009, pp. 311-334, including cover and copyright pages, Edited by Zhiqiang An, John Wiley & Sons, Inc., ISBN 978-0-470-11791-0 [retrieved online: https://doi.org/10.1002/9780470485408.ch13].
Grund M., European Patent Attorney, Grund Intellectual Property Group, Third-Party Observations according to Article 115 EPC regarding 13723933.1, dated Sep. 20, 2021, 5 pages.
U.S. Appl. No. 09/552,219, filed Apr. 19, 2000, issued May 28, 2002 as U.S. Pat. No. 6,395,487.
U.S. Appl. No. 09/552,626, filed Apr. 19, 2000, issued Oct. 8, 2002 as U.S. Pat. No. 6,461,818.
U.S. Appl. No. 13/310,431, filed Dec. 2, 2011.
U.S. Appl. No. 13/416,684, filed Mar. 9, 2012, issued Sep. 20, 2016 as U.S. Pat. No. 9,447,177.
U.S. Appl. No. 13/433,084, filed Mar. 28, 2012, issued Sep. 20, 2016 as U.S. Pat. No. 9,445,581.
U.S. Appl. No. 13/434,361, filed Mar. 29, 2012, issued Feb. 9, 2016 as U.S. Pat. No. 9,253,965.
U.S. Appl. No. 13/740,727, filed Jan. 14, 2013, issued Nov. 29, 2016 as U.S. Pat. No. 9,505,827.
U.S. Appl. No. 13/846,672, filed Mar. 18, 2013, issued Oct. 17, 2017 as U.S. Pat. No. 9,788,534;

(56) References Cited

OTHER PUBLICATIONS

U.S. Appl. No. 13/875,892, filed May 2, 2013, issued Oct. 10, 2017 as U.S. Pat. No. 9,783,593.
U.S. Appl. No. 14/040,405, filed Sep. 27, 2013.
U.S. Appl. No. 14/040,427, filed Sep. 27, 2013.
U.S. Appl. No. 14/052,259, filed Oct. 11, 2013.
U.S. Appl. No. 14/056,434, filed Oct. 17, 2013.
U.S. Appl. No. 14/056,700, filed Oct. 17, 2013.
U.S. Appl. No. 14/056,707, filed Oct. 17, 2013.
U.S. Appl. No. 14/080,630, filed Nov. 14, 2013, issued Jan. 1, 2019 as U.S. Pat. No. 10,165,763.
U.S. Appl. No. 14/137,902, filed Dec. 20, 2013, issued Sep. 6, 2016 as U.S. Pat. No. 9,434,782.
U.S. Appl. No. 14/220,074, filed Mar. 19, 2014, issued Jul. 6, 2021 as U.S. Pat. No. 11,051,497.
U.S. Appl. No. 14/220,095, filed Mar. 19, 2014, issued Oct. 10, 2017 as U.S. Pat. No. 9,783,618.
U.S. Appl. No. 14/220,099, filed Mar. 19, 2014.
U.S. Appl. No. 14/226,598, filed Mar. 26, 2014, issued May 8, 2018 as U.S. Pat. No. 9,963,716.
U.S. Appl. No. 14/497,054, filed Sep. 25, 2014.
U.S. Appl. No. 14/498,685, filed Sep. 26, 2014, issued Apr. 9, 2019 as U.S. Pat. No. 10,251,377.
U.S. Appl. No. 14/516,461, filed Oct. 16, 2014, issued Sep. 4, 2018 as U.S. Pat. No. 10,064,398.
U.S. Appl. No. 14/543,359, filed Nov. 17, 2014, issued Jun. 2, 2020 as U.S. Pat. No. 10,667,501.
U.S. Appl. No. 14/750,870, filed Jun. 25, 2015.
U.S. Appl. No. 14/818,162, filed Aug. 4, 2015, issued Jan. 31, 2023 as U.S. Pat. No. 11,564,380.
U.S. Appl. No. 14/935,010, filed Nov. 6, 2015, issued Nov. 29, 2016 as U.S. Pat. No. 9,504,236.
U.S. Appl. No. 15/016,211, filed Feb. 4, 2016;.
U.S. Appl. No. 15/018,670, filed Feb. 8, 2016, issued Mar. 27, 2018 as U.S. Pat. No. 9,924,705.
U.S. Appl. No. 15/088,805, filed Apr. 1, 2016, issued Dec. 11, 2018 as U.S. Pat. No. 10,149,462.
U.S. Appl. No. 15/095,315, filed Apr. 11, 2016, issued Feb. 20, 2018 as U.S. Pat. No. 9,896,516.
U.S. Appl. No. 15/199,575, filed Jun. 30, 2016.
U.S. Appl. No. 15/214,963, filed Jul. 20, 2016.
U.S. Appl. No. 15/232,122, filed Aug. 9, 2016, issued Mar. 21, 2023 as U.S. Pat. No. 11,606,941.
U.S. Appl. No. 15/251,969, filed Aug. 30, 2016.
U.S. Appl. No. 15/360,502, filed Nov. 23, 2016.
U.S. Appl. No. 15/369,595, filed Dec. 5, 2016.
U.S. Appl. No. 15/383,101, filed Dec. 19, 2016.
U.S. Appl. No. 15/383,188, filed Dec. 19, 2016.
U.S. Appl. No. 15/383,196, filed Dec. 19, 2016; issued Apr. 10, 2018 as U.S. Pat. No. 9,938,357.
U.S. Appl. No. 15/383,202, filed Dec. 19, 2016, issued Apr. 10, 2018 as U.S. Pat. No. 9,938,358.
U.S. Appl. No. 15/383,342, filed Dec. 19, 2016.
U.S. Appl. No. 15/383,353, filed Dec. 19, 2016.
U.S. Appl. No. 15/385,348, filed Dec. 20, 2016.
U.S. Appl. No. 15/385,372, filed Dec. 20, 2016.
U.S. Appl. No. 15/656,897, filed Jul. 21, 2017, issued Aug. 4, 2020 as U.S. Pat. No. 10,730,930.
U.S. Appl. No. 15/690,183, filed Aug. 29, 2017, issued Mar. 12, 2019 as U.S. Pat. No. 10,226,033.
U.S. Appl. No. 15/786,281, filed Oct. 17, 2017.
U.S. Appl. No. 15/948,709, filed Apr. 9, 2018, issued Sep. 15, 2020 as U.S. Pat. No. 10,774,155.
U.S. Appl. No. 15/955,216, filed Apr. 17, 2018.
U.S. Appl. No. 15/973,376, filed May 7, 2018.
U.S. Appl. No. 16/216,666, filed Dec. 11, 2018, issued Apr. 6, 2021 as U.S. Pat. No. 10,966,412.
U.S. Appl. No. 16/296,033, filed Mar. 7, 2019, issued Apr. 12, 2022 as U.S. Pat. No. 11,297,810.
U.S. Appl. No. 16/353,870, filed Mar. 14, 2019; issued Apr. 12, 2022 as U.S. Pat. No. 11,297,811.
U.S. Appl. No. 16/721,326, filed Dec. 19, 2019.
U.S. Appl. No. 16/725,707, filed Dec. 23, 2019.
U.S. Appl. No. 16/869,416, filed May 7, 2020.
U.S. Appl. No. 16/870,365, filed May 8, 2020.
U.S. Appl. No. 16/870,413, filed May 8, 2020.
U.S. Appl. No. 16/886,057, filed May 28, 2020.
U.S. Appl. No. 16/886,394, filed May 28, 2020.
U.S. Appl. No, 16/905,537, filed Jun. 18, 2020.
U.S. Appl. No. 16/905,557, filed Jun. 18, 2020.
U.S. Appl. No. 17/020,997, filed Sep. 15, 2020.
U.S. Appl. No. 17/180,258, filed Feb. 19, 2021; issued Aug. 2, 2022 as U.S. Pat. No. 11,399,522.
U.S. Appl. No. 17/368,266, filed Jul. 6, 2021.
U.S. Appl. No. 17/703,750, filed Mar. 24, 2022.
U.S. Appl. No. 17/707,060, filed Mar. 29, 2022.
U.S. Appl. No. 17/878,628, filed Aug. 1, 2022.
U.S. Appl. No. 18/059,309, filed Nov. 29, 2022.
U.S. Appl. No. 17/943,533, filed Sep. 13, 2022.
U.S. Appl. No. 17/947,884, filed Sep. 19, 2022.
U.S. Appl. No. 18/162,043, filed Jan. 31, 2023.
U.S. Appl. No. 18/166,813, filed Feb. 9, 2023.
Sinzelle L., et al., "Transposition of a reconstructed Harbinger element in human cells and functional homology with two transposon-derived cellular genes," Proceedings of the National Academy of Sciences of the U.S.A., Mar. 2008, vol. 105, Issue No. 12, pp. 4715-4720.
Smith, K., et al., "Rapid generation of fully human monoclonal antibodies specific to a vaccinating antigen," Nature Protocols, 2009, vol. 4 (3), pp. 372-384.
Stephen, R., Cameron McKenna Nabarro Olswang LLP, Response to Opposition to EP 3241435 (Application No. 17174426.1) with supporting documents, dated Jul. 20, 2022, 21 pages.
Taiwanese Patent Office, Search Report, Taiwanese Patent Application No. 107123525, dated Nov. 14, 2022, 1 page.
Tanaka, M., et al., "Somatic chromosomal translocation between Ewsr1 and Fli1 loci leads to dilated cardiomyopathy in a mouse model," Scientific Reports, 2015, vol. 5: 7826, 9 pages.
U.S. Patent and Trademark Office, Office Action issued by Anoop K. Singh, Primary Examiner for U.S. Appl. No. 13/310,431, dated Sep. 7, 2021, 109 pages.
University of California Santa Cruz, "Human Genome Browser GRCh37/hg19 Assembly," Feb. 2009, 3 pages.
Wagner, S., et al., "The diversity of antigen-specific monoclonal antibodies from transgenic mice bearing human immunoglobulin gene miniloci," European Journal of Immunology 1994, vol. 24, pp. 2672-2681.
West, J., et al., "Genome Editing in Large Animals," J Equine Vet Sci. 2016, 41, pp. 1-6.
Wilson, M.H., et al., "PiggyBack Transposon-mediated Gene Transfer in Human Cells, the American Society of Gene Therapy, Molecular Therapy," Jan. 2007, vol. 15, Issue No. 1, pp. 136-145.
Woltjen K. et al., "piggyBac transposition reprograms fibroblast to induced pluripotent stem cells," Nature, Apr. 2009, vol. 458, pp. 766-771.
Wooddard L.E. et al., "piggyBac-ing models and new therapeutic strategies," Trends in Biotechnology, Sep. 2015, vol. 33, Issue No. 9, pp. 525-533.
Zimmerman, A., et al., "Immunoglobulin light chain (IgL) genes in zebrafish: Genomic configurations and inversional rearrangements between (VL-JL-CL) gene clusters," Developmental and comparative immunology, 2008, vol. 32(4), pp. 421-434.
Lefranc M.P., et al., "IMGT Repertoire (IG and TR) Locus representation: mouse (*Musmusculus*) IGL", Molecular Biology of B cells, (Mar. 25, 2012), pp. 37-59, [retrieved from the Internet on Mar. 24, 2023 under https://www.imgt.org/IMGTrepertoire/].
[No Author Listed] IMGT Repertoire (IG and TR), Locus representation: Human (*Homo sapiens*) IGK, dated Nov. 26, 2021, 3 pages [retrieved from the Internet under http://www.imgt.org/IMGrepertoire/index.php?section=LocusGenes&repertoire=locus&species=human&group=IGK/].

(56) References Cited

OTHER PUBLICATIONS

Bergmann-Leitner, E., et al., "Evaluation of immunoglobulin purification methods and their impact on quality and yield of antigen-specific antibodies," Malaria Journal, 2008, vol. 7 (129), 10 pages.
Bychowski M.E., Third-Party Pre-Issuance Submission Under 37 CFR 1.290 in U.S. Appl. No. 17/020,997, dated Sep. 10, 2021, 66 pages.
Canadian IP Office, Protest and Submission of Prior Art, Application No. 2,767,436, dated Oct. 11, 2022, 13 pages.
Casadevall A., et al., "Serum Therapy Revisited: Animal Models of Infection and Development of Passive Antibody Therapy," Antimicrobial Agents and Chemotherapy, Aug. 1994, vol. 38, Issue No. 8, pp. 1695-1702.
Casadevall A., et al., "The convalescent sera option for containing COVID-19," The Journal of Clinical Investigation, 2020, vol. 130, Issue No. 4, pp. 1545-1548.
Ciudad, C., et al., "Deletion of Analysis of the Chinese Hamster Dihydrofolate Reductase Gene Promoter," The Journal of Biological Chemistry, 1988, vol. 263, No. 31, pp. 16274-16282.
Clark K.J., et al., "Pigs taking wing with transposons and recombinases," Genome Biology, 2007, vol. 8, Suppl. I, Article S13, 16 pages.
Collins, A., et al., "Immunoglobulin Light Chain Gene Rearrangements, Receptor Editing and the Development of a Self-Tolerant Antibody Repertoire," Frontiers in Immunology, 2018, vol. 9, pp. 1-12.
Daukss, Dana M., Third-Party Pre-Issuance Submission Under 37 CFR 1.290 in U.S. Appl. No. 17/180,258, dated Oct. 13, 2021, 52 pages.
Dogan, I., et al., "Multiple layers of B cell memory with different effector functions" Nature Immunology 2009, vol. 10, No. 12, pp. 1292-1299.
European Patent Office, Extended European Search Report for Application No. 22168117.4, dated Oct. 24, 2022, 15 pages.
European Patent Office, Decision of the Opposition Division revoking EP2758535, dated Jun. 3, 2019, 17 pages.
European Patent Office, Deleu, Decision of Technical Board of Appeal 3.3.04, relating to Application No. EP11705964.2 (Patent No. EP2582230), dated Apr. 26, 2019 (including Datasheet and Notice of Decision to Refuse), 10 pages.
European Patent Office, Deleu, Summons to Attend Oral Proceedings pursuant to Rule 115(1) EPC, relating to Application No. EP11705964.2 (Patent No. EP2582230), dated Jul. 4, 2017, 10 pages.
European Patent Office, Extended European Search Report for Application No. 22173215.9, dated Dec. 9, 2022, 12 pages.
European Patent Office, Notice of Opposition to European Patent EP3241435 in the name of Kymab Limited pertaining to Application No. 17174426.1, dated Mar. 3, 2022, 44 pages.
Fraser M.J., et al., "Prescise excision of TTAA-specific lepidopteran transposons piggyBac (IFP2) and tagalong (TFP3) from the baculovirus genome in cell lines from two species of Lepidoptera," Insect. Molecular Biology, 1996, vol. 5, Issue No. 2, pp. 141-151.
Fraser, N., et al., "The VH gene repertoire of splenic B cells and somatic hypermutation in systemic lupus erythematosus," Arthritis Research and Therapy, 2003, vol. 5, Issue No. 2, pp. R114-R121.
Genecards, "IGKVI-13 Gene—Immunoglobulin Kappa Va . . . Pseudogene," IGKV1-13 Gene—GeneCards | IGKV1-13 Pseudogene, dated Nov. 4, 2021, 14 pages [retreived online Apr. 11, 2021, https://www.genecards.org/cgi-bin/carddisp.pl?gene=IGKV1-13].
Grund M., European Patent Attorney, Grund Intellectual Property Group, Third-Party Observations according to Article 115 EPC regarding 18153154.2, dated Mar. 18, 2022, 3 pages.
Grund M., European Patent Attorney, Grund Intellectual Property Group, Third-Party Observations according to Article 115 EPC regarding 18153171.6, dated Feb. 2, 2022, 6 pages.
Grund M., European Patent Attorney, Grund Intellectual Property Group, Third-Party Observations according to Article 115 EPC regarding 19207052.2, dated Oct. 28, 2021, 5 pages.
Grund M., European Patent Attorney, Grund Intellectual Properly Group, Third-Party Observations according to Article 115 EPC regarding 20171931.7, dated Dec. 13, 2021, 5 pages.
Grund M., European Patent Attorney, Grund Intellectual Property Group, Third-Party Observations according to Article 115 EPC regarding 20191651.7, dated Nov. 24, 2021, 7 pages.
Grund, M., European Patent Attorney, Grund Intellectual Property Group, Third-Party Observations regarding Application No. EP 20188009.3, dated Jun. 8, 2022, 4 pages.
Hayes Emily A.L., Mewbum Ellis LLP, Supplemental Response on behalf of Regeneron Pharmaceuticals, Inc. regarding Opposition filed Sep. 16, 2021 relating to European Patent No. 3,128,009 (European Appln. No. 16189625.3), dated Dec. 7, 2021, 17 pages.
Hohn B., et al., "Elimination of selection markers from transgenic plants," Current Opinion in Biotechnology, Plant biotechnology, 2001, vol. 12, pp. 139-143.
Ivics Z., et al., "Transposon-mediated genome manipulation in vertebrates," Nature Methods, Jun. 2009, vol. 6, Issue No. 6, pp. 415-422 (including Errata sheet).
Japanese Patent Office, Notice of Reasons for Rejection—Application No. 2021-026065, dated Mar. 22, 2022, together with English translation, 16 pages.
Japanese Patent Office, Notice of Reasons for Rejection—Application No. 2020-500127, dated May 30, 2022, together with English translation, 13 pages.
Kaji K., et al., "Virus-free induction of pluripotency and subsequent excision of reprogramming factors," Nature, Apr. 2009, vol. 458, pp. 771-776.
Kettleborough, C.A., et al., "Isolation of tumor cell-specific single-chain Fv from immunized mice using phage-antibody libraries and the re-construction of whole antibodies from these antibody fragments," Eur. J. Immunol. 1994, vol. 24, pp. 952-958.
Kokubu C. et al., "A transposon-based chromosomal engineering method to survey a large cis-regulatory landscape in mice," Nature Genetics, Aug. 2009, vol. 41, Issue No. 8, pp. 946-954.
Kwon, K., et al., "Instructive role of E2A in early B lymphopoiesis and germinal center B cell development," Immunity 2008, vol. 28, No. 6, pp. 751-762.
Kwon, K., et al., "Supplemental Data Instructive role of E2A in early B lymphopoiesis and germinal center B cell development," Immunity 2008, vol. 28, 24 pages.
Liu L., et al., "IGH V3-23101 and its allele V3-23*03 differ in their capacity to form the canonical human antibody combining site specific for the capsular polysaccharide of Haemophilus influenzae type b," Immunogenetics, 2003, vol. 55, pp. 336-338.
Muñoz-López M., et al., "DNA Transposons: Nature and Applications in Genomics," Current Genomics, 2010, vol. 11, pp. 115-128.
Ni J.M., et al., "Transposon tools hopping in vertebrates," Briefings in Functional Genomics and Proteomics, 2008, vol. 7, Issue No. 6, pp. 444-453.
Nicholls, James, Ja Kemp, Reply to Patentee's Grounds of Appeal, Opposition roceedings in relation to EP Patent No. 3,028,564 B1 (Appln. No. EP1615124.0), dated Nov. 24, 2021, 12 pages.
Nicholls, James, Ja Kemp, Statement of Facts and Arguments in Support of Opposition, Opposition proceedings in relation to EP Patent No. 3,622,813 B1 (Appln. No. EP19207050.6), dated Nov. 17, 2021, 56 pages.
Nicholls, James, Ja Kemp, Third-Party Observations according to Article 115 EPC regarding European Patent Application No. 21169076.3, dated May 27, 2022, 12 pages.
Nitschke, L., et al., "Deletion of the DQ52 Element Within the Ig Heavy Chain Locus Leads to a Selective Reduction in VDJ Recombination and Altered D Gene Usage," The Journal of Immunology, 2001, vol. 166(4), pp. 2540-2552.
Ogle, Ph.D., J.M., European Patent Attorney of Hoffman Eitle, Reply to Patentee's Response of Nov. 16, 2018 In Re Opposition against EP 3028564 (European Appln. No. 16151214.0), dated Feb. 12, 2019, 28 pages.
Ogle, Ph.D., J.M., European Patent Attorney of Hoffman Eitle, Subsequent Written Submission in Response to Patentee's Written Submissions of Jan. 10, 2020 and Jan. 27, 2020 In Re Opposition against EP 3028564 (European Appin. No. 16151214.0), dated Feb. 11, 2020, 10 pages.

(56) References Cited

OTHER PUBLICATIONS

Osterroth, F., et al., "Rapid expression cloning of human immunoglobulin Fab fragments for the analysis of antigen specificity of B cell lymphomas and anti-idiotype lymphoma vaccination," Journal of Immunological Methods 1999, vol. 229, pp. 141-153.
Persic, L., et al., "An integrated vector system for the eukaryotic expression of antibodies or their fragments after selection from phage display libraries," Gene 1997, vol. 187, pp. 9-18.
Porter, Andrew, Declaration for Kymab, Ltd. relating to Patent No. EP 2,792,236 B1, dated Aug. 10, 2018, 24 pages.
Romo-Gonzalez, "Novel substitution polymorphisms of human immunoglobulin VH genes in Mexicans," Human Immunology, 2005, vol. 66, pp. 732-740.
Scarselli, M., et al., "Epitope Mapping of a Bactericidal Monoclonal Antibody against the Factor H Binding Protein of Neisseria meningitidis," The Journal of Molecular Biology, Feb. 2009, vol. 386(1), pp. 97-108.
Lefranc, Marie-Paule, and Gérard Lefranc. Immunoglobulin Facts Book. London: Academic Press, 2011. Print. (pp. 1-428).†

\* cited by examiner
† cited by third party

SEQUENCE LISTING

<160> NUMBER OF SEQ ID NOS: 7

<210> SEQ ID NO 1
<211> LENGTH: 287
<212> TYPE: DNA
<213> ORGANISM: Homo sapiens

<400> SEQUENCE: 1

| | | | | | |
|---|---|---|---|---|---|
| gacatccagt | tgacccagtc | tccatccttc | ctgtctgcat | ctgtaggaga | cagagtcacc | 60 |
| atcacttgct | gggccagtca | gggcattagc | agttatttag | cctggtatca | gcaaaaacca | 120 |
| gggaaagccc | ctaagctcct | gatctatgct | gcatccactt | tgcaaagtgg | ggtcccatca | 180 |
| aggttcagcg | gcagtggatc | tgggacagaa | ttcactctca | caatcagcag | cctgcagcct | 240 |
| gaagattttg | caacttatta | ctgtcaacag | cttaatagtt | accctcc | | 287 |

<210> SEQ ID NO 2
<211> LENGTH: 287
<212> TYPE: DNA
<213> ORGANISM: Homo sapiens

<400> SEQUENCE: 2

| | | | | | |
|---|---|---|---|---|---|
| gaaattgtgt | tgacacagtc | tccagccacc | ctgtctttgt | ctccagggga | aagagccacc | 60 |
| ctctcctgca | gggccagtca | gagtgttagc | agctacttag | cctggtacca | acagaaacct | 120 |
| ggccaggctc | ccaggctcct | catctatgat | gcatccaaca | gggccactgg | catcccagcc | 180 |
| aggttcagtg | gcagtgggtc | tgggacagac | ttcactctca | ccatcagcag | cctagagcct | 240 |
| gaagattttg | cagtttatta | ctgtcagcag | cgtagcaact | ggcctcc | | 287 |

<210> SEQ ID NO 3
<211> LENGTH: 287
<212> TYPE: DNA
<213> ORGANISM: Homo sapiens

<400> SEQUENCE: 3

| | | | | | |
|---|---|---|---|---|---|
| gacatccaga | tgacccagtc | tccatcttcc | gtgtctgcat | ctgtaggaga | cagagtcacc | 60 |
| atcacttgtc | gggcgagtca | gggtattagc | agctggttag | cctggtatca | gcagaaacca | 120 |
| gggaaagccc | ctaagctcct | gatctatgct | gcatccagtt | tgcaaagtgg | ggtcccatca | 180 |
| aggttcagcg | gcagtggatc | tgggacagat | ttcactctca | ccatcagcag | cctgcagcct | 240 |
| gaagattttg | caacttacta | ttgtcaacag | gctaacagtt | tccctcc | | 287 |

<210> SEQ ID NO 4
<211> LENGTH: 287
<212> TYPE: DNA
<213> ORGANISM: Homo sapiens

<400> SEQUENCE: 4

| | | | | | |
|---|---|---|---|---|---|
| gacatccaga | tgacccagtc | tccatcttcc | gtgtctgcat | ctgtaggaga | cagagtcacc | 60 |
| atcacttgtc | gggcgagtca | gggtattagc | agctggttag | cctggtatca | gcagaaacca | 120 |
| gggaaagccc | ctaagctcct | gatctatgct | gcatccagtt | tgcaaagtgg | ggtcccatca | 180 |
| aggttcagcg | gcagtggatc | tgggacagat | ttcactctca | ccatcagcag | cctgcagcct | 240 |
| gaagattttg | caacttacta | ttgtcaacag | gctaacagtt | tccctcc | | 287 |

<210> SEQ ID NO 5
<211> LENGTH: 287
<212> TYPE: DNA
<213> ORGANISM: Homo sapiens

```
<400> SEQUENCE: 5
gccatctgga tgacccagtc tccatcctta ctctctgcat ctacaggaga cagagtcacc     60
atcagttgtc ggatgagtca gggcattagc agttatttag cctggtatca gcaaaaacca    120
gggaaagccc ctgagctcct gatctatgct gcatccactt tgcaaagtgg ggtcccatca    180
aggttcagtg gcagtggatc tgggacagat ttcactctca ccatcagctg cctgcagtct    240
gaagattttg caacttatta ctgtcaacag tattatagtt tccctcc                  287

<210> SEQ ID NO 6
<211> LENGTH: 287
<212> TYPE: DNA
<213> ORGANISM: Homo sapiens

<400> SEQUENCE: 6
gaaattgtgt tgacacagtc tccagccacc ctgtctttgt ctccagggga aagagccacc     60
ctctcctgca gggccagtca gagtgttagc agctacttag cctggtacca gcagaaacct    120
ggccaggctc ccaggctcct catctatgat gcatccaaca gggccactgg catcccagcc    180
aggttcagtg gcagtgggcc tgggacagac ttcactctca ccatcagcag cctagagcct    240
gaagattttg cagtttatta ctgtcagcag cgtagcaact ggcatcc                  287

<210> SEQ ID NO 7
<211> LENGTH: 287
<212> TYPE: DNA
<213> ORGANISM: Homo sapiens

<400> SEQUENCE: 7
gccatccagt tgacccagtc tccatcctcc ctgtctgcat ctgtaggaga cagagtcacc     60
atcacttgcc gggcaagtca gggcattagc agtgctttag cctggtatca gcagaaacca    120
gggaaagctc ctaagctcct gatctatgat gcctccagtt tggaaagtgg ggtcccatca    180
aggttcagcg gcagtggatc tgggacagat ttcactctca ccatcagcag cctgcagcct    240
gaagattttg caacttatta ctgtcaacag tttaatagtt accctcc                  287
```

ANIMALS, REPERTOIRES AND METHODS

CROSS REFERENCE

This application claims the benefit of U.S. 61/818,836 filed 2 May 2013, which is herein incorporated by reference.

The attached sequence listing is hereby incorporated by reference.

FIELD OF THE INVENTION

Antibody Gene Repertoire Sectoring & Gene Segment Inversion

The present invention is directed to the concept of sectoring antibody gene segment repertoires in order to enable the development of novel, synthetic antibody chain repertoires not seen in nature. Sectoring exploits the finite B-cell compartments of non-human vertebrates (such as mice and rats) by artificially biasing the antibody gene segment repertoire available for the production of antibody sequences in the B-cell compartments of individual naïve and immunised vertebrates. A plurality of these vertebrates together are useful as a population in immunisation schedules and research programmes to provide for access to a combined, synthetic antibody gene segment repertoire that is beyond that seen in nature and in prior art transgenic vertebrates in which antibody loci have been engineered.

The present invention is also directed to the realisation of the inventors that sectoring can also alter gene segment expression by providing new arrangements of gene segment clusters relative to other gene segments and regulatory elements in transgenic immunoglobulin loci, thereby providing for new synthetic antibody chain sequence repertoires.

To this end, the present invention provides novel, synthetically-extended antibody repertoires and immunoglobulin heavy and light chain sequence repertoires in non-human vertebrates. The present invention also provides methods of selecting an antibody from said repertoires as well as populations of non-human vertebrates (such as mice or rats) that together provide the novel synthetic (non-naturally occurring) repertoires. The invention also provides for particular non-human vertebrates that are biased to human lambda variable region expression substantially in the absence of kappa chain expression. Such vertebrates are useful in sectoring the kappa and lambda V gene repertoires to provide for novel light chain sequence repertoires according to the invention.

The invention also relates to inversion of vertebrate gene segments and use of these to construct transgenic antibody chain loci in which the inverted gene segments are functional and can contribute to new, synthetic, antibody chain and variable region repertoires.

BACKGROUND

The state of the art provides non-human vertebrates (eg, mice and rats) and cells comprising transgenic immunoglobulin loci, such loci comprising human variable (V), diversity (D) and/or joining (J) segments, and optionally human constant regions. Alternatively, endogenous constant regions of the host vertebrate (eg, mouse or rat constant regions) are provided in the transgenic loci. Methods of constructing such transgenic vertebrates and use of these to generate antibodies and nucleic acids thereof following antigen immunisation are known in the art, eg, see U.S. Pat. No. 7,501,552 (Medarex); U.S. Pat. No. 5,939,598 & U.S. Pat. No. 6,130,364 (Abgenix); WO02/066630, WO2011163311 & WO2011163314 (Regeneron); WO2011004192 & WO2011158009 (Kymab Limited); WO2009076464, WO2009143472, EP1414858, WO2009013620A2, WO2010070263A1 & WO2010109165A2 (Harbour Antibodies); EP1399559 (Crescendo Biologics) and WO2010039900 (Ablexis), the disclosures of which are explicitly incorporated herein including, but not limited to, for the purpose of providing the skilled person with guidance of how to make non-human animals bearing transgenic immunoglobulin loci and to inactivate endogenous loci expression.

It would be desirable to improve upon the prior art transgenic non-human vertebrates to provide for novel and potentially expanded repertoires and diversity of antibodies in naïve and immunised non-human vertebrates bearing transgenic immunoglobulin loci.

SUMMARY OF THE INVENTION

The present inventors addressed this by devising ways of sectoring antibody gene segment repertoires by dividing the repertoire across members of a population of antibody-generating non-human vertebrates. In devising this concept, the inventors realised that the potential for accessing greater gene segment sequence diversity (eg, human antibody gene segment and human antibody variable region diversity) would be made possible by biasing B-cell compartments of individual vertebrates to restricted gene segment sub-repertoires, so that overall the population of vertebrates enables one to access novel gene segment (and resultant antibody sequence) repertoires and potentially explore extended ranges of antibody diversities that are not produced by the prior art transgenic vertebrate collections.

By re-distributing gene segment repertoires by sectoring according to the invention, new arrangements of gene segments in immunoglobulin loci can be provided that are not found in nature or in the prior art transgenic animals. For example, when sectoring a substantially complete human functional VH gene repertoire, it is possible to provide a new location for VH gene segments that are usually distal in the natural human heavy chain locus (in this instance, VH gene segments that are further away from the DJC region of the locus are more distal than those VH gene segments that are closer, ie proximal VH gene segments). This can be done, for example, by placing a distal VH gene segment cluster (eg, 5 to 10 distal human germline VH gene segments) directly upstream of D and JH genes (eg, a substantially complete human D and JH repertoire). This effectively omits the VH gene segments that are between the distal VH gene cluster and the DJ region in a natural human heavy chain locus. In doing so, a synthetic arrangement is made in which distal VH gene segments are now much closer to the influence of proximal regulatory elements. In this respect, it has been observed that proximal V gene segments in natural loci are often recombined more frequently than distal V gene segments. Thus, by moving the distal gene segments more proximally, there is provided the possibility of altering the usage of these gene segments beyond that seen in nature. This aids the provision of novel synthetic repertoires in the present invention. Additionally, this enables the skilled person to omit gene segments that tend to dominate immune responses in vertebrates so that the utility of other gene segments can be more fully explored. The omitted gene segments may, for example, lead to relatively low affinity antibodies that dominate immune antibody repertoires in immunised mice or other non-human vertebrates. The omission removes these undesirable antibodies from the repertoire used for selection of antibody drug candidate leads. Additionally or alternatively, omission of dominating antibodies that bind a specific epitope may be desirable to enable generation and selection of antibodies that bind novel, desirable epitopes on the target antigen, eg, novel neutralising epitopes.

To this end, the invention provides the following.

In a First Configuration

In a first aspect: A method of providing a synthetic antibody heavy chain sequence repertoire, the method comprising providing a heavy chain variable region gene segment repertoire that is divided across the genomes of two or more non-human vertebrates in which endogenous heavy chain expression is substantially inactive, the repertoire gene segments in the genomes being provided as part of transgenic heavy chain loci comprising one or more VH gene segments, one or more D gene segments and one or JH gene segments functionally connected upstream of a heavy chain constant region (eg, Cmu and/or Cgamma), wherein the genomes can express different repertoires of antibody heavy chain sequences derived from VH, D and JH gene segments; Wherein the gene segment repertoire is selected from the group consisting of:

(a) a VH gene repertoire (eg, a human VH gene repertoire or a substantially complete functional human VH gene repertoire);

(b) a D gene repertoire (eg, a human D gene repertoire or a substantially complete functional human D gene repertoire); and (c) a JH gene repertoire (eg, a human JH gene repertoire or a substantially complete functional human JH gene repertoire);

Optionally wherein the D and JH segments in the loci are human D and JH segments.

In a second aspect: A method of providing a synthetic antibody kappa chain sequence repertoire, the method comprising providing a kappa chain variable region gene segment repertoire that is divided across the genomes of two or more non-human vertebrates in which endogenous kappa chain (and optionally also endogenous lambda chain) expression is substantially inactive, the repertoire gene segments in the genomes being provided as part of transgenic light chain loci comprising one or more Vκ gene segments and one or more Jκ gene segments functionally connected upstream of a light chain constant region (eg, Cκ and/or Cλ), wherein the genomes can express different repertoires of antibody kappa chain sequences derived from Vκ and Jκ gene segments;

Wherein the gene segment repertoire is selected from the group consisting of:

(a) a Vκ gene repertoire (eg, a human Vκ gene repertoire or a substantially complete functional human Vκ gene repertoire); and (c) a Jκ gene repertoire (eg, a human Jκ gene repertoire or a substantially complete functional human Jκ gene repertoire);

Optionally wherein the Jκ segments in the loci are human Jκ segments.

In a third aspect: A method of providing a synthetic antibody lambda chain sequence repertoire, the method comprising providing a lambda chain variable region gene segment repertoire that is divided across the genomes of two or more non-human vertebrates in which endogenous lambda chain (and optionally also endogenous kappa chain) expression is substantially inactive, the repertoire gene segments in the genomes being provided as part of transgenic light chain loci comprising one or more Vλ gene segments and one or more Jλ gene segments functionally connected upstream of a light chain constant region (eg, Cκ and/or Cλ), wherein the genomes can express different repertoires of antibody lambda chain sequences derived from Vλ and Jλ gene segments;

Wherein the gene segment repertoire is selected from the group consisting of:

(a) a Vλ gene repertoire (eg, a human Vλ gene repertoire or a substantially complete functional human Vλ gene repertoire); and (c) a Jλ gene repertoire (eg, a human Jλ gene repertoire or a substantially complete functional human Jλ gene repertoire);

Optionally wherein the Jλ segments in the loci are human Jλ segments.

In a fourth aspect: A method of providing a synthetic antibody light chain sequence repertoire, the method comprising providing a Vκ gene repertoire in the genomes of a first group of non-human vertebrates in which endogenous lambda chain (and optionally also endogenous kappa chain) expression is substantially inactive, the Vκ genes in the genomes being provided as part of transgenic light chain loci comprising one or more Jκ gene segments functionally connected upstream of a light chain constant region (eg, Cκ and/or Cλ, eg, human Cλ), wherein the genomes can express repertoires of antibody kappa light chain sequences derived from Vκ and Jκ gene segments substantially in the absence of lambda light chain expression; and a Vλ gene repertoire in the genomes of a second group of non-human vertebrates in which endogenous kappa chain (and optionally also endogenous lambda chain) expression is substantially inactive, the Vλ genes in the genomes being provided as part of transgenic light chain loci comprising one or more Jλ gene segments functionally connected upstream of a light chain constant region (eg, Cκ and/or Cλ, eg, human Cλ), wherein the genomes can express repertoires of antibody lambda light chain sequences derived from human Vλ and Jλ gene segments substantially in the absence of kappa light chain expression;

Optionally wherein the Vκ gene repertoire is a human Vκ gene repertoire (eg, a substantially complete functional human Vκ gene repertoire), the Vλ gene repertoire is a human Vλ gene repertoire (eg, a substantially complete functional human Vλ gene repertoire), the Jκ segments in the loci are human Jκ segments and the Jλ segments in the loci are human Jλ segments; Optionally wherein the genomes of the first and second groups comprise a substantially complete functional VH gene repertoire of a human.

In a fifth aspect: A method of providing a synthetic antibody heavy chain sequence repertoire, the method comprising providing a VH gene repertoire (eg, a substantially complete functional human VH gene repertoire) that is divided across the genomes of two or more non-human vertebrates in which endogenous heavy chain expression is substantially inactive, the VH genes in the genomes being provided as part of transgenic heavy chain loci comprising one or more human JH gene segments and one or more human D gene segments functionally connected upstream of a heavy chain constant region (eg, Cmu and/or Cgamma), wherein the genomes can express different repertoires of antibody heavy chain sequences derived from human VH, D and JH gene segments. Optionally the VH gene repertoire is a human VH gene repertoire.

In a sixth aspect: A method of providing a synthetic antibody heavy chain sequence repertoire, the method comprising providing a JH gene repertoire (eg, a substantially complete functional human JH gene repertoire) that is divided across the genomes of two or more non-human vertebrates in which endogenous heavy chain expression is substantially inactive, the JH genes in the genomes being provided as part of transgenic heavy chain loci comprising one or more human VH gene segments and one or more human D gene segments functionally connected upstream of a heavy chain constant region (eg, Cmu and/or Cgamma), wherein the genomes can express different repertoires of antibody heavy chain sequences derived from human VH, D and JH gene segments. Optionally the JH gene repertoire is a human JH gene repertoire.

In a seventh aspect: A method of providing a synthetic antibody heavy chain sequence repertoire, the method comprising providing a D gene repertoire (eg, a substantially complete functional human JH gene repertoire) that is divided across the genomes of two or more non-human vertebrates in which endogenous heavy chain expression is substantially inactive, the D genes in the genomes being provided as part of transgenic heavy chain loci comprising one or more human VH gene segments and one or more human JH gene segments functionally connected upstream of a heavy chain constant region (eg, Cmu and/or Cgamma), wherein the genomes can express different repertoires of antibody heavy chain sequences derived from human VH, D and JH gene segments. Optionally the D gene repertoire is a human D gene repertoire.

In a Second Configuration

A method of providing a synthetic antibody kappa light chain sequence repertoire, the method comprising providing a Vκ gene repertoire (eg, a substantially complete functional human Vκ gene repertoire) that is divided across the genomes of two or more non-human vertebrates in which endogenous kappa chain (and optionally also endogenous lambda chain) expression is substantially inactive, the Vκ genes in the genomes being provided as part of transgenic light chain loci comprising one or more human Jκ gene segments functionally connected upstream of a light chain constant region (eg, Cκ and/or Cλ), wherein the genomes can express different repertoires of antibody kappa light chain sequences derived from human Vκ and Jκ gene segments. Optionally, the Vκ gene repertoire is a human Vκ gene repertoire.

A method of providing a synthetic antibody kappa light chain sequence repertoire, the method comprising providing a Jκ gene repertoire (eg, a substantially complete functional human Jκ gene repertoire) that is divided across the genomes of two or more non-human vertebrates in which endogenous kappa chain (and optionally also endogenous lambda chain) expression is substantially inactive, the Jκ genes in the genomes being provided as part of transgenic light chain loci comprising one or more human Vκ gene segments functionally connected upstream of a light chain constant region (eg, Cκ and/or Cλ), wherein the genomes can express different repertoires of antibody kappa light chain sequences derived from human Vκ and Jκ gene segments. Optionally, the Jκ gene repertoire is a human Jκ gene repertoire.

In a Third Configuration

A method of providing a synthetic antibody lambda light chain sequence repertoire, the method comprising providing a Vλ gene repertoire (eg, a substantially complete functional human Vλ gene repertoire) that is divided across the genomes of two or more non-human vertebrates in which endogenous lambda chain (and optionally also endogenous kappa chain) expression is substantially inactive, the Vλ genes in the genomes being provided as part of transgenic light chain loci comprising one or more human Jλ gene segments functionally connected upstream of a light chain constant region (eg, Cκ and/or Cλ, eg, human Cλ), wherein the genomes can express different repertoires of antibody lambda light chain sequences derived from human Vλ and Jλ gene segments. Optionally, the Vλ gene repertoire is a human Vλ gene repertoire.

A method of providing a synthetic antibody lambda light chain sequence repertoire, the method comprising providing Jλ gene repertoire (eg, a substantially complete functional human Jλ gene repertoire) that is divided across the genomes of two or more non-human vertebrates in which endogenous lambda chain (and optionally also endogenous kappa chain) expression is substantially inactive, the Jλ genes in the genomes being provided as part of transgenic light chain loci comprising one or more human Vλ gene segments functionally connected upstream of a light chain constant region (eg, Cκ and/or Cλ, eg, human Cλ), wherein the genomes can express different repertoires of antibody lambda light chain sequences derived from human Vλ and Jλ gene segments. Optionally, the Jλ gene repertoire is a human Jλ gene repertoire.

In a Fourth Configuration

A method of providing a synthetic antibody light chain sequence repertoire, the method comprising providing a Vκ gene repertoire (eg, a substantially complete functional human Vκ gene repertoire) in the genomes of a first group of non-human vertebrates in which endogenous lambda chain (and optionally also endogenous kappa chain) expression is substantially inactive, the Vκ genes in the genomes being provided as part of transgenic light chain loci comprising one or more human Jκ gene segments functionally connected upstream of a light chain constant region (eg, Cκ and/or Cλ, eg, human Cλ), wherein the genomes can express repertoires of antibody kappa light chain sequences derived from human Vκ and Jκ gene segments substantially in the absence of kappa light chain expression; and a Vλ gene repertoire (eg, a substantially complete functional human Vλ gene repertoire) in the genomes of a second group of non-human vertebrates in which endogenous kappa chain (and optionally also endogenous lambda chain) expression is substantially inactive, the Vλ genes in the genomes being provided as part of transgenic light chain loci comprising one or more human Jλ gene segments functionally connected upstream of a light chain constant region (eg, Cκ and/or Cλ, eg, human Cλ), wherein the genomes can express repertoires of antibody lambda light chain sequences derived from human Vλ and Jλ gene segments substantially in the absence of kappa light chain expression;

Optionally wherein the genomes of the first and second groups comprise a substantially complete functional VH gene repertoire of a human;

Optionally wherein the Vκ and Vλ gene repertoires are human Vκ and Vλ gene repertoires.

In a Fifth Configuration

A method of providing a synthetic antibody heavy chain sequence repertoire, the method comprising (a) providing a population of transgenic non-human vertebrates (optionally mice or rats), wherein the population provides a repertoire of different human VH gene segments, the repertoire being divided between two or more vertebrates of said population, (b) a first vertebrate of said population comprising a transgenic heavy chain locus comprising one or more human VH gene segments (first VH gene sub-repertoire), D segments and J segments operably connected upstream of a constant region; and (c) a second vertebrate of said population comprising a transgenic heavy chain locus comprising one or more human VH gene segments (second VH gene sub-repertoire), D segments and J segments operably connected upstream of a constant region;

(d) wherein the first VH gene sub-repertoire is different from the second VH gene sub-repertoire, whereby the first vertebrate can produce a heavy chain sequence repertoire that is different from the heavy chain sequence repertoire produced by the second vertebrate.

In a Sixth Configuration

A method of providing a synthetic antibody light chain sequence repertoire, the method comprising (a) providing a population of transgenic non-human vertebrates (optionally mice or rats), wherein the population provides a repertoire of different human VL gene segments, the repertoire being divided between two or more vertebrates of said population, (b) a first vertebrate of said population comprising a transgenic light chain locus comprising one or more human VL gene segments (first VL gene sub-repertoire) and J segments operably connected upstream of a constant region; and (c) a second vertebrate of said population comprising a transgenic light chain locus comprising one or more human VL gene segments (second VL gene sub-repertoire) and J segments operably connected upstream of a constant region;

(d) wherein the first VL gene sub-repertoire is different from the second VL gene sub-repertoire, whereby the first vertebrate can produce a light chain sequence repertoire that is different from the light chain sequence repertoire produced by the second vertebrate.

In a Seventh Configuration

A method of selecting an antibody that binds a predetermined antigen, the method comprising (a) providing a repertoire of antibodies (first repertoire) that bind said antigen, wherein the antibodies comprise human heavy and light chain variable regions and the repertoire comprises
  i. A sub-repertoire of antibodies (lambda sub-repertoire) whose light chain variable regions are produced by rearrangement of a human Vλ gene segment with a human $J_L$ gene segment; and
  ii. A sub-repertoire of antibodies (kappa sub-repertoire) whose light chain variable regions are produced by rearrangement of a human Vκ gene segment with a human $J_L$ gene segment;

(b) selecting one or more antibodies from the lambda sub-repertoire according to a desired antibody characteristic (eg, binding affinity for said antigen);

(c) selecting one or more antibodies from the kappa sub-repertoire according to a desired antibody characteristic; wherein a repertoire (second repertoire) of selected lambda and kappa antibodies is produced, the antibodies of the second repertoire comprising human variable regions that bind said antigen; and (d) Selecting one or more antibodies from said second repertoire on the basis of said desired antibody characteristic;

Wherein in step (a)(i) the lambda sub-repertoire is produced by immunisation of one or more non-human vertebrates (optionally mice or rats) (lambda vertebrates) with said antigen, wherein the lambda vertebrates express more human lambda-type antibodies (antibodies whose light chain variable regions are derived from the rearrangement of a human Vλ gene segment) than kappa-type antibodies (antibodies whose light chain variable regions are derived from the rearrangement of a Vκ gene segment);

Wherein in step (a)(ii) the kappa sub-repertoire is produced immunisation of one or more non-human vertebrates (optionally mice or rats) (kappa vertebrates) with said antigen, wherein the kappa vertebrates express more human kappa-type antibodies (antibodies whose light chain variable regions are derived from the rearrangement of a human Vκ gene segment) than lambda-type antibodies (antibodies whose light chain variable regions are derived from the rearrangement of a Vλ gene segment).

In a Eighth Configuration

A population of transgenic non-human vertebrates (optionally mice or rats), wherein the population provides a repertoire of different human VH gene segments, the repertoire being divided between two or more vertebrates of said population, (a) a first vertebrate of said population comprising a transgenic heavy chain locus comprising one or more human VH gene segments (first VH gene sub-repertoire), D segments and J segments operably connected upstream of a constant region; and (b) a second vertebrate of said population comprising a transgenic heavy chain locus comprising one or more human VH gene segments (second VH gene sub-repertoire), D segments and J segments operably connected upstream of a constant region;

(c) wherein the first VH gene sub-repertoire is different from the second VH gene sub-repertoire for expression of first and second antibody heavy chain sequence repertoires respectively that are different from each other, whereby the population provides a synthetic repertoire of antibody heavy chain sequences.

In a Ninth Configuration

A population of transgenic non-human vertebrates (optionally mice or rats), wherein the population provides a repertoire of different human VL gene segments, the repertoire being divided between two or more vertebrates of said population, (a) a first vertebrate of said population comprising a transgenic light chain locus comprising one or more human VL gene segments (first VL gene sub-repertoire) and J segments operably connected upstream of a constant region; and (b) a second vertebrate of said population comprising a transgenic light chain locus comprising one or more human VL gene segments (second VL gene sub-repertoire) and J segments operably connected upstream of a constant region;

(c) wherein the first VL gene sub-repertoire is different from the second VL gene sub-repertoire for expression of first and second antibody light chain sequence repertoires respectively that are different from each other, whereby the population provides a synthetic repertoire of antibody light chain sequences.

In a Tenth Configuration

A population of non-human vertebrates (optionally mice or rats), wherein the genome of each vertebrate comprises:
(a) One or more transgenic immunoglobulin heavy chain loci, each locus comprising one or more human V gene segments, one or more human D gene segments and one or more human J gene segments upstream of one or more heavy chain constant regions; and
(b) One or more transgenic immunoglobulin light chain loci, each locus comprising one or more human $V_L$ gene segments and one or more human $J_L$ gene segments upstream of one or more light chain constant regions;

Wherein in each vertebrate the gene segments in transgenic heavy chain loci are operably linked to the constant region thereof, and the gene segments in transgenic light chain loci are operably linked to the constant region thereof, so that upon immunisation the vertebrate is capable of producing an antibody comprising heavy chains produced by recombination of a heavy chain locus and light chains produced by recombination of a light chain locus, wherein the heavy and light chains comprise human variable regions;

Wherein the population comprises (i) a first vertebrate type (lambda vertebrates) wherein said light chain loci comprise one or more human Vλ gene segments, wherein following rearrangement the loci express light chain sequences comprising variable region sequences derived from human Vλ gene segments (human lambda light chain sequences), wherein the lambda vertebrates express more lambda light chain sequences than kappa light chain sequences (sequences of light chains comprising variable region sequences derived from Vκ gene segments); and (ii) a second vertebrate type (kappa vertebrates) wherein said light chain loci comprise one or more human Vκ gene segments, wherein following rearrangement the loci express light chain sequences comprising variable region sequences derived from human Vκ gene segments (human kappa light chain sequences), wherein the kappa vertebrates express more kappa light chain sequences than lambda light chain sequences (sequences of light chains comprising variable regions derived from Vλ gene segments);

wherein the vertebrates of said population can be immunised with the same antigen to produce a repertoire of antibodies comprising human heavy and light chain variable regions, wherein the repertoire comprises a sub-repertoire of human lambda antibodies (lambda sub-repertoire) produced by vertebrates of the first type and a sub-repertoire of human kappa antibodies (kappa sub-repertoire) produced by vertebrates of the second type.

In a Eleventh Configuration

A non-human vertebrate (optionally a mouse or rat), wherein the genome of each vertebrate comprises:

(c) One or more transgenic immunoglobulin heavy chain loci, each locus comprising one or more human V gene segments, one or more human D gene segments and one or more human J gene segments upstream of one or more heavy chain constant regions; and (d) One or more transgenic immunoglobulin light chain loci, each locus comprising a human $V_\lambda$ gene segment repertoire and one or more human $J\lambda$ gene segments upstream of one or more light chain constant regions;

Wherein following rearrangement the light chain loci express light chain sequences comprising variable region sequences derived from human Vλ gene segments (human lambda light chain sequences);

Wherein the kappa (and optionally endogenous lambda) light chain expression has been substantially inactivated so that the vertebrate expresses more human lambda light chain sequences than kappa light chain sequences (sequences of light chains comprising variable region sequences derived from Vκ gene segments);

Wherein endogenous heavy chain expression has been substantially inactivated; and Wherein each said transgenic light chain locus comprises a substantially complete functional $V_\lambda$ gene segment repertoire of a human.

In an Twelfth Configuration:

A method of providing a synthetic antibody heavy chain repertoire, the method comprising (a) Dividing a human VH gene segment repertoire (eg, a substantially complete functional human VH gene repertoire) across the genomes of at least first and second non-human vertebrates (eg, mice or rats), the repertoire comprising a first cluster of VH gene segments corresponding to a distal VH gene cluster of the heavy chain locus of a human; and a second cluster of VH gene segments corresponding to a proximal VH gene cluster of the heavy chain locus of a human, wherein the proximal cluster is arranged proximally to the distal cluster in said human locus;

Wherein the distal cluster is provided in a heavy chain locus of said first vertebrate upstream of one or more D gene segments, one or more JH gene segments and one or more constant regions;

Wherein the proximal cluster is provided in a heavy chain locus of said second vertebrate upstream of one or more D gene segments, one or more JH gene segments and one or more constant regions;

Wherein the proximal VH gene cluster is not present between the distal cluster and the D gene segments in the heavy chain locus of the first vertebrate (optionally wherein no further VH gene segments are present between the distal cluster and the D gene segments in the heavy chain locus of the first vertebrate); and (b) Expressing said heavy chain loci of the first and second vertebrates to provide a repertoire of synthetic antibody heavy chains.

A method of providing a synthetic antibody kappa chain repertoire, the method comprising (a) Dividing a human Vκ gene segment repertoire (eg, a substantially complete functional human Vκ gene repertoire) across the genomes of at least first and second non-human vertebrates (eg, mice or rats), the repertoire comprising a first cluster of Vκ gene segments corresponding to a distal Vκ gene cluster of the kappa chain locus of a human; and a second cluster of Vκ gene segments corresponding to a proximal Vκ gene cluster of the kappa chain locus of a human, wherein the proximal cluster is arranged proximally to the distal cluster in said human locus;

Wherein the distal cluster is provided in a kappa chain locus of said first vertebrate upstream of one or more Jκ gene segments and one or more constant regions;

Wherein the proximal cluster is provided in a kappa chain locus of said second vertebrate upstream of one or more Jκ gene segments and one or more constant regions; Wherein the proximal Vκ gene cluster is not present between the distal cluster and the Jκ gene segments in the kappa chain locus of the first vertebrate (optionally wherein no further Vκ gene segments are present between the distal cluster and the Jκ gene segments in the kappa chain locus of the first vertebrate); and (b) Expressing said kappa chain loci of the first and second vertebrates to provide a repertoire of synthetic antibody kappa chains.

A method of providing a synthetic antibody lambda chain repertoire, the method comprising (a) Dividing a human Vλ gene segment repertoire (eg, a substantially complete functional human Vλ gene repertoire) across the genomes of at least first and second non-human vertebrates (eg, mice or rats), the repertoire comprising a first cluster of Vλ gene segments corresponding to a distal Vλ gene cluster of the lambda chain locus of a human; and a second cluster of Vλ gene segments corresponding to a proximal Vλ gene cluster of the lambda chain locus of a human, wherein the proximal cluster is arranged proximally to the distal cluster in said human locus;

Wherein the distal cluster is provided in a lambda chain locus of said first vertebrate upstream of one or more Jλ gene segments and one or more constant regions;

Wherein the proximal cluster is provided in a lambda chain locus of said second vertebrate upstream of one or more Jλ gene segments and one or more constant regions;

Wherein the proximal Vλ gene cluster is not present between the distal cluster and the Jλ gene segments in the lambda chain locus of the first vertebrate (optionally wherein no further Vλ gene segments are present between the distal cluster and the Jλ gene segments in the lambda chain locus of the first vertebrate); and (b) Expressing said lambda chain loci of the first and second vertebrates to provide a repertoire of synthetic antibody lambda chains.

In a Thirteenth Configuration:

A non-human vertebrate (optionally a mouse or a rat) or vertebrate cell (optionally a mouse cell or a rat cell) whose genome comprises a transgenic antibody chain locus comprising one or more human V gene segments and one or more human J gene segments (and optionally one or more human D gene segments) upstream of a constant region, the locus comprising one or more inverted vertebrate species gene segments, the inverted gene segment(s) being present in the locus in a 5'-3' orientation that is opposite to the vertebrate species germline orientation of such segment(s), and wherein the non-human vertebrate or cell is capable of expressing an antibody chain sequence comprising a sequence that is derived from an inverted gene segment.

Thus, the gene segments are naturally present in an opposite orientation to the corresponding CL or Cμ in the germline locus of a vertebrate of the relevant species (eg, human), but by virtue of the present invention these are inverted so that the gene segment orientation is the same as the CL or Cμ.

A non-human vertebrate (optionally a mouse or a rat) or vertebrate cell (optionally a mouse cell or a rat cell) whose genome comprises a transgenic antibody chain locus comprising one or more human V gene segments and one or more human J gene segments (and optionally one or more human D gene segments) upstream of a constant region, wherein the locus comprises one or more inverted human gene segments, the inverted human gene segment(s) being present in the locus in a 5'-3' orientation that is opposite to the human germline orientation of such segment(s), and wherein the vertebrate or cell is capable of expressing an antibody chain sequence comprising a variable region that is derived from recombination of an inverted gene segment.

A method of providing an artificial human antibody variable region repertoire, the method comprising inserting one or more human V gene segment(s) (inverted gene segments) upstream of one or more J gene segments, optionally one or more D gene segments, and a constant region in an antibody chain locus of a non-human vertebrate or non-human vertebrate cell, the V gene segment(s) being present in the locus in a 5'-3' orientation that is opposite to the human germline orientation of such segment(s), and wherein the non-human vertebrate or cell (or a non-human vertebrate progeny derived from the cell) is capable of expressing an antibody chain sequence comprising a variable region sequence that is derived from recombination of an inverted gene segment.

A method of providing an artificial human antibody variable region repertoire, the method comprising isolating serum or lymphoid cells (eg, spleen cells or B-cells) from a vertebrate described above, and optionally isolating from the serum or cells one or more antibodies that specifically bind a predetermined antigen.

K1: comprises an endogenous Ig kappa locus in which has been inserted the human gene segments Vκ1-19 to Jκ5;

K2: comprises an endogenous Ig kappa locus in which has been inserted the human gene segments Vκ2-24 to Jκ5; and K3: comprises an endogenous Ig kappa locus in which has been inserted the human gene segments Vκ2D-40 to Jκ5.

Figure 8:
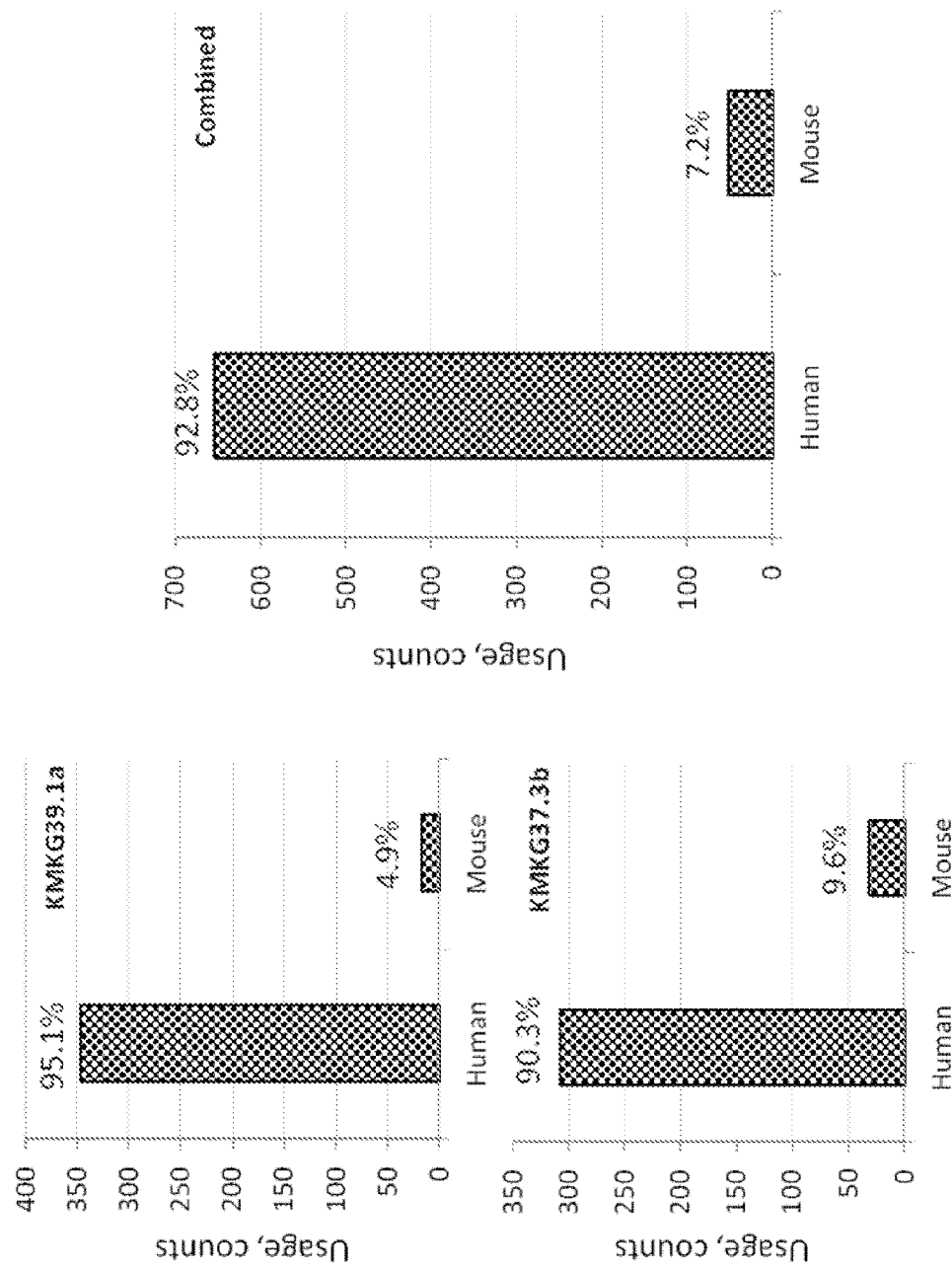

FIG. 8: shows total human Vκ gene segment usage versus mouse Vκ usage in transcripts from mice comprising an insertion of human Vκ and Jκ gene segments into an endogenous mouse kappa locus between the 3'-most mouse Jκ and the mouse Cκ.

K3/KA-K3—the first endogenous kappa allele has three kappa chain locus DNA insertions between the most 3' endogenous Jκ and the mouse Cκ, providing an insertion of 20 human Vκ and Jκ1-Jκ5; and (ii) KA—the second endogenous kappa allele has been inactivated (by insertion of an endogenous interrupting sequence). This arrangement encodes exclusively for kappa light chains from the first endogenous kappa allele.

Figure 9:
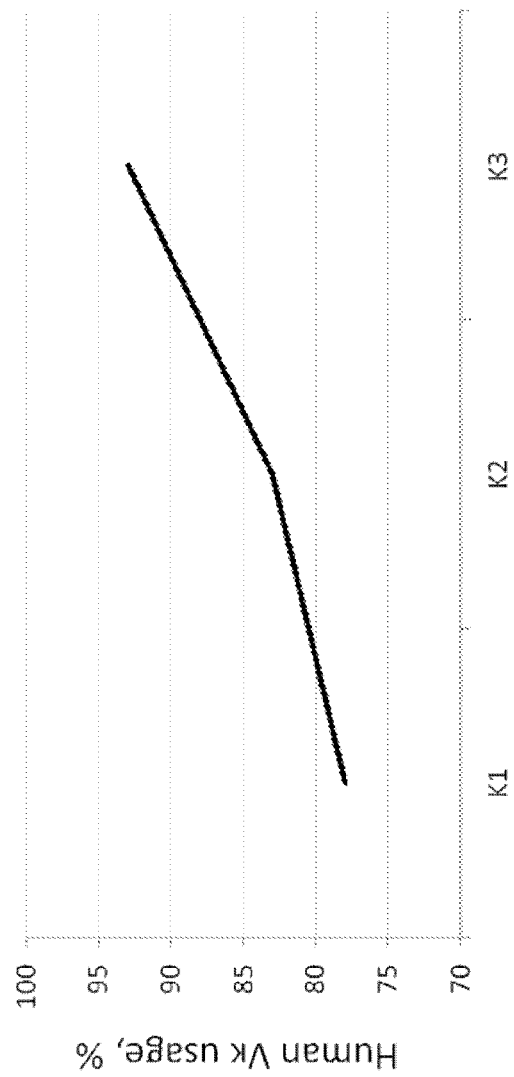

FIG. 9: illustrates the improvement in human Vκ gene segment usage in transcripts (and thus improvement in inactivation of endogenous mouse Vκ gene segment usage) as human kappa locus DNA is inserted in successive BACs 1-3. BAC1 inserts 6 human Vκ and Jκ1-Jκ5 between the 3' endogenous Jκ and the mouse Cκ. BAC2 inserts an additional 8 human Vκ gene segments 5' to the human DNA inserted from the BAC1, resulting in 14 human Vκ and Jκ1-Jκ5 between the 3' endogenous Jκ and the mouse Cκ. BAC3 inserts an additional 6 human Vκ gene segments 5' to the human DNA inserted from the BAC2, resulting in 20 human Vκ and Jκ1-Jκ5 between the 3' endogenous Jκ and the mouse Cκ. With each insertion, the endogenous mouse VJ region is pushed further upstream (5') and inactivation is enhanced.

Figure 10:
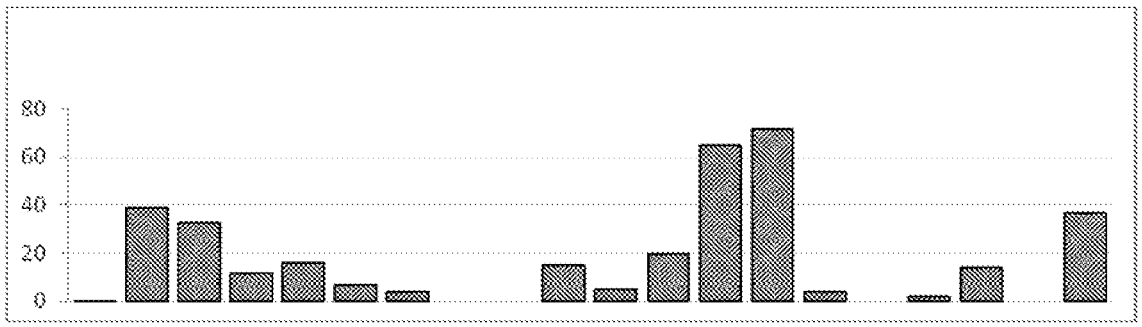

FIG. 10: illustrates the distribution of human Vκ usage at the transcript level from the K3/KA mice.

Figure 11:
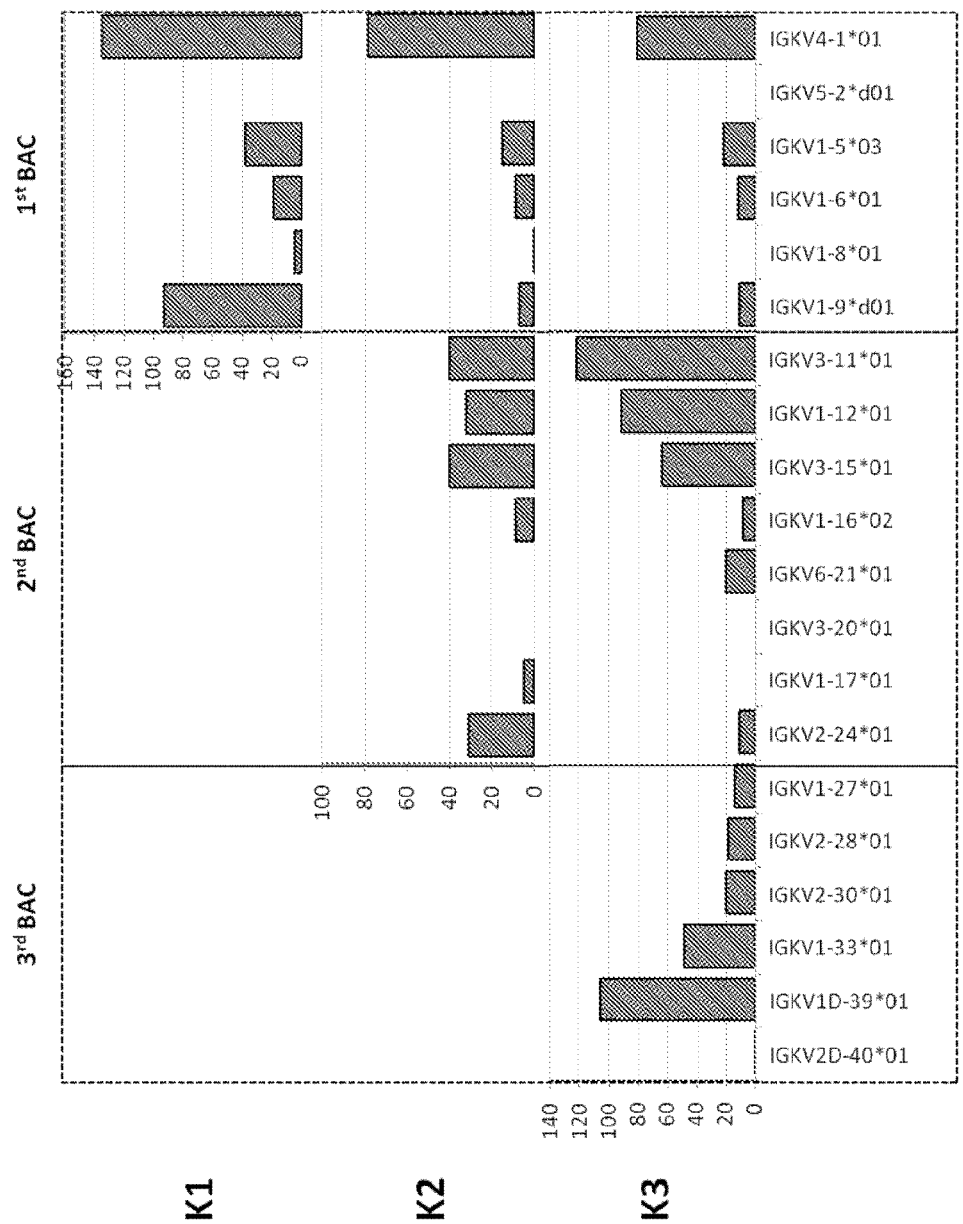

FIG. 11: compares the effect of sectoring the 20 human Vκ gene segment repertoire across three different mice-types (corresponding to insertion of human gene segment DNA from BAC1 only (K1 genotype), BACs1+2 (K2 genotype) and BACs1+2+3 (K3 genotype). Illustrated is the distribution of human Vκ usage at the transcript level from the mice. Different Vκ usage was seen resulting in mice that produced different kappa chain repertoires (and corresponding different human kappa variable region repertoires) as a result of the human gene repertoire sectoring.

Figure 12:
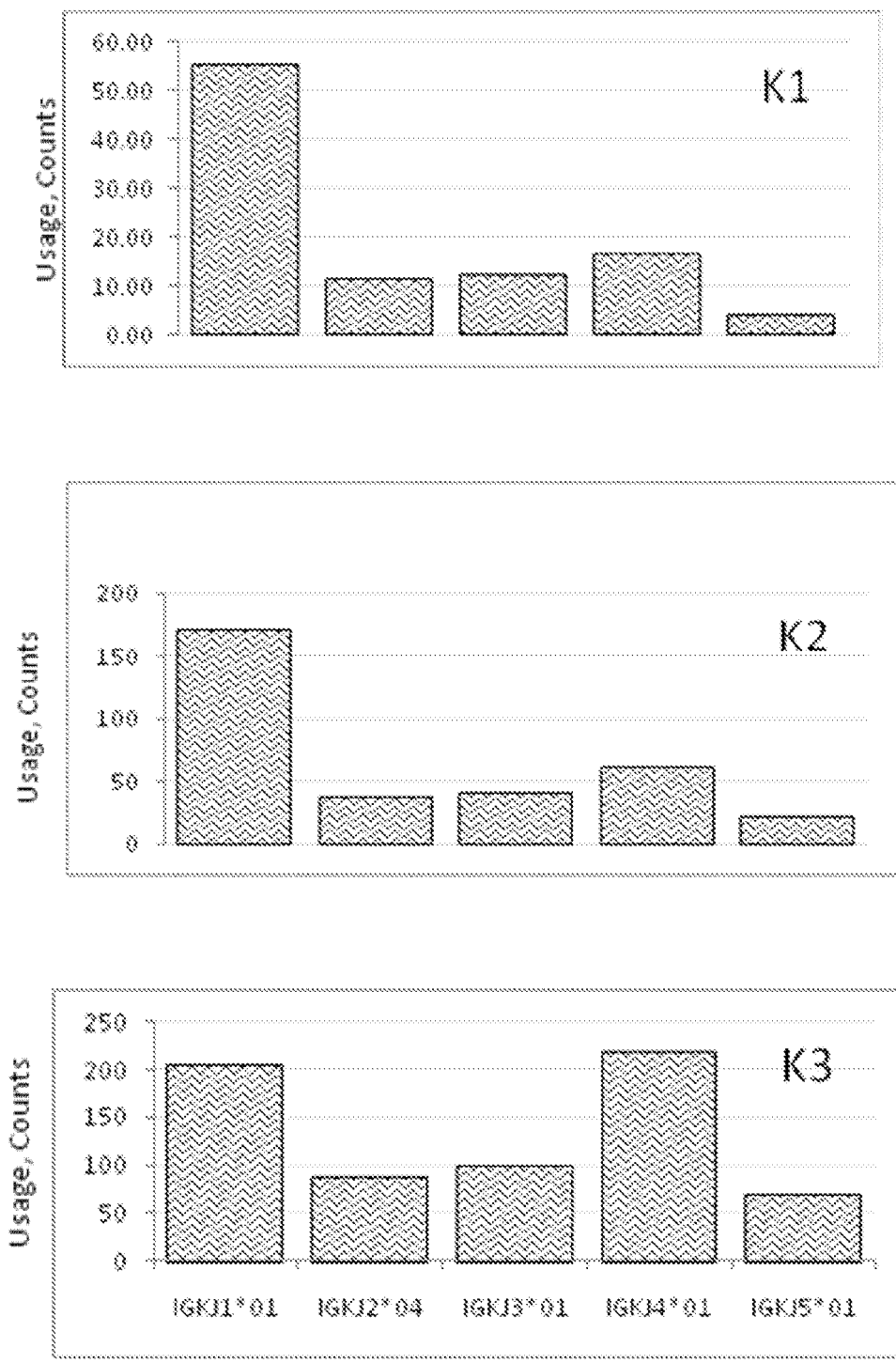

FIG. 12: compares the effect of sectoring the human Jκ gene segment repertoire across three different mice-types (K1, K2 and K3). Illustrated is the distribution of human Jκ usage at the transcript level from the mice. Different Jκ usage was seen resulting in mice that produced different kappa chain repertoires (and corresponding different human kappa variable region repertoires) as a result of the human gene repertoire sectoring.

Figure 13:
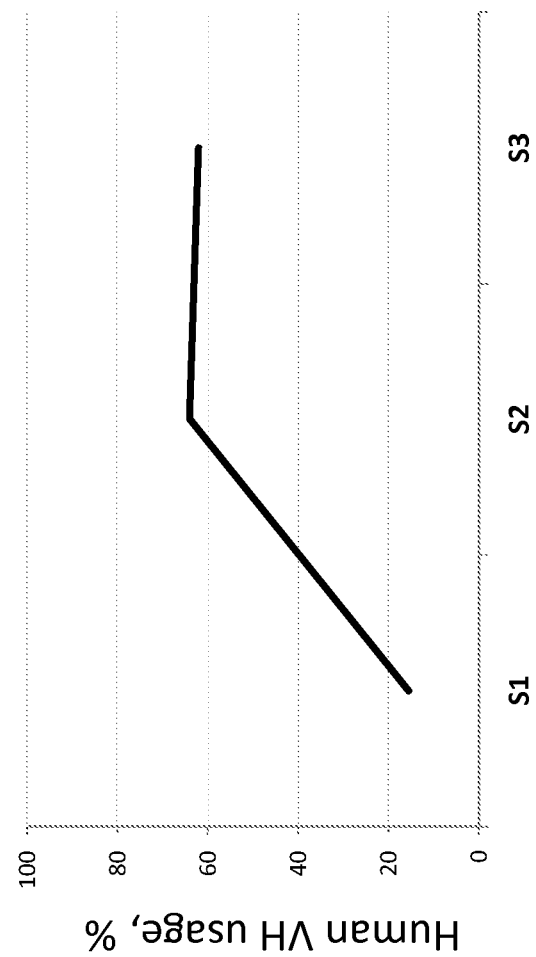

FIG. 13: illustrates the improvement in human VH gene segment usage in transcripts (and thus improvement in inactivation of endogenous mouse VH gene segment usage) as human heavy chain locus DNA is inserted in successive BACs 1-3 (producing S1 chimaeric heavy chain locus (human VDJ gene segments from BAC1 only have been inserted), S2 chimaeric heavy chain locus (human VDJ gene segments from BACs1 & 2 have been inserted) and S3 chimaeric heavy chain locus ((human VDJ gene segments from BACs 1, 2 & 3 have been inserted)). BAC1 inserts 6 human VH and all functional human DH and JH gene segments between the 3' endogenous JH (mouse JH4) and the mouse C-mu. BAC2 inserts an additional 5 human VH gene segments 5' to the human DNA inserted from the BAC1, resulting in 11 human VH and all functional human DH and JH between the 3' endogenous JH4 and the mouse C-mu. BAC3 inserts an additional 7 human VH gene segments 5' to the human DNA inserted from the BAC2, resulting in 18 human VH and all functional human DH and JH between the 3' endogenous JH4 and the mouse C-mu. With each insertion, the endogenous mouse heavy chain VDJ region is pushed further upstream (5') and inactivation is enhanced.

BAC1 human gene segments: VH2-5, 7-4-1, 4-4, 1-3, 1-2, 6-1, and all the human D and JH gene segments D1-1, 2-2, 3-9, 3-10, 4-11, 5-12, 6-13, 1-14, 2-15, 3-16, 4-17, 5-18, 6-19, 1-20, 2-21, 3-22, 4-23, 5-24, 6-25, 1-26 and 7-27; and J1, J2, J3, J4, J5 and J6.

BAC2 human gene segments: VH3-7, 1-8, 3-9, 3-11 and 3-13.

BAC3 human gene segments: VH3-15, 1-18, 3-20, 3-21, 3-23, 1-24 and 2-26.

Figure 14:
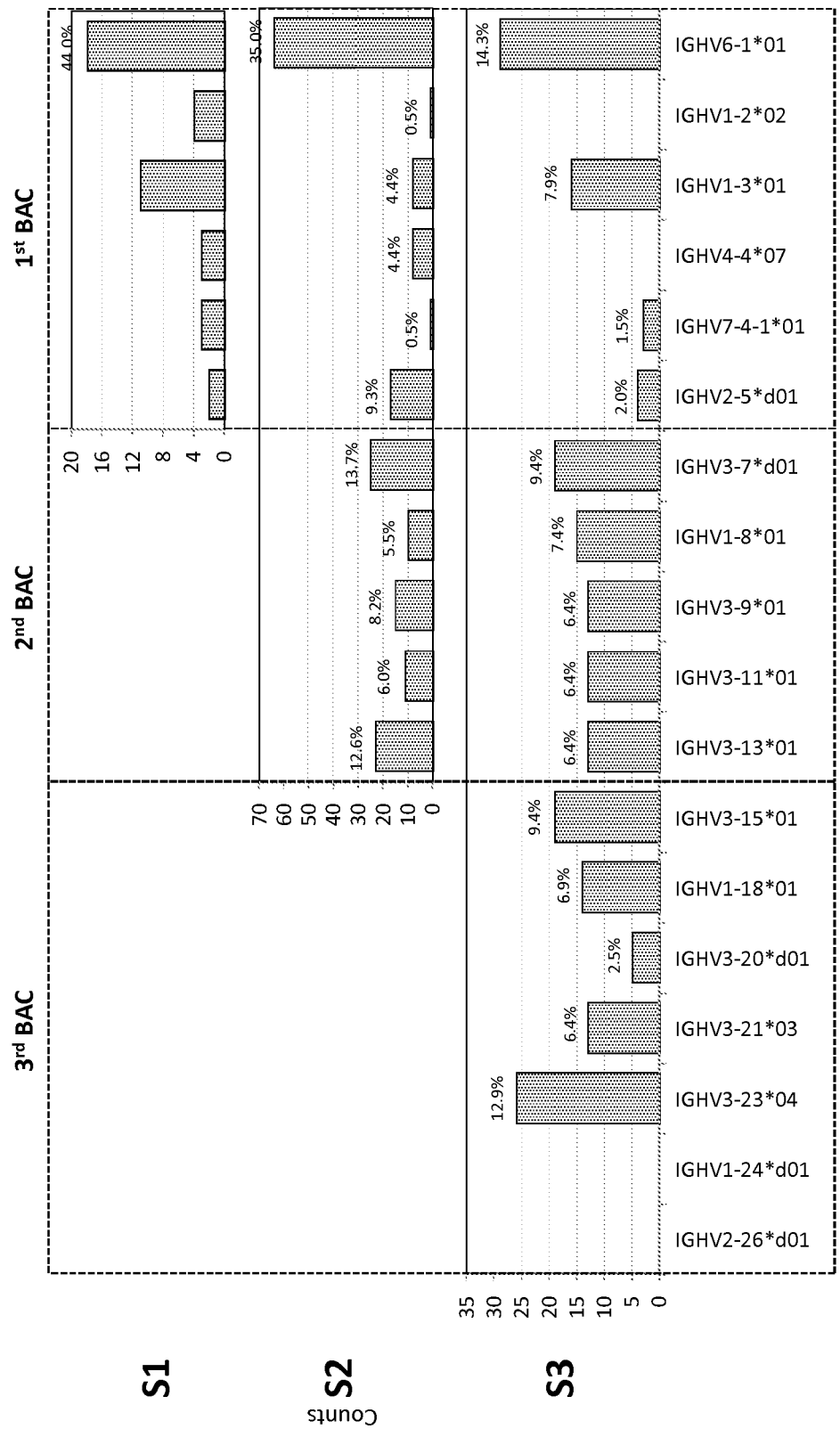

FIG. 14: compares the effect of sectoring the 18 human VH gene segment repertoire across three different mice-types (corresponding to insertion of human gene segment DNA from BAC1 only (S1 genotype), BACs1+2 (S2 genotype) and BACs1+2+3 (S3 genotype). Illustrated is the distribution of human VH usage at the transcript level from the mice. Different VH usage was seen resulting in mice that produced different heavy chain repertoires (and corresponding different human heavy chain variable region repertoires) as a result of the human gene repertoire sectoring.

Figure 15:
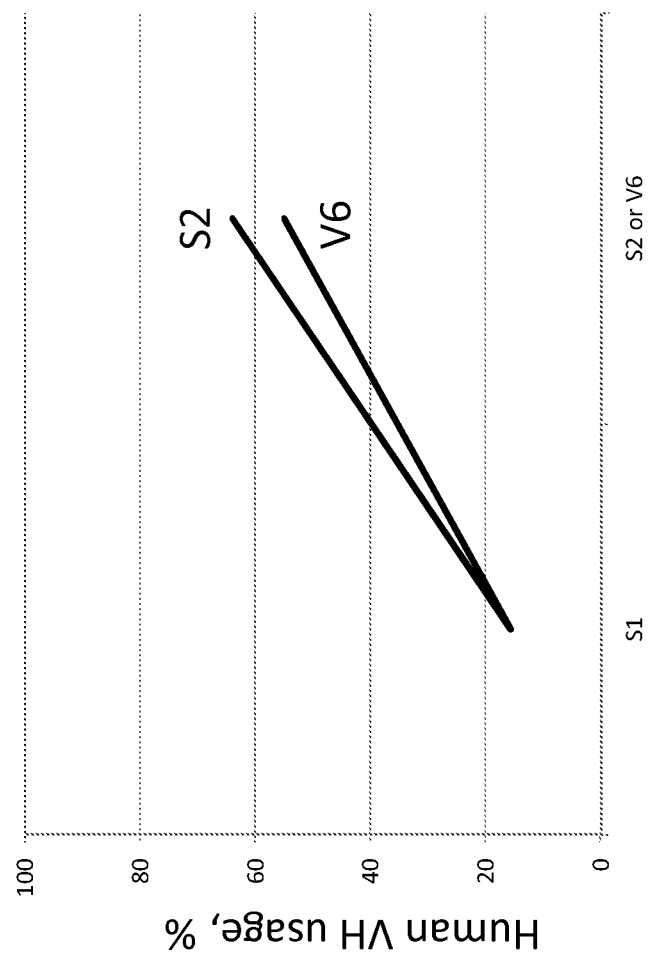

FIG. 15: illustrates the improvement in human VH gene segment usage in transcripts (and thus improvement in inactivation of endogenous mouse VH gene segment usage) as human heavy chain locus DNA is inserted in successive BACs for the S1 chimaeric heavy chain locus (human VDJ gene segments from BAC1 only have been inserted) versus the S2 chimaeric heavy chain locus (human VDJ gene segments from BACs1 & 2 have been inserted) and V6 chimaeric heavy chain locus ((human VDJ gene segments from BACs 1 & 6 have been inserted)). BAC1 inserts 6 human VH and all functional human DH and JH gene segments between the 3' endogenous JH (mouse JH4) and the mouse C-mu. BAC2 inserts an additional 5 human VH gene segments 5' to the human DNA inserted from the BAC1, resulting in 11 human VH and all functional human DH and JH between the 3' endogenous JH4 and the mouse C-mu. BAC6 adds 8 human VH gene segments 5' to the human DNA inserted from BAC1, resulting in 14 human VH and all functional human DH and JH between the 3' endogenous JH4 and the mouse C-mu. With each insertion, the endogenous mouse heavy chain VDJ region is pushed further upstream (5') and inactivation is enhanced.

BAC6 human gene segments: VH3-66, 3-64, 4-61, 4-59, 1-58, 3-53, 5-51 and 3-49.

Figure 16:
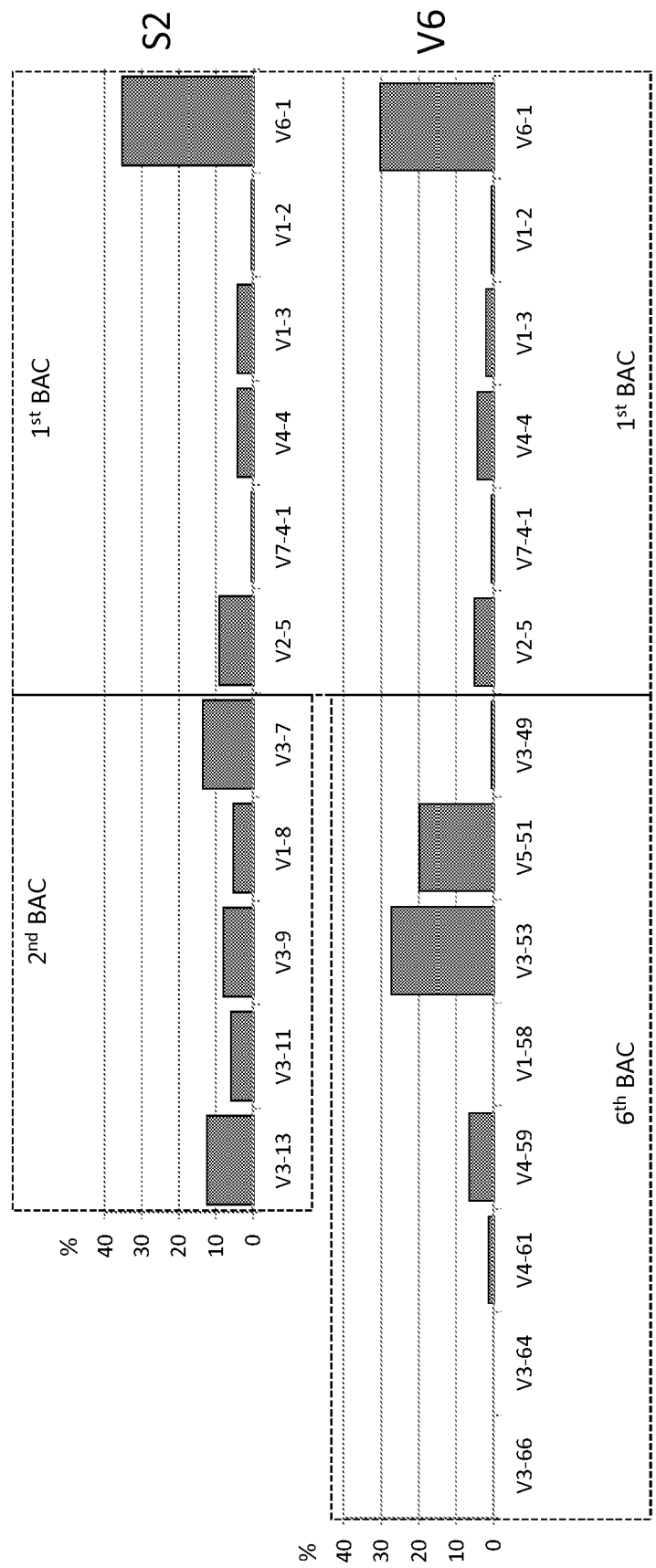

FIG. 16: compares the effect of sectoring a 19 human VH gene segment repertoire across two different mice-types (corresponding to insertion of human gene segment DNA from BACs1+2 (S2 genotype) and BACs1+6 (V6 genotype). Illustrated is the distribution of human VH usage at the transcript level from the mice. Different VH usage was seen resulting in mice that produced different heavy chain repertoires (and corresponding different human heavy chain variable region repertoires) as a result of the human gene repertoire sectoring.

Figure 17:
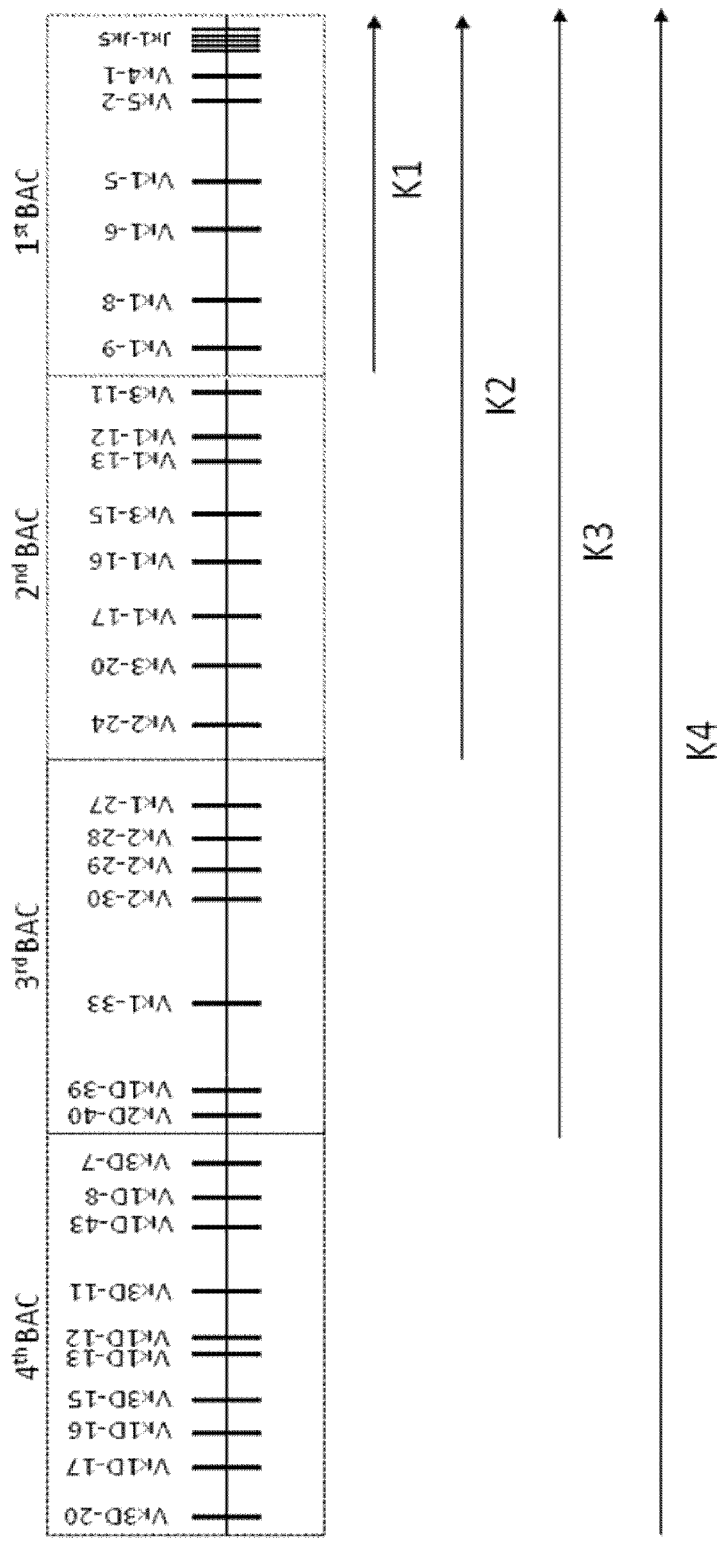

FIG. 17: shows the human gene segment repertoires contained in the first, second, third and fourth BACs used to construct four different mice lines, K1, K2, K3 and K4:—

K4: comprises an endogenous Ig kappa locus in which has been inserted the human gene segments Vκ3D-40 to 3D-7, Vκ2D-40, Vκ1D-39 and Vκ1-33 to Jκ5.

Figure 18:
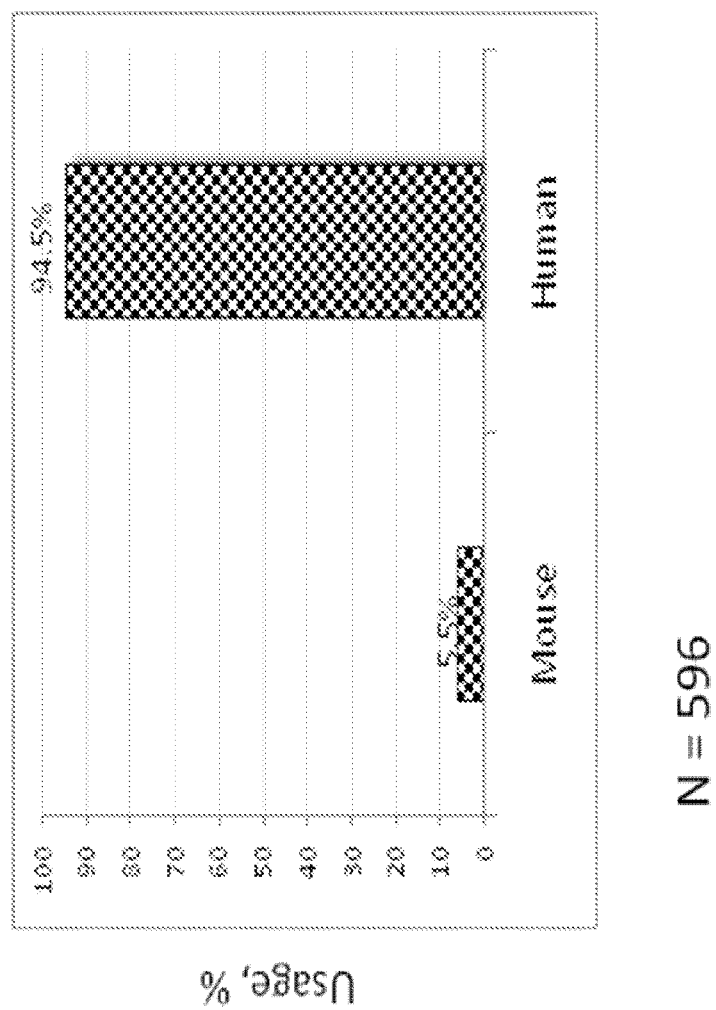

FIG. 18: shows total human Vκ gene segment usage versus mouse Vκ usage in transcripts from K4 mice.

Figure 19:

FIG. 19: illustrates the improvement in human Vκ gene segment usage in transcripts (and thus improvement in inactivation of endogenous mouse Vκ gene segment usage) as human kappa locus DNA is inserted in successive BACs 1-4.

Figure 20:
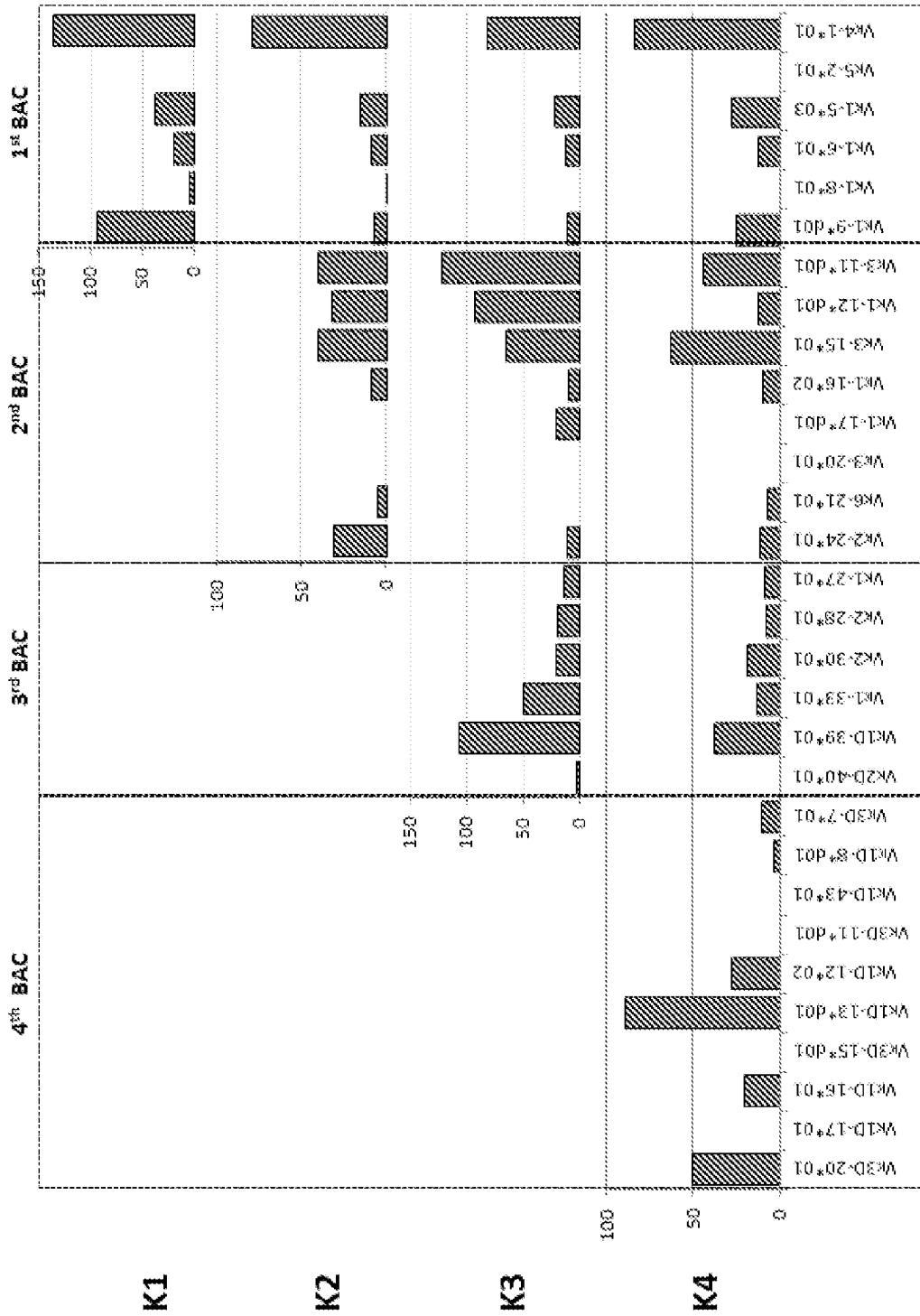

FIG. 20: compares the effect of sectoring a 6, 13, 19 and 29 human Vκ gene segment repertoire across four different mice-types (corresponding to insertion of human gene segment DNA from BAC1 only (K1 genotype), BACs1+2 (K2 genotype), BACs1+2+3 (K3 genotype) and BACs1+2+3+4 (K4 genotype). Illustrated is the distribution of human Vκ usage at the transcript level from the mice. Different Vκ usage was seen resulting in mice that produced different kappa chain repertoires (and corresponding different human kappa variable region repertoires) as a result of the human gene repertoire sectoring. The nucleotide sequence of the Vκ variants mentioned are known in the art (and incorporated herein by reference for possible inclusion in claims herein), eg, known from the IMGT database mentioned herein or 1000 Genomes database (release 1, version 3, 16 Mar.

2012), or are disclosed in the Sequence Listing herein (for variants labelled *d01). NB: Vκ3-20 and Vκ3D-15 were not present in the BACs or mice.

Figure 21:
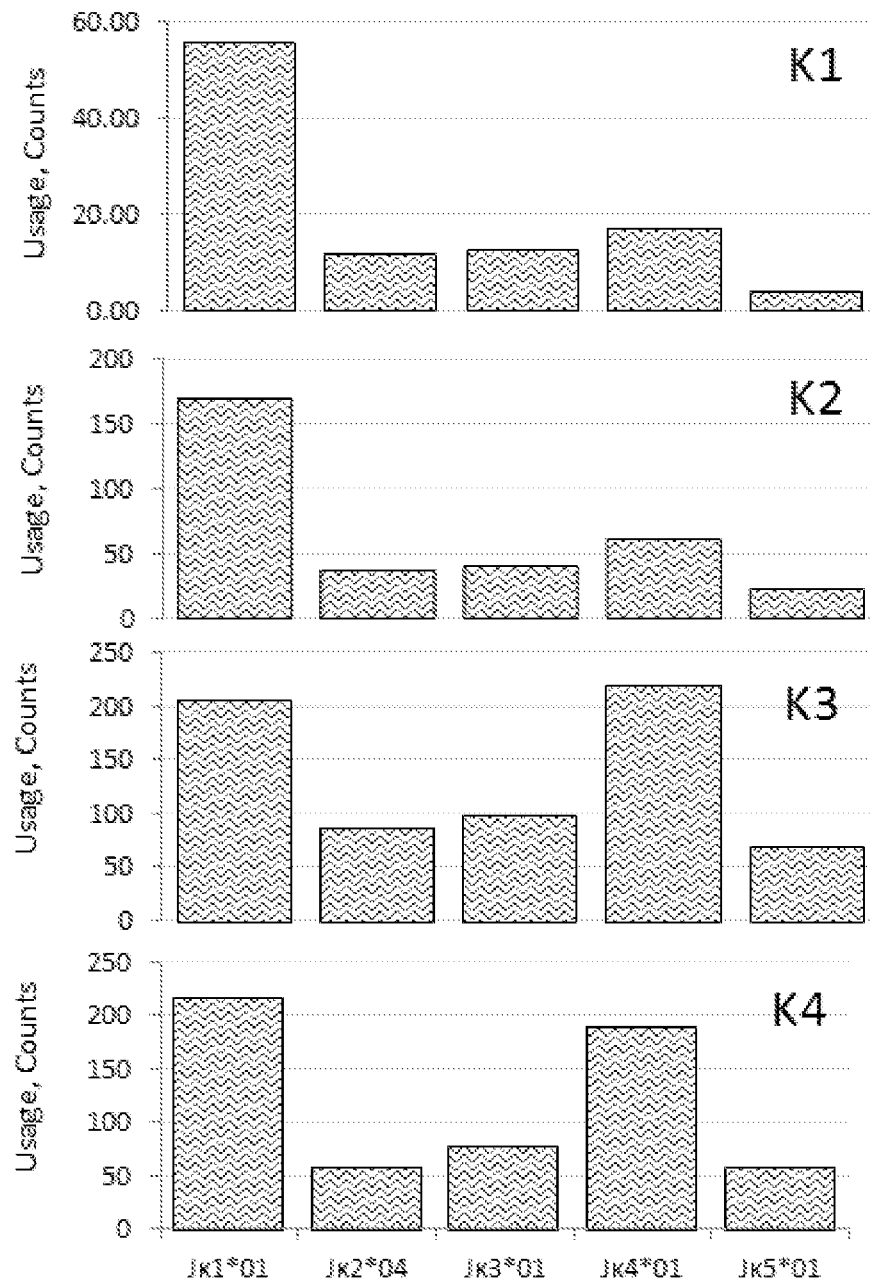

FIG. 21: compares the effect of sectoring the human Jκ gene segment repertoire across four different mice-types (K1, K2, K3 and K4). Illustrated is the distribution of human Jκ usage at the transcript level from the mice. Different Jκ usage was seen resulting in mice that produced different kappa chain repertoires (and corresponding different human kappa variable region repertoires) as a result of the human gene repertoire sectoring.

In some of the figures (eg, FIG. 20), specific human gene segment variants (alleles) are disclosed as having been used to construct the vertebrates exemplifying the aspects of the invention (eg, Vκ2D-40*01, nomenclature being according to IMGT). The sequences (nucleotide and amino acid) of all of these variants eg, as derivable from the IMGT database in the update of Wednesday, 11 Jul. 2012 22:00:09 CEST, are incorporated herein by reference for possible use in claims herein. Also, in embodiments of the invention specific gene segments recited can be provided as one, more or all of the specific variants shown in the figures. Use of such variants is desirable, since they are naturally-occurring in humans and thus are useful for generating Ig loci, cells and vertebrates for generating Ig chains, antibody variable domains and antibodies for use in human medicine.

DETAILED DESCRIPTION OF THE INVENTION

The present invention allows one to dedicate the B-cell compartment of individual vertebrates within the population to a gene segment sub-repertoire from one sector of the overall desired repertoire to be accessed. For example, the invention in one embodiment enables the skilled person to restrict individual vertebrates in the population to one type of light chain (lambda or kappa) predominantly or exclusively, thereby biasing the antibody repertoire within that individual vertebrate to (predominantly) lambda- or kappa-type antibodies. Thus, on an individual vertebrate basis, the finite capacity of the B-cell compartment (the accessible compartment being up to around $2 \times 10^8$ B-cells in a mouse) is controlled artificially to produce antibodies of substantially only the lambda or kappa type in this example. This is important because the potential repertoire encoded by lambda and kappa light chain V and J gene segments totals much more than $2 \times 10^8$. When taken as a whole, however, a population of such vertebrates (ie, a combination of lambda-biased vertebrates with kappa-biased vertebrates) provides for an overall repertoire of antibodies that is not seen in nature (where the B-cell compartments in the prior art vertebrate collections do not have the synthetic restrictions imposed by the present invention). This repertoire according to the present example comprises a sub-repertoire of lambda-type antibodies from vertebrates biased to lambda chain expression as well as a second sub-repertoire of kappa-type antibodies from vertebrates biased to kappa chain expression. Such an approach is quite different from the approach in the art that is directed to providing mice expressing only kappa-type antibodies (perhaps with very low-level lambda-type antibodies at the natural range of 5% in a mouse). Use of such mice ignores the desirability to much more fully explore lambda gene diversity when expressing antibodies. In some prior art examples, transgenic heavy, lambda and kappa chain loci in a single mouse is discussed (eg, see WO02/066630 (Regeneron)), but again here the ratio of lambda:kappa chains is not manipulated to more fully explore the potential lambda as well as kappa diversity. In such mice, diversity is limited by the size of the accessible B-cell compartment so that it is not possible to sample more of the potential VJ light chain repertoire (which is greater than the approximately $2 \times 10^8$ accessible B-cells available in a mouse to express antibodies). Thus, these prior art mice are used in methods that sample only a very small amount of the large potential diversity encoded by recombination of the lambda and kappa V and J gene segments. See the examples below for an illustration.

As will be readily apparent to the skilled person, the operable connection of a gene segment (eg, a V or J gene segment) upstream of a constant region in an Ig locus in any configuration of the invention enables the gene segment to be recombined and expressed in an immunoglobulin chain comprising sequence encoded by the constant region of the locus.

By "divided" in connection with dividing gene segment repertoires between vertebrates of the population, it is meant that the gene segment repertoire is present in the population as a whole, but the genomes of first and second individual members of the population (ie, individual vertebrates) have different collections of gene segments (different "sub-repertoires"), for example, different collections of human VH gene segments. The sub-repertoires can comprise common human gene segments from the overall repertoire (ie, overlapping sub-repertoires) or comprise no common gene segments from the repertoire (ie, non-overlapping sub-repertoires).

In an example, the antibody heavy chain sequence repertoire of the invention is a repertoire of RNA sequences (eg, mRNA) each comprising a sequence derived from the recombination of a human VH gene segment with a D and JH gene segment and a constant region (eg, a C-mu gene segment or C-gamma gene segment). In an example, the antibody heavy chain sequence repertoire is a repertoire of RNA sequences (eg, mRNA) each encoding an antibody heavy chain. In an example, the antibody heavy chain sequence repertoire is a repertoire of antibody heavy chains (eg, provided as part of antibodies). Similarly, an antibody light chain sequence repertoire can be a repertoire of RNA sequences (eg, mRNA) each comprising a sequence derived from the recombination of a human VL gene segment (eg, Vλ or Vκ) with a JL gene segment (eg, Jλ or Jκ respectively) and a constant region (eg, a C-kappa gene segment or C-lambda gene segment). In an example, the antibody light chain sequence repertoire is a repertoire of RNA sequences (eg, mRNA) each encoding an antibody light chain. In an example, the antibody light chain sequence repertoire is a repertoire of antibody light chains (eg, provided as part of antibodies).

The term "antibody" includes monoclonal antibodies (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., dAb, Fab, F(ab')2, and Fv). The term "antibody" also includes H2 antibodies that comprise a dimer of a heavy chain (5'-VH-(optional Hinge)-CH2-CH3-3') and are devoid of a light chain (akin to naturally-occurring H2 antibodies; see, eg, Nature. 1993 Jun. 3; 363(6428):446-8; Naturally occurring antibodies devoid of light chains; Hamers-Casterman C, Atarhouch T, Muyldermans S, Robinson G, Hamers C, Songa E B, Bendahman N, Hamers R). Thus, in an embodiment of the present invention, RNA produced from the transgenic heavy chain locus encodes for heavy chains that re devoid of a CH1 gene segment and comprise no functional antibody light chain. In an example, RNA produced from the transgenic heavy chain locus encodes for VH single variable domains (dAbs; domain antibodies). These can optionally comprise a constant region. Examples of antibodies are classic 4-chain antibodies comprising two heavy chains paired with two light chains (such as, a dimer of 5'-VH-CH1-Hinge-CH2-CH3-3' paired with 5'-VL-CL-3') or H2 antibodies that comprise a dimer of a heavy chain (5'-VH-(optional Hinge)-CH2-CH3-3') and are devoid of a light chain Thus, in an embodiment of the present invention, the heavy chain sequence repertoire encodes for heavy chains that re devoid of a CH1 gene segment and comprise no functional antibody light chain. In an example, the heavy chain sequence repertoire encodes a repertoire of VH single variable domains (dAbs; domain antibodies). These can optionally comprise a constant region.

In an example of any configuration of the invention, a repertoire comprises a plurality of different members (thus, for example, a heavy chain sequence repertoire comprises a plurality of different heavy chain sequences, such as sequences differing in their variable regions). In an example of any configuration of the invention, a repertoire comprises or consists of 2, 3, 4, 5, 6, 7, 8, 9, 10, at least 15, at least 20, at least 30, at least 40, at least 50, at least 60, at least 70, at least 80, at least 90, at least 100, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, or at least $10^{14}$ members. For example, a repertoire of antibody chain sequences or antibodies comprises or consists of at least 100, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, or at least $10^{14}$ antibody chain sequences or antibodies respectively. For example, a repertoire comprises or consists of 2, 3, 4, 5, 6, 7, 8, 9, 10, at least 15, at least 20, at least 30, at least 40, at least 50, at least 60, at least 70, at least 80, at least 90, at least 100, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, or at least $10^{14}$ different members. For example, a repertoire of gene segments (eg, human VH gene segments or VL gene segments or Vλ gene segments or Vκ gene segments) comprises or consists of 2, 3, 4, 5, 6, 7, 8, 9, 10, at least 15, at least 20, at least 30, at least 40, at least 50 gene segments. Optionally, all of the gene segments are different from each other.

A repertoire of human gene segments used in the invention, in one example, comprises additionally non-human gene segments, eg, non-human vertebrate gene segments and/or synthetic gene segments. Such combinations of gene segments is desirable to enhance possible variable region diversity.

In an example of any configuration of the invention, a population comprises a plurality of different members. Thus, for example, a population of transgenic non-human vertebrates (eg, mice or rats) comprises a plurality of vertebrates wherein at least two or more of the vertebrates comprise non-identical genomes. The genomes can, for example, differ in their respective repertoire of human gene segments (eg, human VH gene segments). In an example of any configuration of the invention, a population of non-human vertebrates comprises or consists of 2, 3, 4, 5, 6, 7, 8, 9, 10, at least 15, at least 20, at least 30, at least 40, at least 50, at least 60, at least 70, at least 80, at least 90, at least 100, at least $10^3$ non-human vertebrates. When the population consists of two vertebrates, the genomes of vertebrates are different, eg, the genomes comprise different repertoires of human heavy chain and/or light chain locus gene segments, eg, VH or VL gene segments; or eg, a first of the genomes comprises human lambda locus gene segments (eg, a repertoire of human Vλ and/or Jλ) and (substantially) no human kappa locus gene segments and a second of the genomes comprises human kappa locus gene segments (eg, a repertoire of human Vκ and/or Jκ) and optionally (substantially) no human lambda locus gene segments).

In one embodiment in any configuration of the invention, each vertebrate is a non-human mammal. In one embodiment in any configuration of the invention, the vertebrate is a mouse, rat, rabbit, Camelid (eg, a llama, alpaca or camel), chicken or shark. For example, all vertebrates are of the same vertebrate species, eg, all mice or all rats.

In any configuration of the invention, the inserted human genes may be derived from the same individual or different individuals, or be synthetic or represent human consensus sequences.

Techniques for constructing non-human vertebrates and vertebrate cells whose genomes comprise a transgene containing human V, J and D regions are well known in the art. For example, reference is made to WO2011004192, U.S. Pat. Nos. 7,501,552, 6,673,986, 6,130,364, WO2009076464 and U.S. Pat. No. 6,586,251, the disclosures of which are incorporated herein by reference in their entirety.

In one aspect the human heavy chain gene segments are inserted into the genome so that they are placed under control of the host regulatory sequences (eg, enhancers, promoters and/or switches) or other (non-human, non-host) sequences. In one aspect reference to human coding regions includes both human introns and exons, or in another aspect simply exons and no introns, which may be in the form of cDNA.

Alternatively it is possible to use recombineering in ES cells, or other recombinant DNA technologies, to insert a non human-vertebrate (e.g. mouse) promoter or other control region, such as a promoter for a V region, into a BAC containing a human Ig region. The recombineering step then places a portion of human DNA under control of the mouse promoter or other control region.

In one aspect a (or each) non-human vertebrate of any configuration of the invention is able to generate a diversity of at least $1 \times 10^6$ different functional chimaeric immunoglobulin sequence combinations.

Optionally in any configuration of the invention each constant region is endogenous to the vertebrate and optionally comprises an endogenous switch (when the constant region is a heavy chain constant region). In one embodiment, the constant region comprises a Cgamma (Cγ) gene segment (eg, a human Cgamma) and/or a Smu (Sμ) switch. Switch sequences are known in the art, for example, see Nikaido et al, Nature 292: 845-848 (1981) and also WO2011004192, U.S. Pat. Nos. 7,501,552, 6,673,986, 6,130,364, WO2009/076464 and U.S. Pat. No. 6,586,251, eg, SEQ ID NOs: 9-24 disclosed in U.S. Pat. No. 7,501,552. Optionally the constant region comprises an endogenous S gamma switch and/or an endogenous Smu switch. One or more endogenous switch regions can be provided, in one embodiment, by constructing a transgenic immunoglobulin locus in the vertebrate or cell genome in which at least one human V region, at least one human J region, and optionally at least one human D region, or a rearranged VDJ or VJ region, are inserted into the genome in operable connection with a constant region that is endogenous to the vertebrate or cell. For example, the human V(D)J regions or rearranged VDJ or VJ can be inserted in a cis orientation onto the same chromosome as the endogenous constant region. A trans orientation is also possible, in which the human V(D)J regions or rearranged VDJ or VJ are inserted into one chromosome of a pair (eg, the chromosome 6 pair in a mouse or the chromosome 4 in a rat) and the endogenous constant region is on the other chromosome of the pair, such that trans-switching takes place in which the human V(D)J regions or rearranged VDJ or VJ are spliced inoperable linkage to the endogenous constant region. In this way, the vertebrate can express antibodies having a chain that comprises a variable region encoded all or in part by human V(D)J or a rearranged VDJ or VJ, together with a constant region (eg, a Cgamma or Cmu) that is endogenous to the vertebrate.

Human variable regions are suitably inserted upstream of a non-human vertebrate constant region, the latter comprising all of the DNA required to encode the full constant region or a sufficient portion of the constant region to allow the formation of an effective chimaeric antibody capable of specifically recognising an antigen.

In one aspect the chimaeric antibodies or antibody chains isolated from vertebrates according to the invention have a part of a host constant region sufficient to provide one or more effector functions seen in antibodies occurring naturally in a host vertebrate, for example that they are able interact with Fc receptors, and/or bind to complement.

Reference to a chimaeric antibody or antibody chain having a non-human vertebrate constant region herein therefore is not limited to the complete constant region but also includes chimaeric antibodies or chains which have all of the host constant region, or a part thereof sufficient to provide one or more effector functions. This also applies to non-human vertebrates used in the invention in which human variable region DNA may be inserted into the host genome such that it forms a chimaeric antibody chain with all or part of a host constant region. In one aspect the whole of a host non-human vertebrate constant region is operably linked to human variable region DNA.

The host non-human vertebrate constant region herein is optionally the endogenous host wild-type constant region located at the wild type locus, as appropriate for the heavy or light chain. For example, the human heavy chain DNA is suitably inserted on mouse chromosome 12, suitably adjacent the mouse heavy chain constant region, where the vertebrate is a mouse.

In one optional aspect where the vertebrate is a mouse, the insertion of human DNA, such as a human VDJ region is targeted to the region between the J4 exon and the Cµ locus in the mouse genome IgH locus, and in one aspect is inserted between coordinates 114,667,090 and 114,665,190, suitably at coordinate 114,667,091, after 114,667,090. In one aspect the insertion of a human DNA, such as a human light chain kappa VJ region is targeted into mouse chromosome 6 between coordinates 70,673,899 and 70,675,515, suitably at position 70,674,734, or an equivalent position in the lambda mouse locus on chromosome 16.

All nucleotide co-ordinates for the mouse are those corresponding to NCBI m37 for the mouse C57BL/6J strain, e.g. April 2007 ENSEMBL Release 55.37h, e.g. NCBI37 July 2007 (NCBI build 37) (e.g. UCSC version mm9 see www.genome.ucsc.edu and http://genome.ucsc.edu/FAQ/FAQreleases.html) unless otherwise specified. Human nucleotides coordinates are those corresponding to GRCh37 (e.g. UCSC version hg 19, http://genome.ucsc.edu/FAQ/FAQreleases.html), February 2009 ENSEMBL Release 55. or are those corresponding to NCBI36, Ensemble release 54 unless otherwise specified. Rat nucleotides are those corresponding to RGSC 3.4 Dec. 2004 ENSEMBL release 55.34w, or Baylor College of Medicine HGSC v3.4 Nov. 2004 (e.g., UCSC rn4, see www.genome.ucsc.edu and http://genome.ucsc.edu/FAQ/FAQreleases.html) unless otherwise specified.

In one aspect the host non-human vertebrate constant region for forming the chimaeric antibody may be at a different (non endogenous) chromosomal locus. In this case the inserted human DNA, such as the human variable VDJ or VJ region(s) may then be inserted into the non-human genome at a site which is distinct from that of the naturally occurring heavy or light constant region. The native constant region may be inserted into the genome, or duplicated within the genome, at a different chromosomal locus to the native position, such that it is in a functional arrangement with the human variable region such that chimaeric antibodies of the invention can still be produced.

In one aspect the human DNA is inserted at the endogenous host wild-type constant region located at the wild type locus between the host constant region and the host VDJ region.

Reference to location of the variable region or a gene segment upstream of a constant region means that there is a suitable relative location of the two antibody portions, variable/gene segment and constant, to allow the portions to form a chimaeric antibody or antibody chain in vivo in the vertebrate. Thus, the inserted human DNA and host constant region are in operable connection with one another for antibody or antibody chain production.

In one aspect the inserted human DNA is capable of being expressed with different host constant regions through isotype switching. In one aspect isotype switching does not require or involve trans switching. Insertion of the human variable region DNA on the same chromosome as the relevant host constant region means that there is no need for trans-switching to produce isotype switching.

In the present invention, optionally host non-human vertebrate constant regions are maintained and in an example at least one non-human vertebrate enhancer or other control sequence, such as a switch region, is maintained in functional arrangement with the non-human vertebrate constant region, such that the effect of the enhancer or other control sequence, as seen in the host vertebrate, is exerted in whole or in part in the transgenic animal. This approach is designed to allow the full diversity of the human locus to be sampled, to allow the same high expression levels that would be achieved by non-human vertebrate control sequences such as enhancers, and is such that signalling in the B-cell, for example isotype switching using switch recombination sites, would still use non-human vertebrate sequences.

A non-human vertebrate having such a genome would produce chimaeric antibodies with human variable and non-human vertebrate constant regions, but these are readily humanized, for example in a cloning step.

For example, V (and/or other gene segments) which are naturally inverted in a human genome or are pseudogenes may be omitted from the repertoire provided by the population of the invention.

Reference to "functional" human gene segments in any configuration of the invention acknowledges that in a human Ig locus some V or other gene segments are non-functional pseudogenes (eg, Vλ3-17, Vλ3-15, Vλ3-13, Vλ3-7, Vλ3-6, Vλ2-5, Vλ3-4, Vλ3-2; see the IMGT database: http://www.imgt.org/IMGTrepertoire/index.php?section=LocusGenes&repertoire=locus&species=human&group=IGL). Also, Jλ4-Cλ4 and Jλ5-Cλ5 are not functional in humans. The term "functional" when referring to gene segments excludes pseudogenes. An example of functional human Vλ gene segments is the group Vλ2-18, Vλ3-16, V2-14, Vλ3-12, Vλ2-11, Vλ3-10, Vλ3-9, Vλ2-8, Vλ4-3 and Vλ3-1. An example of functional human Jλ gene segments is the group Jλ1, Jλ2 and Jλ3; or Jλ1, Jλ2 and Jλ7; or Jλ2, Jλ3 and Jλ7; or Jλ1, Jλ2, Jλ3 and Jλ7. An example of functional human Cλ gene segments is the group Cλ1, Cλ2 and Cλ3; or Cλ1, Cλ2 and Cλ7; or Cλ2, Cλ3 and Cλ7; or Cλ1, Cλ2, Cλ3 and Cλ7.

The term "germline configuration" refers to a germline genomic configuration. For example, human immunoglobulin gene segments of a transgenic immunoglobulin locus are in a germline configuration when the relative order of the gene segments is the same as the order of corresponding gene segments in a human germline genome. For example, when the transgenic locus is a heavy chain locus of the invention comprising hypothetical human immunoglobulin gene segments A, B and C, these would be provided in this order (5' to 3' in the locus) when the corresponding gene segments of a human germline genome comprises the arrangement 5'-A-B-C-3'. In an example, when elements of a human immunoglobulin locus (eg, gene segments, enhancers or other regulatory elements) are provided in a transgenic immunoglobulin locus according to the invention, the human Ig locus elements are in germline configuration when the relative order of the gene segments is the same as the order of corresponding gene segments in a human germline genome and human sequences between the elements are included, these corresponding to such sequences between corresponding elements in the human germline genome. Thus, in a hypothetical example the transgenic locus comprises human elements in the arrangement 5'-A-S1-B-S2-C-S3-3', wherein A, B and C are human immunoglobulin gene segments and S1-S3 are human inter-gene segment sequences, wherein the corresponding arrangement 5'-A-S1-B-S2-C-S3-3' is present in a human germline genome. For example, this can be achieved by providing in a transgenic immunoglobulin locus of the invention a DNA insert corresponding to the DNA sequence from A to C in a human germline genome (or the insert comprising the DNA sequence from A to C). The arrangements in human germline genomes and immunoglobulin loci are known in the art (eg, see the IMGT, Kabat and other antibody resources).

As a source of antibody gene segment sequences, the skilled person will also be aware of the following available databases and resources (including updates thereof) the contents of which are incorporated herein by reference:

The Kabat Database (G. Johnson and T. T. Wu, 2002; World Wide Web (www) kabatdatabase.com). Created by E. A. Kabat and T. T. Wu in 1966, the Kabat database publishes aligned sequences of antibodies, T-cell receptors, major histocompatibility complex (MHC) class I and II molecules, and other proteins of immunological interest. A searchable interface is provided by the SeqhuntII tool, and a range of utilities is available for sequence alignment, sequence subgroup classification, and the generation of variability plots. See also Kabat, E. A., Wu, T. T., Perry, H., Gottesman, K., and Foeller, C. (1991) *Sequences of Proteins of Immunological Interest*, 5th ed., NIH Publication No. 91-3242, Bethesda, Md., which is incorporated herein by reference, in particular with reference to human gene segments for use in the present invention.

KabatMan (A. C. R. Martin, 2002; World Wide Web (www) bioinf.org.uk/abs/simkab.html). This is a web interface to make simple queries to the Kabat sequence database.

IMGT (the International ImMunoGeneTics Information System®; M.-P. Lefranc, 2002; World Wide Web (www) imgt.cines.fr). IMGT is an integrated information system that specializes in antibodies, T cell receptors, and MHC molecules of all vertebrate species. It provides a common portal to standardized data that include nucleotide and protein sequences, oligonucleotide primers, gene maps, genetic polymorphisms, specificities, and two-dimensional (2D) and three-dimensional (3D) structures. IMGT includes three sequence databases (IMGT/LIGM-DB, IMGT/MHC-DB, IMGT/PRIMERDB), one genome database (IMGT/GENE-DB), one 3D structure database (IMGT/3Dstructure-DB), and a range of web resources ("IMGT Marie-Paule page") and interactive tools.

V-BASE (I. M. Tomlinson, 2002; World Wide Web (www) mrc-cpe.cam.ac.uk/vbase). V-BASE is a comprehensive directory of all human antibody germline variable region sequences compiled from more than one thousand published sequences. It includes a version of the alignment software DNAPLOT (developed by Hans-Helmar Althaus and Werner Müller) that allows the assignment of rearranged antibody V genes to their closest germline gene segments.

Antibodies—Structure and Sequence (A. C. R. Martin, 2002; World Wide Web (www) bioinf.org.uk/abs). This page summarizes useful information on antibody structure and sequence. It provides a query interface to the Kabat antibody sequence data, general information on antibodies, crystal structures, and links to other antibody-related information. It also distributes an automated summary of all antibody structures deposited in the Protein Databank (PDB). Of particular interest is a thorough description and comparison of the various numbering schemes for antibody variable regions.

AAAAA (A Ho's Amazing Atlas of Antibody Anatomy; A. Honegger, 2001; World Wide Web (www) unizh.ch/~antibody). This resource includes tools for structural analysis, modelling, and engineering. It adopts a unifying scheme for comprehensive structural alignment of antibody and T-cell-receptor sequences, and includes Excel macros for antibody analysis and graphical representation.

WAM (Web Antibody Modeling; N. Whitelegg and A. R. Rees, 2001; World Wide Web (www) antibody.bath.ac.uk). Hosted by the Centre for Protein Analysis and Design at the University of Bath, United Kingdom. Based on the AbM package (formerly marketed by Oxford Molecular) to construct 3D models of antibody Fv sequences using a combination of established theoretical methods, this site also includes the latest antibody structural information.

Mike's Immunoglobulin Structure/Function Page (M. R. Clark, 2001; World Wide Web (www) path.cam.ac.uk/~mrc7/mikeimages.html) These pages provide educational materials on immunoglobulin structure and function, and are illustrated by many colour images, models, and animations. Additional information is available on antibody humanization and Mike Clark's Therapeutic Antibody Human Homology Project, which aims to correlate clinical efficacy and anti-immunoglobulin responses with variable region sequences of therapeutic antibodies.

The Antibody Resource Page (The Antibody Resource Page, 2000; World Wide Web (www) antibodyresource.com). This site describes itself as the "complete guide to antibody research and suppliers." Links to amino acid sequencing tools, nucleotide antibody sequencing tools, and hybridoma/cell-culture databases are provided.

Humanization bY Design (J. Saldanha, 2000; World Wide Web (www) people.cryst.bbk.ac.uk/~ubcg07s). This resource provides an overview on antibody humanization technology. The most useful feature is a searchable database (by sequence and text) of more than 40 published humanized antibodies including information on design issues, framework choice, framework back-mutations, and binding affinity of the humanized constructs.

See also Antibody Engineering Methods and Protocols, Ed. Benny K C Lo, Methods in Molecular Biology™, Human Press. Also at World Wide Web (www) blogsua.com/pdf/antibody-engineering-methods-and-protocolsantibody-engineering-methods-and-protocols.pdf Samples from which B-cells can be obtained include but are not limited to blood, serum, spleen, splenic tissue, bone marrow, lymph, lymph node, thymus, and appendix. Antibodies and immunoglobulin chains can be obtained from each of the previous-mentioned samples and also from the following non-limiting list of B-cells, ascites fluid, hybridomas, and cell cultures.

"Plurality" is used in the ordinary sense of the term and means "at least one" or "more than one".

"Derived from" is used in the ordinary sense of the term. Exemplary synonyms include "produced as", "resulting from", "received from", "obtained from", "a product of", "consequence of", and "modified from" For example, a human variable region of a heavy chain can be derived from recombination of human VH, D and JH gene segments and this reflects the in vivo recombination of these gene segments in, for example, a transgenic heavy chain locus according to the invention with any accompanying mutation (eg, junctional mutation).

In one embodiment in any configuration of the invention, the genome of a or each vertebrate has been modified to prevent or reduce the expression of fully-endogenous antibody. Examples of suitable techniques for doing this can be found in WO2011004192, U.S. Pat. Nos. 7,501,552, 6,673, 986, 6,130,364, WO2009/076464, EP1399559 and U.S. Pat. No. 6,586,251, the disclosures of which are incorporated herein by reference. In one embodiment, the non-human vertebrate VDJ region of the endogenous heavy chain immunoglobulin locus, and optionally VJ region of the endogenous light chain immunoglobulin loci (lambda and/or kappa loci), have been inactivated. For example, all or part of the non-human vertebrate VDJ region is inactivated by inversion in the endogenous heavy chain immunoglobulin locus of the mammal, optionally with the inverted region being moved upstream or downstream of the endogenous Ig locus. For example, all or part of the non-human vertebrate VJ region is inactivated by inversion in the endogenous kappa chain immunoglobulin locus of the mammal, optionally with the inverted region being moved upstream or downstream of the endogenous Ig locus. For example, all or part of the non-human vertebrate VJ region is inactivated by inversion in the endogenous lambda chain immunoglobulin locus of the mammal, optionally with the inverted region being moved upstream or downstream of the endogenous Ig locus. In one embodiment the endogenous heavy chain locus is inactivated in this way as is one or both of the endogenous kappa and lambda loci.

Additionally or alternatively, the or each vertebrate has been generated in a genetic background which prevents the production of mature host B and T lymphocytes, optionally a RAG-1-deficient and/or RAG-2 deficient background. See U.S. Pat. No. 5,859,301 for techniques of generating RAG-1 deficient animals.

In an embodiment, the immunoglobulin loci of the vertebrates differ only in the repertoire of said human gene segments.

The term "immunoglobulin" (Ig) is used interchangeably with "antibody" herein.

An "isolated" antibody is one that has been identified, separated and/or recovered from a component of its production environment (e.g., naturally or recombinantly). Preferably, the isolated polypeptide is free of association with all other components from its production environment, eg, so that the antibody has been isolated to an FDA-approvable or approved standard. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant cells since at least one component of the antibody's natural environment will not be present. Ordinarily, however, an isolated polypeptide or antibody will be prepared by at least one purification step.

An "antibody fragment" comprises a portion of an intact antibody, preferably the antigen binding and/or the variable region of the intact antibody. Examples of antibody fragments include dAb, Fab, Fab', F(ab')2 and Fv fragments; diabodies; linear antibodies; single-chain antibody molecules and multispecific antibodies formed from antibody fragments.

An antibody that "specifically binds to" or is "specific for" a particular polypeptide, antigen, or epitope is one that binds to that particular polypeptide, antigen, or epitope without substantially binding to other polypeptides, antigens or epitopes. For example, binding to the antigen or epitope is specific when the antibody binds with a $K_D$ of 100 μM or less, 10 μM or less, 1 μM or less, 100 nM or less, eg, 10 nM or less, 1 nM or less, 500 pM or less, 100 pM or less, or 10 pM or less. The binding affinity ($K_D$) can be determined using standard procedures as will be known by the skilled person, eg, binding in ELISA and/or affinity determination using surface plasmon resonance (eg, Biacore™ or KinExA™ solution phase affinity measurement which can detect down to fM affinities (Sapidyne Instruments, Idaho)).

"Pharmaceutically acceptable" refers to approved or approvable by a regulatory agency of the USA Federal or a state government or listed in the U.S. Pharmacopeia or other generally recognized pharmacopeia for use in animals, including humans. A "pharmaceutically acceptable carrier, excipient, or adjuvant" refers to an carrier, excipient, or adjuvant that can be administered to a subject, together with an agent, e.g., any antibody or antibody chain described herein, and which does not destroy the pharmacological activity thereof and is nontoxic when administered in doses sufficient to deliver a therapeutic amount of the agent.

In one embodiment of any configuration of the invention when the vertebrate is a mouse, (i) the constant region comprises a mouse or rat Sμ switch and optionally a mouse Cμ region. For example the constant region is provided by the constant region endogenous to the mouse, eg, by inserting human V(D)J region sequences into operable linkage with the endogenous constant region of a mouse genome or mouse cell genome.

In one embodiment of any configuration of the invention when the vertebrate is a rat, (i) the constant region comprises a mouse or rat Sμ switch and optionally a rat Cμ region. For example the constant region is provided by the constant region endogenous to the rat, eg, by inserting human V(D)J region sequences into operable linkage with the endogenous constant region of a rat genome or rat cell genome.

In one embodiment of any configuration of the vertebrate the invention (excluding a kappa vertebrate) the genome comprises an antibody light chain transgene which comprises all or part of the human Igλ locus including at least one human Jλ region and at least one human Cλ region, optionally $C_\lambda 6$ and/or $C_\lambda 7$. Optionally, the transgene comprises a plurality of human Jλ regions, optionally two or more of $J_\lambda 1$, $J_\lambda 2$, $J_\lambda 6$ and $J_\lambda 7$, optionally all of $J_\lambda 1$, $J_\lambda 2$, $J_\lambda 6$ and $J_\lambda 7$. The human lambda immunoglobulin locus comprises a unique gene architecture composed of serial J-C clusters. In order to take advantage of this feature, the invention in optional aspects employs one or more such human J-C clusters inoperable linkage with the constant region in the transgene, eg, where the constant region is endogenous to the non-human vertebrate or non-human vertebrate cell. Thus, optionally the transgene comprises at least one human $J_\lambda$-$C_\lambda$ cluster, optionally at least $J_\lambda 7$-$C_\lambda 7$. The construction of such transgenes is facilitated by being able to use all or part of the human lambda locus such that the transgene comprises one or more J-C clusters in germline configuration, advantageously also including intervening sequences between clusters and/or between adjacent J and C regions in the human locus. This preserves any regulatory elements within the intervening sequences which may be involved in VJ and/or JC recombination and which may be recognised by AID (activation-induced deaminase) or AID homologues.

Where endogenous regulatory elements are involved in CSR (class-switch recombination) in the non-human vertebrate, these can be preserved by including in the transgene a constant region that is endogenous to the non-human vertebrate. In the invention, one can match this by using an AID or AID homologue that is endogenous to the vertebrate or a functional mutant thereof. Such design elements are advantageous for maximising the enzymatic spectrum for SHM (somatic hypermutation) and/or CSR and thus for maximising the potential for antibody diversity.

Optionally, the lambda transgene comprises a human Eλ enhancer. Optionally, the kappa transgene comprises a human Eκ enhancer. Optionally, the heavy chain transgene comprises a heavy chain human enhancer.

In one embodiment of any configuration of the invention the constant region is endogenous to the non-human vertebrate or derived from such a constant region. For example, the vertebrate is a mouse and the constant region is endogenous to the mouse. For example, the vertebrate is a rat and the constant region is endogenous to the rat.

In one embodiment of any configuration of the invention the heavy chain transgene comprises a plurality human IgH V regions, a plurality of human D regions and a plurality of human J regions.

In one embodiment of any configuration of the invention, the vertebrate comprises a heavy chain further transgene, the further transgene comprising at least one human IgH V region, at least one human D region and at least one human J region.

An aspect provides a method of isolating an antibody or nucleotide sequence encoding said antibody, the method comprising (a) immunising (see e.g. Harlow, E. & Lane, D. 1998, 5$^{th}$ edition, Antibodies: A Laboratory Manual, Cold Spring Harbor Lab. Press, Plainview, N.Y.; and Pasqualini and Arap, Proceedings of the National Academy of Sciences (2004) 101:257-259) a vertebrate population according to any configuration or aspect of the invention with an antigen such that the vertebrates produce antibodies; and (b) isolating from immunised vertebrates an antibody that specifically binds to said antigen and/or a nucleotide sequence encoding at least the heavy and/or the light chain variable regions of said antibody;

optionally wherein the variable regions of said antibody are subsequently joined to a human constant region. Such joining can be effected by techniques readily available in the art, such as using conventional recombinant DNA and RNA technology as will be apparent to the skilled person. See e.g. Sambrook, J and Russell, D. (2001, 3'd edition) Molecular Cloning: A Laboratory Manual (Cold Spring Harbor Lab. Press, Plainview, N.Y.).

Suitably an immunogenic amount of the antigen is delivered. The invention also relates to a method for detecting a target antigen comprising detecting an antibody produced as above with a secondary detection agent which recognises a portion of that antibody.

Isolation of the antibody in step (b) can be carried out using conventional antibody selection techniques, eg, panning for antibodies against antigen that has been immobilised on a solid support, optionally with iterative rounds at increasing stringency, as will be readily apparent to the skilled person.

As a further optional step, after step (b) the amino acid sequence of the heavy and/or the light chain variable regions of the antibody are mutated to improve affinity for binding to said antigen. Mutation can be generated by conventional techniques as will be readily apparent to the skilled person, eg, by error-prone PCR. Affinity can be determined by conventional techniques as will be readily apparent to the skilled person, eg, by surface plasmon resonance, eg, using Biacore™.

Additionally or alternatively, as a further optional step, after step (b) the amino acid sequence of the heavy and/or the light chain variable regions of the antibody are mutated to improve one or more biophysical characteristics of the antibody, eg, one or more of melting temperature, solution state (monomer or dimer), stability and expression (eg, in CHO or *E. coli*).

An aspect provides an antibody produced by the method of the invention, optionally for use in medicine, eg, for treating and/or preventing a medical condition or disease in a patient, eg, a human.

An aspect provides a nucleotide sequence encoding the antibody of the invention, optionally wherein the nucleotide sequence is part of a vector. Suitable vectors will be readily apparent to the skilled person, eg, a conventional antibody expression vector comprising the nucleotide sequence together in operable linkage with one or more expression control elements.

An aspect provides a pharmaceutical composition comprising the antibody of the invention and a diluent, excipient or carrier, optionally wherein the composition is contained in an IV container (eg, and IV bag) or a container connected to an IV syringe.

An aspect provides the use of the antibody of the invention in the manufacture of a medicament for the treatment and/or prophylaxis of a disease or condition in a patient, eg a human.

In a further aspect the invention relates to a method for producing an antibody specific to a desired antigen the method comprising immunizing a population of non-human vertebrates as above with a predetermined antigen and recovering a chimaeric antibody (see e.g. Harlow, E. & Lane, D. 1998, 5$^{th}$ edition, Antibodies: A Laboratory Manual, Cold Spring Harbor Lab. Press, Plainview, N.Y.; and Pasqualini and Arap, Proceedings of the National Academy of Sciences (2004) 101:257-259). Suitably an immunogenic amount of the antigen is delivered. The invention also relates to a method for detecting a target antigen comprising detecting an antibody produced as above with a secondary detection agent which recognises a portion of that antibody.

In a further aspect the invention relates to a method for producing a fully humanised antibody comprising immunizing a population of non-human vertebrates as above with a predetermined antigen, recovering a chimaeric antibody or cells expressing the antibody, and then replacing the non-human vertebrate constant region with a human constant region. This can be done by standard cloning techniques at the DNA level to replace the non-human vertebrate constant region with an appropriate human constant region DNA sequence—see e.g. Sambrook, J and Russell, D. (2001, 3'd edition) Molecular Cloning: A Laboratory Manual (Cold Spring Harbor Lab. Press, Plainview, N.Y.).

In a further aspect the invention relates to humanised antibodies and antibody chains produced according to the present invention, both in chimaeric and fully humanised form, and use of said antibodies in medicine. The invention also relates to a pharmaceutical composition comprising such an antibody and a pharmaceutically acceptable carrier or other excipient.

Antibody chains containing human sequences, such as chimaeric human-non-human antibody chains, are considered humanised herein by virtue of the presence of the human protein coding regions region. Fully humanised antibodies may be produced starting from DNA encoding a chimaeric antibody chain of the invention using standard techniques.

Methods for the generation of both monoclonal and polyclonal antibodies are well known in the art, and the present invention relates to both polyclonal and monoclonal antibodies of chimaeric or fully humanised antibodies produced in response to antigen challenge in a population of non-human vertebrates used in the present invention.

In a yet further aspect, chimaeric antibodies or antibody chains generated using the present invention may be manipulated, suitably at the DNA level, to generate molecules with antibody-like properties or structure, such as a human variable region from a heavy chain absent a constant region, for example a domain antibody; or a human variable region with any constant region from either heavy or light chain from the same or different species; or a human variable region with a non-naturally occurring constant region; or human variable region together with any other fusion partner. The invention relates to all such chimaeric antibody derivatives derived from chimaeric antibodies identified using the present invention.

In a further aspect, the invention relates to use of a population of non-human vertebrates of the present invention in the analysis of the likely effects of drugs and vaccines in the context of a quasi-human antibody repertoire.

The invention also relates to a method for identification or validation of a drug or vaccine, the method comprising delivering the vaccine or drug to a population of vertebrates of the invention and monitoring one or more of: the immune response, the safety profile; the effect on disease.

The invention also relates to a kit comprising an antibody or antibody derivative as disclosed herein and either instructions for use of such antibody or a suitable laboratory reagent, such as a buffer, antibody detection reagent.

The invention also relates to a method for making an antibody, or part thereof, the method comprising providing:

(i) a nucleic acid encoding an antibody, or a part thereof, obtained using the population of the present invention; or (ii) sequence information from which a nucleic acid encoding an antibody obtained using the population of the present invention, or part thereof, can be expressed to allow an antibody to be produced.

In an embodiment, each vertebrate of the population of the first aspect of the invention is a non-human vertebrate, mouse or rat, whose genome comprises (a) said transgenic heavy chain locus; and (b) an antibody kappa light chain locus transgene and/or an antibody lambda chain locus transgene;

wherein all of the V, D and J in said transgenes are human V, D and J;

wherein endogenous antibody heavy and light chain expression has been inactivated; and optionally wherein said genome is homozygous for said transgenic heavy and light chain loci.

In an embodiment, the kappa and lambda chain transgenic loci comprise constant regions of said non-human vertebrate species capable of pairing with the constant region of the heavy chain.

In an embodiment, the kappa chain transgenic loci comprises a substantially complete human functional Vκ and Jκ repertoire; and the lambda chain transgene comprises a substantially complete human functional Vλ and Jλ repertoire.

Throughout this text, and with application to any configuration, aspect, embodiment or example of the invention, the term "endogenous" (eg, endogenous constant region) in relation to a non-human vertebrate indicates that the constant region etc is a type of constant region etc that is normally found in the vertebrate (as opposed to an exogenous constant region whose sequence is not normally found in such a vertebrate, eg a human sequence). For example, the endogenous constant region can be those encoded by the wild-type genome of the non-human vertebrate. So, in an example wherein the vertebrate is a mouse, the endogenous constant region would be a mouse constant region. Going further, the endogenous regions are, in an example, strain-matched to the vertebrate. So, in one embodiment, the vertebrate cell is a mouse 129 ES cell, the endogenous constant region would be mouse 129 constant region. In another embodiment, the vertebrate is a JM8 strain mouse, the endogenous constant region would be mouse JM8 constant region. In another embodiment, the vertebrate is a Black 6 mouse, the endogenous constant region would be mouse Black 6 constant region.

In any configuration of the invention, the constant region of the heavy chain transgenic locus is a non-human vertebrate constant region (eg, mouse or rat constant region). Optionally, the constant region is endogenous to said non-human vertebrate. Alternatively, the constant region of the heavy chain transgene is human constant region. For example, the constant region is human and devoid of a CH1. This is useful for producing human H2 antibodies (especially when the vertebrate is not capable of expressing light chains).

In one example of a or each vertebrate used in the invention, the constant region is or comprises a Cmu, eg, a mouse or rat Cmu. For example, where the vertebrate is a mouse the Cmu is an endogenous mouse Cmu. The transgenic heavy chain locus, in an example, comprises a Smu switch 5' of the Cmu and a Cgamma 3' of the Cmu, with a S gamma switch between the Cmu and Cgamma. In an embodiment, the Cmu, Cgamma and switches are endogenous mouse C regions and switches. For example, the C regions and switches are mouse 129 C regions and switches; or the C regions and switches are mouse Black 6 C regions and switches. In another embodiment, the S gamma and C regions are mouse S gamma and C regions, and the Smu is a rat Smu.

In one aspect each vertebrate of the population is a mouse whose genetic background is selected from mouse strains C57BL/6, M129 such as 129/SV, BALB/c, and any hybrid of C57BL/6, M129 such as 129/SV, or BALB/c. In an embodiment, each of these vertebrates have the same genetic background but two or more of the vertebrates of the population differ in their human gene segment repertoires as per the invention.

The invention relates to a method of providing a synthetic antibody heavy chain sequence repertoire in a population of non-human vertebrates, the method comprising (a) providing a population of transgenic non-human vertebrates (optionally mice or rats), wherein the population provides a repertoire of different human VH gene segments, the repertoire being divided between two or more vertebrates of said population, (b) a first vertebrate of said population comprising a transgenic heavy chain locus comprising one or more human VH gene segments (first VH gene sub-repertoire), D segments and J segments operably connected upstream of a constant region; and (c) a second vertebrate of said population comprising a transgenic heavy chain locus comprising one or more human VH gene segments (second VH gene sub-repertoire), D segments and J segments operably connected upstream of a constant region;

(d) wherein the first VH gene sub-repertoire is different from the second VH gene sub-repertoire, whereby the first vertebrate can produce a heavy chain sequence repertoire that is different from the heavy chain sequence repertoire produced by the second vertebrate.

Thus, the population provides an overall heavy chain repertoire comprising the heavy chain sequence repertoires of the first and second vertebrates. The vertebrates in the population can be immunised with the same antigen in a method of selecting and isolating one or more heavy chains (eg, provided as part of antibodies) that specifically bind to the antigen.

The VH gene segments of a repertoire can, in one embodiment, be recombined VH, ie, provided as part of a variable region sequence derived from the recombination of human VH with D and JH (eg, where the VH, D and JH are human).

In an embodiment, the population comprises a third non-human vertebrate, the third vertebrate comprising a transgenic heavy chain locus comprising one or more human VH gene segments (third VH gene sub-repertoire), D segments and J segments operably connected upstream of a constant region; wherein the third VH gene sub-repertoire is different from the first and second VH gene sub-repertoires, whereby the third vertebrate can produce a heavy chain sequence repertoire that is different from the heavy chain sequence repertoire produced by the first and second vertebrates. Thus, the population provides an overall heavy chain repertoire comprising the heavy chain sequence repertoires of the first, second and third vertebrates. The vertebrates in the population can be immunised with the same antigen in a method of selecting and isolating one or more heavy chains (eg, provided as part of antibodies) that specifically bind to the antigen.

In an embodiment, VH gene segment repertoire provided by said population comprises a substantially complete repertoire of functional human VH gene segments; optionally providing at least 6 different human JH gene segments, 27 different human D segments and at least 40 different human VH gene segments.

In an embodiment, the VH gene segment repertoire provided by said population comprises at least 20, 25, 30, 35 or 40 different human VH gene segments.

In an embodiment, the J segments of each transgenic heavy chain locus are human JH gene segments; optionally wherein each heavy chain locus comprises a substantially complete functional repertoire of human JH gene segments.

In an embodiment, each heavy chain locus comprises at least 2, 3, 4, 5 or 6 different human JH gene segments.

In an embodiment, the D segments of each transgenic heavy chain locus are human D gene segments; optionally wherein each heavy chain locus comprises a substantially complete functional repertoire of human D gene segments.

In an embodiment, each heavy chain locus comprises at least 5, 10, 15, 20, 25, 26 or 27 different human D gene segments.

In an embodiment, the heavy chain loci of said vertebrates comprise identical human D and JH gene segment repertoires, but differ in their VH gene repertoires.

In an embodiment, each heavy chain locus comprises at least two human JH gene segments selected from the group consisting of J1, J2, J3, J4, J5 and J6; optionally all of the gene segments of the group.

In an embodiment, each vertebrate comprises human VH gene segments selected from the group consisting of V6-1, V1-2, V1-3, V4-4, V7-41, V2-5, V3-7, V1-8, V3-9, V3-11, V3-15, V1-18, V3-20, V3-21, V3-23, V1-24, V2-26, V4-28, V3-30, V4-31, V3-33, V4-34, V4-39, V3-43, V1-45, V1-46, V3-48, V3-49, V5-51, V3-53, V1-58, V4-59, V4-61, V3-64, V3-66, V1-69, V2-70, V3-72, V3-73 and V3- 74;

wherein the VH gene repertoire comprises a substantially complete human functional VH gene repertoire.

In an embodiment, endogenous antibody heavy chain expression has been inactivated in the vertebrates. For example, less than 10, 5, 4, 3, 2, 1 or 0.5% of heavy chains are provided by endogenous heavy chains (ie, heavy chains whose variable regions are derived from recombination of non-human vertebrate V, D and J gene segments).

In an embodiment, the method of the invention comprises the step of immunising the vertebrates of the population with the same antigen (eg, a human antigen). Thus, the vertebrates are a population and are used as such.

In an embodiment, immunisation of two, more or all of said vertebrates is separated by no more than 12, 9, 6, 5, 4, 3, 2 or 1 months or 3, 2 or 1 week or 6, 5, 4, 3, 2, or 1 day. Thus, the vertebrates are a population and are used as such.

In an embodiment, the method of the invention comprises the step of selecting one or more heavy chains or antibodies from each of said immunised vertebrates on the basis of a common desired antibody or heavy chain characteristic (eg, binding affinity for said antigen), wherein the selected antibodies or heavy chains comprise heavy chain variable region sequences derived from the human VH gene segment repertoire provided by the population.

In an embodiment, the selected antibodies or heavy chains provide a repertoire of selected antibodies or heavy chains (selected repertoire), the method further comprising selecting one or more antibodies or heavy chains from the selected repertoire on the basis of a desired antibody or heavy chain characteristic (eg, binding affinity for said antigen or a different antigen (eg, a related antigen; which is useful for producing bispecific antibodies); or on the basis of the epitope bound by the antibody or heavy chain); optionally wherein the selected repertoire is formed by pooling the selected antibodies or heavy chains.

In an example, the vertebrates share the same genetic background, with the exception of the heavy chain loci thereof (and optionally one or more of the light chain loci thereof).

In any configuration of the invention, in an embodiment vertebrates are derived from transgenic non-human vertebrate ancestor embryonic stem cells that have been genetically modified to include human immunoglobulin locus DNA (eg, human heavy chain V, D and J gene segments and/or human light chain V and J gene segments), the ancestor stem cells being identical or related (eg, clonally related); optionally wherein the genome of the ancestor stem cells comprise a common sequence junction that is a junction between a non-human vertebrate sequence and a human sequence (eg, the ancestor genomes comprise a common transgenic immunoglobulin locus or a common human/non-human vertebrate (eg, human/mouse or human/rat) DNA junction). For example, the genomes comprise a common junction within or at the boundary of one or more of their immunoglobulin chain loci (eg, heavy chain loci and/or light chain loci). For example, the vertebrates of the population are mice whose genomes comprise a common human-mouse DNA junction within their heavy chain loci and/or one or more light chain loci. This is indicative that the mice form a population. For example, by producing variant vertebrates all stemming back from a common ancestor, the vertebrates can all share the same genetic background with the exception of one or more human gene segment repertoires in their genomes. This means that, with the exception of the expression profile resulting from the different gene segment sub-repertoires, there are no other introduced genetic variables between the members of the population, which enhances consistency of performance of the members of the population. This also simplifies breeding to produce the variants making up the population.

The invention provides a method of providing a synthetic antibody light chain sequence repertoire in a population of non-human vertebrates, the method comprising (a) providing a population of transgenic non-human vertebrates (optionally mice or rats), wherein the population provides a repertoire of different human VL gene segments, the repertoire being divided between two or more vertebrates of said population, (b) a first vertebrate of said population comprising a transgenic light chain locus comprising one or more human VL gene segments (first VL gene sub-repertoire) and J segments operably connected upstream of a constant region; and (c) a second vertebrate of said population comprising a transgenic light chain locus comprising one or more human VL gene segments (second VL gene sub-repertoire) and J segments operably connected upstream of a constant region;

(d) wherein the first VL gene sub-repertoire is different from the second VL gene sub-repertoire, whereby the first vertebrate can produce a light chain sequence repertoire that is different from the light chain sequence repertoire produced by the second vertebrate.

Thus, the population provides an overall light chain repertoire comprising the light chain sequence repertoires of the first and second vertebrates. The vertebrates in the population can be immunised with the same antigen in a method of selecting and isolating one or more light chains (eg, provided as part of antibodies) that specifically bind to the antigen.

The VL gene segments of a repertoire can, in one embodiment, be recombined VL, ie, provided as part of a variable region sequence derived from the recombination of human VL with JL (eg, where the VL and JL are human).

In an embodiment, the population comprises a third non-human vertebrate, the third vertebrate comprising a transgenic light chain locus comprising one or more human VL gene segments (third VL gene sub-repertoire) and J segments operably connected upstream of a constant region; wherein the third VL gene sub-repertoire is different from the first and second VL gene sub-repertoires, whereby the third vertebrate can produce a light chain sequence repertoire that is different from the light chain sequence repertoire produced by the first and second vertebrates. Thus, the population provides an overall light chain repertoire comprising the light chain sequence repertoires of the first, second and third vertebrates. The vertebrates in the population can be immunised with the same antigen in a method of selecting and isolating one or more light chains (eg, provided as part of antibodies) that specifically bind to the antigen.

In an embodiment, the J segments of each transgenic light chain locus are human JL gene segments; optionally wherein each light chain locus comprises a substantially complete functional repertoire of human Jκ or Jλ gene segments (eg, each transgenic locus comprises human Vλ gene segments and Jλ gene segments, optionally a substantially complete functional repertoire of human Jλ gene segments; or each transgenic locus comprises human Vκ gene segments and Jκ gene segments, optionally a substantially complete functional repertoire of human Jκ gene segments).

In an embodiment, the repertoire provided by said population comprises a substantially complete repertoire of functional human Vκ gene segments; optionally providing at least 5 different human Jκ gene segments and at least at least 40 different human Vκ gene segments. In an example, the repertoire if provided by a population of non-human vertebrates of the invention, wherein each vertebrate comprises an IgK locus whose Vκ repertoire consists of 30 or less, 20 or less, 14 or less or 6 or less human Vκ gene segment types, as shown in the examples.

In an embodiment, the repertoire provided by said population comprises at least 20, 25, 30, 35 or 40 different human Vκ gene segments.

In an embodiment, the repertoire provided by said population comprises a substantially complete repertoire of functional human Vλ gene segments; optionally providing at least 5 different human Jλ gene segments and at least 40 different human Vλ gene segments.

In an embodiment, the repertoire provided by said population comprises at least 20, 25, 30, 35 or 40 different human Vλ gene segments.

In an embodiment, each light chain locus comprises at least 2, 3, 4, 5 or 6 different human Jκ or Jλ gene segments.

In an embodiment, the light chain loci of said vertebrates comprise identical human JL gene segment repertoires, but differ in their VL gene repertoires.

In an embodiment, endogenous antibody kappa and/or lambda light chain expression has been inactivated in the vertebrates.

In an embodiment, said transgenic light chain loci of the vertebrates are kappa light chain loci (at the endogenous kappa loci, ie, corresponding to the position of a kappa locus in a wild-type non-human vertebrate genome). For example, a transgenic kappa locus can comprise human Vκ gene segments and Jκ gene segments upstream of a constant region (eg, a CH, Cλ or Cκ gene segment; optionally which is an endogenous gene segment). For example, a transgenic kappa locus can comprise human Vλ gene segments and Jλ gene segments upstream of a constant region (eg, a CH, Cλ or Cκ gene segment; optionally which is an endogenous gene segment).

In an embodiment, said transgenic light chain loci of the vertebrates are lambda light chain loci (at the endogenous lambda loci, ie, corresponding to the position of a lambda locus in a wild-type non-human vertebrate genome). For example, a transgenic lambda locus can comprise human Vκ gene segments and Jκ gene segments upstream of a constant region (eg, a CH, Cλ or Cκ gene segment; optionally which is an endogenous gene segment). For example, a transgenic lambda locus can comprise human Vλ gene segments and Jλ gene segments upstream of a constant region (eg, a CH, Cλ or Cκ gene segment; optionally which is an endogenous gene segment).

In an embodiment, the method of the invention comprises the step of immunising the vertebrates of the population with the same antigen (eg, a human antigen). Thus, the vertebrates are a population and are used as such.

In an embodiment, immunisation of two, more or all of said vertebrates is separated by no more than 12, 9, 6, 5, 4, 3, 2 or 1 months or 3, 2 or 1 week or 6, 5, 4, 3, 2, or 1 day. Thus, the vertebrates are a population and are used as such.

In an embodiment, the method of the invention comprises the step of selecting one or more light chains or antibodies from each of said immunised vertebrates on the basis of a common desired antibody or heavy chain characteristic (eg, binding affinity for said antigen), wherein the selected antibodies or light chains comprise light chain variable region sequences derived from the human VL gene segment repertoire provided by the population.

In an embodiment, the selected antibodies or light chains provide a repertoire of selected antibodies or light chains (selected repertoire), the method further comprising selecting one or more antibodies or light chains from the selected repertoire on the basis of a desired antibody or light chain characteristic (eg, binding affinity for said antigen or a different antigen (eg, a related antigen; which is useful for producing bispecific antibodies); or on the basis of the epitope bound by the antibody or light chain); optionally wherein the selected repertoire is formed by pooling the selected antibodies or light chains.

Pooling, as mentioned herein, refers to providing a combination or collection for further use (eg, for further selection of members of the combination or collection on the basis of desirable antibody or antibody chain characteristic). In an example, the members are physically pooled (ie, mixed in a single or a relatively small number of containers, eg, two, three, four, five or six containers).

In an embodiment, the vertebrates share the same genetic background, with the exception of said transgenic light chain loci thereof (and optionally one or more of the heavy chain loci thereof).

In an embodiment, the vertebrates are derived from transgenic non-human vertebrate ancestor embryonic stem cells that have been genetically modified to include human immunoglobulin locus DNA, the ancestor stem cells being identical or related; optionally wherein the genome of the ancestor stem cells comprise a common sequence junction that is a junction between a non-human vertebrate sequence and a human sequence (eg, the ancestor genomes comprise a common transgenic immunoglobulin locus or a common human/non-human vertebrate (eg, human/mouse or human/rat) DNA junction).

The invention provides a method of selecting an antibody that binds a predetermined antigen (eg, a human antigen), the method comprising (a) providing a repertoire of antibodies (first repertoire) that bind said antigen, wherein the antibodies comprise human heavy and light chain variable regions and the repertoire comprises i. A sub-repertoire of antibodies (lambda sub-repertoire) whose light chain variable regions are produced by rearrangement of a human Vλ gene segment with a human $J_L$ gene segment; and ii. A sub-repertoire of antibodies (kappa sub-repertoire) whose light chain variable regions are produced by rearrangement of a human Vκ gene segment with a human $J_L$ gene segment;

(b) selecting one or more antibodies from the lambda sub-repertoire according to a desired antibody characteristic (eg, binding affinity for said antigen);

(c) selecting one or more antibodies from the kappa sub-repertoire according to said desired antibody characteristic;

wherein a repertoire (second repertoire) of selected lambda and kappa antibodies is produced, the antibodies of the second repertoire comprising human variable regions that bind said antigen; and (d) Selecting one or more antibodies from said second repertoire on the basis of a desired antibody characteristic (eg, binding affinity for said antigen);

Wherein in step (a)(i) the lambda sub-repertoire is produced by immunisation of one or more non-human vertebrates (optionally mice or rats) (lambda vertebrates) with said antigen, wherein the lambda vertebrates express more human lambda-type antibodies (antibodies whose light chain variable regions are derived from the rearrangement of a human Vλ gene segment) than kappa-type antibodies (antibodies whose light chain variable regions are derived from the rearrangement of a Vκ gene segment);

Wherein in step (a)(ii) the kappa sub-repertoire is produced by immunisation of one or more non-human vertebrates (optionally mice or rats) (kappa vertebrates) with said antigen, wherein the kappa vertebrates express more human kappa-type antibodies (antibodies whose light chain variable regions are derived from the rearrangement of a human Vκ gene segment) than lambda-type antibodies (antibodies whose light chain variable regions are derived from the rearrangement of a Vλ gene segment).

Each sub-repertoire comprises at least two antibodies, for example, each sub-repertoire comprises or consists of at least 10, 15, 20, 50, 100, $10^3$, $10^4$, $10^5$, $10^6$, $10^7$, $10^8$, $10^9$, $10^{10}$, $10^{11}$, $10^{12}$, $10^{13}$, or $10^{14}$ antibodies.

Examples of a desirable antibody characteristic are affinity for binding a predetermined antigen or epitope (eg, as determined by surface plasmon resonance), completion with a known antibody for binding to a predetermined antigen or epitope, epitopic specificity of the antibody (eg, as determined by X-ray crystallography, competition with a known antibody for antigen binding wherein the known antibody specifically binds to the antigen (eg, as determined by surface plasmon resonance, eg, Biacore™), performance in ELISA or another immunoassay, a desirable biophysical characteristic (eg, melting temperature, pI, solution state, degree of aggregation, storage profile etc).

The lambda-type antibodies can comprise any constant region, eg, Cλ, Cκ or CH (optionally wherein the C is endogenous). The kappa-type antibodies can comprise any constant region, eg, Cλ, Cκ or CH (optionally wherein the C is endogenous).

Methods of immunisation for use in the invention are well known to the skilled person and may involve a classic prime-boost regime, RIMMS or any other protocol. An adjuvant may be administered with the antigen, as is known in the art.

The second repertoire comprises at least two antibodies, for example, each sub-repertoire comprises or consists of at least 10, 15, 20, 50, 100, $10^3$, $10^4$, $10^5$, $10^6$, $10^7$, $10^8$, $10^9$, $10^{10}$, $10^{11}$, $10^{12}$, $10^{13}$, or $10^{14}$ antibodies.

Human heavy chain variable regions are variable regions derived from recombination of a human VH gene segment with a D and JH gene segment (eg, wherein the D and JH gene segments are also human). Human light chain variable regions are variable regions derived from recombination of a human VL gene segment with a JL gene segment (eg, wherein the JL gene segment is also human).

In an embodiment, the lambda vertebrates express substantially no kappa-type antibodies. For example, less than 10, 5, 4, 3, 2, 1 or 0.5% of kappa antibodies are endogenous.

In an embodiment, endogenous kappa antibody expression is substantially inactive in the lambda vertebrates. For example, less than 10, 5, 4, 3, 2, 1 or 0.5% of kappa antibodies are endogenous.

In an embodiment, the kappa vertebrates express substantially no lambda-type antibodies. For example, less than 10, 5, 4, 3, 2, 1 or 0.5% of lambda antibodies are endogenous. Due to the relatively low endogenous lambda expression in mice, when the vertebrates are mice, it may not be necessary to carry out any specific genetic manipulation in the mice to achieve substantially inactive lambda expression.

In an embodiment, endogenous lambda antibody expression is substantially inactive in the kappa vertebrates. For example, less than 10, 5, 4, 3, 2, 1 or 0.5% of lambda antibodies are endogenous. Due to the relatively low endogenous lambda expression in mice, when the vertebrates are mice, it may not be necessary to carry out any specific genetic manipulation in the mice to achieve substantially inactive lambda expression.

In an embodiment, formation (eg, first or last immunisation) of the lambda sub-repertoire is separated by no more than 12, 9, 6, 5, 4, 3, 2 or 1 months or 3, 2 or 1 week or 6, 5, 4, 3, 2, or 1 day from the formation (eg, first or last immunisation) of the kappa sub-repertoire. Thus, the vertebrates form a population and are used as such.

In an embodiment, the second repertoire is formed by pooling the selected lambda and kappa antibodies.

In an embodiment, lambda and kappa antibodies are selected on the basis of affinity of binding to said antigen (higher affinity being preferable to lower affinity).

In an embodiment, affinity is determined by surface plasmon resonance.

In an embodiment, the kappa and lambda vertebrates share the same genetic background, with the exception of the light chain loci thereof (and optionally heavy chain loci thereof).

In an embodiment, the kappa and lambda vertebrates are derived from transgenic non-human vertebrate ancestor embryonic stem cells that have been genetically modified to include human immunoglobulin locus DNA, the ancestor stem cells being identical or related; optionally wherein the genome of the ancestor stem cells comprise a common sequence junction that is a junction between a non-human vertebrate sequence and a human sequence (eg, the ancestor genomes comprise a common transgenic immunoglobulin locus or a common human/non-human vertebrate (eg, human/mouse or human/rat) DNA junction).

The invention provides a population of transgenic non-human vertebrates (optionally mice or rats), wherein the population provides a repertoire of different human VH gene segments, the repertoire being divided between two or more vertebrates of said population, (a) a first vertebrate of said population comprising a transgenic heavy chain locus comprising one or more human VH gene segments (first VH gene sub-repertoire), D segments and J segments operably connected upstream of a constant region; and (b) a second vertebrate of said population comprising a transgenic heavy chain locus comprising one or more human VH gene segments (second VH gene sub-repertoire), D segments and J segments operably connected upstream of a constant region;

(c) wherein the first VH gene sub-repertoire is different from the second VH gene sub-repertoire for expression of first and second antibody heavy chain sequence repertoires respectively that are different from each other, whereby the population provides a synthetic repertoire of antibody heavy chain sequences.

In an embodiment, the population comprises a third non-human vertebrate, the third vertebrate comprising a transgenic heavy chain locus comprising one or more human VH gene segments (third VH gene sub-repertoire), D segments and J segments operably connected upstream of a constant region; wherein the third VH gene sub-repertoire is different from the first and second VH gene sub-repertoires for expression of a third antibody heavy chain sequence repertoire that is different from the first and second antibody heavy chain sequence repertoires, whereby the population provides a synthetic repertoire of antibody heavy chain sequences.

In an embodiment, the vertebrates have been immunised with the same antigen (eg, a human antigen).

In an embodiment, the repertoire provided by said population comprises a substantially complete repertoire of functional human VH gene segments; optionally providing at least 6 different human JH gene segments, 27 different human D segments and at least 40 different human VH gene segments.

In an embodiment, the human VH gene segment repertoire provided by said population comprises at least 20, 25, 30, 35 or 40 different human VH gene segments.

In an embodiment, the J segments of each transgenic heavy chain locus are human JH gene segments; optionally wherein each heavy chain locus comprises a substantially complete functional repertoire of human JH gene segments.

In an embodiment, each heavy chain locus comprises at least 2, 3, 4, 5 or 6 different human JH gene segments.

In an embodiment, the D segments of each transgenic heavy chain locus are human D gene segments; optionally wherein each heavy chain locus comprises a substantially complete functional repertoire of human D gene segments.

In an embodiment, each heavy chain locus comprises at least 5, 10, 15, 20, 25, 26 or 27 different human D gene segments.

In an embodiment, the heavy chain loci of said vertebrates comprise identical human D and JH gene segment repertoires, but differ in their VH gene repertoires.

In an embodiment, each heavy chain locus comprises at least two human JH gene segments selected from the group consisting of J1, J2, J3, J4, J5 and J6; optionally all of the gene segments of the group.

In an embodiment, each heavy chain locus comprises at least 10 human D gene segments selected from the group consisting of D1-1, D2-2, D3-3, D4-4, D5-5, D6-6, D1-7, D2-8, D3-9, D3-10, D4-11, D5-12, D6-13, D1-14, D2-15, D3-16, D4-17, D5-18, D6-19, D1-20, D2-21, D3-22, D4-23, D5-24, D1-26, D6-25 and D7-27; optionally all of the gene segments of the group.

In an embodiment, the population comprises a third vertebrate as described above, wherein each vertebrate comprises human VH gene segments selected from the group consisting of V6-1, V1-2, V1-3, V4-4, V7-41, V2-5, V3-7, V1-8, V3-9, V3-11, V3-15, V1-18, V3-20, V3-21, V3-23, V1-24, V2-26, V4-28, V3-30, V4-31, V3-33, V4-34, V4-39, V3-43, V1-45, V1-46, V3-48, V3-49, V5-51, V3-53, V1-58, V4-59, V4-61, V3-64, V3-66, V1-69, V2-70, V3-72, V3-73 and V3-74; wherein the population provided by the repertoire comprises a substantially complete human functional VH gene repertoire.

In an embodiment, endogenous antibody heavy chain expression has been inactivated in the vertebrates.

In an embodiment, two, more or all of said vertebrates of the population have been immunised with the same antigen, wherein two or more of the immunisations are separated by no more than 12, 9, 6, 5, 4, 3, 2 or 1 months or 3, 2 or 1 week or 6, 5, 4, 3, 2, or 1 day.

In an embodiment, the vertebrates share the same genetic background, with the exception of the heavy chain loci thereof (and optionally one or more of the light chain loci thereof).

In an embodiment, the vertebrates are derived from transgenic non-human vertebrate ancestor embryonic stem cells that have been genetically modified to include human immunoglobulin locus DNA, the ancestor stem cells being identical or related; optionally wherein the genome of the ancestor stem cells comprise a common sequence junction that is a junction between a non-human vertebrate sequence and a human sequence (eg, the ancestor genomes comprise a common transgenic immunoglobulin locus or a common human/non-human vertebrate (eg, human/mouse or human/rat) DNA junction).

The invention provides a population of transgenic non-human vertebrates (optionally mice or rats), wherein the population provides a repertoire of different human VL gene segments, the repertoire being divided between two or more vertebrates of said population, a first vertebrate of said population comprising a transgenic light chain locus comprising one or more human VL gene segments (first VL gene sub-repertoire) and J segments operably connected upstream of a constant region; and a second vertebrate of said population comprising a transgenic light chain locus comprising one or more human VL gene segments (second VL gene sub-repertoire) and J segments operably connected upstream of a constant region;

wherein the first VL gene sub-repertoire is different from the second VL gene sub-repertoire for expression of first and second antibody light chain sequence repertoires respectively that are different from each other, whereby the population provides a synthetic repertoire of antibody light chain sequences.

In an embodiment, the population comprises a third non-human vertebrate, the third vertebrate comprising a transgenic light chain locus comprising one or more human VL gene segments (third VL gene sub-repertoire) and J segments operably connected upstream of a constant region; wherein the third VL gene sub-repertoire is different from the first and second VH gene sub-repertoires for expression of a third antibody light chain sequence repertoire that is different from the first and second antibody light chain sequence repertoires, whereby the population provides a synthetic repertoire of antibody light chain sequences.

In an embodiment, the vertebrates have been immunised with the same antigen (eg, a human antigen).

In an embodiment, the J segments of each transgenic light chain locus are human JL gene segments; optionally wherein each light chain locus comprises a substantially complete functional repertoire of human Jκ or Jλ gene segments.

In an embodiment, the VL gene segment repertoire provided by said population comprises a substantially complete repertoire of functional human Vκ gene segments; optionally providing at least 5 different human Jκ gene segments and at least 40 different human Vκ gene segments.

In an embodiment, the VL gene segment repertoire provided by said population comprises at least 20, 25, 30, 35 or 40 different human Vκ gene segments.

In an embodiment, the VL gene segment repertoire provided by said population comprises a substantially complete repertoire of functional human Vλ gene segments; optionally providing at least 5 different human Jλ gene segments and 30 different human Vλ gene segments.

In an embodiment, the VL gene segment repertoire provided by said population comprises at least 20, 25 or 30 different human Vλ gene segments.

In an embodiment, each light chain locus comprises at least 2, 3, 4, 5 or 6 different human Jκ or Jλ gene segments.

In an embodiment, the light chain loci of said vertebrates comprise identical human JL gene segment repertoires, but differ in their VL gene repertoires.

In an embodiment, endogenous antibody kappa and/or lambda light chain expression has been inactivated in the vertebrates.

In an embodiment, said transgenic light chain loci of the vertebrates are kappa light chain loci.

In an embodiment, said transgenic light chain loci of the vertebrates are lambda light chain loci.

In an embodiment, the light chain loci of said vertebrates comprise identical human JL gene segment repertoires, but differ in their VL gene repertoires.

In an embodiment, each light chain locus comprises at least 2, 3, 4 or 5 human Jκ gene segments or at least 2, 3, 4 or 5 human Jλ gene segments.

In an embodiment, two, more or all of said vertebrates of the population have been immunised with the same antigen, wherein two or more of the immunisations are separated by no more than 12, 9, 6, 5, 4, 3, 2 or 1 months or 3, 2 or 1 week or 6, 5, 4, 3, 2, or 1 day.

In an embodiment, the vertebrates share the same genetic background, with the exception of said transgenic light chain loci thereof (and optionally one or more of the heavy chain loci thereof).

In an embodiment, the vertebrates are derived from transgenic non-human vertebrate ancestor embryonic stem cells that have been genetically modified to include human immunoglobulin locus DNA, the ancestor stem cells being identical or related; optionally wherein the genome of the ancestor stem cells comprise a common sequence junction that is a junction between a non-human vertebrate sequence and a human sequence (eg, the ancestor genomes comprise a common transgenic immunoglobulin locus or a common human/non-human vertebrate (eg, human/mouse or human/rat) DNA junction).

The invention provides a population of non-human vertebrates (optionally mice or rats), wherein the genome of each vertebrate comprises:

One or more transgenic immunoglobulin heavy chain loci, each locus comprising one or more human $V_L$ gene segments, one or more human D gene segments and one or more human J gene segments upstream of one or more heavy chain constant regions; and One or more transgenic immunoglobulin light chain loci, each locus comprising one or more human $V_L$ gene segments and one or more human $J_L$ gene segments upstream of one or more light chain constant regions;

Wherein in each vertebrate the gene segments in transgenic heavy chain loci are operably linked to the constant region thereof, and the gene segments in transgenic light chain loci are operably linked to the constant region thereof, so that upon immunisation the vertebrate is capable of producing an antibody comprising heavy chains produced by recombination of a heavy chain locus and light chains produced by recombination of a light chain locus, wherein the heavy and light chains comprise human variable regions;

Wherein the population comprises (i) a first vertebrate type (lambda vertebrates) wherein said light chain loci comprise one or more human Vλ gene segments, wherein following rearrangement the loci express light chain sequences comprising variable region sequences derived from human Vλ gene segments (human lambda light chain sequences), wherein the lambda vertebrates express more lambda light chain sequences than kappa light chain sequences (sequences of light chains comprising variable region sequences derived from Vκ gene segments); and (ii) a second vertebrate type (kappa vertebrates) wherein said light chain loci comprise one or more human Vκ gene segments, wherein following rearrangement the loci express light chain sequences comprising variable region sequences derived from human Vκ gene segments (human kappa light chain sequences), wherein the kappa vertebrates express more kappa light chain sequences than lambda light chain sequences (sequences of light chains comprising variable regions derived from Vλ gene segments);

wherein the vertebrates of said population can be immunised with the same antigen to produce a repertoire of antibodies comprising human heavy and light chain variable regions, wherein the repertoire comprises a sub-repertoire of human lambda antibodies (lambda sub-repertoire) produced by vertebrates of the first type and a sub-repertoire of human kappa antibodies (kappa sub-repertoire) produced by vertebrates of the second type.

In an embodiment, the vertebrates have been immunised with the same antigen; optionally a human antigen.

In an embodiment, immunisation of the lambda vertebrates is separated by no more than 12, 9, 6, 5, 4, 3, 2 or 1 months or 3, 2 or 1 week or 6, 5, 4, 3, 2, or 1 day from the immunisation of the kappa vertebrates.

In an embodiment, the lambda vertebrates express substantially no kappa-type antibodies.

In an embodiment, endogenous kappa antibody expression is substantially inactive in the lambda vertebrates.

In an embodiment, the kappa vertebrates express substantially no lambda-type antibodies.

In an embodiment, endogenous lambda antibody expression is substantially inactive in the kappa vertebrates.

The invention provides an animal house or a laboratory containing a population according to the invention. For example, vertebrates of the population can be housed in the same cage or in the same collection of cages in the same animal house, building or laboratory. The cages or vertebrates themselves may be labelled so that they are part of the same population or experiment. They may be owned by the same owner, eg, the same company, or in the control of a single person or company. They may be allocated for use in the same research programme or series of related research experiments aimed at discovering one or more antibodies or antibody chains against a common antigen or related antigens. Thus, the vertebrates provide a population and are used as such. It is indicative of a population, that the vertebrates are discussed in the context of the same research programme or immunisation schedule or experiment or set of experiments in a laboratory notebook or a set of laboratory notebooks that relate to the same research programme or immunisation schedule or experiment or set of experiments. For example, such a programme, schedule or experiment(s) may relate to immunisation of the vertebrates of a population with the same antigen.

The invention provides a selected repertoire of antibodies produced according to the method of the invention, or a second repertoire of antibodies produced according to the method of the invention, wherein the antibodies of the selected or second repertoire have been selected for binding a common antigen (eg, a human antigen) from a population of non-human vertebrates.

In an embodiment, in the repertoire, the vertebrates are derived from transgenic non-human vertebrate ancestor embryonic stem cells that have been genetically modified to include human immunoglobulin locus DNA, the ancestor stem cells being identical or related; optionally wherein the genome of the ancestor stem cells comprise a common sequence junction that is a junction between a non-human vertebrate sequence and a human sequence (eg, the ancestor genomes comprise a common transgenic immunoglobulin locus or a common human/non-human vertebrate (eg, human/mouse or human/rat) DNA junction).

In an embodiment, in the repertoire, the population is according to any configuration, aspect, embodiment, example or description of the invention herein.

The invention provides a non-human vertebrate (optionally a mouse or rat), wherein the genome of each vertebrate comprises:

One or more transgenic immunoglobulin heavy chain loci, each locus comprising one or more human V gene segments, one or more human D gene segments and one or more human J gene segments upstream of one or more heavy chain constant regions; and One or more transgenic immunoglobulin light chain loci (eg, lambda loci or kappa loci), each locus comprising a human $V_\lambda$ gene segment repertoire and one or more human Jλ gene segments upstream of one or more light chain constant regions;

Wherein following rearrangement the light chain loci express light chain sequences comprising variable region sequences derived from human Vλ gene segments (human lambda light chain sequences);

Wherein the kappa (and optionally endogenous lambda) light chain expression has been substantially inactivated so that the vertebrate expresses more human lambda light chain sequences than kappa light chain sequences (sequences of light chains comprising variable region sequences derived from Vκ gene segments);

Wherein endogenous heavy chain expression has been substantially inactivated; and Wherein each said transgenic light chain locus comprises a substantially complete functional $V_\lambda$ gene segment repertoire of a human.

Such vertebrates express light chains wherein all or substantially all light chains comprise a human lambda light chain sequence and the vertebrates express substantially no endogenous Ig chains or kappa chains. Such vertebrates are useful as a population of lambda vertebrates for use in the seventh and tenth configuration of the invention (ie, embodiments of the invention where there are separate lambda vertebrates and kappa vertebrates).

For example, less than 10, 5, 4, 3, 2, 1 or 0.5% of kappa antibodies are endogenous or no kappa antibodies are endogenous.

For example, less than 10, 5, 4, 3, 2, 1 or 0.5% of lambda antibodies are endogenous or no lambda antibodies are endogenous. Due to the relatively low endogenous lambda expression in mice, when the vertebrates are mice, it may not be necessary to carry out any specific genetic manipulation in the mice to achieve substantially inactive lambda expression.

For example, less than 10, 5, 4, 3, 2, 1 or 0.5% of heavy antibodies are endogenous or no heavy antibodies are endogenous.

In an embodiment of the vertebrate, each said transgenic light chain locus comprises at least 20, 25, 26, 27, 28 or 29 human $V_\lambda$ gene segments selected from the group consisting of V3-1, V2-8, V3-9, V3-10, V2-11, V3-12, V3-16, V2-18, V3-19, V3-21, V3-22, V2-23, V3-25, V3-27, V1-36, V5-37, V5-39, V1-40, V7-43, V1-44, V5-45, V7-46, V1-74, V9-49, V1-51, V5-52, V6-57, V4-60, V8-61 and V4-69; optionally all of the gene segments of the group.

In an embodiment of the vertebrate, each said transgenic light chain locus comprises a substantially complete functional $J_\lambda$ gene segment repertoire of a human.

In an embodiment of the vertebrate, each said transgenic light chain locus comprises at least 3 or 4 human $J_\lambda$ gene segments selected from the group consisting of J1, J2, J3, J6 and J7; optionally all of the gene segments of the group.

In an embodiment of the vertebrate, each said transgenic heavy chain locus comprises a substantially complete functional VH gene segment repertoire of a human.

In an embodiment of the vertebrate, each said transgenic heavy chain locus comprises at least 30, 35, 36, 37, 38 or 39 human VH gene segments selected from the group consisting of V6-1, V1-2, V1-3, V4-4, V7-41, V2-5, V3-7, V1-8, V3-9, V3-11, V3-15, V1-18, V3-20, V3-21, V3-23, V1-24, V2-26, V4-28, V3-30, V4-31, V3-33, V4-34, V4-39, V3-43, V1-45, V1-46, V3-48, V3-49, V5-51, V3-53, V1-58, V4-59, V4-61, V3-64, V3-66, V1-69, V2-70, V3-72, V3-73 and V3-74; optionally all of the gene segments of the group.

In an embodiment of the vertebrate, each said transgenic heavy chain locus comprises at least 4 or 5 human JH gene segments selected from the group consisting of J1, J2, J3, J4, J5, J6; optionally all of the gene segments of the group.

In an embodiment of the vertebrate, each said transgenic heavy chain locus comprises at least 15, 20, 21, 22, 23, 24, 25 or 26 human D gene segments selected from the group consisting of D1-1, D2-2, D3-3, D4-4, D5-5, D6-6, D1-7, D2-8, D3-9, D3-10, D4-11, D5-12, D6-13, D1-14, D2-15, D3-16, D4-17, D5-18, D6-19, D1-20, D2-21, D3-22, D4-23, D5-24, D1-26, D6-25 and D7-27; optionally all of the gene segments of the group.

The invention provides a population of non-human vertebrates (optionally mice or rats), wherein each vertebrate is according to the invention, wherein the population provides a human VH gene segment repertoire that is divided between two or more vertebrates of said population as per the invention.

The invention provides a population of non-human vertebrates (optionally mice or rats), wherein each vertebrate is according to the invention, wherein the population provides a human VH gene segment repertoire that is divided between first, second and third vertebrates, wherein the first vertebrate comprises a human VH gene repertoire comprising 5 or 6 gene segments from the group consisting of V6-1, V1-2, V1-3, V4-4, V7-41 and V2-5;

the second vertebrate comprises a human VH gene repertoire comprising 15, 16, 17, 18, 19, 20 or 21 gene segments from the group consisting of V3-7, V1-8, V3-9, V3-11, V3-15, V1-18, V3-20, V3-21, V3-23, V1-24, V2-26, V4-28, V3-30, V4-31, V3-33, V4-34, V4-39, V3-43, V1-45, V1-46 and V3-48; and the third vertebrate comprises a human VH gene repertoire comprising 10, 11, 12 or 13 gene segments from the group consisting of V3-49, V5-51, V3-53, V1-58, V4-59, V4-61, V3-64, V3-66, V1-69, V2-70, V3-72, V3-73 and V3-74;

Wherein the VH gene repertoires of the vertebrates are different from each other;

Wherein the population provides a substantially complete functional VH gene segment repertoire of a human and a substantially complete functional V$\lambda$ gene segment of a human, such that following immunisation of the vertebrates of the population with an antigen a synthetic repertoire of antibodies can be produced that is derived from the substantially complete functional human VH and V$\lambda$ repertoires substantially in the absence of kappa chain expression and endogenous heavy chain expression.

In an embodiment of the population, the first vertebrate comprises a human VH gene repertoire consisting of V6-1, V1-2, V1-3, V4-4, V7-41 and V2-5;

the second vertebrate comprises a human VH gene repertoire consisting of V3-7, V1-8, V3-9, V3-11, V3-15, V1-18, V3-20, V3-21, V3-23, V1-24, V2-26, V4-28, V3-30, V4-31, V3-33, V4-34, V4-39, V3-43, V1-45, V1-46 and V3-48; and the third vertebrate comprises a human VH gene repertoire consisting of V3-49, V5-51, V3-53, V1-58, V4-59, V4-61, V3-64, V3-66, V1-69, V2-70, V3-72, V3-73 and V3-74.

In an embodiment of the population, the vertebrates express no kappa light chains at all.

The invention provides a method of isolating an antibody (lambda-type antibody) that binds a predetermined antigen and whose heavy and light chain variable regions are derived from human VH and V$\lambda$ gene segments respectively, the method comprising immunising the vertebrate or the population of vertebrates according to the invention with the antigen and selecting a lambda-type antibody from said vertebrate or population.

The invention provides a pharmaceutical composition comprising an antibody selected as described above or a derivative thereof that binds said antigen, together with a pharmaceutically acceptable diluent, carrier or excipient.

Examples of derivative antibodies (according to any aspect herein) are antibodies that have one or more mutations compared to the isolated antibody (eg, to improve antigen-binding affinity and/or to enhance or inactivate Fc function) Such mutants specifically bind the antigen. Mutation or adaptation to produce a derivative includes, eg, mutation to produce Fc enhancement or inactivation. A derivative can be an antibody following conjugation to a toxic payload or reporter or label or other active moiety. In another example, a chimaeric antibody chain or antibody is modified by replacing one or all human constant regions thereof by a corresponding human constant region. For example, all constant regions of an antibody isolated from such a cell or vertebrate are replaced with human constant regions to produce a fully human antibody (ie, comprising human variable and constant regions). Such an antibody is useful for administration to human patients to reduce anti-antibody reaction by the patient.

The invention provides a method of providing a synthetic antibody heavy chain sequence repertoire, the method comprising providing a heavy chain variable region gene segment repertoire that is divided across the genomes of two or more non-human vertebrates in which endogenous heavy chain expression is substantially inactive, the repertoire gene segments in the genomes being provided as part of transgenic heavy chain loci comprising one or more VH gene segments, one or more D gene segments and one or JH gene segments functionally connected upstream of a heavy chain constant region (eg, Cmu and/or Cgamma), wherein the genomes can express different repertoires of antibody heavy chain sequences derived from VH, D and JH gene segments;

Wherein the gene segment repertoire is selected from the group consisting of:
(a) a VH gene repertoire (eg, a human VH gene repertoire or a substantially complete functional human VH gene repertoire);
(b) a D gene repertoire (eg, a human D gene repertoire or a substantially complete functional human D gene repertoire); and
(c) a JH gene repertoire (eg, a human JH gene repertoire or a substantially complete functional human JH gene repertoire);
Optionally wherein the D and JH segments in the loci are human D and JH segments.

The invention provides a method of providing a synthetic antibody kappa chain sequence repertoire, the method comprising providing a kappa chain variable region gene segment repertoire that is divided across the genomes of two or more non-human vertebrates in which endogenous kappa chain (and optionally also endogenous lambda chain) expression is substantially inactive, the repertoire gene segments in the genomes being provided as part of transgenic light chain loci comprising one or more Vκ gene segments and one or more Jκ gene segments functionally connected upstream of a light chain constant region (eg, Cκ and/or Cλ), wherein the genomes can express different repertoires of antibody kappa chain sequences derived from Vκ and Jκ gene segments;

Wherein the gene segment repertoire is selected from the group consisting of:
(a) a Vκ gene repertoire (eg, a human Vκ gene repertoire or a substantially complete functional human Vκ gene repertoire); and
(c) a Jκ gene repertoire (eg, a human Jκ gene repertoire or a substantially complete functional human Jκ gene repertoire);
Optionally wherein the Jκ segments in the loci are human Jκ segments.

The invention provides a method of providing a synthetic antibody lambda chain sequence repertoire, the method comprising providing a lambda chain variable region gene segment repertoire that is divided across the genomes of two or more non-human vertebrates in which endogenous lambda chain (and optionally also endogenous kappa chain) expression is substantially inactive, the repertoire gene segments in the genomes being provided as part of transgenic light chain loci comprising one or more Vλ gene segments and one or more Jλ gene segments functionally connected upstream of a light chain constant region (eg, Cκ and/or Cλ), wherein the genomes can express different repertoires of antibody lambda chain sequences derived from Vλ and Jλ gene segments;

Wherein the gene segment repertoire is selected from the group consisting of:
(a) a Vλ gene repertoire (eg, a human Vλ gene repertoire or a substantially complete functional human Vλ gene repertoire); and
(c) a Jλ gene repertoire (eg, a human Jλ gene repertoire or a substantially complete functional human Jλ gene repertoire);
Optionally wherein the Jλ segments in the loci are human Jλ segments.

The invention provides a method of providing a synthetic antibody light chain sequence repertoire, the method comprising providing
a Vκ gene repertoire in the genomes of a first group of non-human vertebrates in which endogenous lambda chain (and optionally also endogenous kappa chain) expression is substantially inactive, the Vκ genes in the genomes being provided as part of transgenic light chain loci comprising one or more Jκ gene segments functionally connected upstream of a light chain constant region (eg, Cκ and/or Cλ, eg, human Cλ), wherein the genomes can express repertoires of antibody kappa light chain sequences derived from Vκ and Jκ gene segments substantially in the absence of lambda light chain expression; and
a Vλ gene repertoire in the genomes of a second group of non-human vertebrates in which endogenous kappa chain (and optionally also endogenous lambda chain) expression is substantially inactive, the Vλ genes in the genomes being provided as part of transgenic light chain loci comprising one or more Jλ gene segments functionally connected upstream of a light chain constant region (eg, Cκ and/or Cλ, eg, human Cλ), wherein the genomes can express repertoires of antibody lambda light chain sequences derived from human Vλ and Jλ gene segments substantially in the absence of kappa light chain expression;
Optionally wherein the Vκ gene repertoire is a human Vκ gene repertoire (eg, a substantially complete functional human Vκ gene repertoire), the Vλ gene repertoire is a human Vλ gene repertoire (eg, a substantially complete functional human Vλ gene repertoire), the Jκ segments in the loci are human Jκ segments and the Jλ segments in the loci are human Jλ segments;
Optionally wherein the genomes of the first and second groups comprise a substantially complete functional VH gene repertoire of a human.

The invention provides a population of non-human vertebrates for generating antibodies, the population comprising the first and second groups of vertebrates described above, optionally wherein the vertebrates of the population have been immunised with the same antigen (eg, a human antigen).

The invention provides a synthetic repertoire of antibody heavy chain sequences, antibody light chain sequences, antibody kappa chain sequences, antibody lambda chain sequences, or a repertoire of antibodies obtained from a population of non-human vertebrates according to the invention; or wherein the repertoire is obtained from a vertebrate of the invention.

In an embodiment of the repertoire, the population of vertebrates have been immunised with the same antigen (eg, a human antigen).

In an embodiment of the repertoire, the population of vertebrates are naïve.

In an embodiment of any configuration, the vertebrates are naïve (ie, not immunised with a predetermined antigen, as the term is understood in the art; for example, such a vertebrate that has been kept in a relatively sterile environment as provided by an animal house used for R&D). In another example, the vertebrates have been immunised with a predetermined antigen, eg, an antigen bearing a human epitope. In another example, the population comprises naïve and immunised vertebrates.

In an embodiment of the repertoire, the genomes of the vertebrates comprise a common transgenic immunoglobulin locus or a common human/non-human vertebrate (eg, human/mouse or human/rat) DNA junction.

In an embodiment of the repertoire, the members of the repertoire bind a common antigen and have been generated in the same research programme.

The invention provides a method of providing a synthetic antibody heavy chain repertoire, the method comprising (a) Dividing a human VH gene segment repertoire (eg, a substantially complete functional human VH gene repertoire) across the genomes of at least first and second non-human vertebrates (eg, mice or rats), the repertoire comprising a first cluster of VH gene segments corresponding to a distal VH gene cluster of the heavy chain locus of a human; and a second cluster of VH gene segments corresponding to a proximal VH gene cluster of the heavy chain locus of a human, wherein the proximal cluster is arranged proximally to the distal cluster in said human locus;

Wherein the distal cluster is provided in a heavy chain locus of said first vertebrate upstream of one or more D gene segments, one or more JH gene segments and one or more constant regions;

Wherein the proximal cluster is provided in a heavy chain locus of said second vertebrate upstream of one or more D gene segments, one or more JH gene segments and one or more constant regions;

Wherein the proximal VH gene cluster is not present between the distal cluster and the D gene segments in the heavy chain locus of the first vertebrate (optionally wherein no further VH gene segments are present between the distal cluster and the D gene segments in the heavy chain locus of the first vertebrate); and (b) Expressing said heavy chain loci of the first and second vertebrates to provide a repertoire of synthetic antibody heavy chains.

A cluster of human gene segments (eg, VH gene segments) refers to a collection of gene segments present in a human Ig locus (eg, a human heavy chain locus) from a first gene segment to a second, downstream (more 3') gene segment in a human genome (eg, in a germline human Ig locus). Examples of gene segment arrangements are found in the IMGT database (or by reference to Kabat or the other antibody resources available to the skilled person and described herein). For example, the gene segments in a cluster are all human VH. For example, the gene segments in a cluster are all human Vκ gene segments. For example, the gene segments in a cluster are all human Vλ gene segments. For example, the gene segments in a cluster are all human JH gene segments. For example, the gene segments in a cluster are all human Jλ gene segments. For example, the gene segments in a cluster are all human Jκ gene segments. For example, the gene segments in a cluster are all human D gene segments. For example, a human germline heavy chain Ig locus comprises the following gene cluster (in the 3' to 5' direction, ie, in the proximal to distal direction, ie in the downstream to upstream direction): V6-1, V1-2, V1-3, V4-4, V7-41. For use in the present invention, the V gene segments in this cluster can be provided in this order (the human germline order) or a different order from that shown here. If this cluster is deemed to be a "proximal cluster" in the present invention, a "distal cluster" could be (in the 3' to 5' direction, ie, in the proximal to distal direction, ie in the downstream to upstream direction): V3-49, V5-51, V3-53, V1-58, V4-59, V4-61, V3-64, V3-66, V1-69, V2-70, V3-72, V3-73 and V3-74. A medial cluster (see below) could be (in the 3' to 5' direction, ie, in the proximal to distal direction, ie in the downstream to upstream direction): V3-7, V1-8, V3-9, V3-11, V3-15, V1-18, V3-20, V3-21, V3-23, V1-24, V2-26, V4-28, V3-30, V4-31, V3-33, V4-34, V4-39, V3-43, V1-45, V1-46 and V3-48. In an example, the gene segment clusters are discrete (ie, do not share a common gene segment). In an example two or more clusters are overlapping—for example, a first gene segment cluster (such as a proximal cluster) comprises one or more gene segments that are comprised by a second gene segment cluster (such as a medial or distal cluster) and the first and second clusters are different.

In an embodiment of the method, a third vertebrate comprises a third cluster of VH gene segments corresponding to a medial VH gene cluster of the heavy chain locus of a human, wherein the medial cluster is arranged between the distal and proximal clusters in said human locus; wherein the medial cluster is provided in a heavy chain locus of said third vertebrate upstream of one or more D gene segments, one or more JH gene segments and one or more constant regions; wherein the heavy chain locus of the third vertebrate does not comprise the distal, medial and proximal clusters in an arrangement corresponding to the arrangement of said human (optionally wherein the heavy chain locus of the third vertebrate does not comprise the distal and proximal clusters); the method further comprising expressing said heavy chain locus of the third vertebrate, whereby the repertoire of synthetic antibody heavy chains is provided by expression from the first, second and third vertebrate loci.

In an embodiment of the method, the vertebrates have been immunised with the same antigen (eg, a human antigen).

In an embodiment of the method, the vertebrates are naïve.

In an embodiment of the method, the vertebrates have a common collection of light chain loci. For example, the kappa chain loci alleles are identical in the vertebrates and/or the lambda chain loci alleles are identical in the vertebrates. This simplifies construction of vertebrate variants for producing the population and also simplifies breeding.

In an embodiment, the method comprises comprising selecting one or more antibody heavy chains (eg, as part of an antibodies) from said repertoire according to a desired characteristic (eg, affinity for biding an antigen).

The invention provides a method of providing a synthetic antibody kappa chain repertoire, the method comprising (a) Dividing a human Vκ gene segment repertoire (eg, a substantially complete functional human Vκ gene repertoire) across the genomes of at least first and second non-human vertebrates (eg, mice or rats), the repertoire comprising a first cluster of Vκ gene segments corresponding to a distal Vκ gene cluster of the kappa chain locus of a human; and a second cluster of Vκ gene segments corresponding to a proximal Vκ gene cluster of the kappa chain locus of a human, wherein the proximal cluster is arranged proximally to the distal cluster in said human locus;

Wherein the distal cluster is provided in a kappa chain locus of said first vertebrate upstream of one or more Jκ gene segments and one or more constant regions;

Wherein the proximal cluster is provided in a kappa chain locus of said second vertebrate upstream of one or more Jκ gene segments and one or more constant regions;

Wherein the proximal Vκ gene cluster is not present between the distal cluster and the Jκ gene segments in the kappa chain locus of the first vertebrate (optionally wherein no further Vκ gene segments are present between the distal cluster and the Jκ gene segments in the kappa chain locus of the first vertebrate); and (b) Expressing said kappa chain loci of the first and second vertebrates to provide a repertoire of synthetic antibody kappa chains.

In an embodiment of the method, a third vertebrate comprises a third cluster of Vκ gene segments corresponding to a medial Vκ gene cluster of the kappa chain locus of a human, wherein the medial cluster is arranged between the distal and proximal clusters in said human locus; wherein the medial cluster is provided in a kappa chain locus of said third vertebrate upstream of one or more JK gene segments and one or more constant regions; wherein the kappa chain locus of the third vertebrate does not comprise the distal, medial and proximal clusters in an arrangement corresponding to the arrangement of said human (optionally wherein the kappa chain locus of the third vertebrate does not comprise the distal and proximal clusters); the method further comprising expressing said kappa chain locus of the third vertebrate, whereby the repertoire of synthetic antibody kappa chains is provided by expression from the first, second and third vertebrate loci.

The invention provides a method of providing a synthetic antibody lambda chain repertoire, the method comprising (a) Dividing a human Vλ gene segment repertoire (eg, a substantially complete functional human Vλ gene repertoire) across the genomes of at least first and second non-human vertebrates (eg, mice or rats), the repertoire comprising a first cluster of Vλ gene segments corresponding to a distal Vλ gene cluster of the lambda chain locus of a human; and a second cluster of Vλ gene segments corresponding to a proximal Vλ gene cluster of the lambda chain locus of a human, wherein the proximal cluster is arranged proximally to the distal cluster in said human locus;

Wherein the distal cluster is provided in a lambda chain locus of said first vertebrate upstream of one or more Jλ gene segments and one or more constant regions;

Wherein the proximal cluster is provided in a lambda chain locus of said second vertebrate upstream of one or more Jλ gene segments and one or more constant regions;

Wherein the proximal Vλ gene cluster is not present between the distal cluster and the Jλ gene segments in the lambda chain locus of the first vertebrate (optionally wherein no further Vλ gene segments are present between the distal cluster and the Jλ gene segments in the lambda chain locus of the first vertebrate); and (b) Expressing said lambda chain loci of the first and second vertebrates to provide a repertoire of synthetic antibody lambda chains.

In an embodiment of the method, a third vertebrate comprises a third cluster of Vλ gene segments corresponding to a medial Vλ gene cluster of the lambda chain locus of a human, wherein the medial cluster is arranged between the distal and proximal clusters in said human locus; wherein the medial cluster is provided in a lambda chain locus of said third vertebrate upstream of one or more Jλ gene segments and one or more constant regions; wherein the lambda chain locus of the third vertebrate does not comprise the distal, medial and proximal clusters in an arrangement corresponding to the arrangement of said human (optionally wherein the lambda chain locus of the third vertebrate does not comprise the distal and proximal clusters); the method further comprising expressing said lambda chain locus of the third vertebrate, whereby the repertoire of synthetic antibody lambda chains is provided by expression from the first, second and third vertebrate loci.

In an embodiment of the method, the vertebrates have been immunised with the same antigen (eg, a human antigen).

In an embodiment of the method, the vertebrates are naïve.

In an embodiment of the method, the vertebrates have a common collection of heavy chain loci.

In an embodiment, the method comprises selecting one or more antibody kappa or lambda chains (eg, as part of an antibodies) from said repertoire according to a desired characteristic (eg, affinity for biding an antigen).

As explained in the examples, the inventors carried out sectoring using a repertoire in which they inverted human gene segments that are naturally in an opposite 5'-3' orientation in a human germline genome (eg, see the Ig kappa locus arrangement, eg, as shown in the IMGT database and Lefranc, M.-P., Exp. Clin. Immunogenet., 18, 161-174 (2001)—see 5' gene segments marked with "D"). The distribution of human gene segment usage in transgenic non-human vertebrates surprisingly demonstrated that artificially inverted gene segments were used for rearrangement and expression, the usage unexpectedly being relatively high (FIG. 10). These findings indicate that, although these inverted gene segments are rarely used in humans, they are used in transgenic vertebrates and cells of the invention and can contribute to a transgenic Ig locus expression well once they are inverted to an orientation opposite to a wild-type human germline orientation.

Thus, the invention provides a non-human vertebrate (optionally a mouse or a rat) or vertebrate cell (optionally a mouse cell or a rat cell) whose genome comprises a transgenic antibody chain locus comprising one or more human V gene segments and one or more human J gene segments (and optionally one or more human D gene segments) upstream of a constant region, the locus comprising one or more inverted vertebrate species gene segments, the inverted gene segment(s) being present in the locus in a 5'-3' orientation that is opposite to the vertebrate species germline orientation of such segment(s), and wherein the non-human vertebrate or cell is capable of expressing an antibody chain sequence comprising a sequence that is derived from an inverted gene segment.

In one example, the cell is a B-cell, hybridoma, ES cell or iPS cell. ES cells and iPS cells can be used to develop corresponding non-human vertebrates (vertebrates of the invention) in which the inverted gene segment(s) are functional as the inventors surprisingly observed.

In an embodiment, the inverted gene segment(s) are V gene segments.

In an embodiment, the vertebrate species is selected from human, mouse, rat, rabbit, guinea pig, chicken, a fish, a bird, a reptile, a Camelid, bovine, chimpanzee, a non-human primate and a primate.

In an embodiment, the vertebrate species is human and optionally also the vertebrate of the invention is a mouse or rat.

The invention also provides a non-human vertebrate (optionally a mouse or a rat) or vertebrate cell (optionally a mouse cell or a rat cell) whose genome comprises a transgenic antibody chain locus comprising one or more human V gene segments and one or more human J gene segments (and optionally one or more human D gene segments) upstream of a constant region, wherein the locus comprises one or more inverted human gene segments, the inverted human gene segment(s) being present in the locus in a 5'-3' orientation that is opposite to the human germline orientation of such segment(s), and wherein the vertebrate or cell is capable of expressing an antibody chain sequence comprising a variable region that is derived from recombination of an inverted gene segment.

In an embodiment, the inverted gene segment(s) are or comprise human Vκ gene segment(s).

In an embodiment, the inverted Vκ gene segment(s) comprise one or more or all of Vκ2D-40, 1D-39, 1D-33, 2D-30, 2D-29, 2D-28, 2D-26, 3D-20, 1D-17, 1D-16, 1D-13, 1D-12, 3D-11, 1D-43, 1D-8 and 3D-7 and optionally also 3D-15.

In an embodiment, the locus comprises human Vκ gene segments comprising Vκ4-1 and/or 5-2 with one or more or all of Vκ2D-40, 1D-39, 1D-33, 2D-30, 2D-29, 2D-28, 2D-26, 3D-20, 1D-17, 1D-16, 1D-13, 1D-12, 3D-11, 1D-43, 1D-8 and 3D-7, and optionally also 3D-15, wherein all of the human Vκ gene segments are in the same orientation as the constant region of the locus. Additionally or alternatively, for example, the locus comprises one, more or all of human Vκ2D-40, 1D-39, 1D-33 and 2D-30 3' of one more or all of Vκ3D-7, 1D-8, 1D-43 and 3D-11. In one embodiment, Vκ2D-40, 1D-39, 1D-33 and 2D-30 are present in this order 3' to 5' in the locus. Additionally or alternatively, in one embodiment, Vκ3D-7, 1D-8, 1D-43 and 3D-11 are present in this order 3' to 5' in the locus.

In one example, the 5'-most inverted Vκ gene segment in the locus is Vκ3D-20. In another example, it is Vκ2D-40 (eg, if the sequence of naturally-inverted human Vκ gene segments found in a wild-type human chromosome 2 are provided as this sequence, but in reverse orientation—with Vκ2D-40 as the 5'-most inverted gene segment in the locus of the invention and Vκ3D-7 is the 3'-most inverted gene segment).

In an embodiment, the Vκ gene segment(s) comprise human Vκ2D-40.

In an embodiment, the Vκ gene segment(s) comprise human Vκ1D-39, for example human Vκ2D-40 next to human Vκ1D-39 (eg, in 5' to 3' direction: human Vκ2D-40 next to human Vκ1D-39).

In an embodiment, the constant region is human. In another embodiment, the constant region is a mouse or rat constant region, eg, a constant region endogenous to the non-human vertebrate.

The invention also provides method of providing an artificial human antibody variable region repertoire, the method comprising inserting one or more human V gene segment(s) (inverted gene segments) upstream of one or more J gene segments, optionally one or more D gene segments, and a constant region in an antibody chain locus of a non-human vertebrate or non-human vertebrate cell, the V gene segment(s) being present in the locus in a 5'-3' orientation that is opposite to the human germline orientation of such segment(s), and wherein the non-human vertebrate or cell (or a non-human vertebrate progeny derived from the cell) is capable of expressing an antibody chain sequence comprising a variable region sequence that is derived from recombination of an inverted gene segment.

In an embodiment, the vertebrate or cell or inverted gene segment(s) is as recited above.

The invention also provides a method of providing an artificial human antibody variable region repertoire, the method comprising isolating serum or a lymphoid cell (eg, spleen cell or B-cell) from a vertebrate of the invention, and optionally isolating from the serum or cell one or more antibodies that specifically bind a predetermined antigen.

The invention also provides an antibody isolated in the method described above, or a fragment or derivative thereof.

It will be understood that particular embodiments described herein are shown by way of illustration and not as limitations of the invention and (unless the context states otherwise) embodiments can be applied to any of the configurations of the invention described herein. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. The use of the word "a" or an when used in conjunction with the term "comprising" in the claims and/or the specification may mean "one," but it is also consistent with the meaning of "one or more," "at least one," and "one or more than one." The use of the term or in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps The term or combinations thereof as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

Any part of this disclosure may be read in combination with any other part of the disclosure, unless otherwise apparent from the context.

All of the compositions, populations, vertebrates, antibodies, repertoires and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The present invention is described in more detail in the following non limiting Examples.

EXAMPLES

Example 1: Light Chain Repertoire Sectoring

The inventors realised that the prior art mice provide for immunoglobulin loci in which all of the desired heavy, kappa and lambda gene segment repertoires are provided together in the genome of the cells of the individual mice. In doing this, the inventors realised that the prior art designs have not addressed the limitation of the restricted accessible B-cell component size (around $2\times10^8$ B-cells in a mouse, for example) and the concomitant restriction on the overall antibody chain diversity that can be expressed and accessed in any one mouse.

Figure 1:
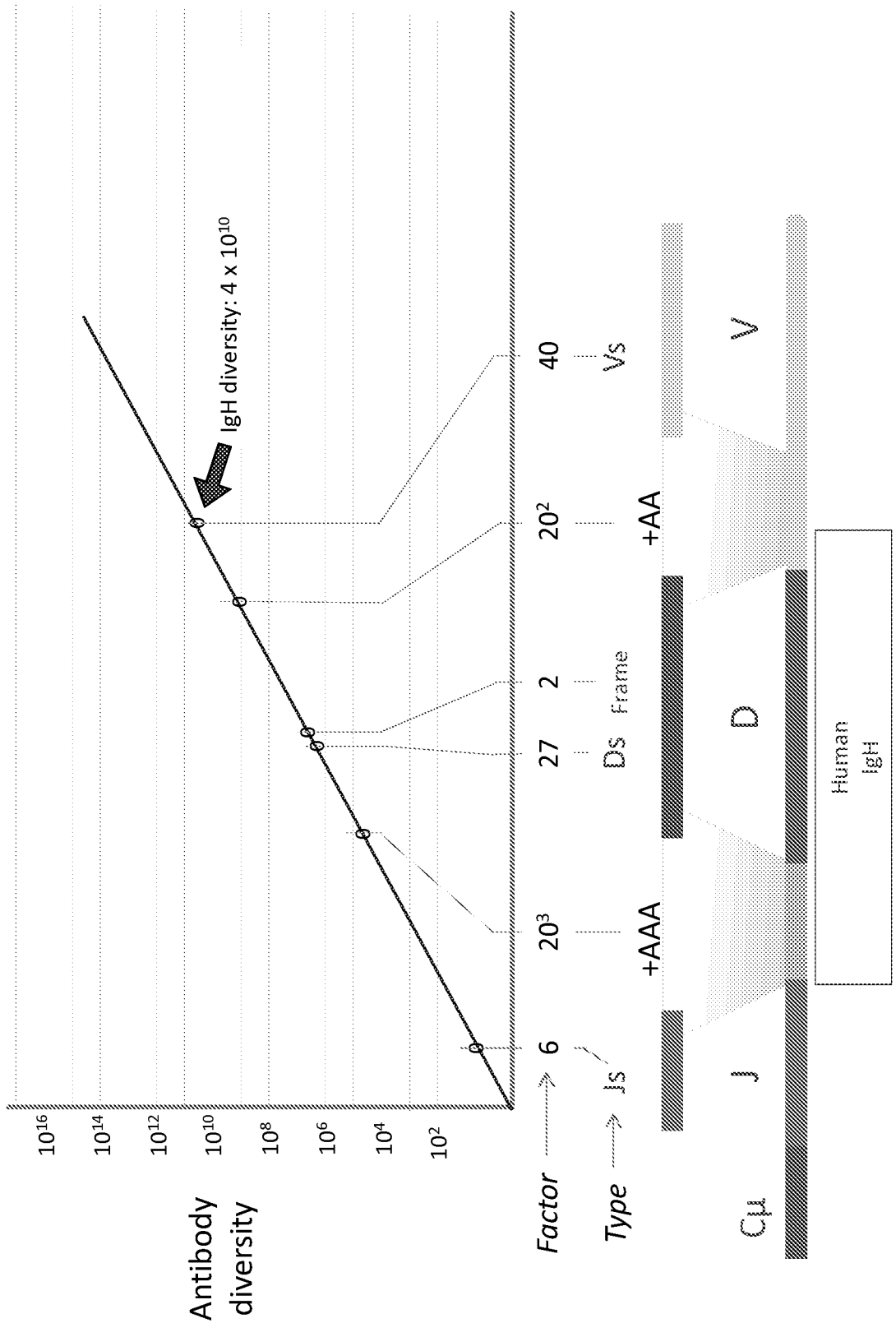
FIG. 1: Schematic showing calculation of potential IgH antibody variable region diversity for a transgenic human immunoglobulin heavy chain locus containing 6 human JH gene segments, 27 human D gene segments and 40 VH gene segments.

This is illustrated by reference to FIGS. 1 to 4. FIG. 1 shows a calculation of potential diversity for a transgenic heavy chain locus comprising a complete functional repertoire of human VH, D and JH gene segments (in this example, 6 different human JH, 27 different human D and 40 different human VH germline gene segments). The calculation takes into account junctional diversity (typically a 3 nucleotide addition at the J-D junction and a 2 nucleotide addition at the D-V junction). The calculation of potential diversity of heavy chain variable region sequences produced by recombination of the gene segments is $4\times10^{10}$.

Figure 2:
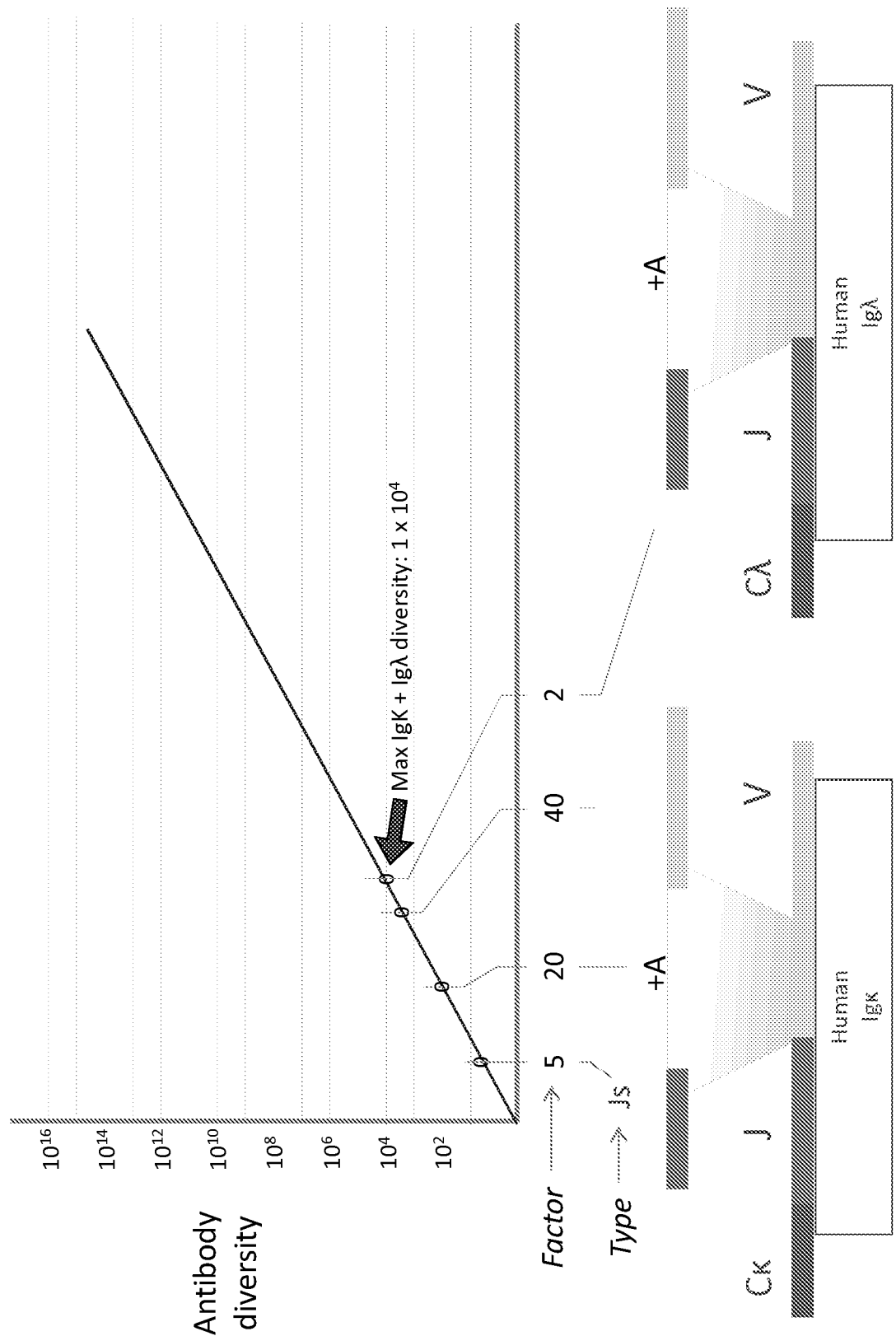
FIG. 2: Schematic showing calculation of potential Igκ and Igλ antibody variable region diversity for transgenic human immunoglobulin light chain kappa and lambda loci, wherein each light chain locus contains 5 human $J_L$ gene segments and 40 $V_L$ gene segments.

FIG. 2 shows a calculation of potential diversity for a transgenic kappa and lambda light chain loci, each comprising a complete functional repertoire of human VH, D and JH gene segments (in this example, 5 different human JL and 40 different human VL germline gene segments in each light chain locus). The calculation takes into account junctional diversity (typically a 1 nucleotide addition at the V-J junction). The calculation of potential diversity of kappa and lambda chain variable region sequences produced by recombination of the gene segments is $1\times10^4$.

Figure 3:
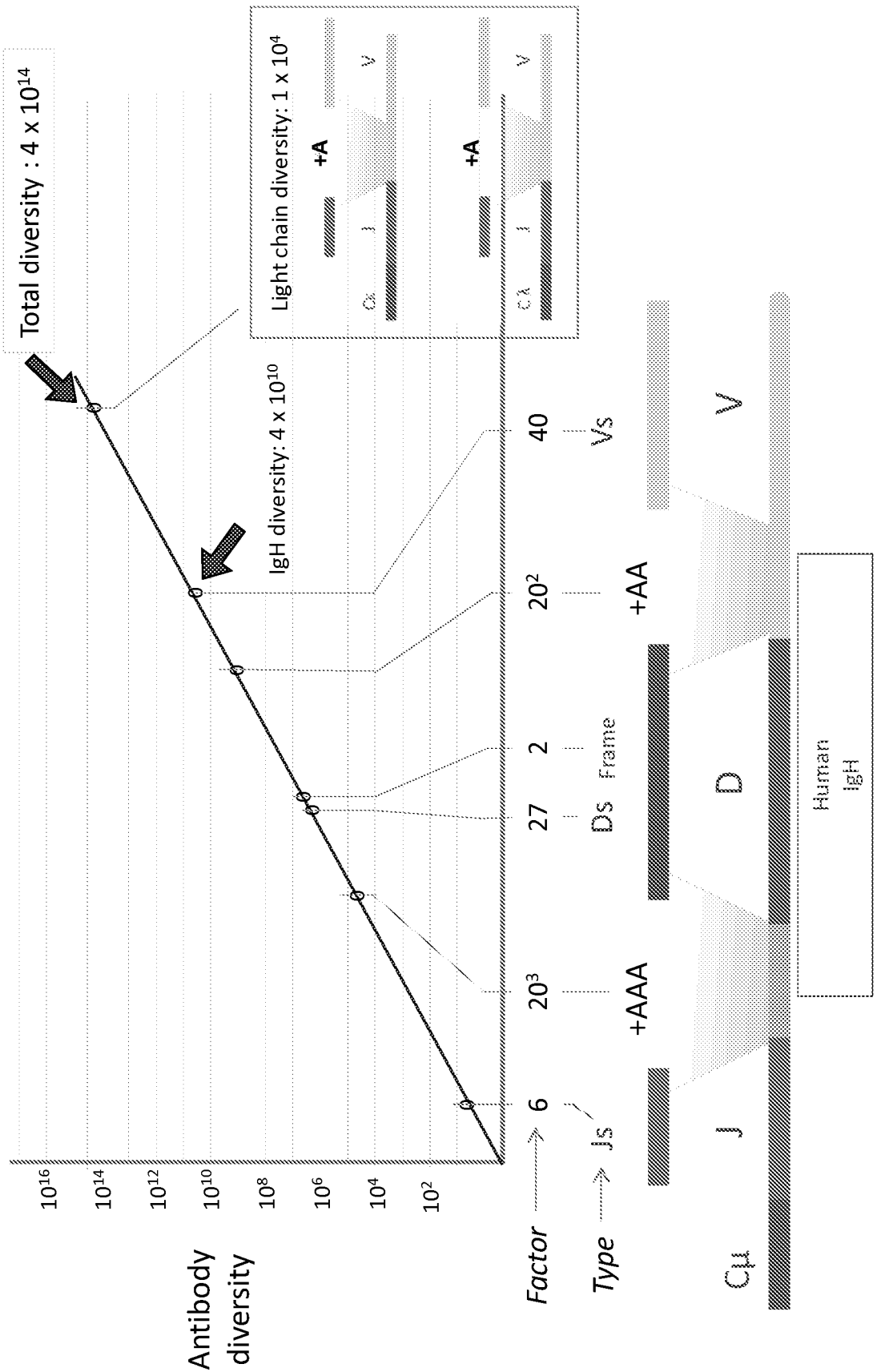
FIG. 3: Schematic showing calculation of potential IgH, Igκ and Igλ antibody variable region diversity for the transgenic human immunoglobulin loci, giving a total potential antibody repertoire size of $4 \times 10^{14}$.

FIG. 3 shows a calculation of potential diversity for transgenic heavy, kappa and lambda light chain loci (ie, the calculation of total potential heavy/light chain variable region combinations). The calculated result is a potential diversity of $4\times10^{14}$.

Figure 4:
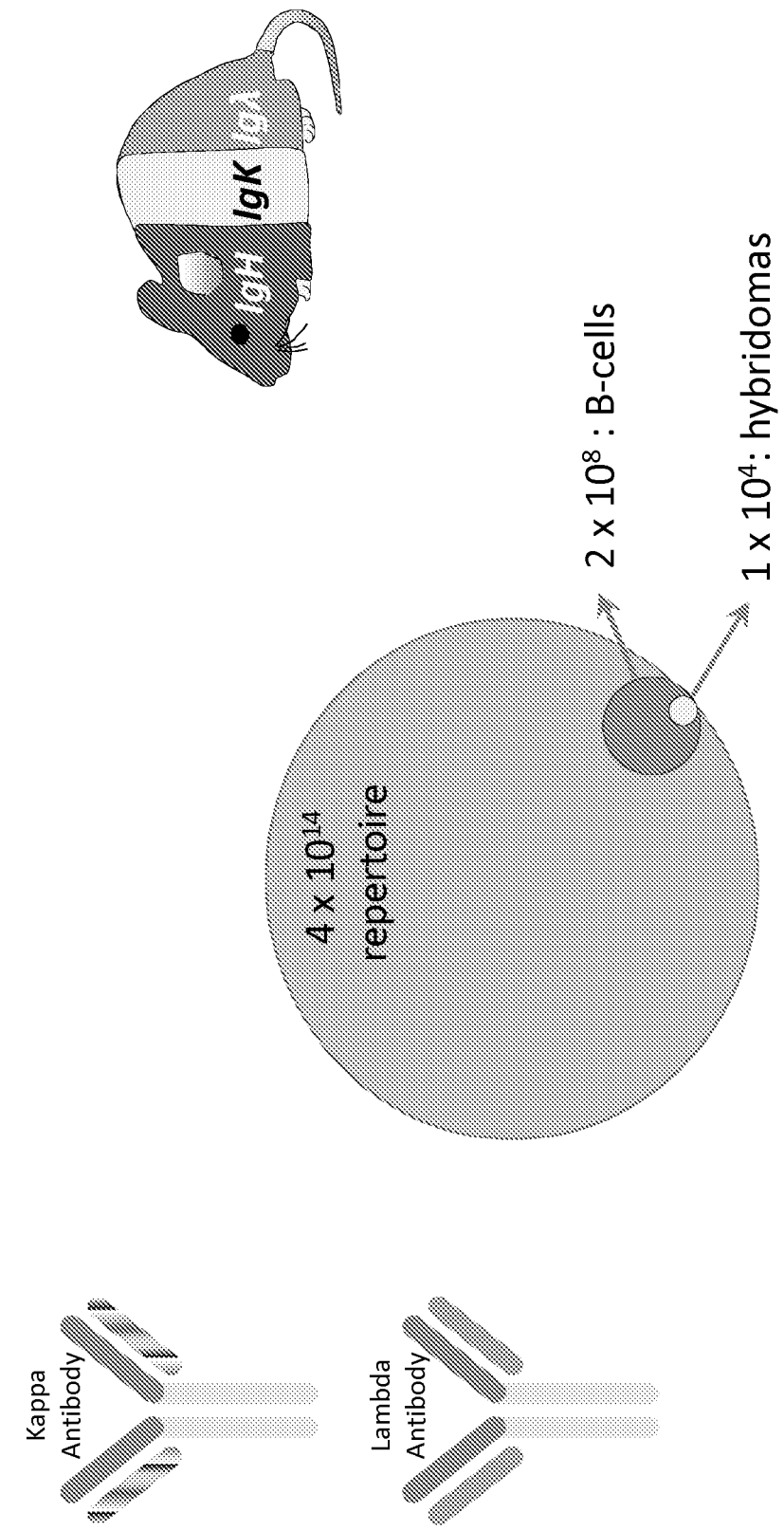
FIG. 4: Schematic showing the typical sampling size in prior art methods of antibody selection from transgenic mice and the typical resultant hybridoma population size.

FIG. 4 schematically illustrates the disadvantage of the existing theoretical designs where mice will comprise human heavy, kappa and lambda gene repertoires together in the same mouse. To date, the state of the art has not reported the successful production of a mouse containing complete functional human heavy, kappa and lambda gene segment repertoires altogether in one mouse genome. Nevertheless, if the skilled person did do this (by, for example, using the complete repertoires described in FIGS. 1-3) from a possible antibody variable region repertoire size of $4\times10^{14}$ only a maximum of around $2\times10^8$ antibodies can be sampled from the accessible B-cell compartment (actually the art often struggles even to sample at anywhere near this level). Thus, a huge amount of the potential diversity cannot be sampled. This is further compounded by the problem of kappa antibody bias in mice to the detriment of sampling the lambda sequence space more fully. There also can be biases in individual V regions that may dominate the immune response following immunisation; in this case, more rarely-used gene segments may not be accessed even though they may provide for desirable antibodies (eg, with desired affinities and/or desired epitopic recognition).

The issue is even more stark when one considers that of the maximum $2\times10^8$ B-cells that can be accessed, typically only a small fraction of these generate hybridomas when using hybridoma generation methods routinely in the art (hybridoma generation being the standard method for enabling workable access to a research and production supply of a desired monoclonal antibody). Typically, after the application of hybridoma generation technologies, only up to around $1\times10^4$ hybridomas can be generated. Thus, the acute problem of poor diversity sampling will be readily apparent to the skilled addressee: of the original potential repertoire, only $1\times10^4$ of the potential $4\times10^{14}$ combinations can maximally be accessed. This is a miniscule amount of the diversity which severely limits the discovery of new and useful antibodies from mice designed according to the prior art concepts.

Figure 5:
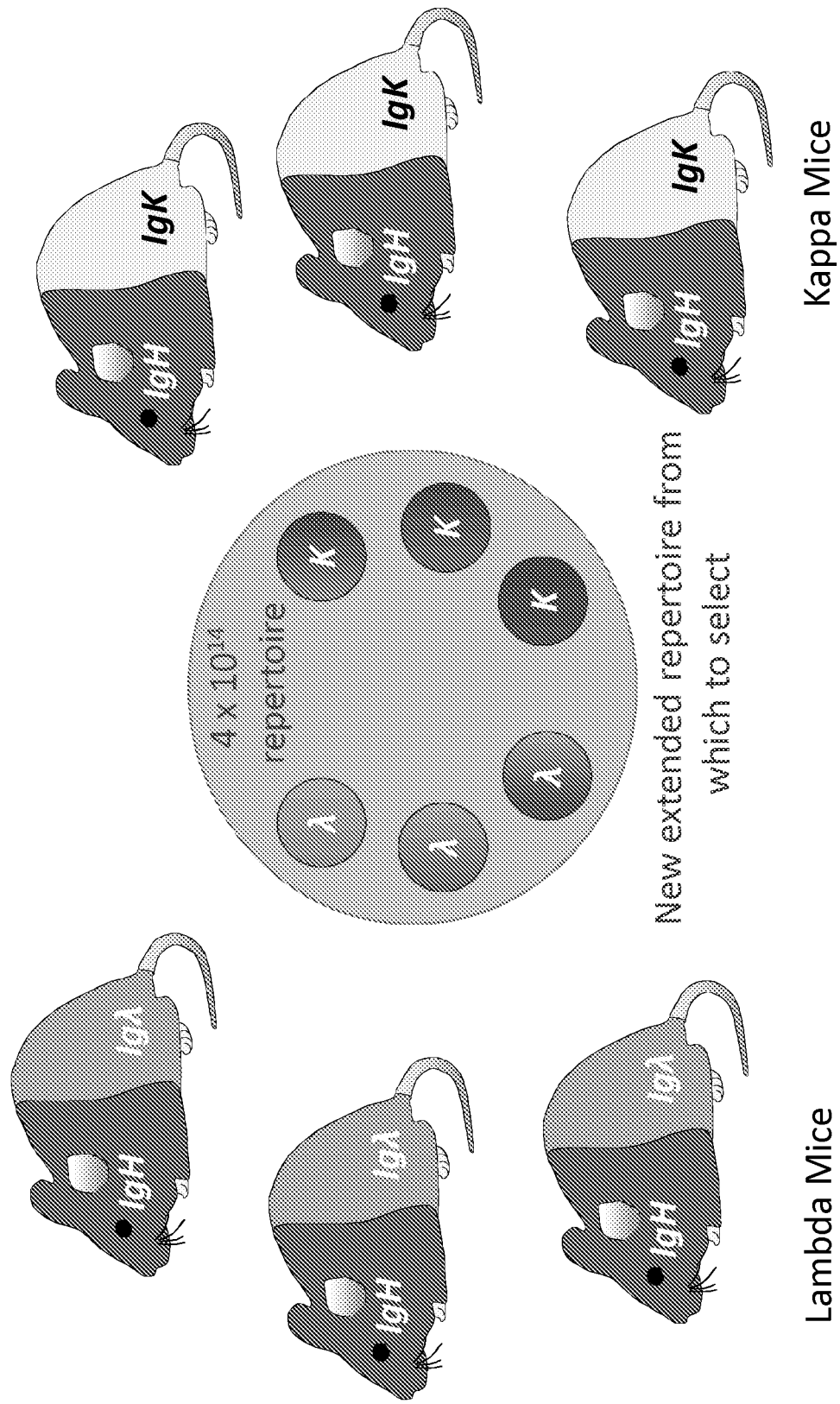
FIG. 5: Schematic showing sectoring of the light chain diversity across several mice in a population according to the invention and the resultant beneficial new and extended repertoire for sampling.

The present inventors have addressed this problem by sectoring the overall desired repertoire in transgenic animals so that the repertoire is instead accessed not in a single genome, but across a plurality of genomes making up a population. This is schematically illustrated in FIG. 5 for an example where the light chain repertoire is sectored to separate lambda gene segment diversity from kappa gene segment diversity. This is possible, for example, by the provision of separate lambda vertebrates and kappa vertebrates according to the invention. In the example of FIG. 5, all mice comprise the same transgenic heavy chain locus (the locus illustrated in FIG. 1 in which there is a complete human functional diversity of V, D and J gene segments). In this example, the complete functional human Vλ gene segment repertoire has been divided across three mice, so that the mice comprise different human Vλ gene segment sub-repertoires (in this case the sub-repertoires are not overlapping, although it is possible for them to overlap as long as they are not identical in their collections of gene segments). Similarly, a complete functional Vκ gene segment repertoire has been sectored across three different kappa vertebrates (right-hand side of the figure). The large circle at the centre of the figure represents the potential overall diversity of $4\times10^{14}$ and each smaller circle represents the accessible B-cell compartment of the respective mice. It can be readily appreciated that this example allows for six individual samplings (sub-repertoires) of the overall potential sequence space. Thus, these sub-repertoires together provide a population diversity in which the overall repertoire size is significantly greater than possible with the conventional design shown in FIG. 4. Furthermore, in addition to significantly extending the repertoire for sampling, importantly the repertoires in the lambda mice are novel, synthetic repertoires that are not seen in conventional transgenic mice that express prior art kappa and lambda antibody ratios together in the same mouse. For example, when the expression of kappa light chain sequences has been inactivated, all antibodies in the lambda mice will comprise lambda light chains, and this is not seen in mice in nature. Similarly (eg, where the endogenous lambda expression is totally inactivated or negligible) in the kappa mice kappa-type antibodies are essentially exclusively expressed. When taken together, the lambda-type and kappa-type repertoires of antibodies expressed in the lambda and kappa mice (both in naïve mice (those not immunised with a predetermined antigen or substantially not exposed to foreign antigen) and immunised mice) provide an overall antibody repertoire that is novel, usefully extended and synthetic (not seen in nature).

Figure 6:
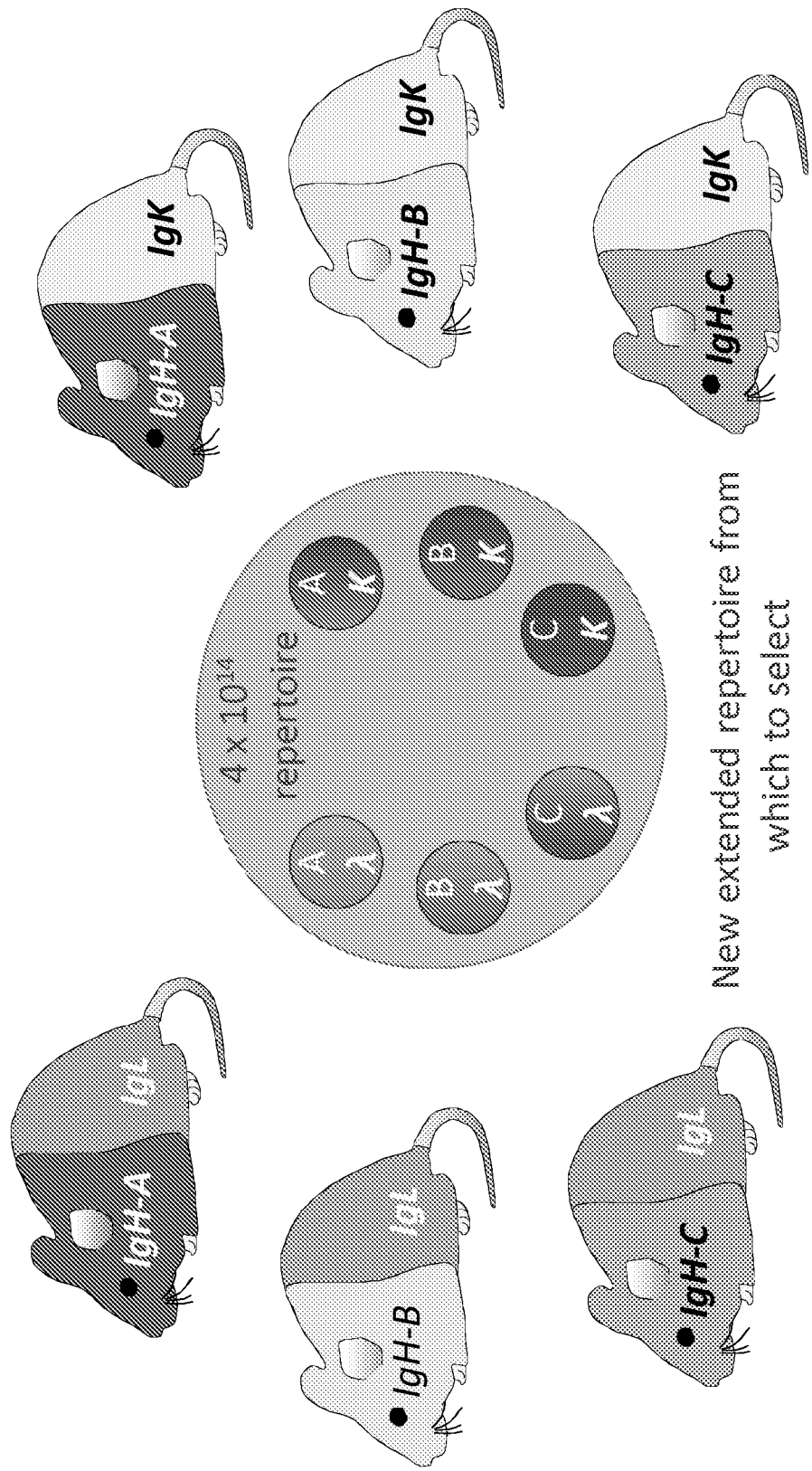
FIG. 6: Schematic showing sectoring of human functional light chain diversity and human functional VH gene segment diversity across several mice in a population according to the invention and the resultant beneficial new and extended repertoire for sampling.

Example 2: Human VH Gene Segment Repertoire & Human Light Chain Repertoire Sectoring FIG. 6 shows a schematic example where the heavy chain VH gene segment repertoire is sectored according to the invention. In this example, the repertoire is a complete human functional VH gene repertoire divided across three mice (mice "A", "B" and "C") as follows:—

A . . . V6-1, V1-2, V1-3, V4-4, V7-41, V2-5, V3-7, V1-8, V3-9, V3-11, V3-15, V1-18, V3-20, V3-21, V3-23, V1-24, V2-26, V4-28, V3-30, V4-31, V3-33, V4-34, V4-39, V3-43, V1-45, V1-46, V3-48, V3-49, V5-51, V3-53, V1-58, V4-59, V4-61, V3-64, V3-66, V1-69, V2-70, V3-72, V3-73 & V3-74

B . . . V6-1, V1-2, V1-3, V4-4, V7-41, V2-5, V4-28, V3-30, V4-31, V3-33, V4-34, V4-39, V3-43, V1-45, V1-46 & V3-48

C . . . V6-1, V1-2, V1-3, V4-4, V7-41, V2-5, V3-49, V5-51, V3-53, V1-58, V4-59, V4-61, V3-64, V3-66, V1-69, V2-70, V3-72, V3-73 & V3-74

In this example, although the V gene repertoires of mice A, B and C overlap, the repertoires are unique. In an alternative example, the repertoires do not overlap, eg, the VH gene repertoires are non-overlapping and comprise or consist of as follows:—

A' . . . V6-1, V1-2, V1-3, V4-4, V7-41 and V2-5

B' . . . V3-7, V1-8, V3-9, V3-11, V3-15, V1-18, V3-20, V3-21, V3-23, V1-24, V2-26, V4-28, V3-30, V4-31, V3-33, V4-34, V4-39, V3-43, V1-45, V1-46 and V3-48

C' . . . V3-49, V5-51, V3-53, V1-58, V4-59, V4-61, V3-64, V3-66, V1-69, V2-70, V3-72, V3-73 and V3-74

In another alternative example, the VH gene repertoires comprise or consist of as follows:—

S . . . V6-1, V1-2, V1-3, V4-4, V7-41, V2-5, V3-7, V1-8, V3-9, V3-11, V3-13, V3-15, V1-18, V3-20, V3-21, V3-23, V1-24 and V2-26

T . . . V4-28, V3-30, V4-31, V3-33, V4-34, V4-39, V3-43, V1-45, V1-46 and V3-48

V . . . V3-49, V5-51, V3-53, V1-58, V4-59, V4-61, V3-64, V3-66, V1-69, V2-70, V3-72, V3- 73 and V3-74

The VH gene sub-repertoire of each mouse is provided in a transgenic heavy chain locus comprising a complete functional human JH gene repertoire and a complete functional human D gene repertoire. Endogenous heavy chain expression is inactivated. It is possible to provide each mouse with the same light chain loci (eg, one or more transgenic lambda locus and one or more transgenic kappa locus, wherein each light chain locus comprises human VL and JL gene segments). In the example of FIG. 6, however, the lambda and kappa gene repertoires have also been sectored according to the invention as per the illustration in FIG. 5. In either example, endogenous kappa chain expression is inactivated in the lambda mice (and endogenous lambda chain expression is optionally inactivated in the kappa mice).

In one example, the JH and D repertoire consists of or comprises

D & JH Repertoire 1

J1, J2, J3, J4, J5 and J6

D1-1, D2-2, D3-9, D3-10, D4-11, D5-12, D6-13, D1-14, D2-15, D3-16, D4-17, D5-18, D6-19, D1-20, D2-21, D3-22, D4-23, D5-24, D1-26 and D7-27

In another example, the JH and D repertoire consists of or comprises

D & JH Repertoire 2

J1, J2, J3, J4, J5 and J6

D1-1, D2-2, D3-3, D4-4, D5-5, D6-6, D1-7, D2-8, D3-9, D3-10, D4-11, D5-12, D6-13, D1-14, D2-15, D3-16, D4-17, D5-18, D6-19, D1-20, D2-21, D3-22, D4-23, D5-24, D1-26 and D7-27

In another alternative example, the VH, DH and JH gene repertoires comprise or consist of human gene segments as follows:—

V, D, J Repertoire 1

V6-1, V1-2, V1-3, V4-4, V7-41, V2-5, V3-7, V1-8, V3-9, V3-11, V3-13, V3-15, V1-18, V3-20, V3-21, V3-23, V1-24 and V2-26 (optionally wherein this represents the 5' to 3' order of the V gene segments)

J1, J2, J3, J4, J5 and J6

D1-1, D2-2, D3-3, D4-4, D5-5, D6-6, D1-7, D2-8, D3-9, D3-10, D4-11, D5-12, D6-13, D1-14, D2-15, D3-16, D4-17, D5-18, D6-19, D1-20, D2-21, D3-22, D4-23, D5-24, D1-26 and D7-27

V, D, J Repertoire 2

V4-28, V3-30, V4-31, V3-33, V4-34, V4-39, V3-43, V1-45, V1-46 and V3-48 (optionally wherein this represents the 5' to 3' order of the V gene segments)

J1, J2, J3, J4, J5 and J6

D1-1, D2-2, D3-3, D4-4, D5-5, D6-6, D1-7, D2-8, D3-9, D3-10, D4-11, D5-12, D6-13, D1-14, D2-15, D3-16, D4-17, D5-18, D6-19, D1-20, D2-21, D3-22, D4-23, D5-24, D1-26 and D7-27 (optionally wherein this represents the 5' to 3' order of the D gene segments)

V, D, J Repertoire 3

V3-49, V5-51, V3-53, V1-58, V4-59, V4-61, V3-64, V3-66, V1-69, V2-70, V3-72, V3-73 and V3-74 (optionally wherein this represents the 5' to 3' order of the V gene segments)

J1, J2, J3, J4, J5 and J6

D1-1, D2-2, D3-3, D4-4, D5-5, D6-6, D1-7, D2-8, D3-9, D3-10, D4-11, D5-12, D6-13, D1-14, D2-15, D3-16, D4-17, D5-18, D6-19, D1-20, D2-21, D3-22, D4-23, D5-24, D1-26 and D7-27 (optionally wherein this represents the 5' to 3' order of the D gene segments)

In an example, a population of first and second non-human vertebrates (eg, mice) according to the invention are provided which differ in their heavy chain gene segment repertoires (and optionally comprise identical human light chain gene segment repertoires), wherein the heavy chain gene segment repertoires comprise identical repertoires of human VH gene segments and different human D gene segment repertoires, Wherein the first vertebrate D gene segment repertoire comprises D1-1, D2-2, D3-9, D3-10, D4-11, D5-12, D6-13, D1-14, D2-15, D3-16, D4-17, D5-18, D6-19, D1-20, D2-21, D3-22, D4-23, D5-24, D1-26 and D7-27;

Wherein the second vertebrate D gene segment repertoire comprises D1-1, D2-2, D3-3, D4-4, D5-5, D6-6, D1-7, D2-8, D3-9, D3-10, D4-11, D5-12, D6-13, D1-14, D2-15, D3-16, D4-17, D5-18, D6-19, D1-20, D2-21, D3-22, D4-23, D5-24, D1-26 and D7-27; and optionally the vertebrates comprise identical JH gene repertoires (eg, J1, J2, J3, J4, J5 and J6).

In an embodiment of this example, each human VH gene segment repertoire comprises or consists of human VH gene segments (a) V6-1, V1-2, V1-3, V4-4, V7-41, V2-5, V3-7, V1-8, V3-9, V3-11, V3-13, V3-15, V1-18, V3-20, V3-21, V3-23, V1-24 and V2-26 and/or (b) V4-28, V3-30, V4-31, V3-33, V4-34, V4-39, V3-43, V1-45, V1-46 and V3-48 and/or (c) V3-49, V5-51, V3-53, V1-58, V4-59, V4-61, V3-64, V3-66, V1-69, V2-70, V3-72, V3-73 and V3-74. For example, each human VH gene segment repertoire comprises or consists of human VH gene segments (a), (b) and (c).

As seen in FIG. 6, each mouse provides a unique sub-repertoire of antibodies and antibody heavy and light chain sequences. The design enables the human Vλ diversity to be explored much more fully than present with prior art designs, due to the sectoring of the kappa and lambda repertoires as explained above. Furthermore, sectoring of the human VH gene repertoire provides for new gene segment arrangements in the heavy chain loci (bringing distal gene segments more proximal and providing non-natural combinations of VH gene segments together in single loci). This enables exploration of the human VH gene diversity more fully as hitherto previously possible. Additionally, in the illustrated design the unique VH gene repertoires are explored separately in mice in the context of lambda vertebrates separately from kappa vertebrates, which in turn provides for novel combinations not seen in nature or hitherto previously possible.

The transgenic mice shown in FIGS. 5 and 6 provide useful sources of antibody and antibody chain repertoires for sampling following immunisation with antigen. For example, all of the mice shown in the population of FIG. 5 or 6 (or a combination of all of the mice in both figures) can be immunised with the same human antigen and desirable antibodies can be selected, eg, for relatively high affinity binding to the antigen or for binding in certain epitopic regions of the antigen (eg, as determined by competition with an anti-antigen antibody of known epitopic specificity). The selected antibodies thereby provide a selected repertoire of antibodies (optionally pooled) from which one or more preferred drug candidates can be selected. This selection can be on the basis of the information already obtained in the first round of selection, and/or a further set of experiments (eg, ELISA and/or surface plasmon resonance (eg, using Biacore™) to determine affinities within the selected repertoire) can be performed to enable the selection from the repertoire.

Figure 7:
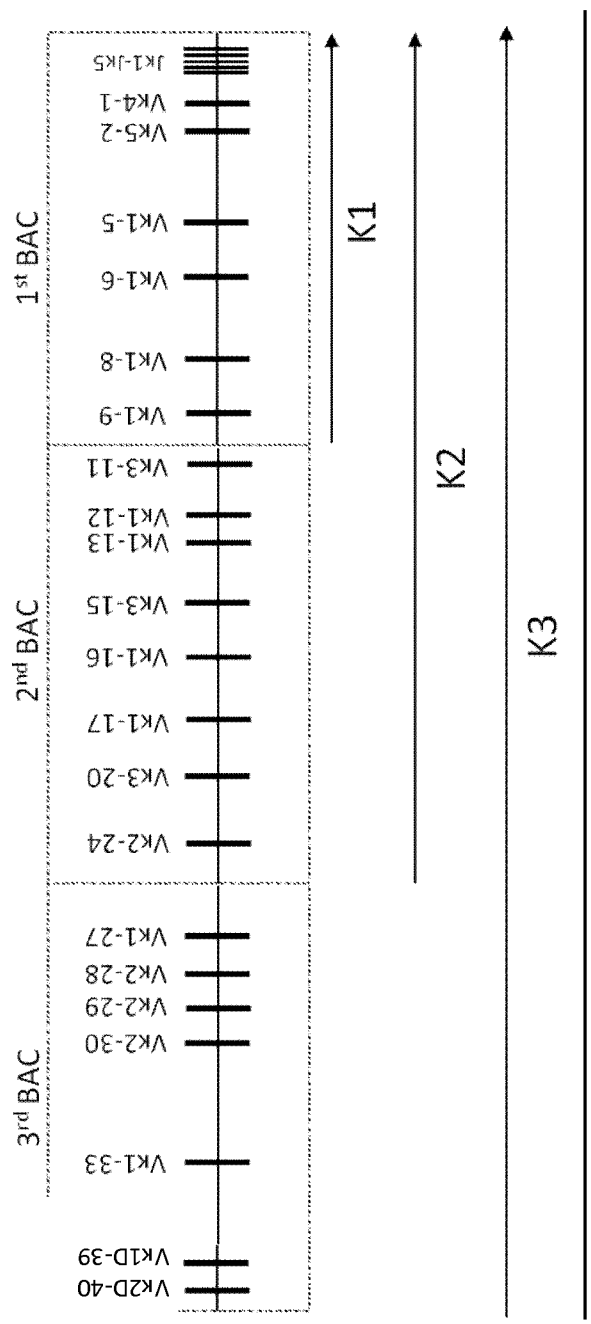
FIG. 7: shows the human gene segment repertoires contained in the first, second and third BACs used to construct three different mice lines, K1, K2 and K3:—

Example 3: Producing New Light Chain & Human Vκ Region Repertoires by Gene Sectoring Human Vκ Gene Repertoires A functional human gene segment repertoire (from Vκ2D-40 to Jκ5, as shown in FIG. 7) was sectored by the inventors to produce three different transgenic kappa chain alleles (denoted K1, K2 and K3) and corresponding mice. The transgenic alleles were expressed in the mice and the kappa chain repertoires were assessed at the RNA transcript level.

Insertion of human kappa gene segments from a 1st IGK BAC into the IGK locus of mouse AB2.1 ES cells (Baylor College of Medicine) was performed to create a light chain allele denoted the K1 allele. The inserted human sequence corresponds to the sequence of human chromosome 2 from position 89312220 to position 89159079 and comprises functional kappa gene segments Vκ1-9, Vκ1-8, Vκ1-6, Vκ1-5, Vκ5-2, Vκ4-1, Jκ1, Jκ2, Jκ3, Jκ4 and Jκ5 (FIG. 7). The insertion was made between positions 70674755 and 70674756 on mouse chromosome 6, which is upstream of the mouse Cκ region. The mouse Vκ and Jκ gene segments were retained in the locus, immediately upstream of (5' of) the inserted human kappa DNA. The mouse lambda loci were left intact.

A second allele, K2 was constructed in which more human functional Vκ gene segments were inserted upstream (5') of the 5'-most Vκ inserted in the K1 allele by the sequential insertion of human DNA from a second BAC. The inserted human sequence from BAC2 corresponds to the sequence of human chromosome 2 from position 89478399 to position 89312221 and comprises functional kappa gene segments Vκ2-24, Vκ1-17, Vκ1-16, Vκ3-15, Vκ1-13, Vκ1-12, Vκ3-11 (FIG. 7).

A third allele, K3 was constructed in which more human functional Vκ gene segments were inserted upstream (5') of the 5'-most Vκ inserted in the K2 allele by the sequential insertion of human DNA from a third BAC. The inserted sequence corresponds to the sequence of human chromosome 2 from position 89889512 to position 89902788 and from position 89609410 to position 89478400, and comprises functional kappa gene segments, Vκ2D-40, Vκ1D-39, Vκ1-33, Vκ2-30, Vκ2-29, Vκ2-28 and Vκ1-27 (FIG. 7).

Human gene segments Vκ2D-40 and Vκ1D-39 are naturally inverted (opposite orientation to other functional gene segments, eg those other Vκ and the Jκ in BACs1-3, when in natural human genomes) and relatively rarely used in humans (see Ig kappa locus representation in the IMGT database and Eur J Immunol. 1994 April; 24(4):827-36, "A directory of human germ-line V kappa segments reveals a strong bias in their usage", J Cox et al). In the current strategy, these gene segment sequences were inverted from their natural state so that they were present in BAC3 in the same 5'-3' orientation as the other human gene segments. The inventors were interested in determining if functionality of gene segments that have been inverted during human evolution can be re-orientated in the transgenic animals, thereby enhancing functionality and thus participation in providing an expressed repertoire.

Mice bearing either the K1, K2 or K3 insertion into an endogenous kappa locus were generated from the ES cells using standard procedures. The other endogenous kappa locus was inactivated in the mice by insertion of an inactivating sequence comprising $neo^R$ into the mouse Jκ-Cκ intron (to produce the "KA" allele). Standard 5'-RACE was carried out to analyse RNA transcripts from the transgenic kappa light chain loci in the K1, K2 and K3 mice.

The K3 mice showed high usage of human Vκ gene segments, 92.8% of rearranged transcripts using human Vκ gene segments and only 7.2% of them using mouse Vκ gene segments (FIG. 8). Compared to K1 and K2, K3 showed improved human Vκ usage (K1: 78%; K2: 83% and K3: 93%) (FIG. 9).

The distribution of human Vκ usage from K3 mice demonstrated that the two transplanted and inverted Vκ2D-40 and Vκ1D-39 surprisingly were used for rearrangement and expression, the usage of Vκ1D-39 unexpectedly being relatively high (FIG. 10). These data indicate that, although these two Vκ gene segments are rarely used in humans, they are used and can contribute to the transgenic IgK locus expression well once they are inverted and have the same orientation to the human Jκ gene segments. Further exemplification of the surprising effect of gene segment inversion according to the invention is shown in Example 6 below.

The distribution of human Vκ usage from K1 to K3 mice also demonstrated that insertion of different repertoires of human Vκ gene segments changes the usage of human Vκs (FIG. 11). While not wishing to be bound by any particular theory, the inventors surmise that this is due to the varying competition among the Vκs, which determine their relative usage. This was also surprisingly observed with the human Jκ usage. For example, the inventors surprisingly observed that with the 3rd BAC insertion, the Jκ4 usage is increased (FIG. 12). Thus, the human Vκ gene repertoire sectoring according to the invention not only altered the repertoire of expressed human Vκ gene segments, but also altered the expressed Jκ profile. Thus, the inventors surprisingly realised that they had discovered a way to provide differing repertoires of antibody chains by gene repertoire sectoring. The collection of K1, K2 and K3 as a combined population is useful, the inventors realised, to produce a novel repertoire of antibody chains and antibodies that can be selected against a desired antigen. For example, the K1, K2 and K3 mice can be immunised with the same human antigen and anti-antigen antibodies from the totally of antibodies in the mice can be selected on the basis of affinity and/or target epitope recognition or another desirable feature.

Further exemplification of sectoring was established by insertion of yet more human IgK DNA (to create K4 mice), as disclosed in Example 6 below.

In summary, the analysis of kappa light chain sequences revealing differential usage and thus differing light chain sequence repertoires could be produced by the gene sectoring technique. The repertoires differed in their human V and J gene segment usage. Additionally, the proportions of particular human gene segments shared by mice could be altered in the expression profiles by the gene sectoring technique of the present invention.

Example 4

Producing New Heavy Chain and Human VH Region Repertoires by Gene Sectoring Human $V_H$ Gene Repertoires A functional human gene segment repertoire (from $V_H2$-26 to $J_H6$, see the IMGT database for the structure of the human IgH locus; http://www.imgt.org/IMGTrepertoire/index.php?section=LocusGenes&repertoire=locus&species=human&group=IGK) was sectored by the inventors to produce three different transgenic heavy chain alleles (denoted S1, S2 and S3) and corresponding mice. The transgenic alleles were expressed in the mice and the heavy chain repertoires were assessed at the RNA transcript level.

Insertion of human heavy gene segments from a 1st IGH BAC into the IGH locus of mouse AB2.1 ES cells (Baylor College of Medicine) was performed to create a heavy chain allele denoted the S1 allele. The inserted human sequence corresponds to the sequence of human chromosome 14 from position 106494908 to position 106328951 and comprises functional heavy gene segments $V_H2$-5, $V_H7$-4-1, $V_H4$-4, $V_H1$-3, $V_H1$-2, $V_H6$-1, D1-1, D2-2, D3-9, D3-10, D4-11, D5-12, D6-13, D1-14, D2-15, D3-16, D4-17, D5-18, D6-19, D1-20, D2-21, D3-22, D4-23, D5-24, D6-25, D1-26, D7-27, $J_H1$, $J_H2$, $J_H3$, $J_H4$, $J_H5$ and $J_H6$ (in 5' to 3' order). The insertion was made between positions 114666435 and 114666436 on mouse chromosome 12, which is upstream of the mouse Cμ region. The mouse $V_H$, D and $J_H$ gene segments were retained in the locus, immediately upstream of (5' of) the inserted human heavy chain DNA.

A second allele, S2 was constructed in which more human functional $V_H$ gene segments were inserted upstream (5') of the 5'-most $V_H$ inserted in the S1 allele by the sequential insertion of human DNA from a second BAC (BAC2). The inserted human sequence from BAC2 corresponds to the sequence of human chromosome 14 from position 106601551 to position 106494909 and comprises functional heavy chain gene segments $V_H3$-13, $V_H3$-11, $V_H3$-9, $V_H1$-8, $V_H3$-7.

A third allele, S3 was constructed in which more human functional $V_H$ gene segments were inserted upstream (5') of the 5'-most $V_H$ inserted in the S2 allele by the sequential insertion of human DNA from a third BAC (BAC3). The inserted sequence corresponds to the sequence of human chromosome 14 from position 106759988 to position 106609301, and comprises functional heavy chain gene segments, $V_H2$-26, $V_H1$-24, $V_H3$-23, $V_H3$-21, $V_H3$-20, $V_H1$-18, and $V_H3$-15.

Mice bearing either the S1, S2 or S3 insertion into an endogenous heavy chain locus were generated from the ES cells using standard procedures. The other endogenous heavy chain locus was inactivated in the mice by insertion of an inactivating sequence comprising neo$^r$ into the mouse $J_H$-Cμ intron (to produce the "HA" allele). Standard 5'-RACE was carried out to analyse RNA transcripts from the transgenic heavy chain light chain loci in the S1, S2 and S3 mice.

The S3 mice showed high usage of human $V_H$ gene segments, 62% of rearranged transcripts using human $V_H$ gene segments and 38% of them using mouse Vκ gene segments (FIG. 13). Human $V_H$ usage was as follows—S1: 16%; S2: 64% and S3: 62% (FIG. 13).

The distribution of human $V_H$ usage from S1 to S3 mice also demonstrated that insertion of different repertoires of human $V_H$ gene segments changes the usage of human $V_H$s (FIG. 14) and thus the repertoire of expressed human heavy chain variable regions is different between the mice. While not wishing to be bound by any particular theory, the inventors surmise that this is due to the varying competition among the $V_H$s, which determine their relative usage. Thus, the inventors realised that they had surprisingly discovered a way to provide differing repertoires of antibody heavy chains and heavy chain variable regions by gene repertoire sectoring. The collection of S1, S2 and S3 as a combined population is useful, the inventors realised, to produce a novel repertoire of antibody heavy chains and antibodies that can be selected against a desired antigen. For example, the S1, S2 and S3 mice (eg, wherein endogenous heavy and light chain expression has been inactivated and optionally where the mice express light chains comprising human variable regions) can be immunised with the same human antigen and anti-antigen antibodies from the totally of antibodies in the mice can be selected on the basis of affinity and/or target epitope recognition or another desirable feature.

Further sectoring of the VH gene repertoire was performed by constructing a fourth heavy chain allele, denoted "V6", in which more human functional $V_H$ gene segments were inserted upstream (5') of the 5'-most $V_H$ inserted in the S1 allele by the sequential insertion of human DNA from a BAC (BAC6). The inserted human sequence from BAC6 corresponds to the sequence of human chromosome 14 from position 107147078 to position 106995083 and comprises functional heavy chain gene segments $V_H3$-66, $V_H3$-64, $V_H4$-61, $V_H4$-59, $V_H1$-58, $V_H3$-53, $V_H5$-51, $V_H3$-49 (FIG. 16).

As shown in FIG. 15, S2 and V6 mice showed greater human VH gene segment usage than S1 mice. The usage in S2 compared to V6 was, furthermore, different. See also FIG. 16.

In summary, the analysis of heavy chain sequences revealing differential usage and thus differing heavy chain and human heavy chain variable region sequence repertoires could be produced by the gene sectoring technique. The repertoires differed in their human $V_H$, D and $J_H$ gene segment usage. Additionally, the proportions of particular human gene segments shared by mice could be altered in the expression profiles by the gene sectoring technique of the present invention (FIGS. 14 & 16).

Example 5

Producing New Heavy Chain and Human V Region Repertoires by Gene Sectoring Human D Gene Repertoires Assessment of D gene segment sectoring can be performed as follows. A functional human gene segment repertoire (from $V_H$2-26 to $J_H$6, see the IMGT database for the structure of the human IgH locus; http://www.imgt.org/IMGTrepertoire/index.php?section=LocusGenes&repertoire=locus&species=human&group=IGK) is sectored to produce two different transgenic heavy chain alleles (denoted S3F and S3FD) and corresponding mice. Endogenous heavy chain variable regions are inactivated by inversion as described in WO2011004192. The transgenic alleles are expressed in the mice and the heavy chain repertoires are assessed at the RNA transcript level.

Using BAC insertion techniques similar to those described for Example 4, human heavy gene segments are inserted from a 1st IGH BAC into the IGH locus of mouse AB2.1 ES cells (Baylor College of Medicine) is performed to create a heavy chain allele denoted the S1 allele. The insertion is made between positions 114666435 and 114666436 on mouse chromosome 12, which is upstream of the mouse Cµ region. The mouse $V_H$, D and $J_H$ gene segments are retained in the locus, immediately upstream of (5' of) the inserted human heavy chain DNA (and subsequently inverted to inactivate at a later stage).

A second allele, S2 is constructed in which more human functional $V_H$ gene segments are inserted upstream (5') of the 5'-most $V_H$ inserted in the 51 allele by the sequential insertion of human DNA from a second BAC (BAC2). The inserted human sequence from BAC2 corresponds to the sequence of human chromosome 14 from position 106601551 to position 106494909 and comprises functional heavy chain gene segments $V_H$3-13, $V_H$3-11, $V_H$3-9, $V_H$1-8, $V_H$3-7.

A third allele, S3 is constructed in which more human functional $V_H$ gene segments is inserted upstream (5') of the 5'-most $V_H$ inserted in the S2 allele by the sequential insertion of human DNA from a third BAC (BAC3). The inserted sequence corresponds to the sequence of human chromosome 14 from position 106759988 to position 106609301, and comprises functional heavy chain gene segments, $V_H$2-26, $V_H$1-24, $V_H$3-23, $V_H$3-21, $V_H$3-20, $V_H$1-18, and $V_H$3-15.

Two different versions of the heavy chain allele are made, differing only in their human D gene segment repertoires:
version 1 (denoted S3F) had a human gene segment repertoire $V_H$2-5, $V_H$7-4-1, $V_H$4-4, $V_H$1-3, $V_H$1-2, $V_H$6-1, D1-1, D2-2, D3-9, D3-10, D4-11, D5-12, D6-13, D1-14, D2-15, D3-16, D4-17, D5-18, D6-19, D1-20, D2-21, D3-22, D4-23, D5-24, D6-25, D1-26, D7-27, $J_H$1, $J_H$2, $J_H$3, $J_H$4, $J_H$5 and $J_H$6 (in 5' to 3' order).
version 2 (denoted S3FD) had a human gene segment repertoire $V_H$2-5, $V_H$7-4-1, $V_H$4-4, $V_H$1-3, $V_H$1-2, $V_H$6-1, D1-1, D2-2, <u>D3-3,D4-4,D5-5,D6-6,D1-7,D2-8</u>, D3-9, D3-10, D4-11, D5-12, D6-13, D1-14, D2-15, D3-16, D4-17, D5-18, D6-19, D1-20, D2-21, D3-22, D4-23, D5-24, D6-25, D1-26, D7-27, $J_H$1, $J_H$2, $J_H$3, $J_H$4, $J_H$5 and $J_H$6 (in 5' to 3' order). The underlined segments do not appear in S3F.

Mice bearing either the S3F or S3FD insertion into an endogenous heavy chain locus are generated from the ES cells using standard procedures. The other endogenous heavy chain locus is inactivated in the mice by insertion of an inactivating sequence comprising neo$^r$ into the mouse $J_H$-Cµ intron (to produce the "HA" allele). Standard 5'-RACE is carried out to analyse RNA transcripts from the transgenic heavy chain light chain loci in the S3F and S3FD mice.

It is expected that the analysis of heavy chain sequences will reveal differential D gene segment usage (even for D segments found in both S3F and S3FD repertoires), and possibly different V and/or J gene segment usage, and thus differing heavy chain and human heavy chain variable region sequence repertoires will be produced by the gene sectoring technique.

Example 6

Plural Inverted Human Gene Segments are Used for Ig Chain Rearrangement & Expression In Example 3, we describe the generation of K1, K2 and K3 mice. K4 mice were generated as follows by the insertion of further DNA from the Vκ gene cluster of human chromosome 2.

A fourth allele, K4 was constructed in which more human functional Vκ gene segments were inserted upstream (5') of the 5'-most Vκ inserted in the K3 allele by the sequential insertion of human DNA from a fourth BAC. The inserted sequence corresponds to the sequence of human chromosome 2 from position [90062244] to position [90276666], and comprises functional kappa gene segments [Vκ3D-20, Vκ1D-17, Vκ1D-16, Vκ1D-13, Vκ1D-12, Vκ3D-11, Vκ1D-43, Vκ1D-8, Vκ3D-7] (FIG. 17). These ten Vκs are in the distal cluster of Vκ segment and naturally in an opposite orientation to the Jκ exons in germline human chromosome 2 but were inverted to the proximal human Jκs and the mouse Cκ in this transgenic allele.

The K4 mice showed high usage of human Vκs, 94.5% of rearranged transcripts using human Vκs and only 5.5% of them using mouse Vκs (FIG. 18). Compared to K1, K2 and K3, K4 showed improved human Vκ usage to K1 and K2 (K1: 78%; K2: 83%), and similar usage to K3 (K3: 93%) (FIG. 19). All the Vκs from the distal cluster are rarely used in human (Cox, J P L et al, "A directory of human germ-lime Vκ segments reveals a strong bias in their usage", Eur. J. Immunol. 1994. 24: 827-836). The distribution of human Vκ usage from K4 mice demonstrated that these Vκs were frequently used for rearrangement and expression (FIG. 20). These data indicate that although these Vκs from the distal cluster are rarely used in human, they are used very well once they are inverted as per the invention. The distribution of human Vκ usage in K4 mice also demonstrated that the insertion of human VκBACs changed the usage of Vκs versus K1 to K3 mice (FIG. 20). We hypothesize that the competition among those Vκs would determine their relative usage. This also applies to the Jκ usage. With the 3$^{rd}$ BAC insertion, the Jκ4 usage is increased and this is retained following the 4$^{th}$ BAC insertion (FIG. 21).

The invention claimed is:

1. A sectored population of mice, wherein the population provides a repertoire of different human immunoglobulin variable light chain (VL) gene segments, the repertoire of VL gene segments being divided between the genomes of at least two or more groups of mice of said population of mice, wherein said population comprises a first group comprising one or more mice and a second group comprising one or more mice, wherein the genome of each mouse of said first and second groups of one or more mice comprises one or more recombinant immunoglobulin light chain (IgL) loci and one or more recombinant immunoglobulin heavy chain (IgH) loci, wherein each said recombinant IgH locus comprising one or more human VH gene segments, one or more human D gene segments and one or more human JH gene segments upstream of one or more constant regions comprising an endogenous CH segment;

wherein each said recombinant IgL locus of said first group of one or more mice of said population comprising human V region DNA consisting essentially of (in 5' to 3' direction):

(i) a first human VL gene segment repertoire consisting essentially of human Vλ gene segments, and (ii) one or more human Jλ gene segments upstream of one or more light chain constant regions at an endogenous light chain locus;

wherein a said recombinant IgL locus of said second group of one or more mice of said population comprising human V region DNA comprising sequentially (in 5' to 3' direction):

(i) a second human VL gene segment repertoire, (ii) one or more human JL gene segments, and (iii) one or more light chain constant regions at an endogenous light chain locus;

wherein said recombinant IgH locus of said population of mice comprises a common human/mouse DNA junction, wherein following rearrangement, (a) said recombinant immunoglobulin light chain locus of the first group of one or more mice expresses recombinant light chains comprising human Vλ Jλ variable regions resulting from rearrangement of human Vλ gene segments of said human Vλ gene segment repertoire and said one or more human A gene segments, and (b) said recombinant immunoglobulin light chain locus of the second group of one or more mice expresses recombinant light chains comprising human VLJL variable regions resulting from rearrangement of human VL gene segments of said second human VL gene segment repertoire and said one or more human JL gene segments, and wherein endogenous kappa IgL expression is substantially inactive in said first group of one or more mice, such that less than 10% of the antibody kappa light chains are endogenous; and wherein endogenous IgH expression is substantially inactive in both said first and second group of one or more mice, such that less than 10% of the antibody heavy chains are endogenous; and wherein said first human VL gene segment repertoire is different from said second human VL gene segment repertoire, and whereby said first group of one or more mice expresses a repertoire of human IgL Variable regions that is different from the repertoire of human IgL Variable regions expressed by said second group of one or more mice; and wherein each mouse of said first and second groups of one or more mice comprises recombinant antibodies comprising human immunoglobulin heavy and light chain V regions which specifically bind the same antigen.

2. The sectored population of claim 1, wherein said first group of one or more mice expresses more light chains comprising human lambda variable regions than kappa variable regions.

3. The sectored population of claim 2, wherein each said recombinant light chain locus of said first group of one or more mice comprises a substantially complete functional Vλ gene segment repertoire of a human.

4. The sectored population of claim 2, wherein the endogenous lambda light chain expression is substantially inactive in each mouse of said first group of one or more mice, such that less than 10% of the antibody lambda light chains are endogenous in each mouse of said first group of one or more mice.

5. The sectored population of claim 2, wherein the human Vλ gene segment repertoire of said first group of one or more mice comprises human lambda chain locus distal Vλ gene cluster gene segments, and wherein human lambda locus proximal Vλ gene cluster gene segments are not present between said distal Vλ gene cluster gene segments and the one or more human Jλ gene segments in the recombinant immunoglobulin lambda chain locus of said first group of one or more mice.

6. The sectored population of claim 2, wherein said recombinant light chain locus of said first group of one or more mice comprises at least 20, 25, 26, 27, 28, 29 or 30 human Vλ gene segments selected from the group consisting of V3-1, V2-8, V3-9, V3-10, V2-11, V3-12, V316, V2-18, V3-19, V3-21, V3-22, V2-23, V3-25, V3-27, V1-36, V5-37, V5-39, V1-40, V7-43, V1-44, V5-45, V7-46, V1-74, V9-49, V1-51, V5-52, V6-57, V4-60, V8-61 and V4-69.

7. The sectored population of claim 2, wherein said recombinant light chain locus of said first group of one or more mice comprises a substantially complete functional Vλ gene segment repertoire and a substantially complete Jλ repertoire of a human.

8. The sectored population of claim 2, wherein said recombinant light chain locus of said first group of one or more mice comprises 3 to 5 human Jλ gene segments selected from the group consisting of J1, J2, J3, J6 and J7.

9. The sectored population of claim 2, wherein said first group of one or more mice expresses endogenous kappa light chain variable region in less than 10% of its antibodies.

10. The sectored population of claim 2, wherein mice of said first group of one or more mice express endogenous kappa light chain variable region in less than 5% of their antibodies.

11. The sectored population of claim 2, wherein mice of said first group of one or more mice express endogenous kappa light chain variable region in less than 0.5% of their antibodies.

12. The sectored population of claim 2, wherein mice of said first group of one or more mice express no antibody comprising endogenous kappa light chain variable region.

13. The sectored population of claim 2, wherein mice of said first group of one or more mice express endogenous heavy chain variable region in less than 10% of their antibodies.

14. The sectored population of claim 2, wherein said first group of one or more mice express endogenous heavy chain variable region in less than 5% of their antibodies.

15. The sectored population of claim 2, wherein mice of said first group of one or more mice express endogenous heavy chain variable region in less than 0.5% of their antibodies.

16. The sectored population of claim 2, wherein mice of said first group of one or more mice express no antibody comprising endogenous heavy chain variable region.

17. The sectored population of claim 2, wherein mice of said first group of one or more mice are functional to express a light chain polypeptide repertoire comprising at least $10^7$ members, each said member comprising a human V region encoded by recombined human Vλ and human Jλ gene segments.

18. The sectored population of claim 2, wherein said recombinant immunoglobulin light chain locus of mice of said first group of one or more mice comprises said human Vλ region gene segments positioned upstream of and operably linked to an endogenous kappa constant region.

19. The sectored population of claim 2, wherein first and second recombinant immunoglobulin light chain loci of mice of said first group of one or more mice comprise said human Vλ region gene segments at an endogenous λ locus.

20. The sectored population of claim 2, wherein each said first and second group of one or more mice expresses endogenous λ light chain.

21. The sectored population of claim 2, wherein said endogenous light chain locus of (iii) is an endogenous λ light chain locus.

22. The sectored population of claim 2, wherein said recombinant immunoglobulin light chain locus of mice of said second group of one or more mice comprises human Vλ region gene segments upstream of an endogenous Cκ gene.

23. The sectored population of claim 2, wherein said human VL gene segment repertoire of said recombinant immunoglobulin light chain locus of mice of said second group of one or more mice consists essentially of human Vκ gene segments, and wherein said one or more human JL gene segments of said recombinant immunoglobulin light chain locus of said second group of one or more mice comprises human Jκ gene segments.

24. The sectored population of claim 23, wherein said human Vκ gene segments and said one or more human Jκ gene segments of said recombinant immunoglobulin light chain locus of said second group of one or more mice are upstream of and operably linked to a kappa light chain constant region.

25. The sectored population of claim 23, wherein said human Vκ gene segments and said one or more human Jκ gene segments of said recombinant immunoglobulin light chain locus of said second group of one or more mice are at an endogenous lambda locus.

26. The sectored population of claim 24 or claim 25, wherein said second group of one or more mice is functional to express a light chain polypeptide repertoire comprising at least 10$^7$ members, each said member comprising a human V region encoded by recombined human Vκ and human Jκ gene segments.

27. The sectored population of claim 2, wherein the endogenous kappa light chain expression is substantially inactive in mice of said second group of one or more mice, such that less than 10% of the antibody kappa light chains in mice of said second group of one or more mice are endogenous.

28. The sectored population of claim 1, wherein the first human V λ gene segment repertoire consists essentially of human Vλ gene segments, and the light chain locus of mice of the first group of one or more mice comprises one or more human Jλ gene segments, and a λ enhancer upstream of a mouse λ enhancer.

29. The sectored population of claim 1, wherein said recombinant immunoglobulin light chain locus of mice of said first group of one or more mice further comprises a human λ enhancer upstream of said one or more light chain constant regions at said endogenous locus.

30. The sectored population of claim 1, wherein said recombinant immunoglobulin light chain locus of mice of said second group of one or more mice further comprises a light chain enhancer upstream of said one or more light chain constant regions at said endogenous locus.

31. The sectored population of claim 1, wherein said antigen is a human antigen.

32. The sectored population of claim 2, wherein each said recombinant light chain locus of said first group of one or more mice comprises at least 30 different human Vλ gene segments.

33. The sectored population of claim 1, wherein said first group of said population comprises two or more mice and wherein said second group of said population comprises two or more mice.

34. The sectored population of claim 1, wherein said first group of said population comprises three or more mice and wherein said second group of said population comprises three or more mice.

* * * * *